(12) United States Patent
Connolly et al.

(10) Patent No.: US 12,221,469 B2
(45) Date of Patent: Feb. 11, 2025

(54) SWITCH RECEPTORS USING IL-9 SIGNALING DOMAINS

(71) Applicants: Parker Institute for Cancer Immunotherapy, San Francisco, CA (US); The Board of Trustees of the Leland Stanford Junior University, Stanford, CA (US)

(72) Inventors: John Connolly, Red Oak, TX (US); Sean Parker, San Francisco, CA (US); Kenan Christopher Garcia, San Francisco, CA (US)

(73) Assignees: PARKER INSTITUTE FOR CANCER IMMUNOTHERAPY, San Francisco, CA (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 18/328,473

(22) Filed: Jun. 2, 2023

(65) Prior Publication Data
US 2023/0303661 A1 Sep. 28, 2023

Related U.S. Application Data

(63) Continuation of application No. 17/946,894, filed on Sep. 16, 2022, now abandoned.

(60) Provisional application No. 63/245,661, filed on Sep. 17, 2021.

(51) Int. Cl.
| | |
|---|---|
| *C12N 5/071* | (2010.01) |
| *C07K 14/705* | (2006.01) |
| *C07K 14/715* | (2006.01) |
| *A61K 39/00* | (2006.01) |
| *C07K 14/71* | (2006.01) |
| *C12N 5/078* | (2010.01) |
| *C12N 5/0783* | (2010.01) |
| *C12N 15/63* | (2006.01) |
| *C12N 15/85* | (2006.01) |

(52) U.S. Cl.
CPC .... *C07K 14/7155* (2013.01); *C07K 14/70578* (2013.01); *A61K 39/4611* (2023.05); *A61K 39/4631* (2023.05); *A61K 39/464406* (2023.05); *A61K 39/464419* (2023.05); *A61K 39/464474* (2023.05); *A61K 2239/23* (2023.05); *A61K 2239/53* (2023.05); *A61K 2239/59* (2023.05); *C07K 14/70503* (2013.01); *C07K 14/70521* (2013.01); *C07K 14/71* (2013.01); *C07K 2319/03* (2013.01); *C07K 2319/32* (2013.01); *C12N 5/0634* (2013.01); *C12N 5/0636* (2013.01); *C12N 15/63* (2013.01); *C12N 15/85* (2013.01)

(58) Field of Classification Search
None
See application file for complete search history.

(56) References Cited

U.S. PATENT DOCUMENTS

| | | |
|---|---|---|
| 2011/0118337 A1 | 5/2011 | Chau et al. |
| 2018/0228842 A1 | 8/2018 | Garcia et al. |
| 2018/0298101 A1* | 10/2018 | Huntington .......... A61K 31/506 |
| 2019/0292533 A1 | 9/2019 | Nager et al. |
| 2019/0359685 A1 | 11/2019 | Tanaka et al. |
| 2020/0216514 A1 | 7/2020 | Fussenegger et al. |
| 2021/0169933 A1 | 6/2021 | Yang et al. |
| 2021/0238258 A1 | 8/2021 | Garcia et al. |
| 2023/0085834 A1 | 3/2023 | Siurala et al. |
| 2023/0110313 A1 | 4/2023 | Connolly et al. |
| 2023/0265147 A1 | 8/2023 | Siurala et al. |
| 2023/0265163 A1 | 8/2023 | Connolly et al. |

FOREIGN PATENT DOCUMENTS

| | | | |
|---|---|---|---|
| WO | WO-2017/029512 A1 | 2/2017 | |
| WO | WO-2019/152660 A1 | 8/2019 | |
| WO | WO-2020163634 A1 * | 8/2020 | ............. A61K 35/17 |
| WO | WO-2021/023987 A1 | 2/2021 | |
| WO | WO-2021/050752 A1 | 3/2021 | |
| WO | WO-2021/141986 A1 | 7/2021 | |
| WO | WO-2021/170666 A1 | 9/2021 | |
| WO | WO-2021/207274 A2 | 10/2021 | |
| WO | WO-2022/192346 A1 | 9/2022 | |
| WO | WO-2023/044453 A1 | 3/2023 | |
| WO | WO-2023/044456 A1 | 3/2023 | |

(Continued)

OTHER PUBLICATIONS

NCBI SEQ ID No. 1-6 and 53-56 Blast results. See attached search results for each SEQ ID No. Searched Nov. 3, 2023. (Year: 2023).*

(Continued)

*Primary Examiner* — Emily A Cordas
*Assistant Examiner* — Constantina E Stavrou
(74) *Attorney, Agent, or Firm* — Mintz, Levin, Cohn, Ferris, Glovsky and Popeo, P.C.

(57) ABSTRACT

The present disclosure generally relates to, inter alia, a class of chimeric switch receptors containing an endodomain of an IL-9 receptor, engineered to modulate transcriptional regulation in a ligand-dependent manner. The disclosure also provides compositions and methods useful for producing such receptors, nucleic acids encoding same, host cells genetically modified with the nucleic acids, as well as methods for modulating gene expression, modulating an activity of a cell, and/or for the treatment of various health conditions or diseases.

20 Claims, 19 Drawing Sheets
Specification includes a Sequence Listing.

(56) References Cited

FOREIGN PATENT DOCUMENTS

| WO | WO-2023/044457 A1 | 3/2023 |
| WO | WO-2023/044461 A2 | 3/2023 |
| WO | WO-2023/044461 A3 | 3/2023 |
| WO | WO-2024/015723 A1 | 1/2024 |

OTHER PUBLICATIONS

Bhattacharya, R. et al. (Mar. 15, 2017). "Impact of genetic variation on three dimensional structure and function of proteins," *PLoS One* 12(3):e0171355, 22 pages.

Chakraborty, S. et al. (May 2019, e-published Apr. 29, 2019). "An Update on Interleukin- 9: From Its Cellular Source and Signal Transduction to Its Role in Immunopathogenesis," *International Journal of Molecular Sciences* 20(9):2113-2129.

International Search Report mailed on Feb. 2, 2023 for PCT Application No. PCT/US2022/076612, filed Sep. 16, 2022, 7 pages.

International Search Report mailed on Mar. 28, 2023, for PCT Application No. PCT/US2022/076618, filed Sep. 16, 2022, 6 pages.

Kalbasi, et al. (Jul. 1, 2021). Abstract NG11 "Orthogonal IL-9 Receptor Signaling Reprograms T Cells to Obviate Conditioning Chemotherapy Before Adoptive Cell Therapy," *Cancer Research* 81(13):NG11.

Kalbasi, A. et al. (Jul. 2022, e-published Jun. 8, 2022). "Potentiating adoptive cell therapy using synthetic IL-9 receptors," *Nature* 607(7918):360-365.

Tokuriki, N. et al. (Oct. 2009, e-published Sep. 16, 2009). "Stability effects of mutations and protein evolvability," *Current Opinion in Structural Biology* 19(5):596-604.

Turnis, M.E. et al. (Jul. 6, 2015). "Inhibitory receptors as targets for cancer immunotherapy," *European Journal of Immunology* 45(7):1892-1905.

Written Opinion mailed on Feb. 2, 2023 for PCT Application No. PCT/US2022/076612, filed Sep. 16, 2022, 6 pages.

Written Opinion mailed on Mar. 28, 2023, for PCT Application No. PCT/US2022/076618, filed Sep. 16, 2022, 7 pages.

\* cited by examiner

| Sequence ID | Ligand-binding domain | Transmembrane domain | Intracellular domain | Linker | pSTAT type | No Ligand Stimulation (gMFI) | Ligand Stimulated (gMFI) | Fold increase in gMFI |
|---|---|---|---|---|---|---|---|---|
| SEQ63+CAR+ | IL21R | IL9R | IL9R | N/A | pSTAT1 | 620 | 1478 | 2.38 |
|  |  |  |  |  | pSTAT3 | 345 | 1831 | 5.31 |
|  |  |  |  |  | pSTAT5 | 700 | 870 | 1.24 |
| SEQ66 | IL15Ra | IL9R | IL9R | N/A | pSTAT1 | 491 | 917 | 1.87 |
|  |  |  |  |  | pSTAT3 | 330 | 594 | 1.80 |
|  |  |  |  |  | pSTAT5 | 669 | 2283 | 3.41 |
| SEQ72+CAR+ | IL4Ra | IL9R | IL9R | N/A | pSTAT1 | 471 | 770 | 1.63 |
|  |  |  |  |  | pSTAT3 | 243 | 444 | 1.83 |
|  |  |  |  |  | pSTAT5 | 536 | 660 | 1.23 |
| SEQ153+CAR+ | IL10Ra | IL9R | IL9R | G4S | pSTAT1 | 261 | 1900 | 7.28 |
|  |  |  |  |  | pSTAT3 | 78 | 1569 | 20.12 |
|  |  |  |  |  | pSTAT5 | 284 | 663 | 2.33 |

FIG. 1

SWITCH RECEPTORS USING IL-9 SIGNALING DOMAINS

CROSS-REFERENCE TO RELATED APPLICATIONS

This application is a continuation of U.S. patent application Ser. No. 17/946,894, filed Sep. 16, 2022, which claims the benefit of U.S. Provisional Patent Application No. 63/245,661, filed Sep. 17, 2021, the disclosures of which are incorporated by reference herein in their entireties.

STATEMENT AS TO RIGHTS TO INVENTIONS MADE UNDER FEDERALLY SPONSORED RESEARCH AND DEVELOPMENT

This invention was made with Government support under Contract AI051321 awarded by the National Institutes of Health. The Government has certain rights in the invention.

REFERENCE TO AN ELECTRONIC SEQUENCE LISTING

The contents of the electronic sequence listing 051288-502001US.xml; Size: 348 Kb; and Date of Creation: Dec. 4, 2022 is hereby incorporated by reference in its entirety.

FIELD

The present disclosure relates generally to synthetic cellular receptors that bind extracellular ligands and have IL-9 endodomains. The disclosure also provides compositions and methods useful for producing such receptors, nucleic acids encoding same, host cells genetically modified with the nucleic acids, as well as methods for modulating gene expression, modulating an activity of a cell, and/or for the treatment of various health conditions or diseases.

BACKGROUND

The manipulation of cells, particularly immune cells, to differentiate, develop specialized functions and expand in numbers is of great clinical interest. Many protein factors that affect these activities are known in the art, including in particular cytokines and chemokines. However, these signaling molecules also have pleiotropic effects on cells not targeted for manipulation, and thus methods of selectively activating signaling in a targeted cell population are desirable. The ability to engineer immune cells to carry out controlled behaviors is of interest in the field. For example, in adoptive immunotherapy T cells are isolated from blood, processed ex vivo, and re-infused into patients. Such T cells have been developed for use in therapeutic applications such as the treatment of cancer, infection, and autoimmune diseases.

A critical challenge in cell based therapies is the ability to engineer receptors that respond to native molecules while also allowing the selective manipulation of immune cells. Some groups have manipulated proteins to bind and respond to modified ligands in a manner independent, or orthogonal, from the influence of the native proteins or ligands. This technology relies on the engineering of both an orthogonal cytokine and an orthogonal receptor, and, relies on the premise that native molecules will not recognize the orthogonal receptor. One of the challenges associated with generating orthogonal ligand-receptor pairs is finding mutations that efficiently prevent activation by the endogenous molecule without otherwise compromising the receptor's structure or intrinsic ability to activate gene transcription. In alternative methods, to modulate signaling in immune cells, the only approach to prevent negative signals delivered by molecules such as PD-1, is to give patients systemic treatment of antagonistic antibodies that bind to PD-1. This approach has the limitation that systemic treatment prevents T cells that are present in the tumor microenvironment and the entire immune system from being inactivated, which in some patients can result in autoimmunity or systemic inflammatory syndrome (Beck et al., 2006, J Clin Oncol 24: 2283-9; Blansfield et al., 2005, J Immunother 28: 593-8; Dougan et al., 2009, Annual Review of Immunology 27: 83-117).

The disclosure provided here provides solutions to the problems existing with previous attempts to manipulate immune cells and potentially offer improved methods for treatments involving cell transfer.

SUMMARY

The present disclosure generally relates to, among other things, chimeric switch receptors containing an endodomain of an IL-9 receptor, engineered to modulate transcriptional regulation in a ligand-dependent manner. The activity of these switch receptors can be controlled by the presence of an extracellular ligand, allowing for spatial and temporal control of specific gene expression in mammalian cells, as well as for use in modulating cell activities or in treating various health conditions, such as diseases.

In one aspect, provided herein are recombinant nucleic acid molecules encoding chimeric receptors that comprise an extracellular portion comprising a binding domain of an endogenous cytokine receptor, an intracellular portion comprising an endodomain of an IL-9 receptor, and a transmembrane domain that joins the extracellular portion and intracellular portion.

In some embodiments, the recombinant nucleic acid molecule further comprises one or more linkers.

In some embodiments, the endogenous cytokine receptor is selected from IL-2rb, IL-2ra, IL-4r, IL-7ra, IL-15ra, and IL-21ra.

In some embodiments, the endogenous cytokine receptor comprises an amino acid sequence having at least 80% sequence identity to an amino acid sequence selected from SEQ ID Nos: 1-6.

In some embodiments, the transmembrane domain is selected from the transmembrane domain of IL-9, IL-7ra, IL-2rb, and TNFR1. In some embodiments, the transmembrane domain comprises an amino acid sequence selected from SEQ ID Nos: 53-56.

In some embodiments, the chimeric receptor comprises an amino acid sequence having at least 80% sequence identity to an amino acid sequence selected from SEQ ID Nos: 63-80.

Another aspect provides recombinant nucleic acid molecules encoding chimeric receptors comprising an extracellular portion comprising a binding domain of an endogenous inhibitory receptor an intracellular portion comprising an endodomain of an IL-9 receptor linked to a BOX1/2 common gamma chain domain; and a transmembrane domain that joins the extracellular portion and the intracellular portion.

In some embodiments, the recombinant nucleic acid molecule further comprises one or more linkers.

In some embodiments, the endogenous inhibitory receptor is selected from TGF-beta R1, TGF-beta R2, IL-10ra, FAS, CTLA4, LAG3, TIM3, PD1, ILT2, ILT3, ILT4, ILT5, and VEGF.

In some embodiments, the endogenous inhibitory receptor comprises an amino acid sequence having at least 80% sequence identity to an amino acid sequence selected from SEQ ID Nos: 7-52.

In some embodiments, the transmembrane domain is selected from the transmembrane domain of IL-9, IL-7ra, IL-2rb, and TNFR1.

In some embodiments, the transmembrane domain is selected from the transmembrane domain of IL-9, IL-7ra, IL-2rb, and TNFR1.

In some embodiments, the chimeric receptor comprises an amino acid sequence having at least 80% sequence identity to an amino acid sequence selected from SEQ ID Nos: 81-203.

Another aspect provides recombinant nucleic acid molecules encoding chimeric receptors comprising an extracellular portion comprising a binding domain of an endogenous inhibitory receptor linked to an agent specific for the common gamma chain; an intracellular portion comprising an endodomain of an IL-9 receptor; and a transmembrane domain that joins the extracellular portion and the intracellular portion.

In some embodiments, the recombinant nucleic acid molecule further comprises one or more linkers.

In some embodiments, the endogenous inhibitory receptor is selected from TGF-beta R1, TGF-beta R2, IL-10ra, FAS, CTLA4, LAG3, TIM3, PD1, ILT2, ILT3, ILT4, ILT5, and VEGF.

In some embodiments, the endogenous inhibitory receptor comprises an amino acid sequence having at least 80% sequence identity to an amino acid sequence selected from SEQ ID Nos: 7-52.

In some embodiments, the transmembrane domain is selected from the transmembrane domain of IL-9, IL-7ra, IL-2rb, and TNFR1. In some embodiments, the transmembrane domain comprises an amino acid sequence selected from SEQ ID Nos: 53-56.

In some embodiments, the agent specific for the common gamma chain comprises a nanobody, a darpin, IL-2, IL-4, IL-7, and scFV.

Another aspect relates to an expression vector comprising the recombinant nucleic acid molecules of the disclosure.

Another aspect relates to a host cell comprising the expression vector of the present disclosure. In some embodiments, the host cell is a mammalian cell. In some embodiments, the host cell is an immune cell.

Another aspect provides a composition comprising a recombinant nucleic acid of the present disclosure.

Another aspect provides a composition of cells comprising the expression vector of the present disclosure.

Another aspect provides a polypeptide encoded by the recombinant nucleic acid the present disclosure.

Another aspect provides a composition of one or more polypeptides encoded by one or more recombinant nucleic acids of the present disclosure.

Another aspect provides a composition of cells capable of expressing the chimeric receptor encoded by the recombinant nucleic acid of the present disclosure.

Another aspect provides a composition of cells comprising a chimeric receptor comprising an amino acid sequence selected from SEQ ID Nos: 63-203.

Another aspect relates to a method for modulating the activity of an immune cell comprising administering, to an immune cell, the recombinant nucleic acid of the present disclosure.

Another aspect relates to a method of treating a subject that involves administering, to the subject, a cell expressing the recombinant nucleic acid of the present disclosure.

In some embodiments, the subject is treated for cancer.

In some embodiments, the subject is treated for autoimmune disease.

In some embodiments, the subject is treated for infection.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 1 shows the pSTAT expression profile in either stimulated or unstimulated primary human T cells transduced with a lentiviral vector encoding switch receptors of SEQ ID NO:63+CAR+(IL21R ECD+IL9R TM+IL9R ICD and CAR 4D5), SEQ ID NO:66 (IL15Ra+IL9R TM+IL9R ICD), SEQ ID NO:72+CAR+(IL4R ECD+IL9R TM+IL9R ICD and CAR 4D5), or SEQ ID NO:153+CAR+(IL10Ra ECD+IL9R TM+IL9R ICD and CAR 4D5).

DETAILED DESCRIPTION OF THE DISCLOSURE

Figure 2:
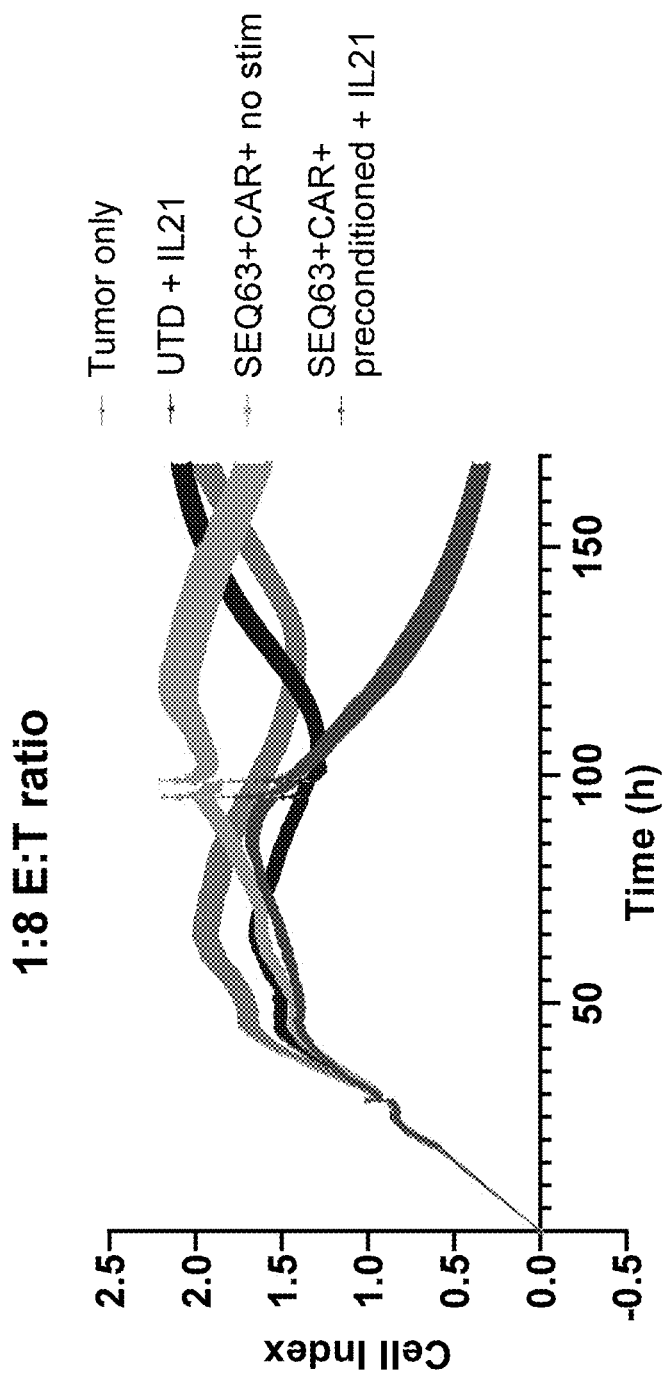
FIG. 2 shows a real-time cytotoxicity assay (RTCA) with T cells co-expressing switch receptor SEQ63 (IL21R ECD+IL9R TM+IL9R ICD) and CAR (4D5) against SKOV-3 human ovarian adenocarcinoma cells expressing HER2. Double-positive T cells (SEQ63+CAR+) were left unstimulated ("no stim") before being added on SKOV-3 tumor cells at a 1:8 effector-to-target ratio, or preconditioned for 48 hours with IL21 before addition to the plate with continued ligand stimulation ("preconditioned+IL21"). Untransduced T cells (UTD) served as control and were added on tumor cells with continued IL21 stimulation ("UTD+IL21").

The present disclosure generally relates to, among other things, chimeric switch receptors containing an endodomain of an IL-9 receptor and a binding domain of an endogenous receptor, wherein the chimeric switch receptor is engineered to modulate transcriptional regulation in a ligand-dependent manner. The activity of these switch receptors can be controlled by the presence of an extracellular ligand, allowing for spatial and temporal control of specific gene expression in mammalian cells, as well as for use in modulating cell activities, immune system responses, or in treating various health conditions, such as diseases. Particularly, the chimeric switch receptor (termed "IL-9 switch receptor"), even though containing the endodomain of an IL-9 receptor, does not require IL-9 for activation and can be tailored to be activated by ligands specific for the binding domains of the endogenous receptors, such as normally inhibitory ligands. This class of chimeric switch receptors is synthetic and recombinant, and does not occur in nature. As described below, the chimeric switch receptors disclosed herein can be synthetic polypeptides, and can be engineered, designed, or modified so as to provide desired and/or improved properties, e.g., modulating transcription. The disclosure also provides compositions and methods useful for producing such receptors, nucleic acids encoding same, cells genetically modified with the nucleic acids, as well as methods for modulating an activity of a cell, modulating immune system, and/or for the treatment of various diseases.

In the following detailed description, the illustrative alternatives described in the detailed description and claims are not meant to be limiting. Other alternatives may be used and other changes may be made without departing from the spirit or scope of the subject matter presented here. It will be readily understood that the aspects, as generally described herein, can be arranged, substituted, combined, and designed in a wide variety of different configurations, all of which are explicitly contemplated and make part of this application.

Definitions

The singular form "a", "an", and "the" include plural references unless the context clearly dictates otherwise. For example, the term "a cell" includes one or more cells, including mixtures thereof. "A and/or B" is used herein to include all of the following alternatives: "A", "B", "A or B", and "A and B."

The terms "administration" and "administering", as used herein, refer to the delivery of a composition or formulation as disclosed herein by an administration route including, but not limited to, intravenous, intra-arterial, intracranial, intramuscular, intraperitoneal, subcutaneous, intramuscular, or combinations thereof. The term includes, but is not limited to, administration by a medical professional and self-administration.

"Cancer" refers to the presence of cells possessing several characteristics typical of cancer-causing cells, such as uncontrolled proliferation, immortality, metastatic potential, rapid growth and proliferation rate, and certain characteristic morphological features. Cancer cells can aggregate into a mass, such as a tumor, or can exist alone within a subject. A tumor can be a solid tumor, a soft tissue tumor, or a metastatic lesion. As used herein, the term "cancer" also encompasses other types of non-tumor cancers. Non-limiting examples include blood cancers or hematological cancers, such as leukemia. Cancer can include premalignant, as well as malignant cancers.

The terms "cell", "cell culture", and "cell line" refer not only to the particular subject cell or cell line but also to the progeny or potential progeny of such a cell, cell culture, or cell line, without regard to the number of transfers or passages in culture. It should be understood that not all progeny are exactly identical to the parental cell. This is because certain modifications may occur in succeeding generations due to either mutations (e.g., deliberate or inadvertent mutations) or environmental influences (e.g., methylation or other epigenetic modifications), such that progeny may not, in fact, be identical to the parent cell, but are still included within the scope of the term as used herein, so long as the progeny retain the same functionality as that of the original cell, cell culture, or cell line.

As used herein "endogenous" refers to any material from or produced inside an organism, cell, tissue or system (e.g., as it would occur in nature or naturally produced).

The term "percent identity", as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the complement of a sequence. This definition also includes sequences that have deletions and/or additions, as well as those that have substitutions. Sequence identity can be calculated over a region that is at least about 20 amino acids or nucleotides in length, or over a region that is 10-100 amino acids or nucleotides in length, or over the entire length of a given sequence. Sequence identity can be calculated using published techniques and widely available computer programs, such as the GCS program package (Devereux et al, *Nucleic Acids Res.* 12:387, 1984), BLASTP, BLASTN, FASTA (Atschul et al., *Mol Biol* 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

As used herein, a "subject" or an "individual" includes animals, such as human (e.g., human subject) and non-human animals. In some embodiments, a "subject" or "individual" is a patient under the care of a physician. Thus, the subject can be a human patient or a subject who has, is at risk of having, or is suspected of having a disease of interest (e.g., cancer) and/or one or more symptoms of the disease. The subject can also be a subject who is diagnosed with a risk of the condition of interest at the time of diagnosis or later. The term "non-human animals" includes all vertebrates, e.g., mammals, e.g., rodents, e.g., mice, non-human primates, and other mammals, such as e.g., sheep, dogs, cows, chickens, and non-mammals, such as amphibians, reptiles, etc.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

All ranges disclosed herein also encompass any and all possible sub-ranges and combinations of sub-ranges thereof. Any listed range can be recognized as sufficiently describing and enabling the same range being broken down into at least equal halves, thirds, quarters, fifths, tenths, etc. As a non-limiting example, each range discussed herein can be readily broken down into a lower third, middle third and upper third, and so forth. As will also be understood by one skilled in the art all language such as "up to", "at least", "greater than", "less than", and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

IL-9 and Common Gamma Chain Receptors

Interleukin-9 (IL-9) is a member of a group of cytokines referred to as the common γ chain cytokines. Common γ chain cytokines exert numerous functions on immune cell survival, function and proliferation. The γc family consists of six members—IL-2, IL-4, IL-7, IL-9, IL-15, and IL-21— which all have unique receptors. Upon receptor ligation, γc cytokines through JAK1 and JAK3 activate various developmental pathways including STAT1, STAT3, STAT5, MAPK, and PI3K/AKT pathways.

An important aspect of γc receptor signaling is positive and negative regulation of pathways to either enhance or repress signaling. Some of the γc cytokines can mediate similar signaling pathways and transcriptional programs (Kovanen P E, Rosenwald A, Fu J, Hurt E M, Lam L T, Giltnane J M, et al. Analysis of Gamma C-Family Cytokine Target Genes. Identification of Dual-Specificity Phosphatase 5 (DUSP5) as a Regulator of Mitogen-Activated Protein Kinase Activity in Interleukin-2 Signaling. *J Biol Chem* (2003) 278(7):5205-13; Osinalde N, Sanchez-Quiles V, Akimov V, Guerra B, Blagoev B, Kratchmarova I. Simultaneous Dissection and Comparison of IL-2 and IL-15 Signaling Pathways by Global Quantitative Phosphoproteomics. *Proteomics* (2015) 15(2-3):520-31), however, physiological differences in cytokine signaling are mediated by competition for γc between the different receptors (Gonnord P, Angermann B R, Sadtler K, Gombos E, Chappert P, Meier-Schellersheim M, et al. A Hierarchy of Affinities Between Cytokine Receptors and the Common Gamma Chain Leads to Pathway Cross-Talk. *Sci Signal* (2018) 11(524)), variability in receptor expression on T cell subsets, a bias for signaling through different STAT molecules, and differences in activation of the MAPK and PI3K pathways (Zeng R, Spolski R, Casas E, Zhu W, Levy D E, Leonard W J. The Molecular Basis of IL-21-Mediated Proliferation. *Blood* (2007) 109(10):4135-42; Gadina M, Sudarshan C, Visconti R, Zhou Y J, Gu H, Neel B G, et al. The Docking Molecule Gab2 is Induced by Lymphocyte Activation and is Involved in Signaling by Interleukin-2 and Interleukin-15 But Not Other Common Gamma Chain-Using Cytokines. *J Biol Chem* (2000) 275(35):26959-66).

The IL-9 receptor alpha (IL-9Rα), a member of the type I hematopoietin receptor superfamily, has high affinity (Kd of approximately 100 pM) for IL-9. This 64-kDa glycoprotein is reported on a variety of hematopoietic cells, particularly T cells. Similar to the other members of the IL-2 receptor family, IL-9Rα also forms a heterotypic receptor complex with the common gamma (γc) chain. In the IL-9R heterocomplex, the IL-9Rα chain is the ligand binding domain and γ chain serves as the signaling subunit. The IL-9Rα subunit is characterized by four extracellular cysteines and the conserved WSXWS motif, while the intracellular domain contains a BOX1 consensus sequence and a serine rich region. IL-9Rα is found in both membrane bound and soluble forms, whereas the γc subunit is observed only in a membrane bound form.

IL-9 binding to IL-9Rα results in the formation the IL-9R heterocomplex. A hallmark of the IL-9R heterocomplex is the absence of any intracellular enzymatic activity, and, therefore, Janus kinases (JAK) need to mediate the phosphorylation of the receptor (Knoops L., Renauld J. C. IL-9 and its receptor: From signal transduction to tumorigenesis. Growth Factors. 2004; 22:207-215). Upon IL-9 binding to the receptor, a conformational change occurs in the IL-9R heterocomplex, which allows JAK molecules to bind to the proline rich BOX1 motif in the membrane-proximal region of IL-9Ra. JAK1 associates with IL-9Ra, whereas JAK3 binds to γc. Phosphorylated JAK1 and JAK3 then mediate the phosphorylation of receptor tyrosine residues. Phosphorylated tyrosine residues act as docking sites for the downstream Src homology 2 (SH2) domain containing signaling molecules such as Signal Transducer and Activator of Transcription (STAT) transcription factors, insulin receptor substrate (IRS), and the adaptors of the Mitogen-Activated Protein Kinase (MAPK) pathways.

Compositions of the Disclosure

As described in greater detail below, one aspect of the present disclosure relates to recombinant nucleic acids encoding chimeric switch receptors that include an extracellular portion comprising a binding domain of an endogenous cytokine receptor or endogenous inhibitory receptor, an intracellular portion comprising an endodomain of an IL-9 receptor, and transmembrane domain that joins the extracellular portion and the intracellular portion. Such receptors are engineered to modulate transcriptional regulation in a ligand-dependent manner with various advantages including the ability to convert an otherwise negative signal into a positive signal in the cell. Thus, the present disclosure also encompasses switch receptors that are able to switch negative signals to positive signals for enhancement of an immune response. The present disclosure also encompasses receptors that are able to bind to an endogenous or exogenously given ligand (e.g. a cytokine) and, regardless of the cytokine, result in activation of STAT5, for example, via the common gamma chain and IL-9 endodomain.

As described in the Examples, certain recombinant nucleic acids encoding chimeric receptors can be tested and validated in T cells. These chimeric receptors are expected to show similar performance in mouse models as well as models in other suitable animals or in vitro systems. The receptors disclosed herein may be engineered into various immune cell types for enhanced discrimination and elimination of tumors, or in recombinant host cells for control of autoimmunity and infection. Accordingly, recombinant host cells and compositions of cells, such as immune cells capable of expressing one of more of the chimeric receptors disclosed herein, are also within the scope of the disclosure. In some embodiments, a composition of cells expresses the chimeric receptor encoded by the recombinant nucleic acid described herein.

Switch Receptors

The present disclosure is based, inter alia, on recombinant nucleic acid molecules encoding chimeric receptors which comprise an endodomain of an IL-9 receptor, thus creating chimeric receptors that can respond to various extracellular ligands while maintaining the ability to initiate intracellular signaling through the IL-9 receptor endodomain. Immune cells expressing these chimeric receptors may be useful in the context of modulating immune cell activity. In some embodiments, the ligand can be added exogenously and not be limited to production within the cell.

As outlined above, some embodiments of the present disclosure relate to recombinant nucleic acid molecules encoding chimeric receptors containing the endodomain of an IL-9 receptor. In particular, the chimeric receptors, even though containing an IL-9 endodomain, do not require binding of IL-9 for the functioning of the receptors. Generally, the chimeric receptors comprise an extracellular portion, an intracellular portion comprising an endodomain of an IL-9 receptor, and a transmembrane domain that joins the extracellular portion and the intracellular portion. In some embodiments, extracellular portion comprises a binding domain of an endogenous cytokine receptor. In some embodiments, the extracellular portion comprises a binding domain of an endogenous inhibitory receptor.

In some embodiments, provided herein is a recombinant nucleic acid encoding a chimeric polypeptide including: (a) an extracellular portion comprising a binding domain of an endogenous cytokine receptor; (b) an intracellular portion comprising an endodomain of an IL-9 receptor; (c) a transmembrane domain that joins the extracellular portion and the intracellular portion.

In some embodiments, provided herein is a recombinant nucleic acid encoding a chimeric polypeptide including: (a) an extracellular portion comprising a binding domain of an endogenous inhibitory receptor; (b) an intracellular portion comprising an endodomain of an IL-9 receptor linked to a BOX1/2 common gamma chain domain; (c) a transmembrane domain that joins the extracellular portion and the intracellular portion.

In some embodiments, provided herein is a recombinant nucleic acid encoding a chimeric polypeptide including: (a) an extracellular portion comprising a binding domain of an endogenous inhibitory receptor linked to an agent specific for the common gamma chain; (b) an intracellular portion comprising an endodomain of an IL-9 receptor; (c) a transmembrane domain that joins the extracellular portion and the intracellular portion.

Extracellular Portions

As outlined above, the extracellular portions of the chimeric receptors (e.g., switch receptors) in some embodiments of the disclosure have a binding domain of an endogenous cytokine receptor or an endogenous inhibitory receptor. A binding domain of an endogenous cytokine receptor can be an extracellular portion of an endogenous cytokine receptor, or a fragment or truncation thereof that can bind a cytokine polypeptide sequence. In some embodiments, the endogenous cytokine receptor is a member of the common gamma chain receptor family. Members of the common gamma chain receptor family are known in the art and are discussed supra. In some embodiments, the endogenous cytokine receptor is selected from IL-2rb, IL-2ra, IL-4r, IL-7ra, IL-15ra, and IL-21ra. As described supra, IL-2rb, IL-2ra, IL-4r, IL-7ra, IL-15ra, and IL-21ra are all part of the common gamma chain family. Therefore, these receptors are capable of recruiting the common gamma chain, upon ligand binding, and signaling can proceed through the IL-9 endodomain.

In one embodiment, the endogenous cytokine receptor comprises the amino acid sequence of IL-2rb (SEQ ID NO:1) below:

AVNGTSQFTCFYNSRANISCVWSQDGALQDTSCQVHAWPDRRRWNQTCELL

PVSQASWACNLILGAPDSQKLTTVDIVTLRVLCREGVRWRVMAIQDFKPFE

NLRLMAPISLQVVHVETHRCNISWEISQASHYFERHLEFEARTLSPGHTWE

EAPLLTLKQKQEWICLETLTPDTQYEFQVRVKPLQGEFTTWSPWSQPLAFR

TKPAALGKDT

In one embodiment, the endogenous cytokine receptor comprises the amino acid sequence of IL-2ra (SEQ ID NO:2) below:

ELCDDDPPEIPHATFKAMAYKEGTMLNCECKRGFRRIKSGSLYMLCTGNSS

HSSWDNQCQCTSSATRNTTKQVTPQPEEQKERKTTEMQSPMQPVDQASLPG

HCREPPPWENEATERIYHFVVGQMVYYQCVQGYRALHRGPAESVCKMTHGK

TRWTQPQLICTGEMETSQFPGEEKPQASPEGRPESETSCLVTTTDFQIQTE

MAATMETSIFTTEYQ

In one embodiment, the endogenous cytokine receptor comprises the amino acid sequence of IL-4 (SEQ ID NO:3) below:

MKVLQEPTCVSDYMSISTCEWKMNGPTNCSTELRLLYQLVFLLSEAHTCIP

ENNGGAGCVCHLLMDDVVSADNYTLDLWAGQQLLWKGSFKPSEHVKPRAPG

-continued
NLTVHTNVSDTLLLTWSNPYPPDNYLYNHLTYAVNIWSENDPADFRIYNVT

YLEPSLRIAASTLKSGISYRARVRAWAQCYNTTWSEWSPSTKWHNSYREPF

EQH

In one embodiment, the endogenous cytokine receptor comprises the amino acid sequence of IL-7ra (SEQ ID NO:4) below:

ESGYAQNGDLEDAELDDYSFSCYSQLEVNGSQHSLTCAFEDPDVNITNLEF

EICGALVEVKCLNFRKLQEIYFIETKKFLLIGKSNICVKVGEKSLTCKKID

LTTIVKPEAPFDLSVVYREGANDFVVTFNTSHLQKKYVKVLMHDVAYRQEK

DENKWTHVNLSSTKLTLLQRKLQPAAMYEIKVRSIPDHYFKGFWSEWSPSY

YFRTPEINNSSGEMD

In one embodiment, the endogenous cytokine receptor comprises the amino acid sequence of IL-15ra (SEQ ID NO:5) below:

ITCPPPMSVEHADIWVKSYSLYSRERYICNSGFKRKAGTSSLTECVLNKAT

NVAHWTTPSLKCIRDPALVHQRPAPPSTVTTAGVTPQPESLSPSGKEPAAS

SPSSNNTAATTAAIVPGSQLMPSKSPSTGTTEISSHESSHGTPSQTTAKNW

ELTASASHQPPGVYPQGHSDTT

In one embodiment, the endogenous cytokine receptor comprises the amino acid sequence of IL-21ra (SEQ ID NO:6) below:

CPDLVCYTDYLQTVICILEMWNLHPSTLTLTWQDQYEELKDEATSCSLHRS

AHNATHATYTCHMDVFHFMADDIFSVNITDQSGNYSQECGSFLLAESIKPA

PPFNVTVTFSGQYNISWRSDYEDPAFYMLKGKLQYELQYRNRGDPWAVSPR

RKLISVDSRSVSLLPLEFRKDSSYELQVRAGPMPGSSYQGTWSEWSDPVIF

QTQSEELKE

In some embodiments, the extracellular portions of the chimeric polypeptides disclosed herein (e.g., IL-9 switch receptors) having at least 80% sequence identity, such as, at least 80%, at least 85%, at least 90%, at least 95%, at least 96%, at least 97%, at least 98%, or 99% sequence identity to a sequence selected from the group consisting of SEQ ID NOS: 1-6 in the Sequence Listing. In some embodiments, the extracellular portion includes an amino acid sequence having at least 90% sequence identity to a sequence selected from the group consisting of SEQ ID NOS: 1-6. In some embodiments, the extracellular portion includes an amino acid sequence having at least 95% sequence identity to a sequence selected from the group consisting of SEQ ID NOS: 1-6. In some embodiments, the extracellular portion includes an amino acid sequence having about 100% sequence identity to a sequence selected from the group consisting of SEQ ID NOS: 1-6. In some embodiments, the extracellular portion includes an amino acid sequence having a sequence selected from the group consisting of SEQ ID NOS: 1-6, wherein one, two, three, four, or five of the amino acid residues in any one of the SEQ ID NOS: 1-6 is substituted by a different amino acid residue.

In another aspect of the present disclosure, the extracellular portion of the chimeric receptor of the disclosure can also comprise a binding domain of an endogenous inhibitory receptor. Specifically, as described supra, in some embodiments, provided herein is a recombinant nucleic acid encoding a chimeric polypeptide including: (a) an extracellular portion comprising a binding domain of an endogenous inhibitory receptor linked to an agent specific for the common gamma chain; (b) an intracellular portion comprising an endodomain of an IL-9 receptor; (c) a transmembrane domain that joins the extracellular portion and the intracellular portion.

As described supra, signaling through the IL-9 endodomain requires recruitment of the common gamma chain. In some embodiments, the binding domains of the extracellular portion of the inhibitory receptors described herein are not able to naturally recruit the common gamma chain in order to elicit signaling through the IL-9 endodomain of the chimeric receptor. Accordingly, in these embodiments, the binding domain of the endogenous inhibitory receptor is linked to an agent specific for the common gamma chain. The binding domain of the inhibitory receptor is linked to the agent specific for the common gamma chain such that both components are able to function in their intended way (e.g., the binding domain is able to bind a ligand and the agent specific for the common gamma chain is able to bind the common gamma chain).

In some embodiments, the agent specific for the common gamma chain comprises agent specific for the common gamma chain comprises a nanobody, a darpin, IL-2, IL-4, IL-7, or an scFv.

In some embodiments, an scFv directed to the common gamma chain is cloned in frame with the extracellular portion of the chimeric receptor, with suitable linker sequences inserted between these components. The binding of the common gamma chain to the scFv will be sufficient to induce chimeric receptor dimerization.

scFVs directed to the common gamma chain as well as their sequences are known in the art and described in WO 2017/021540. However, the use of scFVs directed to the common gamma chain with respect to switch receptors is not disclosed therein.

A binding domain of an endogenous inhibitory receptor can be an extracellular portion of an endogenous inhibitory receptor, or a fragment or truncation thereof that can bind a cytokine polypeptide sequence and subsequently decrease immune activity. For example, a natural inhibitory receptor can reduce T cell proliferation, T cell survival, cytokine release, or immune cell lytic activity upon binding of a natural agonist.

Endogenous inhibitory receptors are well known in the art and are contemplated for use in the compositions described herein (Turnis et al., "Inhibitory Receptors as Targets for Cancer Immunotherapy," *Eur J Immunol* 2015 45(7):1892-1905).

In some embodiments, the endogenous inhibitory receptor signals through trimerization. In some embodiments, the endogenous inhibitory receptor is a member of the TNF receptor superfamily.

In some embodiments, the endogenous inhibitory receptor signals as functional dimers of dimers. In some embodiments, the endogenous inhibitory receptor is a member of the TGF beta superfamily of receptors. Receptors in this family include, for example, Type I, Type II, and Type III receptors. Exemplary members of the Type I receptor family include, without limitation, ACVRL1, ACVR1A, BMPR1A, ACVR1B, TGFβR1, BMPR1B, and ACVR1C. Exemplary members of the Type II receptor family include, without limitation, TGFBR2, BMPR2, ACVR2A, ACVR2B, and AMHR2. TGF βR3 is a member of the Type III family of receptors.

In some embodiments, the endogenous inhibitory receptor signal as dimers. In some embodiments, the endogenous inhibitory receptor is a member of the VEGF family of receptors. Receptors in this family include, for example, VEGFR1, VEGFR2, and VEGFR3.

In some embodiments, the endogenous inhibitory receptor is selected from TGF-beta R1, TGF-beta R2, IL-10ra, FAS, CTLA4, LAGS, TIM3, PD1, ILT2, ILT3, ILT4, ILT5, and VEGF. Thus, in some embodiments, the extracellular portion of the chimeric receptor of the disclosure can be a binding domain of TGF-beta R1, TGF-beta R2, IL-10ra, FAS, CTLA4, LAGS, TIM3, PD1, ILT2, ILT3, ILT4, ILT5, and VEGF.

In one embodiment, the endogenous inhibitory receptor comprises the amino acid sequence of TGFBR1 (SEQ ID NO:7) below:

LQCFCHLCTKDNFTCVTDGLCFVSVTETTDKVIHNSMCIAEIDLIPRDRPF

VCAPSSKTGSVTTTYCCNQDHCNKIELPTTVKSSPGLGPVEL

In one embodiment, the endogenous inhibitory receptor comprises the amino acid sequence of TGFBR2 (SEQ ID NO:8) below:

TIPPHVQKSVNNDMTVTDNNGAVKFPQLCKFCDVRFSTCDNQKSCMSNCSI

TSICEKPQEVCVAVWRKNDENITLETVCHDPKLPYHDFILEDAASPKCIMK

EKKKPGETFFMCSCSSDECNDNIIFSEEYNTSNPDLLLVIFQ

In one embodiment, the endogenous inhibitory receptor comprises the amino acid sequence of IL-10ra (SEQ ID NO:9) below:

HGTELPSPPSVWFEAEFFHHILHWTPIPNQSESTCYEVALLRYGIESWNSI

SNCSQTLSYDLTAVTLDLYHSNGYRARVRAVDGSRHSNWTVTNTRFSVDEV

TLTVGSVNLEIHNGFILGKIQLPRPKMAPANDTYESIFSHFREYEIAIRKV

PGNFTFTHKKVKHENFSLLTSGEVGEFCVQVKPSVASRSNKGMWSKEECIS

LTRQYFTVTN

In one embodiment, the endogenous inhibitory receptor comprises the amino acid sequence of FAS (SEQ ID NO:10) below:

QVTDINSKGLELRKTVTTVETQNLEGLHHDGQFCHKPCPPGERKARDCTVN

GDEPDCVPCQEGKEYTDKAHFSSKCRRCRLCDEGHGLEVEINCTRTQNTKC

RCKPNFFCNSTVCEHCDPCTKCEHGIIKECTLTSNTKCKEEGSRSN

In one embodiment, the endogenous inhibitory receptor comprises the amino acid sequence of CTLA4 (SEQ ID NO:11) below:

KAMHVAQPAVVLASSRGIASFVCEYASPGKATEVRVTVLRQADSQVTEVCA

ATYMMGNELTFLDDSICTGTSSGNQVNLTIQGLRAMDTGLYICKVELMYPP

PYYLGIGNGTQIYVIDPEPCPDSD

In one embodiment, the endogenous inhibitory receptor comprises the amino acid sequence of LAG3 (SEQ ID NO:12) below:

LQPGAEVPVVWAQEGAPAQLPCSPTIPLQDLSLLRRAGVTWQHQPDSGPPA

AAPGHPLAPGPHPAAPSSWGPRPRRYTVLSVGPGGLRSGRLPLQPRVQLDE

RGRQRGDFSLWLRPARRADAGEYRAAVHLRDRALSCRLRLRLGQASMTASP

PGSLRASDWVILNCSFSRPDRPASVHWFRNRGQGRVPVRESPHHHLAESFL

FLPQVSPMDSGPWGCILTYRDGFNVSIMYNLTVLGLEPPTPLTVYAGAGSR

VGLPCRLPAGVGTRSFLTAKWTPPGGGPDLLVTGDNGDFTLRLEDVSQAQA

GTYTCHIHLQEQQLNATVTLAIITVTPKSFGSPGSLGKLLCEVTPVSGQER

FVWSSLDTPSQRSFSGPWLEAQEAQLLSQPWQCQLYQGERLLGAAVYFTEL

SSPGAQRSGRAPGALPAGHL

In one embodiment, the endogenous inhibitory receptor comprises the amino acid sequence of TIM3 (SEQ ID NO:13) below:

SEVEYRAEVGQNAYLPCFYTPAAPGNLVPVCWGKGACPVFECGNVVLRTDE

RDVNYWTSRYWLNGDFRKGDVSLTIENVTLADSGIYCCRIQIPGIMNDEKF

NLKLVIKPAKVTPAPTRQRDFTAAFPRMLTTRGHGPAETQTLGSLPDINLT

QISTLANELRDSRLANDLRDSGATIRIG

In one embodiment, the endogenous inhibitory receptor comprises the amino acid sequence of PD1 (SEQ ID NO:14) below:

FTVTVPKDLYVVEYGSNMTIECKFPVEKQLDLAALIVYWEMEDKNHIQFV

HGEEDLKVQHSSYRQRARLLKDQLSLGNAALQITDVKLQDAGVYRCMISY

GGADYKRITVKVNAPYNKINQRILVVDPVTSEHELTCQAEGYPKAEVIWT

SSDHQVLSGKTTTTNSKREEKLFNVTSTLRINTTTNEIFYCTFRRLDPEE

NHTAELVIPELPLAHPPNER

In one embodiment, the endogenous inhibitory receptor comprises the amino acid sequence of ILT2 (SEQ ID NO:15) below:

GHLPKPTLWAEPGSVITQGSPVTLRCQGGQETQEYRLYREKKTALWITRI

PQELVKKGQFPIPSITWEHAGRYRCYYGSDTAGRSESSDPLELVVTGAYI

KPTLSAQPSPVVNSGGNVILQCDSQVAFDGFSLCKEGEDEHPQCLNSQPH

ARGSSRAIFSVGPVSPSRRWWYRCYAYDSNSPYEWSLPSDLLELLVLGVS

KKPSLSVQPGPIVAPEETLTLQCGSDAGYNRFVLYKDGERDFLQLAGAQP

QAGLSQANFTLGPVSRSYGGQYRCYGAHNLSSEWSAPSDPLDILIAGQFY

DRVSLSVQPGPTVASGENVTLLCQSQGWMQTFLLTKEGAADDPWRLRSTY

QSQKYQAEFPMGPVTSAHAGTYRCYGSQSSKPYLLTHPSDPLELVVSGPS

GGPSSPTTGPTSTSGPEDQPLTPTGSDPQSGLGRHLGV

In one embodiment, the endogenous inhibitory receptor comprises the amino acid sequence of ILT3 (SEQ ID NO:16) below:

QAGPLPKPTLWAEPGSVISWGNSVTIWCQGTLEAREYRLDKEESPAPWDR

QNPLEPKNKARFSIPSMTEDYAGRYRCYYRSPVGWSQPSDPLELVMTGAY

SKPTLSALPSPLVTSGKSVTLLCQSRSPMDTFLLIKERAAHPLLHLRSEH

GAQQHQAEFPMSPVTSVHGGTYRCFSSHGFSHYLLSHPSDPLELIVSGSL

EDPRPSPTRSVSTAAGPEDQPLMPTGSVPHSGLRRHWE

In one embodiment, the endogenous inhibitory receptor comprises the amino acid sequence of ILT4 (SEQ ID NO:17) below:

QTGTIPKPTLWAEPDSVITQGSPVTLSCQGSLEAQEYRLYREKKSASWIT

RIRPELVKNGQFHIPSITWEHTGRYGCQYYSRARWSELSDPLVLVMTGAY

PKPTLSAQPSPVVTSGGRVTLQCESQVAFGGFILCKEGEEEHPQCLNSQP

HARGSSRAIFSVGPVSPNRRWSHRCYGYDLNSPYVWSSPSDLLELLVPGV

SKKPSLSVQPGPVVAPGESLTLQCVSDVGYDRFVLYKEGERDLRQLPGRQ

PQAGLSQANFTLGPVSRSYGGQYRCYGAHNLSSECSAPSDPLDILITGQI

RGTPFISVQPGPTVASGENVTLLCQSWRQFHTFLLTKAGAADAPLRLRSI

HEYPKYQAEFPMSPVTSAHAGTYRCYGSLNSDPYLLSHPSEPLELVVSGP

SMGSSPPPTGPISTPAGPEDQPLTPTGSDPQSGLGRHLGV

In one embodiment, the endogenous inhibitory receptor comprises the amino acid sequence of ILT5 (SEQ ID NO:18) below:

GPFPKPTLWAEPGSVISWGSPVTIWCQGSQEAQEYRLHKEGSPEPLDRNN

PLEPKNKARFSIPSMTEHHAGRYRCHYYSSAGWSEPSDPLEMVMTGAYSK

PTLSALPSPVVASGGNMTLRCGSQKGYHHFVLMKEGEHQLPRTLDSQQLH

SRGFQALFPVGPVTPSHRWRFTCYYYYTNTPWVWSHPSDPLEILPSGVSR

KPSLLTLQGPVLAPGQSLTLQCGSDVGYNRFVLYKEGERDFLQRPGQQPQ

AGLSQANFTLGPVSPSNGGQYRCYGAHNLSSEWSAPSDPLNILMAGQIYD

TVSLSAQPGPTVASGENVTLLCQSWWQFDTFLLTKEGAAHPPLRLRSMYG

AHKYQAEFPMSPVTSAHAGTYRCYGSYSSNPHLLSHPSEPLELVVSGHSG

GSSLPPTGPPSTPGLGRYLE

In one embodiment, the endogenous inhibitory receptor comprises the amino acid sequence of VEGFR1 (SEQ ID NO:19) below:

SKLKDPELSLKGTQHIMQAGQTLHLQCRGEAAHKWSLPEMVSKESERLSI

TKSACGRNGKQFCSTLTLNTAQANHTGFYSCKYLAVPTSKKKETESAIYI

FISDTGRPFVEMYSEIPEIIHMTEGRELVIPCRVTSPNITVTLKKFPLDT

LIPDGKRIIWDSRKGFIISNATYKEIGLLTCEATVNGHLYKTNYLTHRQT

NTIIDVQISTPRPVKLLRGHTLVLNCTATTPLNTRVQMTWSYPDEKNKRA

SVRRRIDQSNSHANIFYSVLTIDKMQNKDKGLYTCRVRSGPSFKSVNTSV

HIYDKAFITVKHRKQQVLETVAGKRSYRLSMKVKAFPSPEVVWLKDGLPA

TEKSARYLTRGYSLIIKDVTEEDAGNYTILLSIKQSNVFKNLTATLIVNV

KPQIYEKAVSSFPDPALYPLGSRQILTCTAYGIPQPTIKWFWHPCNHNHS

EARCDFCSNNEESFILDADSNMGNRIESITQRMAIIEGKNKMASTLVVAD

SRISGIYICIASNKVGTVGRNISFYITDVPNGFHVNLEKMPTEGEDLKLS

CTVNKFLYRDVTWILLRTVNNRTMHYSISKQKMAITKEHSITLNLTIMNV

SLQDSGTYACRARNVYTGEEILQKKEITIRDQEAPYLLRNLSDHTVAISS

STTLDCHANGVPEPQITWFKNNHKIQQEPGIILGPGSSTLFIERVTEEDE

GVYHCKATNQKGSVESSAYLTVQGTSDKSNLE

In one embodiment, the endogenous inhibitory receptor comprises the amino acid sequence of VEGFR2 (SEQ ID NO:20) below:

ASVGLPSVSLDLPRLSIQKDILTIKANTTLQITCRGQRDLDWLWPNNQSG

SEQRVEVTECSDGLFCKTLTIPKVIGNDTGAYKCFYRETDLASVIYVYVQ

DYRSPFIASVSDQHGVVYITENKNKTVVIPCLGSISNLNVSLCARYPEKR

FVPDGNRISWDSKKGFTIPSYMISYAGMVFCEAKINDESYQSIMYIVVVV

GYRIYDVVLSPSHGIELSVGEKLVLNCTARTELNVGIDFNWEYPSSKHQH

KKLVNRDLKTQSGSEMKKFLSTLTIDGVTRSDQGLYTCAASSGLMTKKNS

TFVRVHEKPFVAFGSGMESLVEATVGERVRIPAKYLGYPPPEIKWYKNGI

PLESNHTIKAGHVLTIMEVSERDTGNYTVILTNPISKEKQSHVVSLVVYV

PPQIGEKSLISPVDSYQYGTTQTLTCTVYAIPPPHHIHWYWQLEEECANE

PSQAVSVTNPYPCEEWRSVEDFQGGNKIEVNKNQFALIEGKNKTVSTLVI

QAANVSALYKCEAVNKVGRGERVISFHVTRGPEITLQPDMQPTEQESVSL

WCTADRSTFENLTWYKLGPQPLPIHVGELPTPVCKNLDTLWKLNATMFSN

STNDILIMELKNASLQDQGDYVCLAQDRKTKKRHCVVRQLTVLERVAPTI

TGNLENQTTSIGESIEVSCTASGNPPPQIMWFKDNETLVEDSGIVLKDGN

RNLTIRRVRKEDEGLYTCQACSVLGCAKVEAFFIIEGAQEKTNLE

In one embodiment, the endogenous inhibitory receptor comprises the amino acid sequence of VEGFR3 (SEQ ID NO:21) below:

YSMTPPPTLNITEESHVIDTGDSLSISCRGQHPLEWAWPGAQEEAPATGDKD

SEDTGVVRDCEGTDARPYCKVLLLHEVHANDTGSYVCYYKYIKARIEGTT

AASSYVFVRDFEQPFINKPDTLLVNRKDAMWVPCLVSIPGLNVTLRSQSS

VLWPDGQEVVWDDRRGMLVSTPLLHDALYLQCETTWGDQDFLSNPFLVHI

TGNELYDIQLLPRKSLELLVGEKLVLNCTVWAEFNSGVTFDWDYPGKQAE

RGKWVPERRSQQTHTELSSILTIHNVSQHDLGSYVCKANNGIQRFRESTE

VIVHENPFISVEWLKGPILEATAGDELVKLPVKLAAYPPPEFQWYKDGKA

LSGRHSPHALVLKEVTEASTGTYTLALWNSAAGLRRNISLELVVNVPPQI

HEKEASSPSIYSRHSRQALTCTAYGVPLPLSIQWHWRPWTPCKMFAQRSL

RRRQQQDLMPQCRDWRAVTTQDAVNPIESLDTWTEFVEGKNKTVSKLVIQ

NANVSAMYKCVVSNKVGQDERLIYFYVTTIPDGFTIESKPSEELLEGQPV

LLSCQADSYKYEHLRWYRLNLSTLHDAHGNPLLLDCKNVHLFATPLAASL

EEVAPGARHATLSLSIPRVAPEHEGHYVCEVQDRRSHDKHCHKKYLSVQA

-continued
LEAPRLTQNLTDLLVNVSDSLEMQCLVAGAHAPSIVWYKDERLLEEKSGV

DLADSNQKLSIQRVREEDAGRYLCSVCNAKGCVNSSASVAVEGSEDKGSM

E

A number of other receptor sequences are contemplated for use in the extracellular portions of the chimeric receptors described herein. Such sequences may be used to switch the natural biology of the receptor ligand or provide for localized stimulation of a cell population. Exemplary sequences of the extracellular portions of such receptors are shown in Table 1 below.

| Receptor Extracellular Portion | Amino Acid Sequence | SEQ ID NO |
|---|---|---|
| OPG | ETFPPKYLHYDEETSHQLLCDKCPPGTYLKQHCTAKWKTVCAPCPDHYYTDSWHT SDECLYCSPVCKELQYVKQECNRTHNRVCECKEGRYLEIEFCLKHRSCPPGFGVVQ AGTPERNTV CKRCPDGFFSNETSSKAPCRKHTNCSVFGLLLTQKGNATHDNICSGNSESTQKCGI DVTLCEEAFFRFAVPTKFTPNWLSVLVDNLPGTKVNAESVERIKRQHSSQEQTFQL LKLWKHQN KDQDIVKKIIQDIDLCENSVQRHIGHANLTFEQLRSLMESLPGKKVGAEDIEKTIKAC KPSDQILKLLSLWRIKNGDQDTLKGLMHALKHSKTYHFPKTVTQSLKKTIRFLHSFT MYKLYQKLFLEMIGNQVQSVKISCL | 22 |
| TACI | MSGLGRSRRGGRSRVDQEERFPQGLWTGVAMRSCPEEQYWDPLLGTCMSCKTI CNHQSQRTCAAFCRSLSCRKEQGKFYDHLLRDCISCASICGQHPKQCAYFCENKLR SPVNLPPELRRQRSGEVENNSDNSGRYQGLEHRGSEASPALPGLKLSADQVALVYS | 23 |
| BCMA | MLQMAGQCSQNEYFDSLLHACIPCQLRCSSNTPPLTCQRYCNASVTNSVKGTNA | 24 |
| NGFR | KEACPTGLYTHSGECCKACNLGEGVAQPCGANQTVCEPCLDSVTFSDVVSATEPC KPCTECVGLQSMSAPCVEADDAVCRCAYGYYQDETTGRCEACRVCEAGSGLVFSC QDKQNTVCEE CPDGTYSDEANHVDPCLPCTVCEDTERQLRECTRWADAECEEIPGRWITRSTPPE GSDSTAPSTQEPEAPPEQDLIASTVAGVVTTVMGSSQPVVTRGTTDN | 25 |
| EDAR | EYSNCGENEYYNQTTGLCQECPPCGPGEEPYLSCGYGTKDEDYGCVPCPAEKFSKG GYQICRRHKDCEGFFRATVLTPGDMENDAECGPCLPGYYIVILENRPRNIYGIVIVCY SCLLAPPNTKECVGATSGASANFPGTSGSSTLSPFQHAHKELSGQGHLATA | 26 |
| DCR2 (TNFRSF10D) | ATIPRQDEVPQQTVAPQQQRRSLKEEECPAGSHRSEYTGACNPCTEGVDYTIASN NLPSCLLCTVCKSGQTNKSSCTTTRDTVCQCEKGSFQDKNSPEMCRTCRTGCPRG MVKVSNCTPRSDIKCKNESAASSTGKTPAAEETVTTILGMLASPYH | 27 |
| DCR1 (TNFRSF10C) | ATTARQEEVPQQTVAPQQQRHSFKGEECPAGSHRSEHTGACNPCTEGVDYTNAS NNEPSCFPCTVCKSDQKHKSSCTMTRDTVCQCKEGTFRNENSPEMCRKCSRCPSG EVQVSNCTSWDDIQCVEEFGANATVETPAAEETMNTSPGTPAPAAEETMNTSPG TPAPAAEETMTTSPGTPAPAAEETMTTSPGTPAPAAEETMITSPGTPA | 28 |
| CD40 | EPPTACREKQYLINSQCCSLCQPGQKLVSDCTEFTETECLPCGESEFLDTWNRETHC HQHKYCDPNLGLRVQQKGTSETDTICTCEEGWHCTSEACESCVLHRSCSPGFGVK QIATGVSDTICEPCPVGFFSNVSSAFEKCHPWTSCETKDLVVQQAGTNKTDVVCG PQDRLR | 29 |
| DR4 | ASGTEAAAATPSKVWGSSAGRIEPRGGGRGALPTSMGQHGPSARARAGRAPGP RPAREASPRLRVHKTFKFVVVGVLLQVVPSSAATIKLHDQSIGTQQWEHSPLGELC PPGSHRSEHPGACNRCTEGVGYTNASNNLFACLPCTACKSDEEERSPCTTTRNTAC QCKPGTFRNDNSAEMCRKCSRGCPRGMVKVKDCTPWSDIECVHKESGNGHN | 30 |
| DR6 | QPEQKASNLIGTYRHVDRATGQVLTCDKCPAGTYVSEHCTNTSLRVCSSCPVGTFT RHENGIEKCHDCSQPCPWPMIEKLPCAALTDRECTCPPGMFQSNATCAPHTVCP VGWGVRKKGTETEDVRCKQCARGTFSDVPSSVMKCKAYTDCLSQNLVVIKPGTKE TDNVCGTLPSFSSSTSPSPGTAIFPRPEHMETHEVPSSTYVPKGMNSTESNSSASVR PKVLSSIQEGTVPDNTSSARGKEDVNKTLPNLQVVNHQQGPHHRHILKLLPSMEA TGGEKSSTPIKGPKRGHPRQNLHKHFDINEH | 31 |
| DR5 | ITQQDLAPQQRAAPQQKRSSPSEGLCPPGHHISEDGRDCISCKYGQDYSTHWNDL LFCLRCTRCDSGEVELSPCTTTRNTVCQCEEGTFREEDSPEMCRKCRTGCPRGMVK VGDCTPWSDIECVHKESGTKHSGEVPAVEETVTSSPGTPASPCS | 32 |
| DR3 | QGGTRSPRCDCAGDFHKKIGLFCCRGCPAGHYLKAPCTEPCGNSTCLVCPQDTFLA WENHHNSECARCQACDEQASQVALENCSAVADTRCGCKPGWFVECQVSQCVSS SPFYCQPCLDCGALHRHTRLLCSRRDTDCGTCLPGFYEHGDGCVSCPTSTLGSCPE RCAAVCGWRQ | 33 |
| TNFRSF1B | LPAQVAFTPYAPEPGSTCRLREYYDQTAQMCCSKCSPGQHAKVFCTKTSDTVCDS CEDSTYTQLWNWVPECLSCGSRCSSDQVETQACTREQNRICTCRPGWYCALSKQ EGCRLCAPLRKCRPGFGVARPGTETSDVVCKPCAPGTFSNTTSSTDICRPHQICNV VAIPGNASMDAVCTSTSPTRSMAPGAVHLPQPVSTRSQHTQPTPEPSTAPSTSFLL PMGPSPPAEGSTGD | 34 |

| Receptor Extracellular Portion | Amino Acid Sequence | SEQ ID NO |
|---|---|---|
| TNFRSF1 | LVPHLGDREKRDSVCPQGKYIHPQNNSICCTKCHKGTYLYNDCPGPGQDTDCREC ESGSFTASENHLRHCLSCSKCRKEMGQVEISSCTVDRDTVCGCRKNQYRHYWSEN LFQCFNCSLCLNGTVHLSCQEKQNTVCTCHAGFFLRENECVSCSNCKKSLECTKLCL PQIENVKGTEDSGTT | 35 |
| BMPR1B | KKEDGESTAPTPRPKVLRCKCHHHCPEDSVNNICSTDGYCFTMIEEDDSGLPVVTS GCLGLEGSDFQCRDTPIPHQRRSIECCTERNECNKDLHPTLPPLKNRDFVDGPIHH R | 36 |
| BMPR1A | QNLDSMLHGTGMKSDSDQKKSENGVTLAPEDTLPFLKCYCSGHCPDDAINNTCIT NGHCFAIIEEDDQGETTLASGCMKYEGSDFQCKDSPKAQLRRTIECCRTNLCNQYL QPTLPPVVIGPFFDGSIR | 37 |
| BMPR2 | SQNQERLCAFKDPYQQDLGIGESRISHENGTILCSKGSTCYGLWEKSKGDINLVKQ GCWSHIGDPQECHYEECVVTTTPPSIQNGTYRFCCCSTDLCNVNFTENFPPPDTTP LSPPHSFNRDET | 38 |
| CSF3R | ECGHISVSAPIVHLGDPITASCIIKQNCSHLDPEPQILWRLGAELQPGGRQQRLSDG TQESIITLPHLNHTQAFLSCCLNWGNSLQILDQVELRAGYPPAIPHNLSCLMNLTTS SLICQWEPGPETHLPTSFTLKSFKSRGNCQTQGDSILDCVPKDGQSHCCIPRKHLLL YQNMGIWVQAENALGTSMSPQLCLDPMDVVKLEPPMLRTMDPSPEAAPPQAG CLQLCWEPWQPGLHINQKCELRHKPQRGEASWALVGPLPLEALQYELCGLLPATA YTLQIRCIRWPLPGHWSDWSPSLELRTTERAPTVRLDTWWRQRQLDPRTVQLFW KPVPLEEDSGRIQGYVVSWRPSGQAGAILPLCNTTELSCTFHLPSEAQEVALVAYNS AGTSRPTPVVFSESRGPALTRLHAMARDPHS LWVGWEPPNPWPQGYVIEWGLGPPSASNSNKTWRMEQNGRATGFLLKENIRP FQLYEIIVTPLYQDTMGPSQHVYAYSQEMAPSHAPELHLKHIGKTWAQLEWVPEP PELGKSPLTHYTIFWTNAQNQSFSAILNASSRGFVLHGLEPASLYHIHLMAASQAG ATNSTVLTLMTLTPEGSELH | 39 |
| CSF1R | IPVIEPSVPELVVKPGATVTLRCVGNGSVEWDGPPSPHWTLYSDGSSSILSTNNATF QNTGTYRCTEPGDPLGGSAAIHLYVKDPARPWNVLAQEVVVFEDQDALLPCLLTD PVLEAGVSLVRVRGRPLMRHTNYSFSPWHGFTIHRAKFIQSQDYQCSALMGGRK VMSISIRLKVQKVIPGPPALTLVPAELVRIRGEAAQIVCSASSVDVNFDVFLQHNNT KLAIPQQSDFHNNRYQKVLTLNLDQVDFQHAGNYSCVASNVQGKHSTSMFFRVV ESAYLNLSSEQNLIQEVTVGEGLNLKVMVEAYPGLQGFNWTYLGPFSDHQPEPKL ANATTKDTYRHTFTLSLPRLKPSEAGRYSFLARNPGGWRALTFELTRYPPEVSVIW TFINGSGTLLCAASGYPQPNVTWLQCSGHTDRCDEAQVLQVWDDPYPEVLSQEP FHKVTVQSLLTVETLEHNQTYECRAHNSVGSGSWAFIPISAGAHTHPPDEFLFTP | 40 |
| Activin R1A | MEDEKPKVNPKLYMCVCEGLSCGNEDHCEGQQCFSSLSINDGFHVYQKGCFQVY EQGKMTCKTPPSPGQAVECCQGDWCNRNITAQLPTKGKSFPGTQNFHLE | 41 |
| Activin R1B | SGPRGVQALLCACTSCLQANYTCETDGACMVSIFNLDGMEHHVRTCIPKVELVPA GKPFYCLSSEDLRNTHCCYTDYCNRIDLRVPSGHLKEPEHPSMWGPVE | 42 |
| Activin R1C | LSPGLKCVCLLCDSSNFTCQTEGACWASVMLTNGKEQVIKSCVSLPELNAQVFCHS SNNVTKTECCFTDFCNNITLHLPTASPNAPKLGPME | 43 |
| Activin R2B | SGRGEAETRECIYYNANWELERTNQSGLERCEGEQDKRLHCYASWRNSSGTIELVK KGCWLDDFNCYDRQECVATEENPQVYFCCCEGNFCNERFTHLPEAGGPEVTYEPP PTAPTLLT | 44 |
| Activin R2A | AILGRSETQECLFFNANWEKDRTNQTGVEPCYGDKDKRRHCFATWKNISGSIEIVK QGCWLDDINCYDRTDCVEKKDSPEVYFCCCEGNMCNEKFSYFPEMEVTQPTSNP VTPKPP | 45 |
| TIGIT | MMTGTIETTGNISAEKGGSIILQCHLSSTTAQVTQVNWEQQDQLLAICNADLGW HISPSFKDRVAPGPGLGLTLQSLTVNDTGEYFCIYHTYPDGTYTGRIFLEVLESSVAE HGARFQIP | 46 |
| FCGR2B | TPAAPPKAVLKLEPQWINVLQEDSVTLTCRGTHSPESDSIQWFHNGNLIPTHTQPS YRFKANNNDSGEYTCQTGQTSLSDPVHLTVLSEWLVLQTPHLEFQEGETIVLRCHS WKDKPLVKVTFFQNGKSKKFSRSDPNFSIPQANHSHSGDYHCTGNIGYTLYSSKPV TITVQAP | 47 |
| FCGR1 | QVDTTKAVITLQPPWVSVFQEETVTLHCEVLHLPGSSSTQWFLNGTATQTSTPSYR ITSASVNDSGEYRCQRGLSGRSDPIQLEIHRGWLLLQVSSRVFTEGEPLALRCHAW KDKLVYNVLYYRNGKAPKFFHWNSNLTILKTNISHNGTYHCSGMGKHRYTSAGISV TVKELFPAPVLNASVTSPLLEGNLVTLSCETKLLLQRPGLQYFSFYMGSKTLRGRNT SSEYQILTARREDSGLYWCEAATEDGNVLKRSPELELQVLGLQLPTPVWFH | 48 |

| Receptor Extracellular Portion | Amino Acid Sequence | SEQ ID NO |
|---|---|---|
| 2B4 | CQGSADHVVSISGVPLQLQPNSIQTKVDSIAWKKLLPSQNGFHHILKWENGSLPSN TSNDRFSFIVKNLSLLIKAAQQQDSGLYCLEVTSISGKVQTATFQVFVFESLLPDKVE KPRLQGQGKILDRGRCQVALSCLVSRDGNVSYAWYRGSKLIQTAGNLTYLDEEVDI NGTHTYTCNVSNPVSWESHTLNLTQDCQNAHQEFRFWP | 49 |
| LAIR1 | QEEDLPRPSISAEPGTVIPLGSHVTFVCRGPVGVQTFRLERESRSTYNDTEDVSQAS PSESEARFRIDSVSEGNAGPYRCIYYKPPKWSEQSDYLELLVKETSGGPDSPDTEPG SSAGPTQRPSDNSHNEHAPASQGLKAEHLY | 50 |
| CD5 | RLSWYDPDFQARLTRSNSKCQGQLEVYLKDGWHMVCSQSWGRSSKQWEDPSQ ASKVCQRLNCGVPLSLGPFLVTYTPQSSIICYGQLGSFSNCSHSRNDMCHSLGLTCL EPQKTTPPTTRPPPTTTPEPTAPPRLQLVAQSGGQHCAGVVEFYSGSLGGTISYEA QDKTQDLENFLCNNLQCGSFLKHLPETEAGRAQDPGEPREHQPLPIQWKIQNSSC TSLEHCFRKIKPQKSGRVLALLCSGFQPKVQSRLVGGSSICEGTVEVRQGAQWAAL CDSSSARSSLRWEEVCREQQCGSVNSYRVLDAGDPTSRGLFCPHQKLSQCHELWE RNSYCKKVFVTCQDPNP | 51 |
| TWEAKR | EQAPGTAPCSRGSSWSADLDKCMDCASCRARPHSDFCLGCAAAPPAPFRLLWP | 52 |

In some embodiments, the extracellular portions of the chimeric polypeptides disclosed herein (e.g., IL-9 switch receptors) having at least 80% sequence identity, such as, at least 80%, at least 85%, at least 90%, at least 95%, at least 96%, at least 97%, at least 98%, or 99% sequence identity to a sequence selected from the group consisting of SEQ ID NOS: 7-52 in the Sequence Listing. In some embodiments, the extracellular portion includes an amino acid sequence having at least 90% sequence identity to a sequence selected from the group consisting of SEQ ID NOS: 7-52. In some embodiments, the extracellular portion includes an amino acid sequence having at least 95% sequence identity to a sequence selected from the group consisting of SEQ ID NOS: 7-52. In some embodiments, the extracellular portion includes an amino acid sequence having about 100% sequence identity to a sequence selected from the group consisting of SEQ ID NOS: 7-52. In some embodiments, the extracellular portion includes an amino acid sequence having a sequence selected from the group consisting of SEQ ID NOS: 7-52, wherein one, two, three, four, or five of the amino acid residues in any one of the SEQ ID NOS: 7-52 is substituted by a different amino acid residue.

domain can be positioned such that it directly or indirectly connects, or joins, the extracellular portion of the chimeric switch receptor to the intracellular portion of the chimeric switch receptor. This includes, but is not limited to recombinant fusions, covalent bonds, disulfide bonds, ionic bonds, hydrogen bonds, electrostatic bonds, and the like. Transmembrane domains may be a hydrophobic alpha helix that spans the cell membrane. The transmembrane domain associated with the endodomain is commonly used. However, in some embodiments, the transmembrane domain of TNFR1 is used in combination with extracellular portions from the TNF superfamily (e.g., DCR2, TNFRSF1, etc.) to stabilize the receptor structure.

The transmembrane domain can have any length. In some embodiments, the transmembrane domain includes 1 amino acid or 10 amino acids or 20 amino acids or 50 amino acids or 60 amino acids or 70 amino acids or 80 amino acids or 100 amino acids or 120 amino acids or 140 amino acids or 160 amino acids or 180 amino acids or 200 amino acids or 250 amino acids or 300 amino acids or any number therebetween.

In some embodiments, the transmembrane domain is selected from the transmembrane domain of IL-9, IL-7ra, IL-2rb, and TNFR1. Exemplary amino sequences of transmembrane domains for use herein are shown in Table 2.

TABLE 2

Transmembrane domain sequences

| Transmembrane domain | Amino acid sequence | SEQ ID NO |
|---|---|---|
| IL-9 | LIPPWGWPGNTLVAVSIFLLLTGPTYLLFKLSPR | 53 |
| IL-7ra | PILLTISILSFFSVALLVILACVLW | 54 |
| IL-2rb | IPWLGHLLVGLSGAFGFIILVYLLI | 55 |
| TNFR1 | VLLPLVIFFGLCLLSLLFIGLMY | 56 |

Transmembrane Domain (TMD)

As outlined above, the chimeric switch receptors of the disclosure also include a transmembrane domain that joins the extracellular portion and the intracellular portion of the chimeric receptor.

The transmembrane domain is a region, which can be generally hydrophobic, and crosses the cell membrane. This In some embodiments, the transmembrane domain comprises the transmembrane domain of IL-9. In some embodiments, the transmembrane domain comprises the amino acid sequence of LIPPWGWPGNTLVAVSIFLLLTGPTYLLFKLSPR (SEQ ID NO: 53).

In some embodiments, the transmembrane domain comprises the transmembrane domain of TNFR1. In some embodiments, the transmembrane domain comprises the amino acid sequence of VLLPLVIFFGLCLLSLLFIGLMY (SEQ ID NO: 56).

In some embodiments, the transmembrane domain includes an amino acid sequence exhibiting at least 70%, at least 75%, at least 80%, at least 85%, at least 90%, at least 95%, at least 96%, at least 97%, at least 98%, at least 99% sequence identity to one or more of SEQ ID NOS: 53-56 in the Sequence Listing. In some embodiments, the transmembrane domain includes an amino acid sequence having at least 90% sequence identity to a sequence selected from the group consisting of SEQ ID NOS: 53-56. In some embodiments, the transmembrane domain includes an amino acid sequence having at least 95% sequence identity to a sequence selected from the group consisting of SEQ ID NOS: 53-56. In some embodiments, the transmembrane domain includes an amino acid sequence having about 100% sequence identity to one or more of SEQ ID NOS: 53-56. In some embodiments, the transmembrane domain includes an amino acid sequence having a sequence selected from the group consisting of SEQ ID NOS: 53-56, wherein one, two, three, four, or five of the amino acid residues in any one of the SEQ ID NOS: 53-56 is substituted by a different amino acid residue.

Endodomain

In some embodiments, the endodomain is responsible for receptor clustering/dimerization after antigen binding and for initiation of signal transduction to the cell.

As outlined above, the chimeric receptors of the disclosure include an endodomain of an IL-9 receptor.

In some embodiments, the amino acid sequence for the IL-9 receptor endodomain is as follows in SEQ ID NO: 57 below:

VKRIFYQNVPSPAMFFQPLYSVHNGNFQTWMGAHGAGVLLSQDCAGTPQG

ALEPCVQEATALLTCGPARPWKSVALEEEQEGPGTRLPGNLSSEDVLPAG

CTEWRVQTLAYLPQEDWAPTSLTRPAPPDSEGSRSSSSSSSSNNNNYCAL

GCYGGWHLSALPGNTQSSGPIPALACGLSCDHQGLETQQGVAWVLAGHCQ

RPGLHEDLQGMLLPSVLSKARSWTF

In other embodiments, amino acid numbers 292 to 521 of IL-9Rα (NCBI REFSEQ: NP_002177.2) can be used.

Alternatively, a truncated fragment of said endodomain of the IL-9 receptor chain also may be used. For example, the truncated fragment comprises up to 250 amino acids, or is 50 to 200 amino acids or 80 to 150 amino acids of the ILR cytoplasmic domain.

As described supra, one aspect of the present disclosure relates to a recombinant nucleic acid encoding a chimeric receptor including: (a) an extracellular portion comprising a binding domain of an endogenous inhibitory receptor; (b) an intracellular portion comprising an endodomain of an IL-9 receptor linked to a BOX1/2 common gamma chain domain; (c) a transmembrane domain that joins the extracellular portion and the intracellular portion. Extracellular portions comprising binding domains of inhibitory receptors are described above and are useful in the chimeric receptors described infra as well. In this category of chimeric receptors, signaling through the IL-9 endodomain requires recruitment of the common gamma chain. In some embodiments, the binding domains of the extracellular portion of the chimeric receptors described herein are not able to naturally recruit the common gamma chain in order to elicit signaling through the IL-9 endodomain of the chimeric receptor. Accordingly, in these embodiments, the endodomain of the IL-9 receptor can be linked to BOX1/2 domain. Receptors of the common gamma chain family contain two regions at the cytoplasmic tail, termed Box 1 and Box 2. These domains are critical for the association of JAKs with the receptor (see for example, Murakami M, Narazaki M, Hibi M, Yawata H, Yasukawa K, Hamaguchi M, Taga T, Kishimoto T (1991) Critical cytoplasmic region of the interleukin 6 signal transducer gp130 is conserved in the cytokine receptor family. *Proc Natl Acad Sci USA* 88:11349-11353). Generally, the Box1 domain contains a proline-rich segment of amino acid residues, and the Box2 domain contains a hydrophobic segment of amino acid residues.

In some embodiments, the chimeric receptor comprises a BOX1/2 domain of the following amino acid sequence of SEQ ID NO: 58

ERTMPRIPTLKNLEDLVTEYHGNFSAWSGVSKGLAESLQPDYSERLCLVS

EIPPKGGALGEGPGASPCNQHSPYWAPPCYTLKPET

Linkers

The nucleic acid encoding the chimeric receptor can further comprise a linker between any of the portions or domains described above. As used herein, the term "linker" generally refers to an oligopeptide or polypeptide that functions to link a one region of a nucleic acid to another region of a nucleic acid. The spacer or linker may comprise up to 300 amino acids, 0-100 amino acids, 25-50 amino acids, 10-15 amino acids, for example.

Linkers useful in the chimeric receptors described herein include those in Table 3 below.

| Linker | Amino acid sequence | SEQ ID NO |
|---|---|---|
| Gly Ser Linker | GGGGSGGGGSGGGGS | 59 |
| Q-Pro Linker | QPQPQPQPQPQP | 60 |
| K-Pro Linker | KPKPKPKPKPKP | 61 |

In some embodiments, the linker is a Gly Ser Linker. In some embodiments, the linker comprising the amino acid sequence GGGGSGGGGSGGGGS (SEQ ID NO:59).

In some embodiments, the linker is a Q-Pro Linker. In some embodiments, the linker comprising the amino acid sequence QPQPQPQPQPQP (SEQ ID NO:60).

In some embodiments, no linker is present.

In some embodiments, the linker can be a 2A self-cleaving peptide. 2A peptide are a class of 18-22 amino acid peptides, which can result in ribosomal skipping during translation of a protein in a cell. In some embodiments, a linker, such as a 2A peptide, can be included to link the nucleic acid region encoding the chimeric receptor of the disclosure to another nucleic acid region encoding a chimeric antigen receptor (CAR). In some embodiments, the CAR is anti-HER2 CAR (4D5).

Signal Sequence

A "signal sequence" can also included at the beginning of the coding sequence of the chimeric receptors disclosed herein. This sequence encodes a signal peptide, N-terminal to the mature polypeptide, that directs the host cell to translocate the polypeptide. Translocation signal sequences can be found associated with a variety of proteins native to eukaryotes and prokaryotes, and are often functional in both types of organisms.

An exemplary signal sequence that can be used in the chimeric receptors herein includes the amino acid sequence of: MAAPALSWRLPLLILLLPLATSWASA (SEQ ID NO: 62)

Nucleic Acid Molecules

Provided herein are various nucleic acid molecules including nucleotide sequences encoding the chimeric receptors of the disclosure. In some embodiments, expression cassettes and expression vectors contain these nucleic acid molecules operably linked to heterologous nucleic acid sequences such as, for example, regulatory sequences which allow in vivo expression of the receptor in a host cell.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. A nucleic acid molecule can be double-stranded or single-stranded (e.g., a sense strand or an antisense strand). A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

Nucleic acid molecules of the present disclosure can be of any length, including for example, between about 1.5 Kb and about 50 Kb, between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

In some embodiments, provided herein is a nucleic acid molecule including a nucleotide sequence encoding a chimeric polypeptide including: (a) an extracellular portion comprising a binding domain of an endogenous cytokine receptor; (b) a transmembrane domain; and (c) an intracellular portion comprising an endodomain of an IL-9 receptor.

In one embodiment, the nucleic acid molecule includes a sequence encoding a chimeric polypeptide including: (a) a binding domain of IL-21; (b) a transmembrane domain of IL-9; and (c) an endodomain of an IL-9 receptor.

In one embodiment, the nucleic acid molecule includes a sequence encoding a chimeric polypeptide including: (a) a binding domain of IL-4; (b) a transmembrane domain of IL-9; and (c) an endodomain of an IL-9 receptor.

In one embodiment, the nucleic acid molecule includes a sequence encoding a chimeric polypeptide including: (a) a binding domain of IL-15Ra; (b) a transmembrane domain of IL-9; and (c) an endodomain of an IL-9 receptor.

In one embodiment, the nucleic acid molecule includes a sequence encoding a chimeric polypeptide including: (a) a binding domain of IL-10Ra; (b) a transmembrane domain of IL-9; and (c) an endodomain of an IL-9 receptor.

In some embodiments, provided herein is a nucleic acid molecule including a nucleotide sequence encoding a chimeric polypeptide including: (a) an extracellular portion comprising a binding domain of an endogenous inhibitory receptor; (b) a transmembrane domain; and (c) an intracellular portion comprising an endodomain of an IL-9 receptor linked to a BOX1/2 common gamma chain domain.

The orientation of the endodomain of the IL-9 receptor linked to a BOX 1/2 common gamma chain domain may be altered depending upon desired structure and function. For example, the intracellular portion can comprise, in an N- to C-terminal direction, an endomain of an IL-9 receptor, a linker, and a BOX 1/2 common gamma chain domain. Alternatively, the intracellular portion can comprise, in an N- to C-terminal direction, a BOX 1/2 common gamma chain domain, a linker, and an endomain of an IL-9 receptor.

In one embodiment, the nucleic acid molecule includes a sequence encoding a chimeric polypeptide including: (a) a binding domain of Fas; (b) a transmembrane domain of IL-9; and (c) an endodomain of an IL-9 receptor linked to a BOX1/2 common gamma chain domain.

In some embodiments, provided herein is a nucleic acid molecule including a nucleotide sequence encoding a chimeric polypeptide including: (a) an extracellular portion comprising a binding domain of an endogenous inhibitory receptor linked to an agent specific for the common gamma chain; (b) a transmembrane domain; and (c) an intracellular portion comprising an endodomain of an IL-9 receptor.

The orientation of the extracellular portion comprising a binding domain of an endogenous inhibitory receptor linked to an agent specific for the common gamma chain may be altered depending upon desired structure and function. For example, the extracellular portion can comprise, in an N- to C-terminal direction, a binding domain of an endogenous inhibitory receptor, a linker, and an agent specific for the common gamma chain. Alternatively, the extracellular portion can comprise, in an N- to C-terminal direction, an agent specific for the common gamma chain, a linker, and a binding domain of an endogenous inhibitory receptor.

In some embodiments, the nucleotide sequence is incorporated into an expression cassette or an expression vector. It will be understood that an expression cassette generally includes a construct of genetic material that contains coding sequences and enough regulatory information to direct proper transcription and/or translation of the coding sequences in a recipient cell, in vivo and/or ex vivo. Generally, the expression cassette may be inserted into a vector for targeting to a desired host cell and/or into a subject. As such, in some embodiments, an expression cassette of the disclosure include a coding sequence for the chimeric polypeptide as disclosed herein, which is operably linked to expression control elements, such as a promoter, and optionally, any or a combination of other nucleic acid sequences that affect the transcription or translation of the coding sequence.

In some embodiments, the nucleotide sequence is incorporated into a cloning vector or an expression vector. It will be understood by one skilled in the art that the term "vector" generally refers to a recombinant polynucleotide construct designed for transfer between host cells, and that may be used for the purpose of transformation, e.g., the introduction of heterologous DNA into a host cell. As such, in some embodiments, the vector can be a replicon, such as a plasmid, phage, or cosmid, into which another DNA segment may be inserted so as to bring about the replication of the inserted segment. In some embodiments, the expression vector can be an integrating vector. In some embodiments, the nucleotide sequence is incorporated into a cloning vector.

As described above in relation to linkers, the nucleic acid sequence encoding a chimeric receptor as described herein can also encode a CAR. Each may each be provided on separate expression vectors, each nucleic acid sequence being operably linked to one or more expression control elements to achieve expression of the CAR and chimeric receptor in the target cell, the vectors being co-transfected into the target cell. Alternatively, the nucleic acid sequences encoding the CAR and the chimeric receptor may each be provided on a single vector each nucleic acid sequence under the control of one or more expression control elements to achieve expression of the associated nucleic acid sequence. Alternatively, both nucleic acid sequences may be under the control of a single promoter with intervening or downstream control elements that facilitate co-expression of the two sequences from the vector.

In some embodiments, the expression vector can be a viral vector. As will be appreciated by one of skill in the art, the term "viral vector" is widely used to refer either to a nucleic acid molecule (e.g., a transfer plasmid) that includes virus-derived nucleic acid elements that generally facilitate transfer of the nucleic acid molecule or integration into the genome of a cell or to a viral particle that mediates nucleic acid transfer. Viral particles will generally include various viral components and sometimes also host cell components in addition to nucleic acid(s). The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus, which is a genus of retrovirus.

In some embodiments, provided herein are nucleic acid molecules encoding a polypeptide with an amino acid sequence having at least about 80%, 90%, 95%, 96%, 97%, 98%, 99%, or 100% sequence identity to a chimeric receptor disclosed herein. In some embodiments, provided herein are nucleic acid molecules encoding a polypeptide with an amino acid sequence having at least about 80%, 90%, 95%, 96%, 97%, 98%, 99%, or 100% sequence identity to any one of SEQ ID NOS: 63-203 as identified in the Sequence Listing.

The nucleic acid sequences encoding the chimeric receptors can be optimized for expression in the host cell of interest. For example, the G-C content of the sequence can be adjusted to average levels for a given cell, as calculated by reference to known genes expressed in the host cell. Methods for codon usage optimization are known in the art. Codon usages within the coding sequence of the chimeric receptor disclosed herein can be optimized to enhance expression in the host cell, such that about 1%, about 5%, about 10%, about 25%, about 50%, about 75%, or up to 100% of the codons within the coding sequence have been optimized for expression in a particular host cell.

Some embodiments disclosed herein relate to vectors or expression cassettes including a recombinant nucleic acid molecule encoding the chimeric receptors disclosed herein. The expression cassette generally contains coding sequences and sufficient regulatory information to direct proper transcription and/or translation of the coding sequences in a recipient cell, in vivo and/or ex vivo. The expression cassette may be inserted into a vector for targeting to a desired host cell and/or into a subject. An expression cassette can be inserted into a plasmid, cosmid, virus, autonomously replicating polynucleotide molecule, phage, as a linear or circular, single-stranded or double-stranded, DNA or RNA polynucleotide molecule, derived from any source, capable of genomic integration or autonomous replication, including a nucleic acid molecule where one or more nucleic acid sequences has been linked in a functionally operative manner, i.e., operably linked. 101601 Also provided herein are vectors, plasmids, or viruses containing one or more of the nucleic acid molecules encoding a chimeric receptor disclosed herein. The nucleic acid molecules can be contained within a vector that is capable of directing their expression in, for example, a cell that has been transformed/transduced with the vector. Suitable vectors for use in eukaryotic and prokaryotic cells are known in the art and are commercially available, or readily prepared by a skilled artisan. See for example, Sambrook, J., & Russell, D. W. (2012). *Molecular Cloning: A Laboratory Manual* (4th ed.). Cold Spring Harbor, NY: Cold Spring Harbor Laboratory and Sambrook, J., & Russel, D. W. (2001). *Molecular Cloning: A Laboratory Manual* (3rd ed.). Cold Spring Harbor, NY: Cold Spring Harbor Laboratory (jointly referred to herein as "Sambrook"); Ausubel, F. M. (1987). *Current Protocols in Molecular Biology*. New York, NY: Wiley (including supplements through 2014); Bollag, D. M. et al. (1996). *Protein Methods*. New York, NY: Wiley-Liss; Huang, L. et al. (2005). *Nonviral Vectors for Gene Therapy*. San Diego: Academic Press; Kaplitt, M. G. et al. (1995). *Viral Vectors: Gene Therapy and Neuroscience Applications*. San Diego, CA: Academic Press; Lefkovits, I. (1997). *The Immunology Methods Manual: The Comprehensive Sourcebook of Techniques*. San Diego, CA: Academic Press; Doyle, A. et al. (1998). *Cell and Tissue Culture: Laboratory Procedures in Biotechnology*. New York, NY: Wiley; Mullis, K. B., Ferre, F. & Gibbs, R. (1994). *PCR: The Polymerase Chain Reaction*. Boston: Birkhauser Publisher; Greenfield, E. A. (2014). *Antibodies: A Laboratory Manual* (2nd ed.). New York, NY: Cold Spring Harbor Laboratory Press; Beaucage, S. L. et al. (2000). *Current Protocols in Nucleic Acid Chemistry*. New York, NY: Wiley, (including supplements through 2014); and Makrides, S. C. (2003). *Gene Transfer and Expression in Mammalian Cells*. Amsterdam, NL: Elsevier Sciences B. V., the disclosures of which are incorporated herein by reference).

DNA vectors can be introduced into eukaryotic cells via conventional transformation or transfection techniques. Suitable methods for transforming or transfecting host cells can be found in Sambrook et al. (2012, supra) and other standard molecular biology laboratory manuals, such as, calcium phosphate transfection, DEAE-dextran mediated transfection, transfection, microinjection, cationic lipid-mediated transfection, electroporation, transduction, scrape loading, ballistic introduction, nucleoporation, hydrodynamic shock, and infection.

Viral vectors that can be used in the disclosure include, for example, retrovirus vectors, adenovirus vectors, and adeno-associated virus vectors, lentivirus vectors, herpes virus, simian virus 40 (SV40), and bovine papilloma virus vectors (see, for example, Gluzman (Ed.), *Eukaryotic Viral Vectors*, CSH Laboratory Press, Cold Spring Harbor, N.Y.). For example, a chimeric receptor as disclosed herein can be produced in a eukaryotic host, such as a mammalian cells (e.g., COS cells, NIH 3T3 cells, or HeLa cells). These cells are available from many sources, including the American Type Culture Collection (Manassas, VA). In selecting an expression system, care should be taken to ensure that the components are compatible with one another. Artisans of ordinary skill are able to select and design expression systems suitable and functional in a selected engineered cell. If further guidance is required in selecting an expression system, skilled artisans may consult P. Jones, "Vectors: Cloning Applications", John Wiley and Sons, New York, N.Y., 2009).

The nucleic acid molecules provided can contain naturally occurring sequences, or sequences that differ from those that occur naturally, but, due to the degeneracy of the genetic code, encode the same polypeptide, e.g., antibody. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (e.g., either a sense or an antisense strand).

Recombinant Cells and Cell Cultures

The nucleic acid of the present disclosure can be introduced into a host cell, such as, for example, a human T lymphocyte, to produce a host cell containing the recombinant nucleic acid molecule. Accordingly, some embodiments of the disclosure relate to methods for making a host cell, including (a) providing a cell capable of protein expression and (b) contacting the provided cell with a recombinant nucleic acid of the disclosure.

Introduction of the nucleic acid molecules of the disclosure into cells can be achieved by methods known to those skilled in the art such as, for example, viral infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Accordingly, in some embodiments, the nucleic acid molecules can be delivered by viral or non-viral delivery vehicles known in the art. For example, the nucleic acid molecule can be stably integrated in the host genome, or can be episomally replicating, or present in the recombinant cell as a mini-circle expression vector for transient expression. Accordingly, in some embodiments, the nucleic acid molecule is maintained and replicated in the recombinant cell as an episomal unit. In some embodiments, the nucleic acid molecule is stably integrated into the genome of the recombinant cell. Stable integration can be achieved using classical random genomic recombination techniques or with more precise techniques such as guide RNA-directed CRISPR/Cas9 genome editing, or DNA-guided endonuclease genome editing with NgAgo (*Natronobacterium gregoryi* Argonaute), or TALENs genome editing (transcription activator-like effector nucleases). In some embodiments, the nucleic acid molecule is present in the recombinant cell as a mini-circle expression vector for transient expression.

The nucleic acid molecules can be encapsulated in a viral capsid or a lipid nanoparticle, or can be delivered by viral or non-viral delivery means and methods known in the art, such as electroporation. For example, introduction of nucleic acids into cells may be achieved by viral transduction. In a non-limiting example, adeno-associated virus (AAV) is engineered to deliver nucleic acids to target cells via viral transduction. Several AAV serotypes have been described, and all of the known serotypes can infect cells from multiple diverse tissue types. AAV is capable of transducing a wide range of species and tissues in vivo with no evidence of toxicity, and it generates relatively mild innate and adaptive immune responses.

Lentiviral-derived vector systems are also useful for nucleic acid delivery and gene therapy via viral transduction. Lentiviral vectors offer several attractive properties as gene-delivery vehicles, including: (i) sustained gene delivery through stable vector integration into host genome; (ii) the capability of infecting both dividing and non-dividing cells; (iii) broad tissue tropisms, including important gene- and cell-therapy-target cell types; (iv) no expression of viral proteins after vector transduction; (v) the ability to deliver complex genetic elements, such as polycistronic or intron-containing sequences; (vi) a potentially safer integration site profile; and (vii) a relatively easy system for vector manipulation and production.

In some embodiments, host cells can be genetically engineered (e.g., transduced or transformed or transfected) with, for example, a vector construct of the present application that can be, for example, a viral vector or a vector for homologous recombination that includes nucleic acid sequences homologous to a portion of the genome of the host cell, or can be an expression vector for the expression of the polypeptides of interest. These cells can be either untransformed cells or cells that have already been transfected with at least one nucleic acid molecule.

In some embodiments, the recombinant cell is a prokaryotic cell or a eukaryotic cell. In some embodiments, the cell is in vivo. In some embodiments, the cell is ex vivo. In some embodiments, the cell is in vitro. In some embodiments, the recombinant cell is a prokaryotic cell including a recombinant nucleic acid as disclosed herein. In some embodiments, the recombinant prokaryotic cell includes a recombinant nucleic acid which is a cloning vector. In some embodiments, the recombinant cell is a eukaryotic cell. In some embodiments, the recombinant cell is an animal cell. In some embodiments, the animal cell is a mammalian cell. In some embodiments, the animal cell is a human cell. In some embodiments, the cell is a non-human primate cell. In some embodiments, the mammalian cell is an immune cell, a neuron, an epithelial cell, and endothelial cell, or a stem cell. In some embodiments, the recombinant cell is an immune system cell, e.g., a lymphocyte (e.g., a T cell or NK cell), or a dendritic cell. In some embodiments, the immune cell is a B cell, a monocyte, a natural killer (NK) cell, a basophil, an eosinophil, a neutrophil, a dendritic cell, a macrophage, a regulatory T cell, a helper T cell ($T_H$), a cytotoxic T cell ($T_{CTL}$), or other T cell. In some embodiments, the immune system cell is a T lymphocyte.

In some embodiments, the cell is a stem cell. In some embodiments, the cell is a hematopoietic stem cell. In some embodiments of the cell, the cell is a lymphocyte. In some embodiments, the cell is a precursor T cell or a T regulatory (Treg) cell. In some embodiments, the cell is a CD34+, CD8+, or a CD4+ cell. In some embodiments, the cell is a CD8+T cytotoxic lymphocyte cell selected from the group consisting of naïve CD8+ T cells, central memory CD8+ T cells, effector memory CD8+ T cells, and bulk CD8+ T cells. In some embodiments of the cell, the cell is a CD4+T helper lymphocyte cell selected from the group consisting of naïve CD4+ T cells, central memory CD4+ T cells, effector memory CD4+ T cells, and bulk CD4+ T cells. In some embodiments, the cell can be obtained by leukapheresis performed on a sample obtained from a subject. In some embodiments, the subject is a human patient.

In one embodiment, the cell expressing the recombinant nucleic acid molecule described herein is a T-cell which has been modified to surface express a chimeric antigen receptor (a 'CAR-T' cell). As used herein, a CAR-T cell may be engineered to express a chimeric receptor of the present disclosure. CARs useful in the practice of the present disclosure can be prepared in accordance with principles well known in the art. See e.g., Eshhaar et al. U.S. Pat. No. 7,741,465 B1 issued Jun. 22, 2010; Sadelain, et al (2013) Cancer Discovery 3(4):388-398; Jensen and Riddell (2015)

Current Opinions in Immunology 33:9-15; Gross, et al. (1989) PNAS(USA) 86(24): 10024-10028; Curran, et al. (2012) J Gene Med 14(6): 405-15. Examples of commercially available CAR-T cell products that may be modified to incorporate a chimeric receptor of the present disclosure include axicabtagene ciloleucel (marketed as Yescarta® commercially available from Gilead Pharmaceuticals) and tisagenlecleucel (marketed as Kymriah® commercially available from Novartis).

In some embodiments, the recombinant cell further includes a first and a second nucleic acid molecule as disclosed herein, wherein the first nucleic acid molecule and the second nucleic acid molecule do not have the same sequence. In some embodiments, the recombinant cell further includes a first and a second chimeric polypeptide as disclosed herein, wherein the first chimeric polypeptide and the second chimeric polypeptide do not have the same sequence. In some embodiments, the first second chimeric polypeptide is a CAR. In some embodiments, the first chimeric polypeptide modulates the expression and/or activity of the second chimeric polypeptide.

In some embodiments, the recombinant cell further includes an expression cassette or vector encoding a protein of interest operably linked to a promoter, wherein expression of the protein is modulated by the chimeric receptor's transcriptional effector. In some embodiments, the protein of interest is heterologous to the recombinant cell. In some embodiments, the heterologous protein is one that is not normally found in the cell, e.g., not normally produced by the cell. In some embodiments, the expression vector encodes a copy of a protein that is already present in the cell. Exemplary types of proteins suitable for use with the compositions and methods disclosed herein include cytokines, cytotoxins, chemokines, immunomodulators, pro-apoptotic factors, anti-apoptotic factors, hormones, differentiation factors, dedifferentiation factors, immune cell receptors, or reporters.

In another aspect, provided herein are compositions of cells comprising an expression vector described herein. Cell cultures including at least one host cell as disclosed herein, and a culture medium are also contemplated. Generally, the culture medium can be any suitable culture medium for culturing the cells described herein. Techniques for transforming a wide variety of the above-mentioned cells and species are known in the art and described in the technical and scientific literature. Accordingly, cell cultures including at least one recombinant cell as disclosed herein are also within the scope of this application. Methods and systems suitable for generating and maintaining cell cultures are known in the art.

Pharmaceutical Compositions

In some embodiments, the nucleic acids, host cells, and/or polypeptides (i.e., chimeric receptors) of the disclosure can be incorporated into compositions, including pharmaceutical compositions. Such compositions include one or more of the recombinant nucleic acids, host cells, and/or polypeptides (i.e., chimeric receptors) as disclosed herein. The composition can also contain a pharmaceutically acceptable excipient, e.g., a carrier.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be generally to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above.

In some embodiments, the chimeric receptors of the disclosure can also be administered by transfection or infection using methods known in the art, including but not limited to the methods described in McCaffrey et al. (Nature 418:6893, 2002), Xia et al. (Nature Biotechnol. 20:1006-10, 2002), or Putnam (Am. J. Health Syst. Pharm. 53:151-60, 1996, erratum at Am. J. Health Syst. Pharm. 53:325, 1996).

As described in greater detail below, in some embodiments, the host cells of the disclosure can be formulated for administration to a subject using techniques known to the skilled artisan. For example, formulations comprising populations of recombinant cells can include pharmaceutically acceptable excipient(s). Excipients included in the formulations will have different purposes depending, for example, on the recombinant cells used and the mode of administration. Examples of generally used excipients included, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents. The formulations comprising recombinant cells can have been prepared and cultured in the absence of non-human components, e.g., in the absence of animal serum. A formulation can include one population of recombinant cells, or more than one, such as two, three, four, five, six or more populations of recombinant cells.

Formulations comprising population(s) of recombinant cells can be administered to a subject using modes and techniques known to the skilled artisan. Exemplary modes include, but are not limited to, intravenous injection. Other modes include, without limitation, intratumoral, intradermal, subcutaneous (S.C., s.q., sub-Q, Hypo), intramuscular (i.m.), intraperitoneal (i.p.), intra-arterial, intramedullary, intracardiac, intra-articular (joint), intrasynovial (joint fluid area), intracranial, intraspinal, and intrathecal (spinal fluids). Devices useful for parenteral injection of infusion of the formulations can be used to effect such administration.

Methods of the Disclosure
Methods for Modulating an Activity of a Cell

In one aspect, provided herein are methods for modulating an activity of an immune cell. The methods involve administering, to an immune cell, the recombinant nucleic acid as described herein. One skilled in the art upon reading the present disclosure will appreciate that the disclosed methods can be carried out in vivo, ex vivo, or in vitro.

Non-limiting exemplary cellular activities that can be modulated using the methods provide herein include, but are not limited to, gene expression, proliferation, apoptosis, non-apoptotic death, differentiation, dedifferentiation, migration, secretion of a gene product, cellular adhesion, and cytolytic activity.

In some embodiments, the expression of a gene product of the cell is modulated.

In some embodiments, the gene product in the cell is selected from the group consisting of a chemokine, a chemokine receptor, a chimeric antigen receptor, a cytokine, a cytokine receptor, a differentiation factor, a growth factor, a growth factor receptor, a hormone, a metabolic enzyme, a pathogen-derived protein, a proliferation inducer, a receptor, an RNA guided nuclease, a site-specific nuclease, a T cell receptor (TCR) or a component thereof, a chimeric antigen receptor (CAR), a toxin, a toxin-derived protein, a transcriptional effector, a transcriptional activator, a transcriptional repressor, a translation regulator, a translational activator, a translational repressor, an activating immuno-receptor, an antibody, an apoptosis inhibitor, an apoptosis inducer, an engineered T cell receptor, an immuno-activator, an immuno-inhibitor, and an inhibiting immuno-receptor.

In cases where expression of a chemokine or a cytokine is modulated, in some embodiments, the expression of cytokines and chemokines is modulated such that there is an increase in type-1 polarization following ligand stimulation relative to controls. Exemplary cytokine and chemokines that can be modulated include, without limitation, FGF2, GMCSF, IFNa, IFNg, IL-10, IL-17, IL-12, IL-2, IL-3, IL-6, IP-10, MIP1a, and RANTES.

Methods of measuring levels of cytokines and chemokines are known in the art. Levels of cytokines and chemokines can be measured, for example, by enzyme-linked immunosorbent assay (ELISA), bead based systems (e.g. Luminex), the Cytokine Bead Array (Pharmingen) and array-based systems (e.g., EMD Biosciences' ProteoPlex).

In some embodiments, the modulation of an activity of an immune cell can involve alteration of cell signaling events within the cell. As described herein, the IL-9 receptor endodomain signals through JAK1 and JAK3 to activate various developmental pathways including STAT1, STAT3, STAT5, MAPK, and PI3K/AKT pathways. Activation of STAT family members through ligand mediated phosphorylation is believed to confer advantages in effector function, polarization and proliferation to T cells. This, in some embodiments, administration of the recombinant nucleic acid encoding the chimeric switch receptor described herein induces phosphorylation of STAT1, STAT3, and/or STAT5 when stimulated with ligand. Methods for measuring the phosphorylation status of one or more proteins is known in the art and includes, for example, western blot and phospho flow cytometry as described in the Examples herein.

Cell death (e.g., apoptosis and non-apoptotic cell death) can also be modulated by the methods described herein. In some embodiments, administration of the recombinant nucleic acid encoding the chimeric switch receptor described herein can result in increased cell death of a target cell. By way of example, real-time cytotoxicity assays can be used to analyze whether or not cells expressing a chimeric switch receptor of the present disclosure show increased cytotoxicity when exposed to ligand. In some embodiments, cells expressing a chimeric switch receptor of the present disclosure demonstrate improved killing of target cells when stimulated with ligand over unstimulated controls.

Methods of Treatment

Administration of any one of the therapeutic compositions described herein, e.g., chimeric receptors, nucleic acids, host cells, and pharmaceutical compositions, can be used to treat patients for relevant diseases, such as cancers, autoimmune diseases, and infections. In some embodiments, the recombinant nucleic acids, host cells, and pharmaceutical compositions described herein can be incorporated into therapeutic agents for use in methods of treating or aiding in the treatment of a subject who has, who is suspected of having, or who may be at high risk for developing one or more diseases.

One aspect of the present disclosure is directed to a method of treating a subject that involves administering, to the subject, a chimeric switch receptor of the present disclosure or a cell expressing the recombinant nucleic acid of the present disclosure.

In one embodiment, the subject is treated for cancer. A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma. In particular, treatment of melanoma, kidney cancer (e.g. renal carcinoma) or bladder cancer is contemplated.

In some embodiments the cancer is an EBV or HPV positive cancer.

In one embodiment, the subject is treated for autoimmune disease. Exemplary autoimmune diseases include Crohn's disease and Multiple Sclerosis.

In one embodiment, the subject is treated for infection. An infection may be any infection or infectious disease, e.g. bacterial, viral, fungal, or parasitic infection. In some embodiments it may be particularly desirable to treat chronic/persistent infections, e.g. where such infections are associated with T cell dysfunction or T cell exhaustion. It is well established that T cell exhaustion is a state of T cell dysfunction that arises during many chronic infections (including viral, bacterial and parasitic), as well as in cancer (Wherry Nature Immunology Vol. 12, No. 6, p 492-499, June 2011).

Examples of bacterial infections that may be treated include infection by *Bacillus* spp., *Bordetella pertussis, Clostridium* spp., *Corynebacterium* spp., *Vibrio chloerae, Staphylococcus* spp., *Streptococcus* spp. *Escherichia, Klebsiella, Proteus, Yersinia, Erwina, Salmonella, Listeria* sp, *Helicobacter pylori*, mycobacteria (e.g. *Mycobacterium tuberculosis*) and *Pseudomonas aeruginosa*. For example, the bacterial infection may be sepsis or tuberculosis. Examples of viral infections that may be treated include infection by Epstein-Barr virus, influenza virus, measles virus, hepatitis B virus (HBV), hepatitis C virus (HCV), human immunodeficiency virus (HIV), lymphocytic choriomeningitis virus (LCMV), Herpes simplex virus and human papilloma virus.

Examples of fungal infections that may be treated include infection by *Alternaria* sp, *Aspergillus* sp, *Candida* sp and *Histoplasma* sp. The fungal infection may be fungal sepsis or histoplasmosis. Examples of parasitic infections that may be treated include infection by *Plasmodium* species (e.g. *Plasmodium falciparum, Plasmodium yoeli, Plasmodium ovale, Plasmodium vivax*, or *Plasmodium chabaudi chabaudi*). The parasitic infection may be a disease such as malaria, leishmaniasis and toxoplasmosis Administration of Recombinant Cells to a Subject In some embodiments, the methods of the disclosure involve administering an effective amount or number of the recombinants cells to a subject in need of such treatment. This administering step can be accomplished using any method of implantation delivery in the art. For example, the recombinant cells can be infused directly in the subject's bloodstream or otherwise administered to the subject.

In some embodiments, the methods disclosed herein include administering, which term is used interchangeably with the terms "introducing", implanting", and "transplanting", recombinant cells into a subject, by a method or route that results in at least partial localization of the introduced cells at a desired site such that a desired effect(s) is/are produced. The recombinant cells or their differentiated progeny can be administered by any appropriate route that results in delivery to a desired location in the subject where at least a portion of the administered cells or components of the cells remain viable. The period of viability of the cells after administration to a subject can be as short as a few hours, e.g., twenty-four hours, to a few days, to as long as several years, or even the lifetime of the subject, i.e., long-term engraftment.

When provided prophylactically, the recombinant cells described herein can be administered to a subject in advance of a symptom or indication of a disease or condition to be treated. Accordingly, in some embodiments the prophylactic administration of a recombinant cell population prevents the occurrence of symptoms of the disease or condition.

When provided therapeutically in some embodiments, recombinant cells are provided at (or after) the onset of a symptom or indication of a disease or condition, e.g., upon the onset of disease or condition.

For use in the various embodiments described herein, an effective amount of recombinant cells as disclosed herein, can be at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof. The recombinant cells can be derived from one or more donors or can be obtained from an autologous source. In some embodiments, the recombinant cells are expanded in culture prior to administration to a subject in need thereof.

In some embodiments, the delivery of a recombinant cell composition (e.g., a composition including a plurality of recombinant cells according to any of the cells described herein) into a subject by a method or route results in at least partial localization of the cell composition at a desired site. A composition including recombinant cells can be administered by any appropriate route that results in effective treatment in the subject, e.g., administration results in delivery to a desired location in the subject where at least a portion of the composition delivered, e.g., at least $1\times10^4$ cells, is delivered to the desired site for a period of time. Modes of administration include injection, infusion, instillation. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. In some embodiments, the route is intravenous. For the delivery of cells, delivery by injection or infusion is a standard mode of administration.

In some embodiments, the recombinant cells are administered systemically, e.g., via infusion or injection. For example, a population of recombinant cells are administered other than directly into a target site, tissue, or organ, such that it enters, the subject's circulatory system and, thus, is subject to metabolism and other similar biological processes.

The efficacy of a treatment including any of the compositions provided herein for the treatment of a disease or condition can be determined by a skilled clinician. However, one skilled in the art will appreciate that a treatment is considered effective if any one or all of the signs or symptoms or markers of disease are improved or ameliorated. Efficacy can also be measured by failure of a subject to worsen as assessed by decreased hospitalization or need for medical interventions (e.g., progression of the disease is halted or at least slowed). Methods of measuring these indicators are known to those of skill in the art and/or described herein. Treatment includes any treatment of a disease in a subject or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

In some embodiments of the disclosed methods, the subject is a mammal. In some embodiments, the mammal is a human.

Additional Therapies

As discussed above, the recombinant cells, and pharmaceutical compositions described herein can be administered in combination with one or more additional therapeutic agents such as, for example, chemotherapeutics or anti-cancer agents or anti-cancer therapies. Administration "in combination with" one or more additional therapeutic agents includes simultaneous (concurrent) and consecutive administration in any order. In some embodiments, the one or more additional therapeutic agents, chemotherapeutics, anti-cancer agents, or anti-cancer therapies is selected from the group consisting of chemotherapy, radiotherapy, immunotherapy, hormonal therapy, toxin therapy, and surgery. "Chemotherapy" and "anti-cancer agent" are used interchangeably herein. Various classes of anti-cancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Accordingly, in some embodiments, the disclosed treatment methods further include administering to the subject a second therapy. Generally, the second therapy can be any therapy known in the art. Non-limiting examples of therapies suitable for use in combination with the therapeutic compositions disclosed herein include chemotherapy, radiotherapy, immunotherapy, hormonal therapy, toxin therapy, and surgery. In some embodiments, the second therapy includes one or more additional therapeutic agents such as, for example, chemotherapeutics or anti-cancer agents or anti-cancer therapies. In some embodiments, the first therapy and the second therapy are administered together in the same composition. In some embodiments, the first therapy and the second therapy are administered in separate compositions. In some embodiments, the first therapy and the second therapy are administered at the same time. In some embodiments, the first therapy and the second therapy are administered sequentially. In some embodiments, the first therapy is administered before the second therapy. In some embodiments, the first therapy is administered after the second therapy. In some embodiments, the first therapy and the second therapy are administered in rotation.

Systems and Kits

Also provided herein are kits including the recombinant nucleic acids, recombinant cells, or pharmaceutical compositions provided and described herein as well as written instructions for making and using the same. For example, provided herein, in some embodiments, are kits that include one or more of the following: (i) a recombinant nucleic acids as described herein, (ii) a recombinant cell as described herein, and (iii) a pharmaceutical composition as described herein. In some embodiments, the systems and/or kits of the disclosure further include one or more syringes (including pre-filled syringes) and/or catheters (including pre-filled syringes) used to administer one any of the provided recombinant nucleic acids, recombinant cells, or pharmaceutical compositions to a subject. In some embodiments, a kit can have one or more additional therapeutic agents that can be administered simultaneously or sequentially with the other kit components for a desired purpose, e.g., for modulating an activity of a cell, inhibiting a target cancer cell, or treating a disease in a subject in need thereof.

Any of the above-described systems and kits can further include one or more additional reagents, where such additional reagents can be selected from: dilution buffers; reconstitution solutions, wash buffers, control reagents, control expression vectors, negative control polypeptides, positive control polypeptides, reagents for in vitro production of the chimeric receptor polypeptides.

In some embodiments, a system or kit can further include instructions for using the components of the kit to practice the methods. The instructions for practicing the methods are generally recorded on a suitable recording medium. For example, the instructions can be printed on a substrate, such as paper or plastic, etc. The instructions can be present in the kits as a package insert, in the labeling of the container of the kit or components thereof (i.e., associated with the packaging or sub-packaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the internet), are provided. An example of this embodiment is a kit that includes a web address where the instructions can be viewed and/or from which the instructions can be downloaded. As with the instructions, this means for obtaining the instructions can be recorded on a suitable substrate.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

Throughout this specification, various patents, patent applications and other types of publications (e.g., journal articles, electronic database entries, etc.) are referenced. The disclosure of all patents, patent applications, and other publications cited herein are hereby incorporated by reference in their entirety to the same extent as if each individual publication or patent application was specifically and individually indicated to be incorporated by reference.

EXAMPLES

The practice of the present disclosure will employ, unless otherwise indicated, conventional techniques of molecular biology, microbiology, cell biology, biochemistry, nucleic acid chemistry, and immunology, which are well known to those skilled in the art. Such techniques are explained fully in the literature cited above.

Additional embodiments are disclosed in further detail in the following examples, which are provided by way of illustration and are not in any way intended to limit the scope of this disclosure or the claims.

Example 1

Cloning of chimeric receptors. DNA encoding the binding domains of IL-2rb, IL-2ra, IL-4r, IL-7ra, IL-15ra, IL-21ra, TGF-beta R1, TGF-beta R2, IL-10ra, FAS, CTLA4, LAGS, TIM3, PD1, ILT2, ILT3, ILT4, ILT5, VEGF; the transmembrane domains of IL-9, IL-7ra and IL-2rb; the endodomain of the IL-9 receptor; the BOX 1/2 common gamma chain domain; and an agent specific for the common gamma chain are cloned, in various configurations, into mammalian expression vectors driven by a CMV or elongation factor (EF)-1 promoter. The vector contains a mammalian selection cassette.

Similarly, DNA encoding the binding domains of IL-2rb, IL-2ra, IL-4r, IL-7ra, IL-15ra, IL-21ra, TGF-beta R1, TGF-beta R2, IL-10ra, FAS, CTLA4, LAG3, TIM3, PD1, ILT2, ILT3, ILT4, ILT5, VEGF; the transmembrane domains of IL-9, IL-7ra and IL-2rb; the endodomain of the IL-9 receptor; the BOX 1/2 common gamma chain domain; and an agent specific for the common gamma chain are cloned, in various configurations, into lentiviral vectors.

Example 2

Lentivirus expression. Lentivirus is produced as previously described in [Tiscornia G. et al. Nature Protocols 27 Jun. 2006; doi: 10.1038/nprot.2006.37].

Example 3

Assessment of surface expression of chimeric receptors. Mammalian expression constructs encoding for chimeric receptors are transfected into 293 cells using methods well known in the art such as lipofection 2000 (Invitrogen) or electroporation. 24 to 48 hours later, cell surface expression is assessed by flow cytometry using fluorescently labeled antibodies specific for the ectodomains chimeric receptors. An example would be FITC labeled anti-IL4R antibody for 293 cells transduced with construct 73.

Alternatively, Jurkat T cell are transduced with purified lentivirus expressing the chimeric receptors of interest at an MOI of 20. 24 to 48 hours later, cell surface expression is assessed by flow cytometry using fluorescently labeled antibodies specific for the ectodomains chimeric receptors.

Example 4

Ligand stimulation and STAT5 activation. Transfected 293 cells and virally transduced Jurkat T cells are stimulated with individual ligands to analyze the ability of the ligands to bind the chimeric receptors and induce STAT5 activation. Briefly, after stimulation with ligand for various time points, cells are lysed and protein is collected. The phosphorylation status of STAT5 is analyzed by Western Blot using phosphor STAT5 specific antibodies and assessed relative to a negative control comprising an empty vector. STAT5 phosphorylation status of ligand activated cells relative to empty vector controls is also assessed by flow cytometry as previously described. (http://rhlccflow.facilities.northwestern.edu/files/2011/09/intracellular-phospho-protein-staining.pdf)

Example 5

STAT5 reporter assay. STAT5 reporter assays are done in 293 cells for activated JAK1-3 induced activity. Cells are seeded in a 48 well plate. The next day, cells are transfected by Lipofectamine 2000 (Invitrogen) with the STAT5-Luciferase vector and an internal control plasmid together with other plasmids expressing genes of interest. 24 hours later, the cells are stimulated with appropriate ligand for various time points, then lysed and subjected to internal control fluorescence and luciferase luminescence measurement using a plate reader. The reporter gene activity is shown after being normalized against internal control readings.

Example 6

Ligand stimulation and cytokine expression. Jurkat T cell are transduced with purified lentivirus expressing the chimeric receptors of interest. 24 to 48 hours later, cells are stimulated with appropriate ligands for various time points from 0, 15, 30 45 and 60 minutes. Cells are then collected for analysis of expression of IFNγ, IL-4, IL-5, IP-10, IL-2, MIP1α, MIP1β, and TNFα using intracellular flow cytometry. Supernatants from the culture are collected analyzed for the expression of 30 cytokines and chemokines (Thermo Fisher) (https://www.thermofisher.com/order/catalog/product/LHC6003M#/LHC6003M) by Luminex analysis.

Example 7

Cytotoxicity Assays. The ability of the recombinant nucleic acids described herein to stimulate CTL cytotoxicity can be measured by methods known to the skilled person. Cytotoxicity of a T cell to a given target cell can be investigated, for example, using any of the methods reviewed in Zaritskaya et al. Expert Rev Vaccines (2011), 9(6):601-616, hereby incorporated by reference in its entirety. Additionally, the ability of the chimeric cytokine receptor to enhanced cell killing of a GPC3 CAR is assessed by measuring cellular killing of cell line targets in real time by electrical impedance as described in (https://www.ncbi.nlm.nih.gov/pmc/articles/PMC5834184/). GPC3 CAR (scFv-41BB-CD3) expressing Lentivirus will be purchased from Creative Biolabs (CAR-M0158-YC) and used to transduce T cells. Briefly, T cells will be isolated from the PBMC fraction of peripheral blood by negative selection. Cells will be stimulated with TransAct (Miltenyi) for 72 hours in the presence of IL-2 prior to Lentiviral transduction. Cells will be incubated for 48 hours and CAR expressing cells sorted by FACS. The CAR positive fraction will then be transduced with the chimeric cytokine receptor constructs. Cell surface expression of the chimeric cytokine receptor will be assessed 48 hours post transduction, by flow cytometry. Cells will be stimulated with the appropriate ligand for an additional 48 hours, washed and cultured with HEPG2 target cells on XCellegence plates (https://www.agilent.com/en/product/cell-analysis/real-time-cell-analysis/rtca-analyzers/xcelligence-rtca-mp-multiple-plates-741230). Transduced T cells and target cells will be cocultured for 96 hours. Target killing will be measured in real time according to the manufacturer's protocol.

Example 8

Materials and Methods for Examples 9-12
Cloning of chimeric receptors. DNA encoding the binding domains of various endogenous cytokine and inhibitory receptors; the transmembrane domains of IL-9 or TNFR1; the endodomain of the IL-9 receptor; and/or the BOX 1/2 common gamma chain domain; were cloned, in various configurations, into pTRPE backbone lentiviral transfer plasmid. Some receptors were co-expressed with anti-HER2 CAR (4D5) via a 2A linker sequence. The 4D5 amino acid sequence is as follows:

(SEQ ID NO: 204)
MDFQVQIFSFLLISASVIMSRGDIQMTQSPSSLSASVGDRVTITCRASQD

VNTAVAWYQQKPGKAPKLLIYSASFLYSGVPSRFSGSRSGTDFTLTISSL

QPEDFATYYCQQHYTTPPTFGQGTKVEIKRTGSTSGSGKPGSGEGSEVQL

VESGGGLVQPGGSLRLSCAASGFNIKDTYIHWVRQAPGKGLEWVARIYPT

NGYTRYADSVKGRFTISADTSKNTAYLQMNSLRAEDTAVYYCSRWGGDGF

GGAVHTRGLDFACDIYIWAPLAGTCGVLLLSLVITLYCKRGRKKLLYIFK

QPFMRPVQTYAMDVWGQGTLVTVSSTTTPAPRPPTPAPTIASQPLSLRPE

ACRPAATQEEDGCSCRFPEEEEGGCELRVKFSRSADAPAYKQGQNQLYNE

LNLGRREEYDVLDKRRGRDPEMGGKPRRKNPQEGLYNELQKDKMAEAYSE

IGMKGERRRGKGHDGLYQGLSTATKDTYDALHMQALPPR*

Similarly, DNA encoding the binding domains of IL-21R, IL-15ra, IL-4ra, IL-10ra, IL-7ra, TWEAKR, CTLA4, TIM3, LAG3, PD1, DCR1, CD40, Fas, Dr4, TNFRSF1B, TGFBR2, TIGIT, 2B4; the transmembrane domains of IL-9 and TNFR1; the endodomain of the IL-9 receptor; the BOX 1/2 common gamma chain domain; were cloned, in various configurations, into lentiviral vectors.

Assessment of surface expression of chimeric receptors. Lentiviral transfer plasmids encoding for chimeric receptors were transfected into 293 cells using Lipofectamine 3000 and 500 ng of lentiviral expression plasmids. 24 hours later, cell surface expression was assessed by flow cytometry using fluorescently labeled antibodies specific for the ectodomains of the chimeric receptors. Expression of chimeric receptors on primary human T cells was measured by transducing primary human T cells with a dilution series of lentiviral supernatants and analyzed by flow cytometry 72 hours later.

Lentivirus. Lentiviruses for transduction of primary human CD3+ T cells were produced in 293T cells by lipofection (Lipofectamine 3000, Thermo Fisher Scientific) of transfer and packaging plasmids, and purified by ultra-centrifugation. T cells activated with human CD3/CD28 Dynabeads (3:1 beads to cell ratio) in the presence of recombinant IL-7 and IL-15 were infected with lentiviruses one day after activation, de-beaded on Day 3, and expanded until Day 5.

Flow Cytometry. Flow cytometric detection of chimeric cytokine receptors and chimeric antigen receptors was performed by incubating lentivirally transduced primary human T cells with receptor-specific antibodies for 20 minutes in room temperature in the dark followed by acquisition of at least 10,000 events on FACSymphony A3 flow cytometer (BD Biosciences). Data was analyzed with FlowJo software (BD Biosciences). Transiently transfected 293T cells were treated similarly to detect chimeric cytokine receptors and chimeric antigen receptors 24 hours after lipofection (Lipofectamine 3000, Thermo Fisher Scientific) of 500 ng of lentiviral expression plasmids.

pSTAT Detection. In phosphoflow experiments, transduced human T cells were stimulated by addition of ligands for 30 minutes at 37° C., and the reaction was terminated by fixation with 1.5% paraformaldehyde (PFA) for 15 min at room temperature with agitation. Cells were washed and permeabilized with ice-cold 100% methanol for 60 minutes on ice or stored at −80° C. overnight. Cells were washed with FACS buffer before staining with pSTAT antibodies (Thermo Fisher Scientific) for 1 h at 4° C. in the dark. Cells were washed and analyzed on FACSymphony A3 flow cytometer. Data represent the mean fluorescence intensity (MFI).

xCELLigence Real-Time Cell Analysis. Tumor cell killing was assessed using the xCELLigence Real-Time Cell Analysis (RTCA) Analyzer (Agilent). SKOV-3 human ovarian adenocarcinoma tumor cells were seeded on a 96-well xCELLigence E-Plate at 10,000 cells per well. Twenty-four hours later, transduced T cells with or without 48 hours of pre-incubation with ligands for switch receptors were added in triplicate at various effector-to-target ratios with or without continued ligand stimulation. At the end of the assay, supernatant from each experimental well of the E-Plate was harvested, centrifuged to remove debris, then immediately frozen at −80 C.

Cytokine Multiplex Analysis. Samples were analyzed for cytokines and chemokines using the Milliplex cytokine assay kit (Millipore) as per manufacturer's protocol. Briefly, samples were diluted 1:2.5 assay diluent buffer and loaded onto a Millipore Multiscreen BV 96-well filter plate. Serial dilutions of cytokine standards were prepared in parallel and added to the plate. Milliplex 42-Plex Cytokine beads were vortexed for 30 sec. and 25 ul was added to each well with culture supernatants. Samples were then incubated on a plate shaker at 600 rpm in the dark at room temperature for 2 hours. The plate was applied to a Millipore Multiscreen Vacuum Manifold, washed twice with 50 µl of assay buffer (PBS, pH7.4, 1% BSA, 0.05% Tween20, 0.05% sodium azide), and each well resuspended with 75 µl assay buffer. 25 µl of biotinylated Anti-Human Multi-Cytokine Reporter was added to each well. The plate was incubated on a plate shaker at 600 rpm in the dark at room temperature for 1.5 hours. Streptavidin-Phycoerythrin was diluted 1:12.5 in assay buffer, and then 25 µl was added directly to each well. The plate was incubated on a plate shaker at 600 rpm in the dark at room temperature for 30 minutes. 25 µl of stop solution (0.2% (v/v) formaldehyde in PBS, pH 7.4) was added to each well and incubated at room temperature for 5 minutes. The plate was then applied to the vacuum manifold and each well resuspended in 125 µl assay buffer and shaken for 1 minute. Assay plate was the transferred to the Bio-Plex Luminex 200 XYP instrument for analysis. Cytokine concentrations were calculated using Bio-Plex Manager 6.2 software with a 5 parameter curve fitting algorithm applied for standard curve calculations.

Example 9

Chimeric Switch Receptors are Expressed on the Surface of Cells

In order to analyze whether the chimeric switch receptors were able to be correctly folded and expressed on the surface of cells, 293T cells were transiently transfected with lentiviral transfer plasmids encoding for the chimeric switch receptors. 24 hours later, cell surface expression was assessed by flow cytometry. The expression levels of various constructs are shown in Table 4 below.

TABLE 4

| Sequence ID | Ligand-binding domain | Trans-membrane domain | Intra-cellular domain | Linker | % expression transduced sample | % expression control sample | % positive cells | % double-positive cells |
|---|---|---|---|---|---|---|---|---|
| SEQ63 + CAR+ | IL21R | IL9R | IL9R | N/A | 45.4 | 0.031 | | 45.369 |
| SEQ72 + CAR+ | IL4Ra | IL9R | IL9R | N/A | 16.7 | 0.5 | | 16.2 |
| SEQ89 + CAR+ | CTLA4 | IL9R | IL9R | G$_4$S | 28.8 | 0.72 | | 28.08 |
| SEQ90 + CAR+ | CTLA4 | IL9R | IL9R | QP | 26.6 | 0.22 | | 26.38 |
| SEQ91 | TIM3 | IL9R | IL9R | G$_4$S | 21.5 | 3.42 | 18.08 | |
| SEQ93 | LAG3 | IL9R | IL9R | QP | 1.33 | 0.13 | 1.2 | |
| SEQ94 | LAG3 | IL9R | IL9R | G$_4$S | 3.35 | 2.25 | 1.1 | |
| SEQ95 + CAR+ | PD1 | IL9R | IL9R | G$_4$S | 18.3 | 0.49 | | 17.81 |
| SEQ96 + CAR+ | PD1 | IL9R | IL9R | QP | 12.2 | 0.21 | | 11.99 |
| SEQ109 | DCR1 | IL9R | IL9R | G$_4$S | 26 | 11.2 | 14.8 | |
| SEQ110 | DCR1 | IL9R | IL9R | QP | 17.6 | 7.66 | 9.94 | |
| SEQ111 | CD40 | IL9R | IL9R | G$_4$S | 24 | 1.42 | 22.58 | |
| SEQ112 | CD40 | IL9R | IL9R | QP | 19.2 | 0.31 | 18.89 | |
| SEQ113 + CAR+ | Fas | IL9R | IL9R | G$_4$S | 22.9 | 1.1 | | 21.8 |
| SEQ114 + CAR+ | Fas | IL9R | IL9R | QP | 24.9 | 1.03 | | 23.87 |
| SEQ115 | DR4 | IL9R | IL9R | G$_4$S | 54.5 | 34.7 | 19.8 | |
| SEQ116 | DR4 | IL9R | IL9R | QP | 38.3 | 21.4 | 16.9 | |
| SEQ123 | TNFRSF1B | IL9R | IL9R | G$_4$S | 44.9 | 1.59 | 43.31 | |
| SEQ124 | TNFRSF1B | IL9R | IL9R | QP | 52.2 | 1.11 | 51.09 | |
| SEQ153 + CAR+ | IL10Ra | IL9R | IL9R | G$_4$S | 19.2 | 0.68 | | 18.52 |
| SEQ155 | TGFBR2 | IL9R | IL9R | G$_4$S | 6.22 | 0.45 | 5.77 | |
| SEQ156 | TGFBR2 | IL9R | IL9R | QP | 10.7 | 0.17 | 10.53 | |
| SEQ159 + CAR+ | TIGIT | IL9R | IL9R | G$_4$S | 13.8 | 0.16 | | 13.64 |
| SEQ160 + CAR+ | TIGIT | IL9R | IL9R | QP | 19.9 | 0.023 | | 19.877 |
| SEQ165 | 2B4 | IL9R | IL9R | G$_4$S | 30.4 | 28.5 | 1.9 | |
| SEQ166 | 2B4 | IL9R | IL9R | QP | 18.1 | 15.3 | 2.8 | |
| SEQ187 | DCR1 | TNFR1 | IL9R | G$_4$S | 35.3 | 15.5 | 19.8 | |
| SEQ188 | DCR1 | TNFR1 | IL9R | QP | 47 | 11.4 | 35.6 | |
| SEQ189 | CD40 | TNFR1 | IL9R | G$_4$S | 31.1 | 1.03 | 30.07 | |
| SEQ190 | CD40 | TNFR1 | IL9R | QP | 29 | 1.45 | 27.55 | |
| SEQ193 | DR4 | TNFR1 | IL9R | G$_4$S | 65.8 | 45.3 | 20.5 | |
| SEQ194 | DR4 | TNFR1 | IL9R | QP | 63.7 | 49.6 | 14.1 | |
| SEQ200 | TNFRSF1B | TNFR1 | IL9R | G$_4$S | 29.1 | 1.31 | 27.79 | |
| SEQ201 | TNFRSF1B | TNFR1 | IL9R | QP | 47.3 | 0.95 | 46.35 | |

As demonstrated by the data in Table 4, all constructs exhibited some level of cell surface expression in 293T cells. These results indicate that the constructs produced properly folded proteins capable of endocytic transport and resistant to general proteolysis.

Constructs that exhibited cell surface expression in 293T cells were then packaged in lentivirus and titered on human primary T cells. The expression analysis over transduced primary human T cells is show in Table 5 below

TABLE 5

| Sequence ID | Ligand-binding domain | Trans-membrane domain | Intra-cellular domain | Linker | Fold-dilution of lentivirus | % positive T cells | % double-positive T cells (average of duplicates) | % positive T cells in unstained T cells (average of duplicates) | % positive T cells in stained un-transduced T cells (endogenous expression) |
|---|---|---|---|---|---|---|---|---|---|
| SEQ63 + CAR+ | IL21R | IL9R | IL9R | N/A | 2 | | 61 | 0.46 | 20.6 |
| | | | | | 6 | | 39.85 | | |
| | | | | | 18 | | 28.4 | | |
| | | | | | 54 | | 14.8 | | |
| | | | | | 162 | | 4.725 | | |
| | | | | | 486 | | 0.845 | | |
| | | | | | 1458 | | 0.495 | | |
| SEQ66 | IL15Ra | IL9R | IL9R | N/A | 2 | 63.1 | | 0.2 | 32.3 |
| | | | | | 6 | 60.6 | | | |
| | | | | | 18 | 33.85 | | | |
| | | | | | 54 | 40.6 | | | |

TABLE 5-continued

| Sequence ID | Ligand-binding domain | Trans-membrane domain | Intra-cellular domain | Linker | Fold-dilution of lentivirus | % positive T cells | % double-positive T cells (average of duplicates) | % positive T cells in unstained T cells (average of duplicates) | % positive T cells in stained un-transduced T cells (endogenous expression) |
|---|---|---|---|---|---|---|---|---|---|
| | | | | | 162 | 39.6 | | | |
| | | | | | 486 | 38 | | | |
| | | | | | 1458 | 36 | | | |
| SEQ69 | IL7Ra | IL9R | IL9R | N/A | 2 | 90.6 | | 1.02 | 55.5 |
| | | | | | 6 | 83.4 | | | |
| | | | | | 18 | 77.25 | | | |
| | | | | | 54 | 66.6 | | | |
| | | | | | 162 | 60.45 | | | |
| | | | | | 486 | 54.4 | | | |
| | | | | | 1458 | 52.8 | | | |
| SEQ72 + CAR+ | IL4Ra | IL9R | IL9R | N/A | 2 | | 38.95 | 0.15 | 44.6 |
| | | | | | 6 | | 29.85 | | |
| | | | | | 18 | | 18.1 | | |
| | | | | | 54 | | 10.8 | | |
| | | | | | 162 | | 7.01 | | |
| | | | | | 486 | | 2.915 | | |
| | | | | | 1458 | | 1.41 | | |
| SEQ89 + CAR+ | CTLA4 | IL9R | IL9R | G$_4$S | 2 | | 30 | N/A | N/A |
| | | | | | 6 | | 18.45 | | |
| | | | | | 18 | | 9.895 | | |
| | | | | | 54 | | 3.97 | | |
| | | | | | 162 | | 1.355 | | |
| | | | | | 486 | | 0.635 | | |
| | | | | | 1458 | | 0.485 | | |
| SEQ90 + CAR+ | CTLA4 | IL9R | IL9R | QP | 2 | | 41.3 | 0.058 | 0.63 |
| | | | | | 6 | | 31.5 | | |
| | | | | | 18 | | 20.05 | | |
| | | | | | 54 | | 12.6 | | |
| | | | | | 162 | | 3.06 | | |
| | | | | | 486 | | 1.255 | | |
| | | | | | 1458 | | 0.68 | | |
| SEQ91 | TIM3 | IL9R | IL9R | G$_4$S | 2 | 83.4 | | 1.71 | 88.4 |
| | | | | | 6 | 84.15 | | | |
| | | | | | 18 | 85.5 | | | |
| | | | | | 54 | 81.8 | | | |
| | | | | | 162 | 88.3 | | | |
| | | | | | 486 | 86.6 | | | |
| | | | | | 1458 | 77 | | | |
| | | | | | 4374 | 84.9 | | | |
| SEQ95 + CAR+ | PD1 | IL9R | IL9R | G$_4$S | 2 | | 32.45 | 0.027 | 0.64 |
| | | | | | 6 | | 18.75 | | |
| | | | | | 18 | | 14.45 | | |
| | | | | | 54 | | 6.965 | | |
| | | | | | 162 | | 2.43 | | |
| | | | | | 486 | | 1.19 | | |
| | | | | | 1458 | | 0.88 | | |
| SEQ96 + CAR+ | PD1 | IL9R | IL9R | QP | 2 | | 30.5 | 0.01 | 85.8 |
| | | | | | 6 | | 25.1 | | |
| | | | | | 18 | | 12.85 | | |
| | | | | | 54 | | 9.4 | | |
| | | | | | 162 | | 3.31 | | |
| | | | | | 486 | | 1.33 | | |
| | | | | | 1458 | | 0.645 | | |
| SEQ109 | DCR1 | IL9R | IL9R | G$_4$S | 2 | 77.8 | | 0.033 | 0.7 |
| | | | | | 6 | 60.95 | | | |
| | | | | | 18 | 44.6 | | | |
| | | | | | 54 | 29.45 | | | |
| | | | | | 162 | 13.4 | | | |
| | | | | | 486 | 4.285 | | | |
| | | | | | 1458 | 2.985 | | | |
| SEQ110 | DCR1 | IL9R | IL9R | QP | 2 | 89.1 | | 0.059 | 1.14 |
| | | | | | 6 | 74.9 | | | |
| | | | | | 18 | 49.65 | | | |
| | | | | | 54 | 28.9 | | | |
| | | | | | 162 | 15.6 | | | |
| | | | | | 486 | 10.755 | | | |
| | | | | | 1458 | 8.61 | | | |
| SEQ111 | CD40 | IL9R | IL9R | G$_4$S | 2 | 50.25 | | 0.44 | 12.1 |
| | | | | | 6 | 48.2 | | | |
| | | | | | 18 | 38.1 | | | |
| | | | | | 54 | 40.25 | | | |
| | | | | | 162 | 21.8 | | | |

TABLE 5-continued

| Sequence ID | Ligand-binding domain | Trans-membrane domain | Intra-cellular domain | Linker | Fold-dilution of lentivirus | % positive T cells | % double-positive T cells (average of duplicates) | % positive T cells in unstained T cells (average of duplicates) | % positive T cells in stained un-transduced T cells (endogenous expression) |
|---|---|---|---|---|---|---|---|---|---|
| | | | | | 486 | 9.285 | | | |
| | | | | | 1458 | 9.3 | | | |
| SEQ112 | CD40 | IL9R | IL9R | QP | 2 | 85.05 | | 0.049 | 3.41 |
| | | | | | 6 | 78.2 | | | |
| | | | | | 18 | 62.4 | | | |
| | | | | | 54 | 39.1 | | | |
| | | | | | 162 | 31.75 | | | |
| | | | | | 486 | 13.65 | | | |
| | | | | | 1458 | 12.13 | | | |
| SEQ113 + CAR+ | Fas | IL9R | IL9R | G$_4$S | 2 | | 42.45 | N/A | N/A |
| | | | | | 6 | | 17.3 | | |
| | | | | | 18 | | 8.735 | | |
| | | | | | 54 | | 4.84 | | |
| | | | | | 162 | | 2.05 | | |
| | | | | | 486 | | 0.98 | | |
| | | | | | 1458 | | 0.625 | | |
| SEQ114 + CAR+ | Fas | IL9R | IL9R | QP | 2 | | 87.15 | 0.34 | 98.1 |
| | | | | | 6 | | 81.25 | | |
| | | | | | 18 | | 71.4 | | |
| | | | | | 54 | | 54.15 | | |
| | | | | | 162 | | 30 | | |
| | | | | | 486 | | 13 | | |
| | | | | | 1458 | | 4.52 | | |
| SEQ116 | DR4 | IL9R | IL9R | QP | 2 | 93.1 | | 0.2 | 33.9 |
| | | | | | 6 | 87.85 | | | |
| | | | | | 18 | 77.75 | | | |
| | | | | | 54 | 63.8 | | | |
| | | | | | 162 | 50.1 | | | |
| | | | | | 486 | 39 | | | |
| | | | | | 1458 | 34.6 | | | |
| SEQ123 | TNFRSF1B | IL9R | IL9R | G$_4$S | 2 | 90.9 | | 0.019 | 68.5 |
| | | | | | 6 | 86.45 | | | |
| | | | | | 18 | 77.85 | | | |
| | | | | | 54 | 57.75 | | | |
| | | | | | 162 | 78 | | | |
| | | | | | 486 | 72.45 | | | |
| | | | | | 1458 | 72.5 | | | |
| SEQ124 | TNFRSF1B | IL9R | IL9R | QP | 2 | 81.05 | | 0.086 | 72.7 |
| | | | | | 6 | 78.25 | | | |
| | | | | | 18 | 70 | | | |
| | | | | | 54 | 70.75 | | | |
| | | | | | 162 | 71.9 | | | |
| | | | | | 486 | 73.6 | | | |
| | | | | | 1458 | 71.65 | | | |
| SEQ154 + CAR+ | IL10Ra | IL9R | IL9R | QP | 2 | | 28.2 | 0.33 | 1.34 |
| | | | | | 6 | | 22.4 | | |
| | | | | | 18 | | 10.9 | | |
| | | | | | 54 | | 4.49 | | |
| | | | | | 162 | | 1.635 | | |
| | | | | | 486 | | 1.055 | | |
| | | | | | 1458 | | 1.075 | | |
| SEQ155 | TGFBR2 | IL9R | IL9R | G$_4$S | 2 | 27.55 | | 0.67 | 0.68 |
| | | | | | 6 | 17.6 | | | |
| | | | | | 18 | 14.14 | | | |
| | | | | | 54 | 4.305 | | | |
| | | | | | 162 | 1.425 | | | |
| | | | | | 486 | 2.1 | | | |
| | | | | | 1458 | 1.6 | | | |
| SEQ156 | TGFBR2 | IL9R | IL9R | QP | 2 | 77.45 | | 0.056 | 68.9 |
| | | | | | 6 | 76.8 | | | |
| | | | | | 18 | 70.55 | | | |
| | | | | | 54 | 70.9 | | | |
| | | | | | 162 | 63.45 | | | |
| | | | | | 486 | 67.5 | | | |
| | | | | | 1458 | 71.05 | | | |
| SEQ171 | TWEAKR | IL9R | IL9R | G$_4$S | 2 | 77.35 | | 0.54 | 62.8 |
| | | | | | 6 | 68.45 | | | |
| | | | | | 18 | 53.65 | | | |
| | | | | | 54 | 46.8 | | | |
| | | | | | 162 | 59.7 | | | |
| | | | | | 486 | 63.4 | | | |
| | | | | | 1458 | 63.75 | | | |

TABLE 5-continued

| Sequence ID | Ligand-binding domain | Trans-membrane domain | Intra-cellular domain | Linker | Fold-dilution of lentivirus | % positive T cells | % double-positive T cells (average of duplicates) | % positive T cells in unstained T cells (average of duplicates) | % positive T cells in stained untransduced T cells (endogenous expression) |
|---|---|---|---|---|---|---|---|---|---|
| SEQ172 | TWEAKR | IL9R | IL9R | QP | 2 | 74 | | 0.39 | 32.9 |
| | | | | | 6 | 53.85 | | | |
| | | | | | 18 | 44.9 | | | |
| | | | | | 54 | 47.4 | | | |
| | | | | | 162 | 36.45 | | | |
| | | | | | 486 | 34.75 | | | |
| | | | | | 1458 | 34.1 | | | |
| SEQ173 | TWEAKR | TNFR1 | IL9R | G$_4$S | 2 | 92.7 | | 0.37 | 30.5 |
| | | | | | 6 | 80.85 | | | |
| | | | | | 18 | 64.65 | | | |
| | | | | | 54 | 46.55 | | | |
| | | | | | 162 | 36.1 | | | |
| | | | | | 486 | 32.95 | | | |
| | | | | | 1458 | 31 | | | |
| SEQ174 | TWEAKR | TNFR1 | IL9R | QP | 2 | 87.2 | | 0.29 | 23.6 |
| | | | | | 6 | 68.95 | | | |
| | | | | | 18 | 47.75 | | | |
| | | | | | 54 | 37.15 | | | |
| | | | | | 162 | 30 | | | |
| | | | | | 486 | 25.7 | | | |
| | | | | | 1458 | 26.75 | | | |
| SEQ187 | DCR1 | TNFR1 | IL9R | G$_4$S | 2 | 86.65 | | 0.16 | 4.81 |
| | | | | | 6 | 70.25 | | | |
| | | | | | 18 | 50.15 | | | |
| | | | | | 54 | 29 | | | |
| | | | | | 162 | 19.8 | | | |
| | | | | | 486 | 6.475 | | | |
| | | | | | 1458 | 3.325 | | | |
| SEQ188 | DCR1 | TNFR1 | IL9R | QP | 2 | 63.85 | | 0.02 | 8.63 |
| | | | | | 6 | 60.8 | | | |
| | | | | | 18 | 48.65 | | | |
| | | | | | 54 | 35.7 | | | |
| | | | | | 162 | 15.08 | | | |
| | | | | | 486 | 14.7 | | | |
| | | | | | 1458 | 8.65 | | | |
| SEQ189 | CD40 | TNFR1 | IL9R | G$_4$S | 2 | 91.05 | | 0.079 | 11.9 |
| | | | | | 6 | 79 | | | |
| | | | | | 18 | 55.8 | | | |
| | | | | | 54 | 24.3 | | | |
| | | | | | 162 | 20.55 | | | |
| | | | | | 486 | 10.65 | | | |
| | | | | | 1458 | 10.365 | | | |
| SEQ190 | CD40 | TNFR1 | IL9R | QP | 2 | 58.15 | | 0.32 | 34 |
| | | | | | 6 | 56.3 | | | |
| | | | | | 18 | 53.5 | | | |
| | | | | | 54 | 48.5 | | | |
| | | | | | 162 | 38.65 | | | |
| | | | | | 486 | 33.15 | | | |
| | | | | | 1458 | 31.3 | | | |
| SEQ193 | DR4 | TNFR1 | IL9R | G$_4$S | 2 | 86 | | 0.22 | 40 |
| | | | | | 6 | 69.3 | | | |
| | | | | | 18 | 61 | | | |
| | | | | | 54 | 50.3 | | | |
| | | | | | 162 | 48.85 | | | |
| | | | | | 486 | 47 | | | |
| | | | | | 1458 | 43.2 | | | |
| SEQ194 | DR4 | TNFR1 | IL9R | QP | 2 | 87 | | 0.089 | 60.6 |
| | | | | | 6 | 84.3 | | | |
| | | | | | 18 | 83.4 | | | |
| | | | | | 54 | 84.15 | | | |
| | | | | | 162 | 75.6 | | | |
| | | | | | 486 | 74 | | | |
| | | | | | 1458 | 64.85 | | | |
| SEQ200 | TNFRSF1B | TNFR1 | IL9R | G$_4$S | 2 | 96.95 | | 1.84 | 93.6 |
| | | | | | 6 | 95.35 | | | |
| | | | | | 18 | 93.65 | | | |
| | | | | | 54 | 94.25 | | | |
| | | | | | 162 | 92.7 | | | |
| | | | | | 486 | 91.65 | | | |
| | | | | | 1458 | 92 | | | |
| SEQ201 | TNFRSF1B | TNFR1 | IL9R | QP | 2 | 95.85 | | 0.39 | 92.8 |
| | | | | | 6 | 96.2 | | | |

TABLE 5-continued

| Sequence ID | Ligand-binding domain | Trans-membrane domain | Intra-cellular domain | Linker | Fold-dilution of lentivirus | % positive T cells | % double-positive T cells (average of duplicates) | % positive T cells in unstained T cells (average of duplicates) | % positive T cells in stained un-transduced T cells (endogenous expression) |
|---|---|---|---|---|---|---|---|---|---|
| | | | | | 18 | 94.15 | | | |
| | | | | | 54 | 93.5 | | | |
| | | | | | 162 | 94.15 | | | |
| | | | | | 486 | 92.1 | | | |
| | | | | | 1458 | 93.8 | | | |

As demonstrated in Table 5 above, lentiviruses for all constructs were successfully produced and transduced primary human T cells exhibited at least some level of cell surface expression. Despite their general resistance to viral transduction and sensitivity unfolded protein responses (UPR) [Lopez-Soto et al., "Cancer-induced Endoplasmic Reticulum Stress in T Cells Subverts Immunosurveillance," Cell Metabolism 28(6):803-805 (2018); Li et al., "The Emerging Roles of Endoplasmic Reticulum Stress in Balancing Immunity and Tolerance in Health and Diseases: Mechanisms and Opportunities," Front. Immunol. Volum 10, Article 3154], the constructs produced properly folded proteins capable of endocytic transport and resistant to general proteolysis in primary T cells.

Example 10

Expression of Chimeric Switch Receptors Results in Phosphorylation of STAT Receptors Some constructs were then tested for their ability to induce phosphorylation of STAT1, STAT3, and/or STAT5. Briefly, primary human T cells were transduced with a lentiviral vector encoding switch receptors of SEQ ID NO:63+CAR+(IL21R ECD+IL9R TM+IL9R ICD and CAR 4D5), SEQ ID NO:66 (IL15Ra+IL9R TM+IL9R ICD), SEQ ID NO:72+CAR+(IL4R ECD+IL9R TM+IL9R ICD and CAR 4D5), or SEQ ID NO:153+CAR+(IL10Ra ECD+IL9R TM+IL9R ICD and CAR 4D5). Cells transduced with SEQ ID NO:63+CAR+ were left either unstimulated or stimulated with 200 ng/mL IL-21 for 30 minutes. Cells transduced with SEQ ID NO:66 were left either unstimulated or stimulated with 200 ng/mL IL-15 for 30 minutes. Cells transduced with SEQ ID NO:72+CAR+ were left either unstimulated or stimulated with 200 ng/mL IL-4 for 30 minutes. Cells transduced with SEQ ID NO:153+CAR+ were left either unstimulated or stimulated with 200 ng/mL IL-4 for 30 minutes. The fold increase in gMFI of ligand stimulated versus no stimulation was calculated and is shown in FIG. 1.

As shown in FIG. 1, all constructs induced phosphorylation of STAT1, STAT3, and STAT5 when stimulated with ligand. Activation of STAT family members through ligand mediated phosphorylation is believed to confer advantages in effector function, polarization and proliferation to T cells.

Example 11

Figure 3:
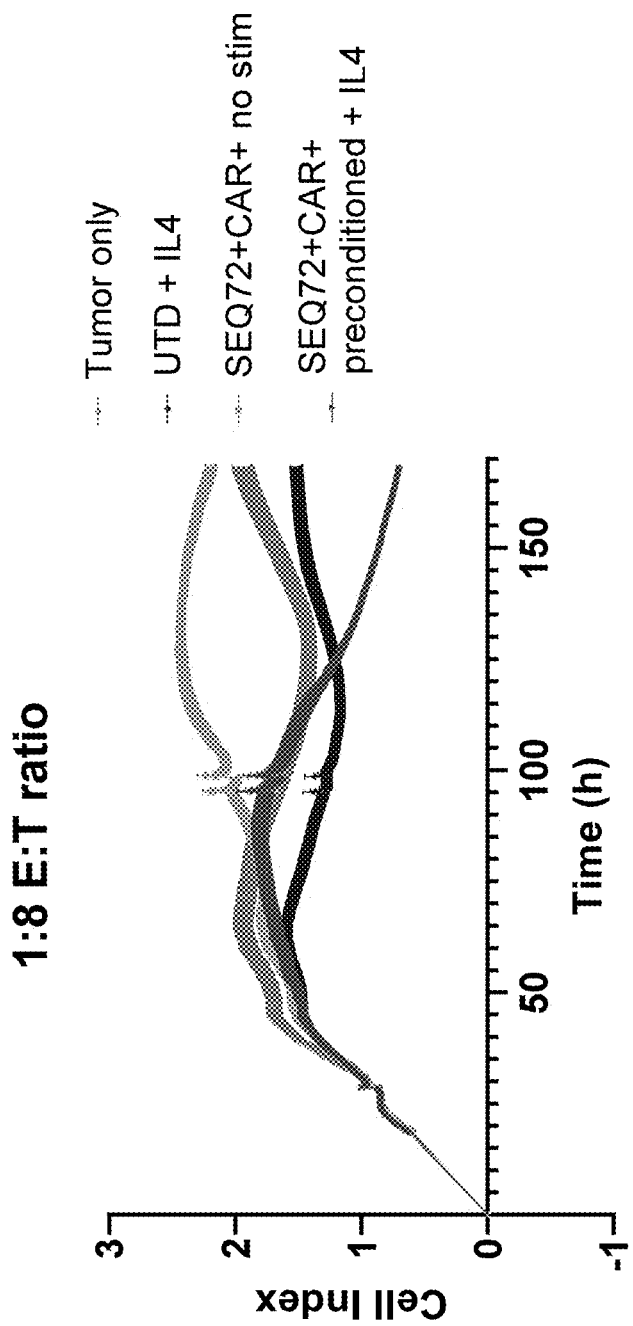
FIG. 3 shows a real-time cytotoxicity assay (RTCA) with T cells co-expressing switch receptor SEQ72 (IL4R ECD+IL9R TM+IL9R ICD) and CAR (4D5) against SKOV-3 human ovarian adenocarcinoma cells expressing HER2. Double-positive T cells (SEQ72+CAR+) were left unstimulated ("no stim") before being added on SKOV-3 tumor cells at a 1:8 effector-to-target ratio, or preconditioned for 48 hours with IL4 before addition to the plate with continued ligand stimulation ("preconditioned+IL4"). Untransduced T cells (UTD) served as control and were added on tumor cells with continued IL4 stimulation ("UTD+IL4").
Figure 4:
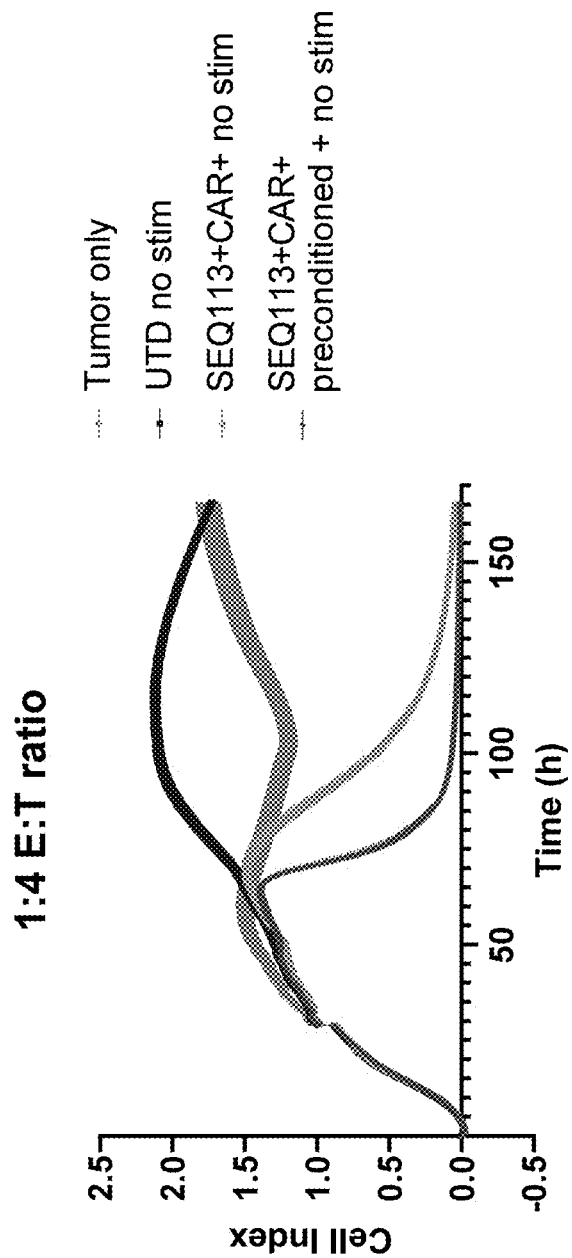
FIG. 4 shows a real-time cytotoxicity assay (RTCA) with T cells co-expressing switch receptor SEQ113 (Fas ECD+IL9R TM+IL9R ICD) and CAR (4D5) against SKOV-3 human ovarian adenocarcinoma cells expressing HER2. Double-positive T cells (SEQ113+CAR+) were left unstimulated ("no stim") before being added on SKOV-3 tumor cells at a 1:4 effector-to-target ratio, or preconditioned for 48 hours with FasL before addition to the plate ("preconditioned+no stim"). Untransduced T cells (UTD) served as control and were added on tumor cells unstimulated ("UTD+no stim").

Primary T Cells Expressing Chimeric Switch Receptors Exhibit Enhanced Tumor Cell Killing Real-time cytotoxicity assays were then used to analyze whether or not cells expressing a chimeric switch receptor of the present disclosure would show increased cytotoxicity when exposed to ligand. As shown in FIGS. 2-4, upon stimulation with ligand, cells expressing either SEQ ID NO:63+CAR+(IL21R ECD+IL9R TM+IL9R ICD and CAR 4D5) (FIG. 2), SEQ ID NO:72+CAR+(IL4R ECD+IL9R TM+IL9R ICD and CAR 4D5) (FIG. 3), or SEQ ID NO:113+CAR+(Fas ECD+IL9R TM+IL9R ICD and CAR 4D5) (FIG. 4), demonstrated an increase in killing of SKOV-3 human ovarian adenocarcinoma cells expressing HER2 when preconditioned with ligand as compared to untransduced, stimulated cells. Consistent with the observed activation of STAT transcription factors following ligand stimulation, T cells transduced with hybrid IL9R receptors demonstrated improved killing over unstimulated controls. It should be noted that in the case of Seq ID NO 113, the presence of natural ligand (TNFSF6) increases background killing in the assay. That said, the addition of exogenous ligand enhances T cell killing above controls.

Example 12

Figure 5:
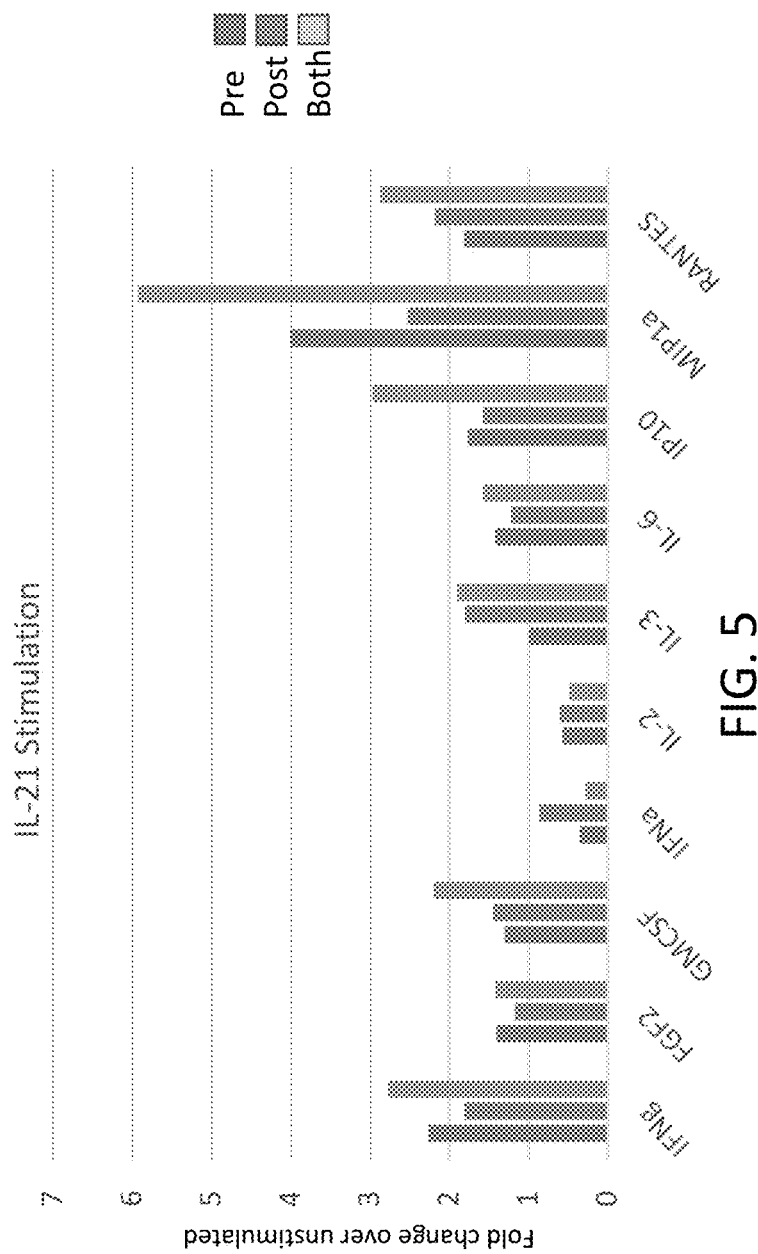
FIG. 5 shows hybrid cytokine receptors induce functional activation of T cells in response to ligand stimulation. T cells were transduced with hybrid cytokine receptor SEQ63 (IL21R ECD+IL9R TM+IL9R ICD) and CAR (4D5) and cocultured with IL-21 (i) before, (ii) during, or (iii) before+during, co-culture with target cells for 160 hrs. Cell culture supernatants were collected and the concentrations of effector cytokines measured by Luminex assay. The graph depicts fold change over unstimulated.
Figure 6:
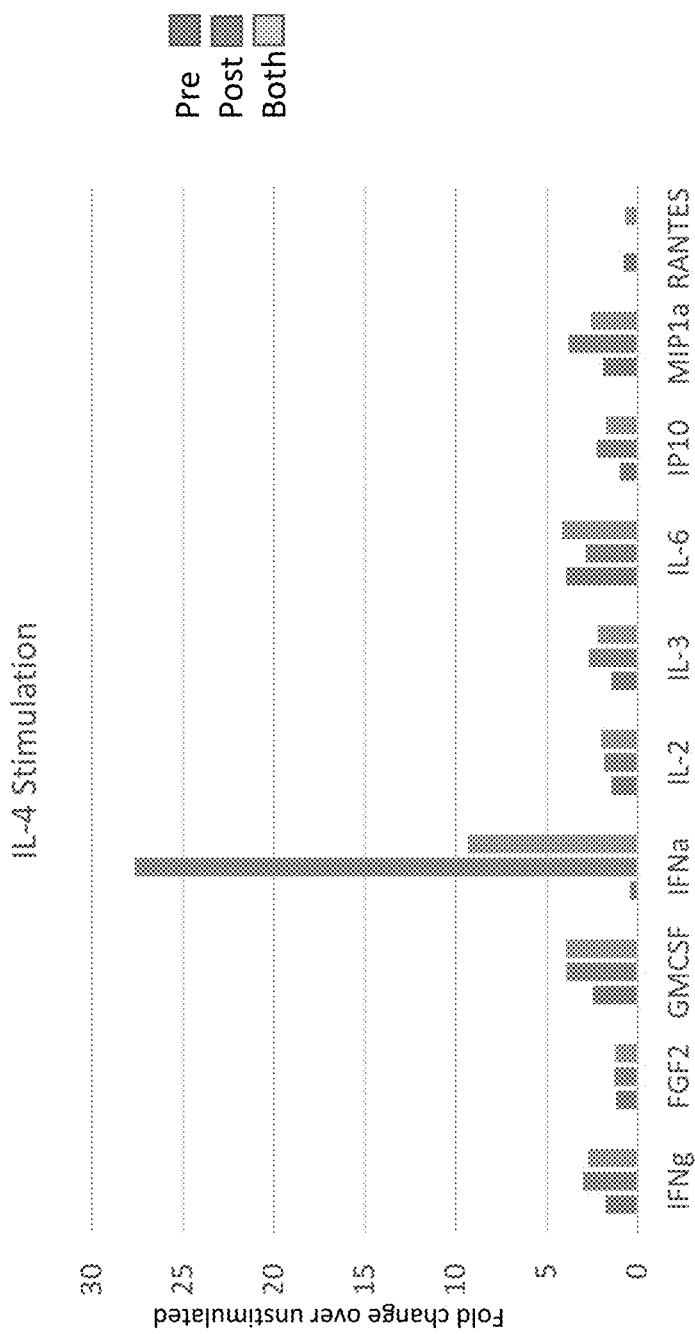
FIG. 6 shows hybrid cytokine receptors induce functional activation of T cells in response to ligand stimulation. T cells were transduced with hybrid cytokine receptor SEQ72 (IL4R ECD+IL9R TM+IL9R ICD) and CAR (4D5) and cocultured with IL-4 (i) before, (ii) during, or (iii) before+during, co-culture with target cells for 160 hrs. Cell culture supernatants were collected and the concentrations of effector cytokines measured by Luminex assay. The graph depicts fold change over unstimulated.
Figure 7:
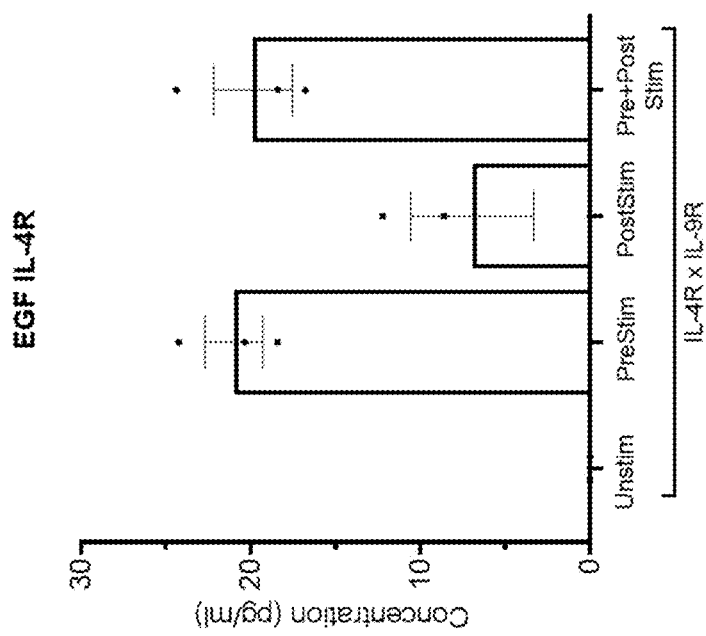
FIG. 7 shows hybrid cytokine receptors induce functional activation of T cells in response to ligand stimulation. T cells were transduced with hybrid cytokine receptor SEQ72 (IL4R ECD+IL9R TM+IL9R ICD) and CAR (4D5) and cocultured with IL-4 (i) before, (ii) during, or (iii) before+during, co-culture with target cells for 160 hrs. Cell culture supernatants were collected and the concentrations of effector cytokines measured by Luminex assay. The graphs shows concentration of EGF in pg/mL.
Figure 8A:
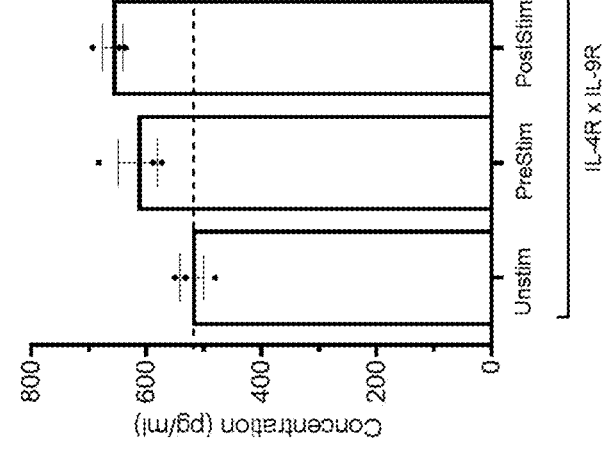
FIGS. 8A-8B show hybrid cytokine receptors induce functional activation of T cells in response to ligand stimulation. T cells were transduced with hybrid cytokine receptors SEQ63 (IL21R ECD+IL9R TM+IL9R ICD) and CAR (4D5) (FIG. 8A) and SEQ72 (IL4R ECD+IL9R TM+IL9R ICD) and CAR (4D5) (FIG. 8B) and cocultured with their respective ligands (i) before, (ii) during, or (iii) before+during, co-culture with target cells for 160 hrs. Cell culture supernatants were collected and the concentrations of effector cytokines measured by Luminex assay. The graphs shows concentration of FGF-2 in pg/mL.
Figure 8B:
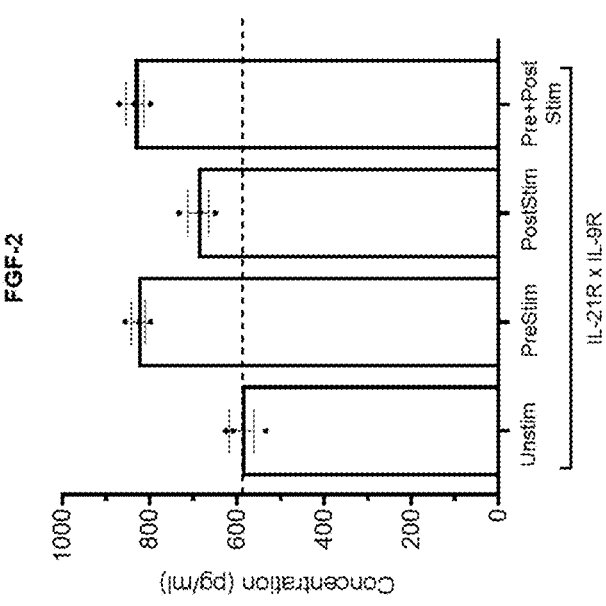
Figure 9A:
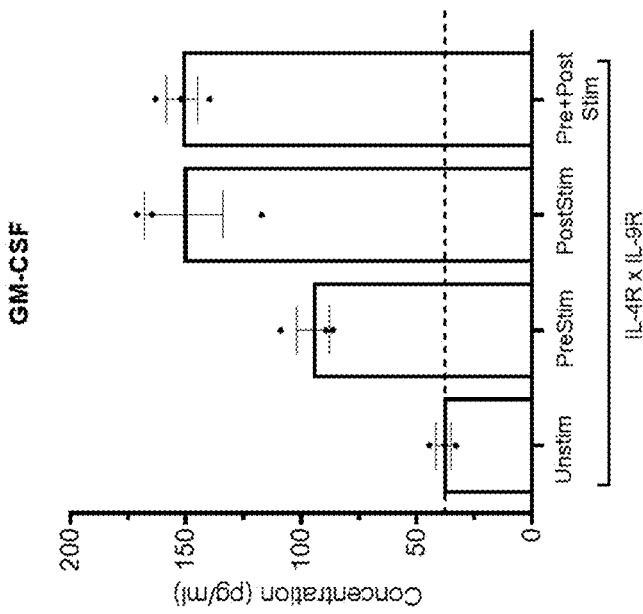
FIGS. 9A-9B show hybrid cytokine receptors induce functional activation of T cells in response to ligand stimulation. T cells were transduced with hybrid cytokine receptors SEQ63 (IL21R ECD+IL9R TM+IL9R ICD) and CAR (4D5) (FIG. 9A) and SEQ72 (IL4R ECD+IL9R TM+IL9R ICD) and CAR (4D5) (FIG. 9B) and cocultured with their respective ligands (i) before, (ii) during, or (iii) before+during, co-culture with target cells for 160 hrs. Cell culture supernatants were collected and the concentrations of effector cytokines measured by Luminex assay. The graphs shows concentration of GM-CSF in pg/mL.
Figure 9B:
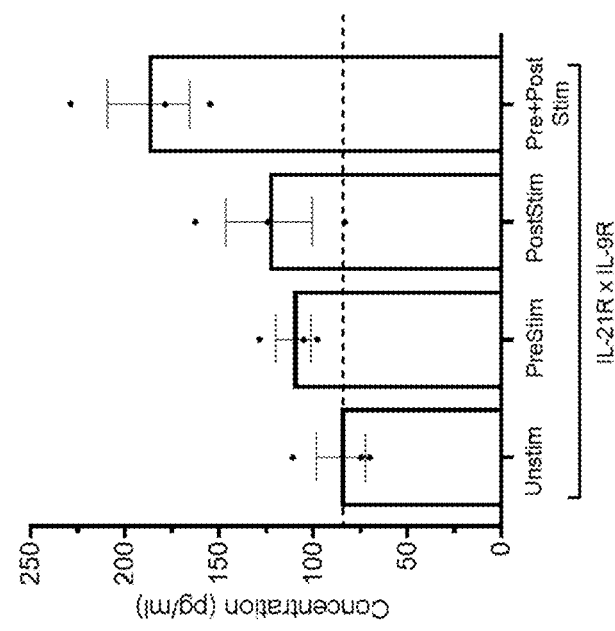
Figure 10:
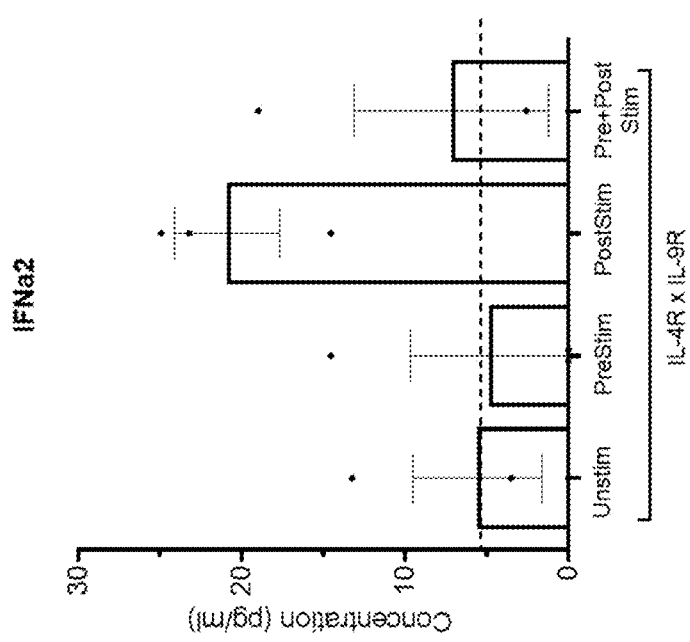
FIG. 10 shows hybrid cytokine receptors induce functional activation of T cells in response to ligand stimulation. T cells were transduced with hybrid cytokine receptor SEQ72 (IL4R ECD+IL9R TM+IL9R ICD) and CAR (4D5) and cocultured with its respective ligand (i) before, (ii) during, or (iii) before+during, co-culture with target cells for 160 hrs. Cell culture supernatants were collected and the concentrations of effector cytokines measured by Luminex assay. The graphs shows concentration of IFNa2 in pg/mL.
Figure 11B:
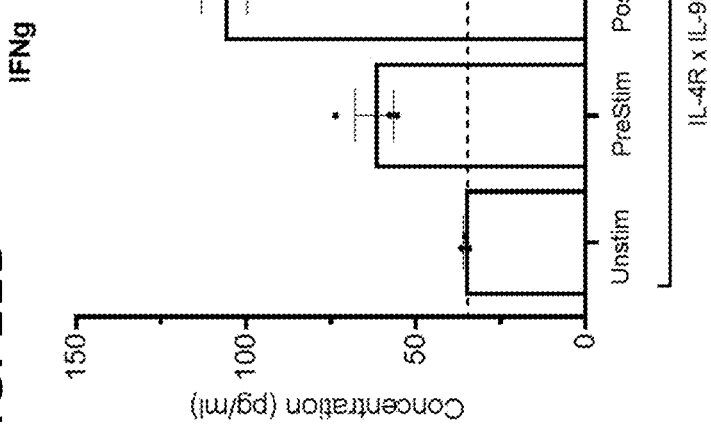
FIGS. 11A-11B show hybrid cytokine receptors induce functional activation of T cells in response to ligand stimulation. T cells were transduced with hybrid cytokine receptors SEQ63 (IL21R ECD+IL9R TM+IL9R ICD) and CAR (4D5) (FIG. 11A) and SEQ72 (IL4R ECD+IL9R TM+IL9R ICD) and CAR (4D5) (FIG. 11B) and cocultured with their respective ligands (i) before, (ii) during, or (iii) before+during, co-culture with target cells for 160 hrs. Cell culture supernatants were collected and the concentrations of effector cytokines measured by Luminex assay. The graphs shows concentration of IFNg in pg/mL.
Figure 11A:
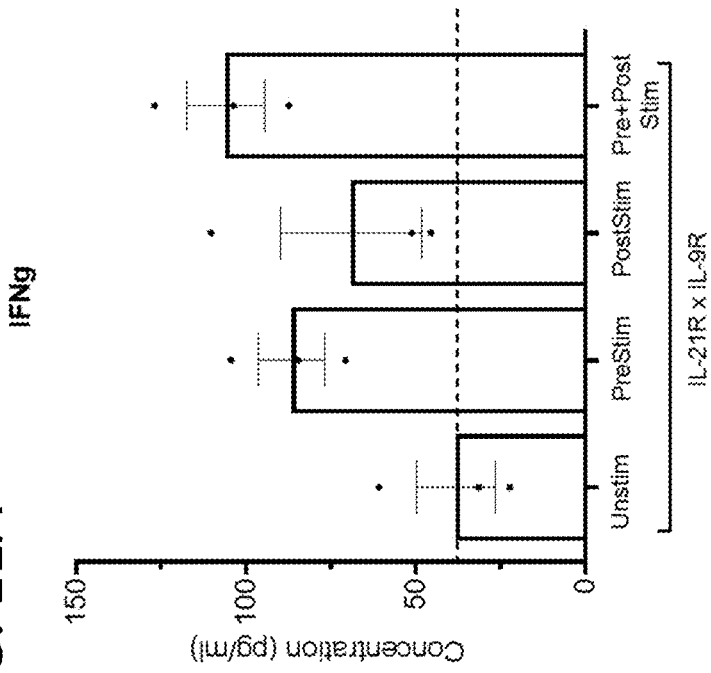
Figure 12:
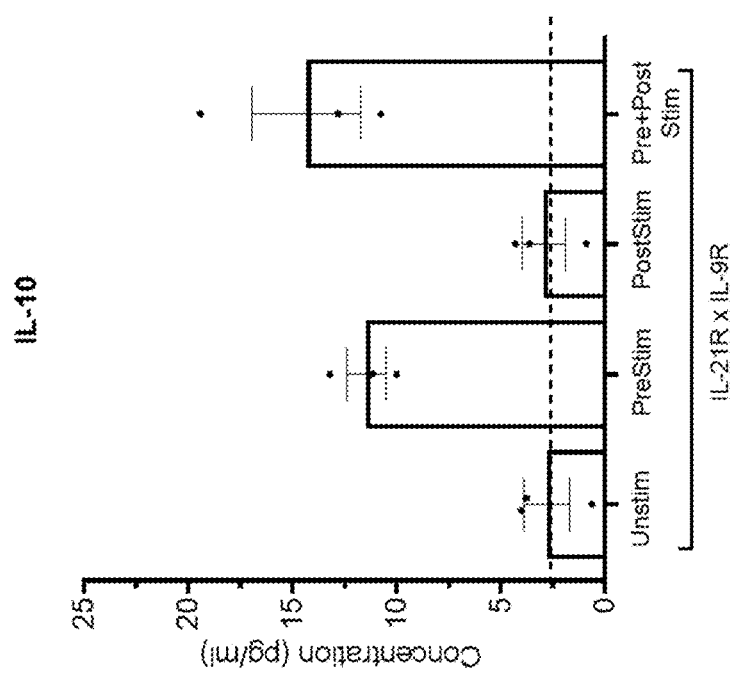
FIG. 12 shows hybrid cytokine receptors induce functional activation of T cells in response to ligand stimulation. T cells were transduced with hybrid cytokine receptor SEQ63 (IL21R ECD+IL9R TM+IL9R ICD) and CAR (4D5) and cocultured with its respective ligand (i) before, (ii) during, or (iii) before+during, co-culture with target cells for 160 hrs. Cell culture supernatants were collected and the concentrations of effector cytokines measured by Luminex assay. The graphs shows concentration of IL-10 in pg/mL.
Figures 13A, 13B:
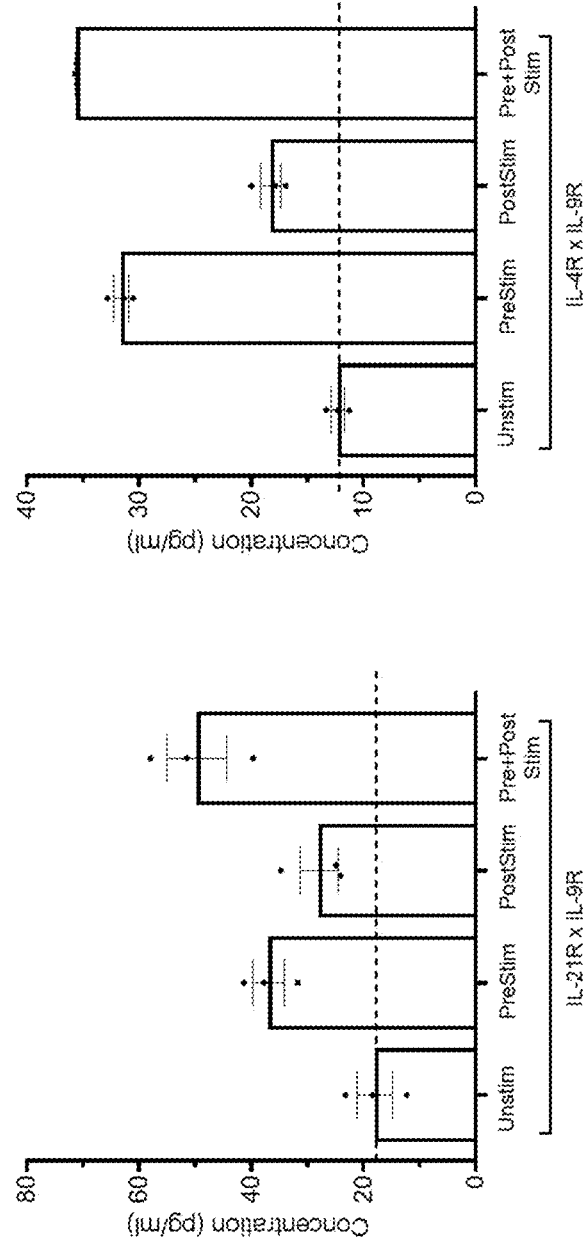
FIGS. 13A-13B show hybrid cytokine receptors induce functional activation of T cells in response to ligand stimulation. T cells were transduced with hybrid cytokine receptors SEQ63 (IL21R ECD+IL9R TM+IL9R ICD) and CAR (4D5) (FIG. 13A) and SEQ72 (IL4R ECD+IL9R TM+IL9R ICD) and CAR (4D5) (FIG. 13B) and cocultured with their respective ligands (i) before, (ii) during, or (iii) before+during, co-culture with target cells for 160 hrs. Cell culture supernatants were collected and the concentrations of effector cytokines measured by Luminex assay. The graphs shows concentration of IL-1a in pg/mL.
Figure 14:
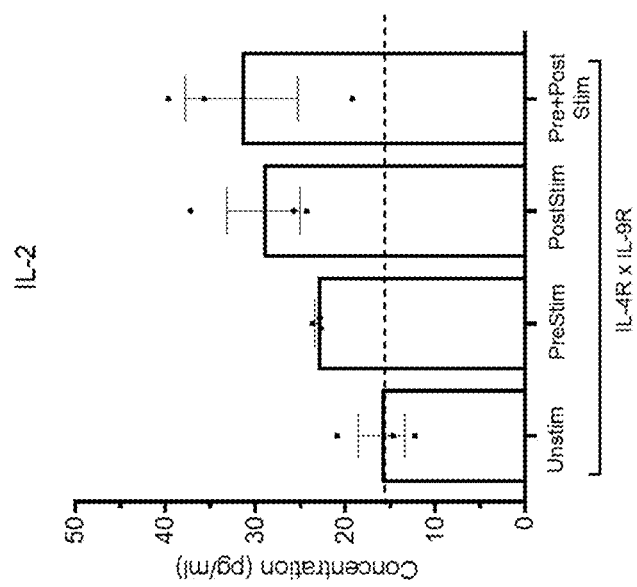
FIG. 14 shows hybrid cytokine receptors induce functional activation of T cells in response to ligand stimulation. T cells were transduced with hybrid cytokine receptor SEQ72 (IL4R ECD+IL9R TM+IL9R ICD) and CAR (4D5) and cocultured with its respective ligand (i) before, (ii) during, or (iii) before+during, co-culture with target cells for 160 hrs. Cell culture supernatants were collected and the concentrations of effector cytokines measured by Luminex assay. The graphs shows concentration of IL-2 in pg/mL.
Figure 15A:
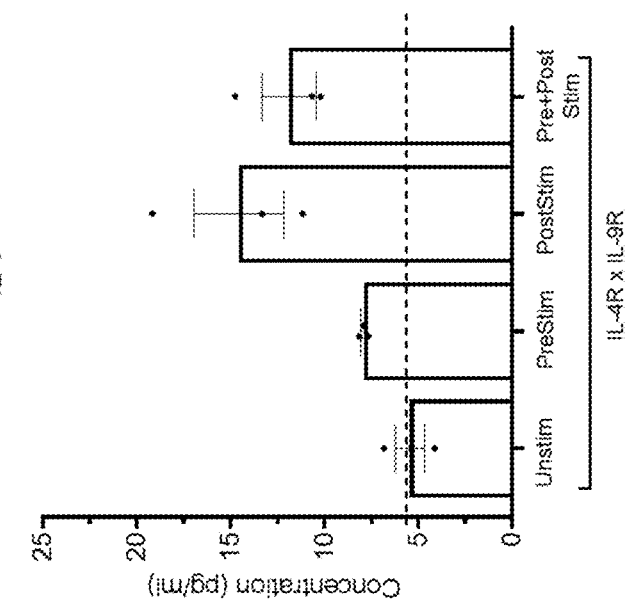
FIGS. 15A-15B show hybrid cytokine receptors induce functional activation of T cells in response to ligand stimulation. T cells were transduced with hybrid cytokine receptors SEQ63 (IL21R ECD+IL9R TM+IL9R ICD) and CAR (4D5) (FIG. 15A) and SEQ72 (IL4R ECD+IL9R TM+IL9R ICD) and CAR (4D5) (FIG. 15B) and cocultured with their respective ligands (i) before, (ii) during, or (iii) before+during, co-culture with target cells for 160 hrs. Cell culture supernatants were collected and the concentrations of effector cytokines measured by Luminex assay. The graphs shows concentration of IL-3 in pg/mL.
Figure 15B:
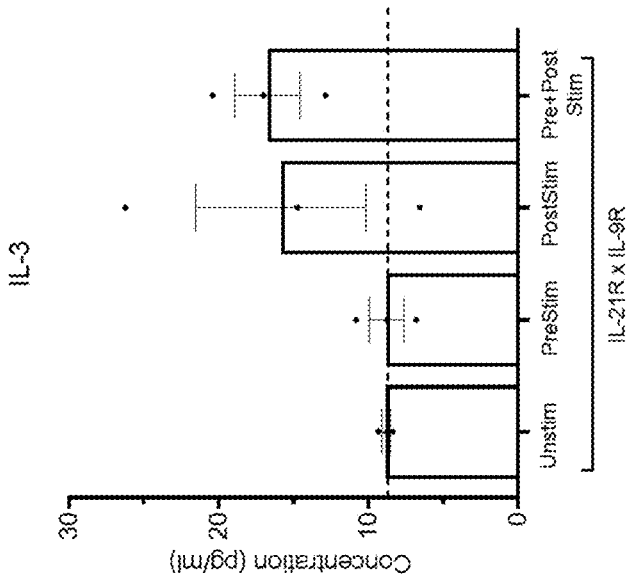
Figure 16B:
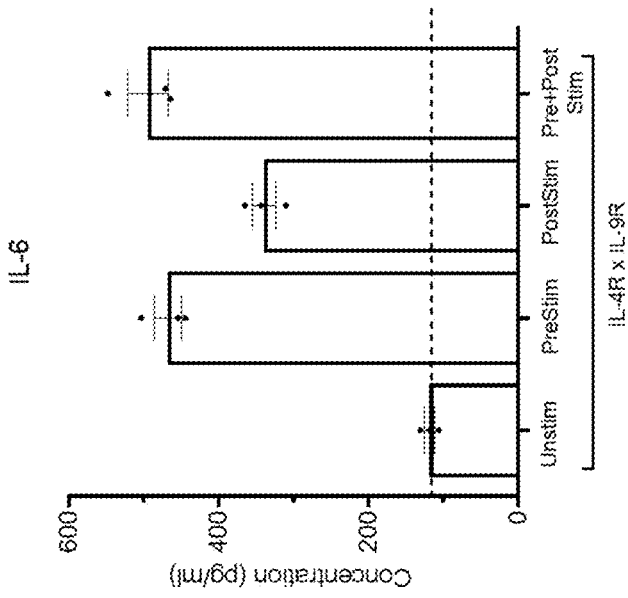
FIGS. 16A-16B show hybrid cytokine receptors induce functional activation of T cells in response to ligand stimulation. T cells were transduced with hybrid cytokine receptors SEQ63 (IL21R ECD+IL9R TM+IL9R ICD) and CAR (4D5) (FIG. 16A) and SEQ72 (IL4R ECD+IL9R TM+IL9R ICD) and CAR (4D5) (FIG. 16B) and cocultured with their respective ligands (i) before, (ii) during, or (iii) before+during, co-culture with target cells for 160 hrs. Cell culture supernatants were collected and the concentrations of effector cytokines measured by Luminex assay. The graphs shows concentration of IL-6 in pg/mL.
Figure 16A:
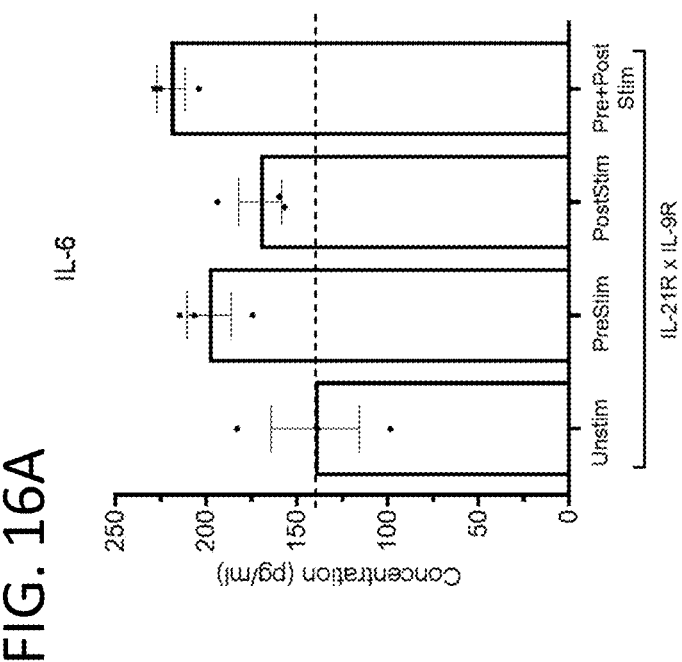
Figure 17B:
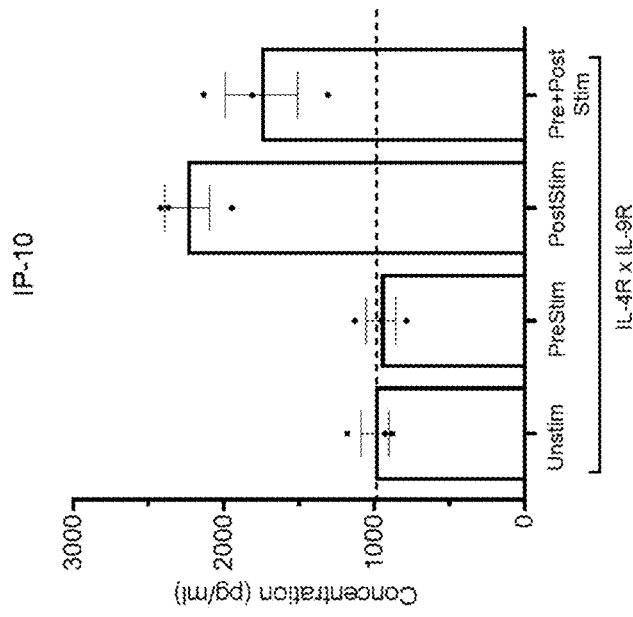
FIGS. 17A-17B show hybrid cytokine receptors induce functional activation of T cells in response to ligand stimulation. T cells were transduced with hybrid cytokine receptors SEQ63 (IL21R ECD+IL9R TM+IL9R ICD) and CAR (4D5) (FIG. 17A) and SEQ72 (IL4R ECD+IL9R TM+IL9R ICD) and CAR (4D5) (FIG. 17B) and cocultured with their respective ligands (i) before, (ii) during, or (iii) before+during, co-culture with target cells for 160 hrs. Cell culture supernatants were collected and the concentrations of effector cytokines measured by Luminex assay. The graphs shows concentration of IP-10 in pg/mL.
Figure 17A:
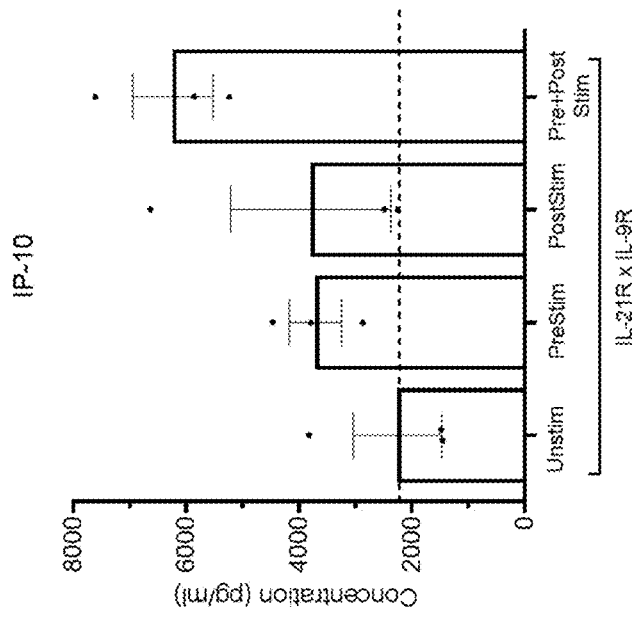
Figure 18B:
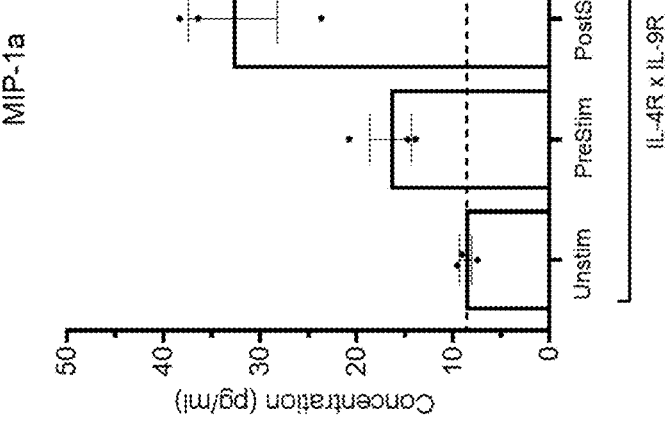
FIGS. 18A-18B show hybrid cytokine receptors induce functional activation of T cells in response to ligand stimulation. T cells were transduced with hybrid cytokine receptors SEQ63 (IL21R ECD+IL9R TM+IL9R ICD) and CAR (4D5) (FIG. 18A) and SEQ72 (IL4R ECD+IL9R TM+IL9R ICD) and CAR (4D5) (FIG. 18B) and cocultured with their respective ligands (i) before, (ii) during, or (iii) before+during, co-culture with target cells for 160 hrs. Cell culture supernatants were collected and the concentrations of effector cytokines measured by Luminex assay. The graphs shows concentration of MIP-1a in pg/mL.
Figure 18A:
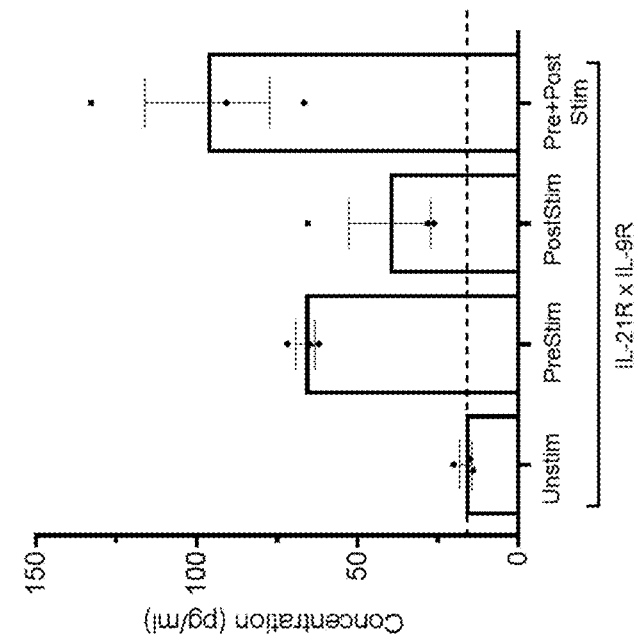
Figure 19:
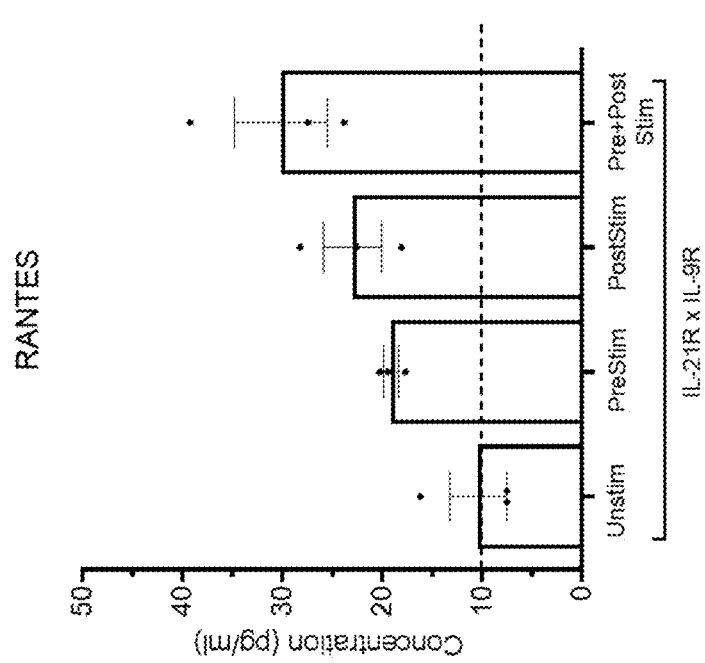
FIG. 19 shows hybrid cytokine receptors induce functional activation of T cells in response to ligand stimulation. T cells were transduced with hybrid cytokine receptor SEQ63 (IL21R ECD+IL9R TM+IL9R ICD) and CAR (4D5) and cocultured with its respective ligand (i) before, (ii) during, or (iii) before+during, co-culture with target cells for 160 hrs. Cell culture supernatants were collected and the concentrations of effector cytokines measured by Luminex assay. The graphs shows concentration of RANTES in pg/mL.

Primary T Cells Expressing Chimeric Switch Receptors Exhibit Increased Cytokine and Chemokine Activity Culture supernatants from primary human T cells transduced with either SEQ ID NO:63+CAR+(IL21R ECD+IL9R TM+IL9R ICD and CAR 4D5) (FIG. 5) or SEQ ID NO:72+CAR+(IL4R ECD+IL9R TM+IL9R ICD and CAR 4D5) (FIG. 6) were then analyzed for the presence of cytokines and chemokines. Supernatants were taken from cells stimulated with ligand before the real-time cytotoxicity assay of Example 11 (first bar, "pre"), cells stimulated with ligand during the real-time cytotoxicity assay of Example 11 (second bar, "post"), or cells stimulated at both points in the real-time cytotoxicity assay of Example 11 (third bar, "both"). The fold increase over unstimulated was calculated and is shown in FIGS. 5 and 6. As shown in FIGS. 5 and 6, several cytokines and chemokines, such as IFNg, FGF2, GMCSF, IL-3, IL-6, IP10, MIP1a, and RANTES, demonstrated increased production. The magnitude and quality of cytokines produced following ligand stimulation (either "pre", "post" or "both") indicates a robust improvement in T cell response with hybrid-IL9R engagement. Furthermore, the pattern of cytokine response indicates an increase in type-1 polarization following ligand stimulation relative to controls.

FIGS. 7-19 depict results from the same experiment, however, the data is shown in concentration of cytokine or chemokine (in pg·mL) for each of the above described experimental conditions. Similarly, the magnitude and quality of cytokines produced following ligand stimulation (either "pre", "post" or "both") indicates a robust improvement in T cell response with hybrid-IL9R engagement, and the pattern of cytokine response indicates an increase in type-1 polarization following ligand stimulation relative to controls.

What is claimed is:

1. A recombinant nucleic acid molecule encoding a chimeric receptor, said chimeric receptor comprising:
   an extracellular portion comprising a binding domain of an endogenous cytokine receptor, wherein the extracellular portion does not bind IL-9;
   an intracellular portion comprising an endodomain of an IL-9 receptor; and
   a transmembrane domain that joins the extracellular portion and the intracellular portion, wherein the chimeric receptor induces signaling through the IL-9 endodomain upon extracellular ligand binding, and wherein the chimeric receptor comprises an amino acid sequence having at least 80% sequence identity to an amino acid sequence selected from SEQ ID Nos: 63-80.

2. The recombinant nucleic acid molecule of claim 1 further comprising one or more linkers.

3. The recombinant nucleic acid molecule of claim 1, wherein the endogenous cytokine receptor is selected from IL-2rb, IL-2ra, IL-4r, IL-7ra, IL-15ra, and IL-21ra.

4. The recombinant nucleic acid molecule according to claim 1, wherein the endogenous cytokine receptor comprises an amino acid sequence having at least 80% sequence identity to an amino acid sequence selected from SEQ ID Nos: 1-6.

5. The recombinant nucleic acid molecule according to claim 1, wherein the transmembrane domain is selected from the transmembrane domain of IL-9, IL-7ra, IL-2rb, and TNFR1.

6. The recombinant nucleic acid molecule according to claim 5, wherein the transmembrane domain comprises an amino acid sequence selected from SEQ ID Nos: 53-56.

7. The recombinant nucleic acid molecule according to claim 1, wherein the recombinant nucleic acid molecule is incorporated into a vector.

8. The recombinant nucleic acid molecule according to claim 1, wherein the chimeric receptor comprises the amino acid sequence selected from SEQ ID Nos: 63 and 72.

9. The recombinant nucleic acid molecule according to claim 1, further comprising a signal sequence.

10. The recombinant nucleic acid molecule according to claim 9, wherein the signal sequence comprises the amino acid sequence of MAAPALSWRLPLLILLLPLATSWASA (SEQ ID NO: 62).

11. The recombinant nucleic acid molecule according to claim 1 further comprising a 2A linker.

12. The recombinant nucleic acid molecule according to claim 1 further comprising a nucleic acid sequence encoding a chimeric antigen receptor.

13. An expression vector comprising the recombinant nucleic acid molecule of claim 1.

14. A recombinant cell comprising the recombinant nucleic acid construct according to claim 1.

15. The recombinant cell of claim 14, wherein the recombinant cell is a eukaryotic cell.

16. The recombinant cell of claim 15, wherein the eukaryotic cell is an animal cell.

17. The recombinant cell of claim 16, wherein the animal cell is a mammalian cell.

18. The recombinant cell of claim 17, wherein the mammalian cell is an immune cell, a neuron, an epithelial cell, and endothelial cell, or a stem cell.

19. The recombinant cell of claim 18, wherein the recombinant cell is an immune cell or a dendritic cell.

20. The recombinant cell of claim 19, wherein the immune cell is a B cell, a monocyte, a natural killer (NK) cell, a basophil, an eosinophil, a neutrophil, a dendritic cell, a macrophage, a regulatory T cell, a helper T cell ($T_H$), a cytotoxic T cell ($T_{CTL}$), or other T cell.

* * * * *

SEQUENCE LISTING

```
Sequence total quantity: 205
SEQ ID NO: 1                moltype = AA  length = 214
FEATURE                     Location/Qualifiers
REGION                      1..214
                            note = MISC_FEATURE - IL-2rb
source                      1..214
                            mol_type = protein
                            organism = synthetic construct
SEQUENCE: 1
AVNGTSQFTC FYNSRANISC VWSQDGALQD TSCQVHAWPD RRRWNQTCEL LPVSQASWAC   60
NLILGAPDSQ KLTTVDIVTL RVLCREGVRW RVMAIQDFKP FENLRLMAPI SLQVVHVETH  120
RCNISWEISQ ASHYFERHLE FEARTLSPGH TWEEAPLLTL KQKQEWICLE TLTPDTQYEF  180
QVRVKPLQGE FTTWSPWSQP LAFRTKPAAL GKDT                              214

SEQ ID NO: 2                moltype = AA  length = 219
FEATURE                     Location/Qualifiers
REGION                      1..219
                            note = MISC_FEATURE - IL-2ra
source                      1..219
                            mol_type = protein
                            organism = synthetic construct
SEQUENCE: 2
ELCDDDPPEI PHATFKAMAY KEGTMLNCEC KRGFRRIKSG SLYMLCTGNS SHSSWDNQCQ   60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SCLVTTTDFQ IQTEMAATME TSIFTTEYQ                         219

SEQ ID NO: 3                moltype = AA  length = 207
FEATURE                     Location/Qualifiers
REGION                      1..207
                            note = MISC_FEATURE - IL-4
source                      1..207
                            mol_type = protein
                            organism = synthetic construct
SEQUENCE: 3
MKVLQEPTCV SDYMSISTCE WKMNGPTNCS TELRLLYQLV FLLSEAHTCI PENNGGAGCV   60
CHLLMDDVVS ADNYTLDLWA GQQLLWKGSF KPSEHVKPRA PGNLTVHTNV SDTLLLTWSN  120
PYPPDNYLYN HLTYAVNIWS ENDPADFRIY NVTYLEPSLR IAASTLKSGI SYRARVRAWA  180
QCYNTTTWSEW SPSTKWHNSY REPFEQH                                    207

SEQ ID NO: 4                moltype = AA  length = 219
FEATURE                     Location/Qualifiers
REGION                      1..219
                            note = MISC_FEATURE - IL-7ra
source                      1..219
                            mol_type = protein
                            organism = synthetic construct
SEQUENCE: 4
ESGYAQNGDL EDAELDDYSF SCYSQLEVNG SQHSLTCAFE DPDVNITNLE FEICGALVEV   60
KCLNFRKLQE IYFIETKKFL LIGKSNICVK VGEKSLTCKK IDLTTIVKPE APFDLSVVYR  120
EGANDFVVTF NTSHLQKKYV KVLMHDVAYR QEKDENKWTH VNLSSTKLTL LQRKLQPAAM  180
YEIKVRSIPD HYFKGFWSEW SPSYYFRTPE INNSSGEMD                         219

SEQ ID NO: 5                moltype = AA  length = 175
FEATURE                     Location/Qualifiers
REGION                      1..175
                            note = MISC_FEATURE - IL-15ra
source                      1..175
                            mol_type = protein
                            organism = synthetic construct
SEQUENCE: 5
ITCPPPMSVE HADIWVKSYS LYSRERYICN SGFKRKAGTS SLTECVLNKA TNVAHWTTPS   60
LKCIRDPALV HQRPAPPSTV TTAGVTPQPE SLSPSGKEPA ASSPSSNNTA ATTAAIVPGS  120
QLMPSKSPST GTTEISSHES SHGTPSQTTA KNWELTASAS HQPPGVYPQG HSDTT       175

SEQ ID NO: 6                moltype = AA  length = 213
FEATURE                     Location/Qualifiers
REGION                      1..213
                            note = MISC_FEATURE - IL-21ra
source                      1..213
                            mol_type = protein
                            organism = synthetic construct
SEQUENCE: 6
CPDLVCYTDY LQTVICILEM WNLHPSTLTL TWQDQYEELK DEATSCSLHR SAHNATHATY   60
TCHMDVFHFM ADDIFSVNIT DQSGNYSQEC GSFLLAESIK PAPPFNVTVT FSGQYNISWR  120
SDYEDPAFYM LKGKLQYELQ YRNRGDPWAV SPRRKLISVD SRSVSLLPLE FRKDSSYELQ  180
VRAGPMPGSS YQGTWSEWSD PVIFQTQSEE LKE                               213
```

```
SEQ ID NO: 7              moltype = AA   length = 93
FEATURE                   Location/Qualifiers
REGION                    1..93
                          note = MISC_FEATURE - TGFBR1
source                    1..93
                          mol_type = protein
                          organism = synthetic construct
SEQUENCE: 7
LQCFCHLCTK DNFTCVTDGL CFVSVTETTD KVIHNSMCIA EIDLIPRDRP FVCAPSSKTG     60
SVTTTYCCNQ DHCNKIELPT TVKSSPGLGP VEL                                 93

SEQ ID NO: 8              moltype = AA   length = 144
FEATURE                   Location/Qualifiers
REGION                    1..144
                          note = MISC_FEATURE - TGFBR2
source                    1..144
                          mol_type = protein
                          organism = synthetic construct
SEQUENCE: 8
TIPPHVQKSV NNDMIVTDNN GAVKFPQLCK FCDVRFSTCD NQKSCMSNCS ITSICEKPQE     60
VCVAVWRKND ENITLETVCH DPKLPYHDFI LEDAASPKCI MKEKKKPGET FFMCSCSSDE    120
CNDNIIFSEE YNTSNPDLLL VIFQ                                          144

SEQ ID NO: 9              moltype = AA   length = 214
FEATURE                   Location/Qualifiers
REGION                    1..214
                          note = MISC_FEATURE - IL-10ra
source                    1..214
                          mol_type = protein
                          organism = synthetic construct
SEQUENCE: 9
HGTELPSPPS VWFEAEFFHH ILHWTPIPNQ SESTCYEVAL LRYGIESWNS ISNCSQTLSY     60
DLTAVTLDLY HSNGYRARVR AVDGSRHSNW TVTNTRFSVD EVTLTVGSVN LEIHNGFILG    120
KIQLPRPKMA PANDTYESIF SHFREYEIAI RKVPGNFTFT HKKVKHENFS LLTSGEVGEF    180
CVQVKPSVAS RSNKGMWSKE ECISLTRQYF TVTN                               214

SEQ ID NO: 10             moltype = AA   length = 148
FEATURE                   Location/Qualifiers
REGION                    1..148
                          note = MISC_FEATURE - FAS
source                    1..148
                          mol_type = protein
                          organism = synthetic construct
SEQUENCE: 10
QVTDINSKGL ELRKTVTTVE TQNLEGLHHD GQFCHKPCPP GERKARDCTV NGDEPDCVPC     60
QEGKEYTDKA HFSSKCRRCR LCDEGHGLEV EINCTRTQNT KCRCKPNFFC NSTVCEHCDP    120
CTKCEHGIIK ECTLTSNTKC KEEGSRSN                                      148

SEQ ID NO: 11             moltype = AA   length = 126
FEATURE                   Location/Qualifiers
REGION                    1..126
                          note = MISC_FEATURE - CTLA4
source                    1..126
                          mol_type = protein
                          organism = synthetic construct
SEQUENCE: 11
KAMHVAQPAV VLASSRGIAS FVCEYASPGK ATEVRVTVLR QADSQVTEVC AATYMMGNEL     60
TFLDDSICTG TSSGNQVNLT IQGLRAMDTG LYICKVELMY PPPYYLGIGN GTQIYVIDPE    120
PCPDSD                                                              126

SEQ ID NO: 12             moltype = AA   length = 428
FEATURE                   Location/Qualifiers
REGION                    1..428
                          note = MISC_FEATURE - LAG3
source                    1..428
                          mol_type = protein
                          organism = synthetic construct
SEQUENCE: 12
LQPGAEVPVV WAQEGAPAQL PCSPTIPLQD LSLLRRAGVT WQHQPDSGPP AAAPGHPLAP     60
GPHPAAPSSW GPRPRRYTVL SVGPGGLRSG RLPLQPRVQL DERGRQRGDF SLWLRPARRA    120
DAGEYRAAVH LRDRALSCRL RLRLGQASMT ASPPGSLRAS DWVILNCSFS RPDRPASVHW    180
FRNRGQGRVP VRESPHHHLA ESFLFLPQVS PMDSGPWGCI LTYRDGFNVS IMYNLTVLGL    240
EPPTPLTVYA GAGSRVGLPC RLPAGVGTRS FLTAKWTPPG GGPDLLVTGD NGDFTLRLED    300
VSQAQAGTYT CHIHLQEQQL NATVTLAIIT VTPKSFGSPG SLGKLLCEVT PVSGQERFVW    360
SSLDTPSQRS FSGPWLEAQE AQLLSQPWQC QLYQGERLLG AAVYFTELSS PGAQRSGRAP    420
GALPAGHL                                                            428

SEQ ID NO: 13             moltype = AA   length = 181
FEATURE                   Location/Qualifiers
```

```
REGION                         1..181
                               note = MISC_FEATURE - TIM3
source                         1..181
                               mol_type = protein
                               organism = synthetic construct
SEQUENCE: 13
SEVEYRAEVG QNAYLPCFYT PAAPGNLVPV CWGKGACPVF ECGNVVLRTD ERDVNYWTSR    60
YWLNGDFRKG DVSLTIENVT LADSGIYCCR IQIPGIMNDE KFNLKLVIKP AKVTPAPTRQ   120
RDFTAAFPRM LTTRGHGPAE TQTLGSLPDI NLTQISTLAN ELRDSRLAND LRDSGATIRI   180
G                                                                  181

SEQ ID NO: 14                  moltype = AA  length = 220
FEATURE                        Location/Qualifiers
REGION                         1..220
                               note = MISC_FEATURE - PD1
source                         1..220
                               mol_type = protein
                               organism = synthetic construct
SEQUENCE: 14
FTVTVPKDLY VVEYGSNMTI ECKFPVEKQL DLAALIVYWE MEDKNIIQFV HGEEDLKVQH    60
SSYRQRARLL KDQLSLGNAA LQITDVKLQD AGVYRCMISY GGADYKRITV KVNAPYNKIN   120
QRILVVDPVT SEHELTCQAE GYPKAEVIWT SSDHQVLSGK TTTTNSKREE KLFNVTSTLR   180
INTTTNEIFY CTFRRLDPEE NHTAELVIPE LPLAHPPNER                         220

SEQ ID NO: 15                  moltype = AA  length = 438
FEATURE                        Location/Qualifiers
REGION                         1..438
                               note = MISC_FEATURE - ILT2
source                         1..438
                               mol_type = protein
                               organism = synthetic construct
SEQUENCE: 15
GHLPKPTLWA EPGSVITQGS PVTLRCQGGQ ETQEYRLYRE KKTALWITRI PQELVKKGQF    60
PIPSITWEHA GRYRCYYGSD TAGRSESSDP LELVVTGAYI KPTLSAQPSP VVNSGGNVIL   120
QCDSQVAFDG FSLCKEGEDE HPQCLNSQPH ARGSSRAIFS VGPVSPSRRW WYRCYAYDSN   180
SPYEWSLPSD LLELLVLGVS KKPSLSVQPG PIVAPEETLT LQCGSDAGYN RFVLYKDGER   240
DFLQLAGAQP QAGLSQANFT LGPVSRSYGG QYRCYGAHNL SSEWSAPSDP LDILIAGQFY   300
DRVSLSVQPG PTVASGENVT LLCQSQGWMQ TFLLTKEGAA DDPWRLRSTY QSQKYQAEFP   360
MGPVTSAHAG TYRCYGSQSS KPYLLTHPSD PLELVVSGPG GGPSSPTTGP TSTSGPEDQP   420
LTPTGSDPQS GLGRHLGV                                                438

SEQ ID NO: 16                  moltype = AA  length = 238
FEATURE                        Location/Qualifiers
REGION                         1..238
                               note = MISC_FEATURE - ILT3
source                         1..238
                               mol_type = protein
                               organism = synthetic construct
SEQUENCE: 16
QAGPLPKPTL WAEPGSVISW GNSVTIWCQG TLEAREYRLD KEESPAPWDR QNPLEPKNKA    60
RFSIPSMTED YAGRYRCYYR SPVGWSQPSD PLELVMTGAY SKPTLSALPS PLVTSGKSVT   120
LLCQSRSPMD TFLLIKERAA HPLLHLRSEH GAQQHQAEFP MSPVTSVHGG TYRCFSSHGF   180
SHYLLSHPSD PLELIVSGSL EDPRPSPTRS VSTAAGPEDQ PLMPTGSVPH SGLRRHWE     238

SEQ ID NO: 17                  moltype = AA  length = 440
FEATURE                        Location/Qualifiers
REGION                         1..440
                               note = MISC_FEATURE - ILT4
source                         1..440
                               mol_type = protein
                               organism = synthetic construct
SEQUENCE: 17
QTGTIPKPTL WAEPDSVITQ GSPVTLSCQG SLEAQEYRLY REKKSASWIT RIRPELVKNG    60
QFHIPSITWE HTGRYGCQYY SRARWSELSD PLVLVMTGAY PKPTLSAQPS PVVTSGGRVT   120
LQCESQVAFG GFILCKEGEE EHPQCLNSQP HARGSSRAIF SVGPVSPNRR WSHRCYGYDL   180
NSPYVWSSPS DLLELLVPGV SKKPSLSVQP GPVVAPGESL TLQCVSDVGY DRFVLYKEGE   240
RDLRQLPGRQ PQAGLSQANF TLGPVSRSYG GQYRCYGAHN LSSECSAPSD PLDILITGQI   300
RGTPFISVQP GPTVASGENV TLLCQSWRQF HTFLLTKAGA ADAPLRLRSI HEYPKYQAEF   360
PMSPVTSAHA GTYRCYGSLN SDPYLLSHPS EPLELVVSGP SMGSSPPPTG PISTPAGPED   420
QPLTPTGSDP QSGLGRHLGV                                              440

SEQ ID NO: 18                  moltype = AA  length = 420
FEATURE                        Location/Qualifiers
REGION                         1..420
                               note = MISC_FEATURE - ILT5
source                         1..420
                               mol_type = protein
                               organism = synthetic construct
SEQUENCE: 18
```

```
GPFPKPTLWA EPGSVISWGS PVTIWCQGSQ EAQEYRLHKE GSPEPLDRNN PLEPKNKARF    60
SIPSMTEHHA GRYRCHYYSS AGWSEPSDPL EMVMTGAYSK PTLSALPSPV VASGGNMTLR   120
CGSQKGYHHF VLMKEGEHQL PRTLDSQQLH SRGFQALFPV GPVTPSHRWR FTCYYYYTNT   180
PWVWSHPSDP LEILPSGVSR KPSLLTLQGP VLAPGQSLTL QCGSDVGYNR FVLYKEGERD   240
FLQRPGQQPQ AGLSQANFTL GPVSPSNGGQ YRCYGAHNLS SEWSAPSDPL NILMAGQIYD   300
TVSLSAQPGP TVASGENVTL LCQSWWQFDT FLLTKEGAAH PPLRLRSMYG AHKYQAEFPM   360
SPVTSAHAGT YRCYGSYSSN PHLLSHPSEP LELVVSGHSG GSSLPPTGPP STPGLGRYLE   420

SEQ ID NO: 19           moltype = AA   length = 732
FEATURE                 Location/Qualifiers
REGION                  1..732
                        note = MISC_FEATURE - VEGFR1
source                  1..732
                        mol_type = protein
                        organism = synthetic construct
SEQUENCE: 19
SKLKDPELSL KGTQHIMQAG QTLHLQCRGE AAHKWSLPEM VSKESERLSI TKSACGRNGK    60
QFCSTLTLNT AQANHTGFYS CKYLAVPTSK KKETESAIYI FISDTGRPFV EMYSEIPEII   120
HMTEGRELVI PCRVTSPNIT VTLKKFPLDT LIPDGKRIIW DSRKGFIISN ATYKEIGLLT   180
CEATVNGHLY KTNYLTHRQT NTIIDVQIST PRPVKLLRGH TLVLNCTATT PLNTRVQMTW   240
SYPDEKNKRA SVRRRIDQSN SHANIFYSVL TIDKMQNKDK GLYTCRVRSG PSFKSVNTSV   300
HIYDKAFITV KHRKQQVLET VAGKRSYRLS MKVKAFPSPE VVWLKDGLPA TEKSARYLTR   360
GYSLIIKDVT EEDAGNYTIL LSIKQSNVFK NLTATLIVNV KPQIYEKAVS SFPDPALYPL   420
GSRQILTCTA YGIPQPTIKW FWHPCNHNHS EARCDFCSNN EESFILDADS NMGNRIESIT   480
QRMAIIEGKN KMASTLVVAD SRISGIYICI ASNKVGTVGR NISFYITDVP NGFHVNLEKM   540
PTEGEDLKLS CTVNKFLYRD VTWILLRTVN NRTMHYSISK QKMAITKEHS ITLNLTIMNV   600
SLQDSGTYAC RARNVYTGEE ILQKKEITIR DQEAPYLLRN LSDHTVAISS STTLDCHANG   660
VPEPQITWFK NNHKIQQEPG IILGPGSSTL FIERVTEEDE GVYHCKATNQ KGSVESSAYL   720
TVQGTSDKSN LE                                                       732

SEQ ID NO: 20           moltype = AA   length = 745
FEATURE                 Location/Qualifiers
REGION                  1..745
                        note = MISC_FEATURE - VEGFR2
source                  1..745
                        mol_type = protein
                        organism = synthetic construct
SEQUENCE: 20
ASVGLPSVSL DLPRLSIQKD ILTIKANTTL QITCRGQRDL DWLWPNNQSG SEQRVEVTEC    60
SDGLFCKTLT IPKVIGNDTG AYKCFYRETD LASVIYVYVQ DYRSPFIASV SDQHGVVYIT   120
ENKNKTVVIP CLGSISNLNV SLCARYPEKR FVPDGNRISW DSKKGFTIPS YMISYAGMVF   180
CEAKINDESY QSIMYIVVVV GYRIYDVVLS PSHGIELSVG EKLVLNCTAR TELNVGIDFN   240
WEYPSSKHQH KKLVNRDLKT QSGSEMKKFL STLTIDGVTR SSGLYTCAA SSGLMTKKNS   300
TFVRVHEKPF VAFGSGMESL VEATVGERVR IPAKYLGYPP PEIKWYKNGI PLESNHTIKA   360
GHVLTIMEVS ERDTGNYTVI LTNPISKEKQ SHVVSLVVYV PPQIGEKSLI SPVDSYQYGT   420
TQTLTCTVYA IPPPHHIHWY WQLEEECANE PSQAVSVTNP YPCEEWRSVE DFQGGNKIEV   480
NKNQFALIEG KNKTVSTLVI QAANVSALYK CEAVNKVGRG ERVISFHVTR GPEITLQPDM   540
QPTEQESVSL WCTADRSTFE NLTWYKLGPQ PLPIHVGELP TPVCKNLDTL WKLNATMFSN   600
STNDILIMEL KNASLQDQGD YVCLAQDRKT KKRHCVVRQL TVLERVAPTI TGNLENQTTS   660
IGESIEVSCT ASGNPPPQIM WFKDNETLVE DSGIVLKDGN RNLTIRRVRK EDEGLYTCQA   720
CSVLGCAKVE AFFIIEGAQE KTNLE                                         745

SEQ ID NO: 21           moltype = AA   length = 751
FEATURE                 Location/Qualifiers
REGION                  1..751
                        note = MISC_FEATURE - VEGFR3
source                  1..751
                        mol_type = protein
                        organism = synthetic construct
SEQUENCE: 21
YSMTPPTLNI TEESHVIDTG DSLSISCRGQ HPLEWAWPGA QEAPATGDKD SEDTGVVRDC    60
EGTDARPYCK VLLLHEVHAN DTGSYVCYYK YIKARIEGTT AASSYVFVRD FEQPFINKPD   120
TLLVNRKDAM WVPCLVSIPG LNVTLRSQSS VLWPDGQEVY WDDRRGMLVS TPLLHDALYL   180
QCETTWGDQD FLSNPFLVHI TGNELYDIQL LPRKSLELLV GEKLVLNCTV WAEFNSGVTF   240
DWDYPGKQAE RGKWVPERRS QQTHTELSSI LTIHNVSQHD LGSYVCKANN GIQRFRESTE   300
VIVHENPFIS VEWLKGPILE ATAGDELVKL PVKLAAYPPP EFQWYKDGKA LSGRHSPHAL   360
VLKEVTEAST GTYTLALWNS AAGLRRNISL ELVVNVPPQI HEKEASSPSI YSRHSRQALT   420
CTAYGVPLPL SIQWHWRPWT PCKMFAQRSL RRRQQQDLML QCRDWRAVTT QDAVNPIESL   480
DTWTEFVEGK NKTVSKLVIQ NANVSAMYKC VVSNKVGQDE RLIYFYVTTI PDGFTIESKP   540
SEELLEGQPV LLSCQADSYK YEHLRWYRLN LSTLHDAHGN PLLLDCKNVH LFATPLAASL   600
EEVAPGRAHA TLSLSIPRVA PEHEGHYVCE VQDRRSHDKH CHKKYLSVQA LEAPRLTQNL   660
TDLLVNVSDS LEMQCLVAGA HAPSIVWYKD ERLLEEKSGV DLADSNQKLS IQRVREEDAG   720
RYLCSVCNAK GCVNSSASVA VEGSEDKGSM E                                  751

SEQ ID NO: 22           moltype = AA   length = 380
FEATURE                 Location/Qualifiers
REGION                  1..380
                        note = MISC_FEATURE - OPG
source                  1..380
```

```
                        mol_type = protein
                        organism = synthetic construct
SEQUENCE: 22
ETFPPKYLHY DEETSHQLLC DKCPPGTYLK QHCTAKWKTV CAPCPDHYYT DSWHTSDECL    60
YCSPVCKELQ YVKQECNRTH NRVCECKEGR YLEIEFCLKH RSCPPGFGVV QAGTPERNTV   120
CKRCPDGFFS NETSSKAPCR KHTNCSVFGL LLTQKGNATH DNICSGNSES TQKCGIDVTL   180
CEEAFRRFAV PTKFTPNWLS VLVDNLPGTK VNAESVERIK RQHSSQEQTF QLLKLWKHQN   240
KDQDIVKKII QDIDLCENSV QRHIGHANLT FEQLRSLMES LPGKKVGAED IEKTIKACKP   300
SDQILKLLSL WRIKNGDQDT LKGLMHALKH SKTYHFPKTV TQSLKKTIRF LHSFTMYKLY   360
QKLFLEMIGN QVQSVKISCL                                              380

SEQ ID NO: 23           moltype = AA   length = 165
FEATURE                 Location/Qualifiers
REGION                  1..165
                        note = MISC_FEATURE - TACI
source                  1..165
                        mol_type = protein
                        organism = synthetic construct
SEQUENCE: 23
MSGLGRSRRG GRSRVDQEER FPQGLWTGVA MRSCPEEQYW DPLLGTCMSC KTICNHQSQR    60
TCAAFCRSLS CRKEQGKFYD HLLRDCISCA SICGQHPKQC AYFCENKLRS PVNLPPELRR   120
QRSGEVENNS DNSGRYQGLE HRGSEASPAL PGLKLSADQV ALVYS                   165

SEQ ID NO: 24           moltype = AA   length = 54
FEATURE                 Location/Qualifiers
REGION                  1..54
                        note = MISC_FEATURE - BCM4
source                  1..54
                        mol_type = protein
                        organism = synthetic construct
SEQUENCE: 24
MLQMAGQCSQ NEYFDSLLHA CIPCQLRCSS NTPPLTCQRY CNASVTNSVK GTNA          54

SEQ ID NO: 25           moltype = AA   length = 222
FEATURE                 Location/Qualifiers
REGION                  1..222
                        note = MISC_FEATURE - NGFR
source                  1..222
                        mol_type = protein
                        organism = synthetic construct
SEQUENCE: 25
KEACPTGLYT HSGECCKACN LGEGVAQPCG ANQTVCEPCL DSVTFSDVVS ATEPCKPCTE    60
CVGLQSMSAP CVEADDAVCR CAYGYYQDET TGRCEACRVC EAGSGLVFSC QDKQNTVCEE   120
CPDGTYSDEA NHVDPCLPCT VCEDTERQLR ECTRWADAEC EEIPGRWITR STPPEGSDST   180
APSTQEPEAP PEQDLIASTV AGVVTTVMGS SQPVVTRGTT DN                      222

SEQ ID NO: 26           moltype = AA   length = 161
FEATURE                 Location/Qualifiers
REGION                  1..161
                        note = MISC_FEATURE - EDAR
source                  1..161
                        mol_type = protein
                        organism = synthetic construct
SEQUENCE: 26
EYSNCGENEY YNQTTGLCQE CPPCGPGEEP YLSCGYGTKD EDYGCVPCPA EKFSKGGYQI    60
CRRHKDCEGF FRATVLTPGD MENDAECGPC LPGYYMLENR PRNIYGMVCY SCLLAPPNTK   120
ECVGATSGAS ANFPGTSGSS TLSPFQHAHK ELSGQGHLAT A                       161

SEQ ID NO: 27           moltype = AA   length = 156
FEATURE                 Location/Qualifiers
REGION                  1..156
                        note = MISC_FEATURE - DCR2 (TNFRSF10D)
source                  1..156
                        mol_type = protein
                        organism = synthetic construct
SEQUENCE: 27
ATIPRQDEVP QQTVAPQQQR RSLKEEECPA GSHRSEYTGA CNPCTEGVDY TIASNNLPSC    60
LLCTVCKSGQ TNKSSCTTTR DTVCQCEKGS FQDKNSPEMC RTCRTGCPRG MVKVSNCTPR   120
SDIKCKNESA ASSTGKTPAA EETVTTILGM LASPYH                             156

SEQ ID NO: 28           moltype = AA   length = 211
FEATURE                 Location/Qualifiers
REGION                  1..211
                        note = MISC_FEATURE - DCR1 (TNFRSF10C)
source                  1..211
                        mol_type = protein
                        organism = synthetic construct
SEQUENCE: 28
ATTARQEEVP QQTVAPQQQR HSFKGEECPA GSHRSEHTGA CNPCTEGVDY TNASNNEPSC    60
```

```
FPCTVCKSDQ KHKSSCTMTR DTVCQCKEGT FRNENSPEMC RKCSRCPSGE VQVSNCTSWD    120
DIQCVEEFGA NATVETPAAE ETMNTSPGTP APAAEETMNT SPGTPAPAAE ETMTTSPGTP    180
APAAEETMTT SPGTPAPAAE ETMITSPGTP A                                   211

SEQ ID NO: 29           moltype = AA   length = 173
FEATURE                 Location/Qualifiers
REGION                  1..173
                        note = MISC_FEATURE - CD40
source                  1..173
                        mol_type = protein
                        organism = synthetic construct
SEQUENCE: 29
EPPTACREKQ YLINSQCCSL CQPGQKLVSD CTEFTETECL PCGESEFLDT WNRETHCHQH     60
KYCDPNLGLR VQQKGTSETD TICTCEEGWH CTSEACESCV LHRSCSPGFG VKQIATGVSD    120
TICEPCPVGF FSNVSSAFEK CHPWTSCETK DLVVQQAGTN KTDVVCGPQD RLR           173

SEQ ID NO: 30           moltype = AA   length = 216
FEATURE                 Location/Qualifiers
REGION                  1..216
                        note = MISC_FEATURE - DR4
source                  1..216
                        mol_type = protein
                        organism = synthetic construct
SEQUENCE: 30
ASGTEAAAAT PSKVWGSSAG RIEPRGGGRG ALPTSMGQHG PSARARAGRA PGPRPAREAS     60
PRLRVHKTFK FVVVGVLLQV VPSSAATIKL HDQSIGTQOW EHSPLGELCP PGSHRSEHPG    120
ACNRCTEGVG YTNASNNLFA CLPCTACKSD EEERSPCTTT RNTACQCKPG TFRNDNSAEM    180
CRKCSRGCPR GMVKVKDCTP WSDIECVHKE SGNGHN                              216

SEQ ID NO: 31           moltype = AA   length = 308
FEATURE                 Location/Qualifiers
REGION                  1..308
                        note = MISC_FEATURE - DR6
source                  1..308
                        mol_type = protein
                        organism = synthetic construct
SEQUENCE: 31
QPEQKASNLI GTYRHVDRAT GQVLTCDKCP AGTYVSEHCT NTSLRVCSSC PVGTFTRHEN     60
GIEKCHDCSQ PCPWPMIEKL PCAALTDREC TCPPGMFQSN ATCAPHTVCP VGWGVRKKGT    120
ETEDVRCKQC ARGTFSDVPS SVMKCKAYTD CLSQNLVVIK PGTKETDNVC GTLPSFSSST    180
SPSPGTAIFP RPEHMETHEV PSSTYVPKGM NSTESNSSAS VRPKVLSSIQ EGTVPDNTSS    240
ARGKEDVNKT LPNLQVVNHQ QGPHHRHILK LLPSMEATGG EKSSTPIKGP KRGHPRQNLH    300
KHFDINEH                                                             308

SEQ ID NO: 32           moltype = AA   length = 155
FEATURE                 Location/Qualifiers
REGION                  1..155
                        note = MISC_FEATURE - DR5
source                  1..155
                        mol_type = protein
                        organism = synthetic construct
SEQUENCE: 32
ITQQDLAPQQ RAAPQQKRSS PSEGLCPPGH HISEDGRDCI SCKYGQDYST HWNDLLFCLR     60
CTRCDSGEVE LSPCTTTRNT VCQCEEGTFR EEDSPEMCRK CRTGCPRGMV KVGDCTPWSD    120
IECVHKESGT KHSGEVPAVE ETVTSSPGTP ASPCS                               155

SEQ ID NO: 33           moltype = AA   length = 175
FEATURE                 Location/Qualifiers
REGION                  1..175
                        note = MISC_FEATURE - DR3
source                  1..175
                        mol_type = protein
                        organism = synthetic construct
SEQUENCE: 33
QGGTRSPRCD CAGDFHKKIG LFCCRGCPAG HYLKAPCTEP CGNSTCLVCP QDTFLAWENH     60
HNSECARCQA CDEQASQVAL ENCSAVADTR CGCKPGWFVE CQVSQCVSSS PFYCQPCLDC    120
GALHRHTRLL CSRRDTDCGT CLPGFYEHGD GCVSCPTSTL GSCPERCAAV CGWRQ         175

SEQ ID NO: 34           moltype = AA   length = 235
FEATURE                 Location/Qualifiers
REGION                  1..235
                        note = MISC_FEATURE - TNFRSF1B
source                  1..235
                        mol_type = protein
                        organism = synthetic construct
SEQUENCE: 34
LPAQVAFTPY APEPGSTCRL REYYDQTAQM CCSKCSPGQH AKVFCTKTSD TVCDSCEDST     60
YTQLWNWVPE CLSCGSRCSS DQVETQACTR EQNRICTCRP GWYCALSKQE GCRLCAPLRK    120
CRPGFGVARP GTETSDVVCK PCAPGTFSNT TSSTDICRPH QICNVVAIPG NASMDAVCTS    180
```

```
TSPTRSMAPG AVHLPQPVST RSQHTQPTPE PSTAPSTSFL LPMGPSPPAE GSTGD        235

SEQ ID NO: 35          moltype = AA   length = 182
FEATURE                Location/Qualifiers
REGION                 1..182
                       note = MISC_FEATURE - TNFRSF1
source                 1..182
                       mol_type = protein
                       organism = synthetic construct
SEQUENCE: 35
LVPHLGDREK RDSVCPQGKY IHPQNNSICC TKCHKGTYLY NDCPGPGQDT DCRECESGSF    60
TASENHLRHC LSCSKCRKEM GQVEISSCTV DRDTVCGCRK NQYRHYWSEN LFQCFNCSLC   120
LNGTVHLSCQ EKQNTVCTCH AGFFLRENEC VSCSNCKKSL ECTKLCLPQI ENVKGTEDSG   180
TT                                                                 182

SEQ ID NO: 36          moltype = AA   length = 113
FEATURE                Location/Qualifiers
REGION                 1..113
                       note = MISC_FEATURE - BMPR1B
source                 1..113
                       mol_type = protein
                       organism = synthetic construct
SEQUENCE: 36
KKEDGESTAP TPRPKVLRCK CHHHCPEDSV NNICSTDGYC FTMIEEDDSG LPVVTSGCLG    60
LEGSDFQCRD TPIPHQRRSI ECCTERNECN KDLHPTLPPL KNRDFVDGPI HHR          113

SEQ ID NO: 37          moltype = AA   length = 129
FEATURE                Location/Qualifiers
REGION                 1..129
                       note = MISC_FEATURE - BMPR1A
source                 1..129
                       mol_type = protein
                       organism = synthetic construct
SEQUENCE: 37
QNLDSMLHGT GMKSDSDQKK SENGVTLAPE DTLPFLKCYC SGHCPDDAIN NTCITNGHCF    60
AIIEEDDQGE TTLASGCMKY EGSDFQCKDS PKAQLRRTIE CCRTNLCNQY LQPTLPPVVI   120
GPFFDGSIR                                                          129

SEQ ID NO: 38          moltype = AA   length = 124
FEATURE                Location/Qualifiers
REGION                 1..124
                       note = MISC_FEATURE - BMPR2
source                 1..124
                       mol_type = protein
                       organism = synthetic construct
SEQUENCE: 38
SQNQERLCAF KDPYQQDLGI GESRISHENG TILCSKGSTC YGLWEKSKGD INLVKQGCWS    60
HIGDPQECHY EECVVTTTPP SIQNGTYRFC CCSTDLCNVN FTENFPPPDT TPLSPPHSFN   120
RDET                                                               124

SEQ ID NO: 39          moltype = AA   length = 603
FEATURE                Location/Qualifiers
REGION                 1..603
                       note = MISC_FEATURE - CSF3R
source                 1..603
                       mol_type = protein
                       organism = synthetic construct
SEQUENCE: 39
ECGHISVSAP IVHLGDPITA SCIIKQNCSH LDPEPQILWR LGAELQPGGR QQRLSDGTQE    60
SIITLPHLNH TQAFLSCCLN WGNSLQILDQ VELRAGYPPA IPHNLSCLMN LTTSSLICQW   120
EPGPETHLPT SFTLKSFKSR GNCQTQGDSI LDCVPKDGQS HCCIPRKHLL LYQNMGIWVQ   180
AENALGTSMS PQLCLDPMDV VKLEPPMLRT MDPSPEAAPP QAGCLQLCWE PWQPGLHINQ   240
KCELRHKPQR GEASWALVGP LPLEALQYEL CGLLPATAYT LQIRCIRWPL PGHWSDWSPS   300
LELRTTERAP TVRLDTWWRQ RQLDPRTVQL FWKPVPLEED SGRIQGYVVS WRPSGQAGAI   360
LPLCNTTELS CTFHLPSEAQ EVALVAYNSA GTSRPTPVVF SESRGPALTR LHAMARDPHS   420
LWVGWEPPNP WPQGYVIEWG LGPPSASNSN KTWRMEQNGR ATGFLLKENI RPFQLYEIIV   480
TPLYQDTMGP SQHVYAYSQE MAPSHAPELH LKHIGKTWAQ LEWVPEPPEL GKSPLTHYTI   540
FWTNAQNQSF SAILNASSRG FVLHGLEPAS LYHIHLMAAS QAGATNSTVL TLMTLTPEGS   600
ELH                                                                603

SEQ ID NO: 40          moltype = AA   length = 498
FEATURE                Location/Qualifiers
REGION                 1..498
                       note = MISC_FEATURE - CSF1R
source                 1..498
                       mol_type = protein
                       organism = synthetic construct
SEQUENCE: 40
IPVIEPSVPE LVVKPGATVT LRCVGNGSVE WDGPPSPHWT LYSDGSSSIL STNNATFQNT    60
```

```
GTYRCTEPGD PLGGSAAIHL YVKDPARPWN VLAQEVVVFE DQDALLPCLL TDPVLEAGVS    120
LVRVRGRPLM RHTNYSFSPW HGFTIHRAKF IQSQDYQCSA LMGGRKVMSI SIRLKVQKVI    180
PGPPALTLVP AELVRIRGEA AQIVCSASSV DVNFDVFLQH NNTKLAIPQQ SDFHNNRYQK    240
VLTLNLDQVD FQHAGNYSCV ASNVQGKHST SMFFRVVESA YLNLSSEQNL IQEVTVGEGL    300
NLKVMVEAYP GLQGFNWTYL GPFSDHQPEP KLANATTKDT YRHTFTLSLP RLKPSEAGRY    360
SFLARNPGGW RALTFELTLR YPPEVSVIWT FINGSGTLLC AASGYPQPNV TWLQCSGHTD    420
RCDEAQVLQV WDDPYPEVLS QEPFHKVTVQ SLLTVETLEH NQTYECRAHN SVGSGSWAFI    480
PISAGAHTHP PDEFLFTP                                                  498

SEQ ID NO: 41           moltype = AA  length = 103
FEATURE                 Location/Qualifiers
REGION                  1..103
                        note = MISC_FEATURE - Activin R1A
source                  1..103
                        mol_type = protein
                        organism = synthetic construct
SEQUENCE: 41
MEDEKPKVNP KLYMCVCEGL SCGNEDHCEG QQCFSSLSIN DGFHVYQKGC FQVYEQGKMT     60
CKTPPSPGQA VECCQGDWCN RNITAQLPTK GKSFPGTQNF HLE                      103

SEQ ID NO: 42           moltype = AA  length = 103
FEATURE                 Location/Qualifiers
REGION                  1..103
                        note = MISC_FEATURE - Activin R1B
source                  1..103
                        mol_type = protein
                        organism = synthetic construct
SEQUENCE: 42
SGPRGVQALL CACTSCLQAN YTCETDGACM VSIFNLDGME HHVRTCIPKV ELVPAGKPFY     60
CLSSEDLRNT HCCYTDYCNR IDLRVPSGHL KEPEHPSMWG PVE                      103

SEQ ID NO: 43           moltype = AA  length = 92
FEATURE                 Location/Qualifiers
REGION                  1..92
                        note = MISC_FEATURE - Activin R1C
source                  1..92
                        mol_type = protein
                        organism = synthetic construct
SEQUENCE: 43
LSPGLKCVCL LCDSSNFTCQ TEGACWASVM LTNGKEQVIK SCVSLPELNA QVFCHSSNNV     60
TKTECCFTDF CNNITLHLPT ASPNAPKLGP ME                                  92

SEQ ID NO: 44           moltype = AA  length = 119
FEATURE                 Location/Qualifiers
REGION                  1..119
                        note = MISC_FEATURE - Activin R2B
source                  1..119
                        mol_type = protein
                        organism = synthetic construct
SEQUENCE: 44
SGRGEAETRE CIYYNANWEL ERTNQSGLER CEGEQDKRLH CYASWRNSSG TIELVKKGCW     60
LDDFNCYDRQ ECVATEENPQ VYFCCCEGNF CNERFTHLPE AGGPEVTYEP PPTAPTLLT     119

SEQ ID NO: 45           moltype = AA  length = 116
FEATURE                 Location/Qualifiers
REGION                  1..116
                        note = MISC_FEATURE - Activin R2A
source                  1..116
                        mol_type = protein
                        organism = synthetic construct
SEQUENCE: 45
AILGRSETQE CLFFNANWEK DRTNQTGVEP CYGDKDKRRH CFATWKNISG SIEIVKQGCW     60
LDDINCYDRT DCVEKKDSPE VYFCCCEGNM CNEKFSYFPE MEVTQPTSNP VTPKPP        116

SEQ ID NO: 46           moltype = AA  length = 120
FEATURE                 Location/Qualifiers
REGION                  1..120
                        note = MISC_FEATURE - TIGIT
source                  1..120
                        mol_type = protein
                        organism = synthetic construct
SEQUENCE: 46
MMTGTIETTG NISAEKGGSI ILQCHLSSTT AQVTQVNWEQ QDQLLAICNA DLGWHISPSF     60
KDRVAPGPGL GLTLQSLTVN DTGEYFCIYH TYPDGTYTGR IFLEVLESSV AEHGARFQIP    120

SEQ ID NO: 47           moltype = AA  length = 175
FEATURE                 Location/Qualifiers
REGION                  1..175
                        note = MISC_FEATURE - FCGR2B
```

```
source                  1..175
                        mol_type = protein
                        organism = synthetic construct
SEQUENCE: 47
TPAAPPKAVL KLEPQWINVL QEDSVTLTCR GTHSPESDSI QWFHNGNLIP THTQPSYRFK    60
ANNNDSGEYT CQTGQTSLSD PVHLTVLSEW LVLQTPHLEF QEGETIVLRC HSWKDKPLVK   120
VTFFQNGKSK KFSRSDPNFS IPQANHSHSG DYHCTGNIGY TLYSSKPVTI TVQAP        175

SEQ ID NO: 48           moltype = AA  length = 277
FEATURE                 Location/Qualifiers
REGION                  1..277
                        note = MISC_FEATURE - FCGR1
source                  1..277
                        mol_type = protein
                        organism = synthetic construct
SEQUENCE: 48
QVDTTKAVIT LQPPWVSVFQ EETVTLHCEV LHLPGSSSTQ WFLNGTATQT STPSYRITSA    60
SVNDSGEYRC QRGLSGRSDP IQLEIHRGWL LLQVSSRVFT EGEPLALRCH AWKDKLVYNV   120
LYYRNGKAFK FFHWNSNLTI LKTNISHNGT YHCSGMGKHR YTSAGISVTV KELFPAPVLN   180
ASVTSPLLEG NLVTLSCETK LLLQRPGLQL YFSFYMGSKT LRGRNTSSEY QILTARREDS   240
GLYWCEAATE DGNVLKRSPE LELQVLGLQL PTPVWFH                            277

SEQ ID NO: 49           moltype = AA  length = 208
FEATURE                 Location/Qualifiers
REGION                  1..208
                        note = MISC_FEATURE - 2B4
source                  1..208
                        mol_type = protein
                        organism = synthetic construct
SEQUENCE: 49
CQGSADHVVS ISGVPLQLQP NSIQTKVDSI AWKKLLPSQN GFHHILKWEN GSLPSNTSND    60
RFSFIVKNLS LLIKAAQQQD SGLYCLEVTS ISGKVQTATF QVFVFESLLP DKVEKPRLQG   120
QGKILDRGRC QVALSCLVSR DGNVSYAWYR GSKLIQTAGN LTYLDEEVDI NGTHTYTCNV   180
SNPVSWESHT LNLTQDCQNA HQEFRFWP                                      208

SEQ ID NO: 50           moltype = AA  length = 144
FEATURE                 Location/Qualifiers
REGION                  1..144
                        note = MISC_FEATURE - LAIR1
source                  1..144
                        mol_type = protein
                        organism = synthetic construct
SEQUENCE: 50
QEEDLPRPSI SAEPGTVIPL GSHVTFVCRG PVGVQTFRLE RESRSTYNDT EDVSQASPSE    60
SEARFRIDSV SEGNAGPYRC IYYKPPKWSE QSDYLELLVK ETSGGPDSPD TEPGSSAGPT   120
QRPSDNSHNE HAPASQGLKA EHLY                                          144

SEQ ID NO: 51           moltype = AA  length = 348
FEATURE                 Location/Qualifiers
REGION                  1..348
                        note = MISC_FEATURE - CD5
source                  1..348
                        mol_type = protein
                        organism = synthetic construct
SEQUENCE: 51
RLSWYDPDFQ ARLTRSNSKC QGQLEVYLKD GWHMVCSQSW GRSSKQWEDP SQASKVCQRL    60
NCGVPLSLGP FLVTYTPQSS IICYGQLGSF SNCSHSRNDM CHSLGLTCLE PQKTTPPTTR   120
PPPPTTTPEPT APPRLQLVAQ SGGQHCAGVV EFYSGSLGGT ISYEAQDKTQ DLENFLCNNL   180
QCGSFLKHLP ETEAGRAQDP GEPREHQPLP IQWKIQNSSC TSLEHCFRKI KPQKSGRVLA   240
LLCSGFQPKV QSRLVGGSSI CEGTVEVRQG AQWAALCDSS SARSSLRWEE VCREQQCGSV   300
NSYRVLDAGD PTSRGLFCPH QKLSQCHELW ERNSYCKKVF VTCQDPNP                348

SEQ ID NO: 52           moltype = AA  length = 53
FEATURE                 Location/Qualifiers
REGION                  1..53
                        note = MISC_FEATURE - TWEAKR
source                  1..53
                        mol_type = protein
                        organism = synthetic construct
SEQUENCE: 52
EQAPGTAPCS RGSSWSADLD KCMDCASCRA RPHSDFCLGC AAPPAPFRL LWP            53

SEQ ID NO: 53           moltype = AA  length = 34
FEATURE                 Location/Qualifiers
REGION                  1..34
                        note = MISC_FEATURE - IL-9
source                  1..34
                        mol_type = protein
                        organism = synthetic construct
```

```
SEQUENCE: 53
LIPPWGWPGN TLVAVSIFLL LTGPTYLLFK LSPR                                       34

SEQ ID NO: 54           moltype = AA  length = 25
FEATURE                 Location/Qualifiers
REGION                  1..25
                        note = MISC_FEATURE - IL-7ra
source                  1..25
                        mol_type = protein
                        organism = synthetic construct
SEQUENCE: 54
PILLTISILS FFSVALLVIL ACVLW                                                 25

SEQ ID NO: 55           moltype = AA  length = 25
FEATURE                 Location/Qualifiers
REGION                  1..25
                        note = MISC_FEATURE - IL-2rb
source                  1..25
                        mol_type = protein
                        organism = synthetic construct
SEQUENCE: 55
IPWLGHLLVG LSGAFGFIIL VYLLI                                                 25

SEQ ID NO: 56           moltype = AA  length = 23
FEATURE                 Location/Qualifiers
REGION                  1..23
                        note = MISC_FEATURE - TNFR1
source                  1..23
                        mol_type = protein
                        organism = synthetic construct
SEQUENCE: 56
VLLPLVIFFG LCLLSLLFIG LMY                                                   23

SEQ ID NO: 57           moltype = AA  length = 225
FEATURE                 Location/Qualifiers
REGION                  1..225
                        note = MISC_FEATURE - IL-9
source                  1..225
                        mol_type = protein
                        organism = synthetic construct
SEQUENCE: 57
VKRIFYQNVP SPAMFFQPLY SVHNGNFQTW MGAHGAGVLL SQDCAGTPQG ALEPCVQEAT           60
ALLTCGPARP WKSVALEEEQ EGPGTRLPGN LSSEDVLPAG CTEWRVQTLA YLPQEDWAPT          120
SLTRPAPPDS EGSRSSSSSS SSNNNNYCAL GCYGGWHLSA LPGNTQSSGP IPALACGLSC          180
DHQGLETQQG VAWVLAGHCQ RPGLHEDLQG MLLPSVLSKA RSWTF                          225

SEQ ID NO: 58           moltype = AA  length = 86
FEATURE                 Location/Qualifiers
REGION                  1..86
                        note = MISC_FEATURE - BOX1/2
source                  1..86
                        mol_type = protein
                        organism = synthetic construct
SEQUENCE: 58
ERTMPRIPTL KNLEDLVTEY HGNFSAWSGV SKGLAESLQP DYSERLCLVS EIPPKGGALG           60
EGPGASPCNQ HSPYWAPPCY TLKPET                                                86

SEQ ID NO: 59           moltype = AA  length = 15
FEATURE                 Location/Qualifiers
REGION                  1..15
                        note = MISC_FEATURE - Gly Ser Linker
source                  1..15
                        mol_type = protein
                        organism = synthetic construct
SEQUENCE: 59
GGGGSGGGGS GGGGS                                                            15

SEQ ID NO: 60           moltype = AA  length = 12
FEATURE                 Location/Qualifiers
REGION                  1..12
                        note = MISC_FEATURE - Q-Pro Linker
source                  1..12
                        mol_type = protein
                        organism = synthetic construct
SEQUENCE: 60
QPQPQPQPQP QP                                                               12

SEQ ID NO: 61           moltype = AA  length = 12
FEATURE                 Location/Qualifiers
```

```
REGION                  1..12
                        note = MISC_FEATURE - K-Pro Linker
source                  1..12
                        mol_type = protein
                        organism = synthetic construct
SEQUENCE: 61
KPKPKPKPKP KP                                                           12

SEQ ID NO: 62           moltype = AA  length = 26
FEATURE                 Location/Qualifiers
REGION                  1..26
                        note = MISC_FEATURE - Exemplary signal sequence
source                  1..26
                        mol_type = protein
                        organism = synthetic construct
SEQUENCE: 62
MAAPALSWRL PLLILLLPLA TSWASA                                            26

SEQ ID NO: 63           moltype = AA  length = 472
FEATURE                 Location/Qualifiers
REGION                  1..472
                        note = MISC_FEATURE - IL21r/IL9R
source                  1..472
                        mol_type = protein
                        organism = synthetic construct
SEQUENCE: 63
CPDLVCYTDY LQTVICILEM WNLHPSTLTL TWQDQYEELK DEATSCSLHR SAHNATHATY        60
TCHMDVFHFM ADDIFSVNIT DQSGNYSQEC GSFLLAESIK PAPPFNVTVT FSGQYNISWR       120
SDYEDPAFYM LKGKLQYELQ YRNRGDPWAV SPRRKLISVD SRSVSLLPLE FRKDSSYELQ       180
VRAGPMPGSS YQGTWSEWSD PVIFQTQSEE LKELIPPWGW PGNTLVAVSI FLLLTGPTYL       240
LFKLSPRVKR IFYQNVPSPA MFFQPLYSVH NGNFQTWMGA HGAGVLLSQD CAGTPQGALE       300
PCVQEATALL TCGPARPWKS VALEEEQEGP GTRLPGNLSS EDVLPAGCTE WRVQTLAYLP       360
QEDWAPTSLT RPAPPDSEGS RSSSSSSSSN NNNYCALGCY GGWHLSALPG NTQSSGPIPA       420
LACGLSCDHQ GLETQQGVAW VLAGHCQRPG LHEDLQGMLL PSVLSKARSW TF              472

SEQ ID NO: 64           moltype = AA  length = 463
FEATURE                 Location/Qualifiers
REGION                  1..463
                        note = MISC_FEATURE - IL21r/IL9R/IL7RaTM
source                  1..463
                        mol_type = protein
                        organism = synthetic construct
SEQUENCE: 64
CPDLVCYTDY LQTVICILEM WNLHPSTLTL TWQDQYEELK DEATSCSLHR SAHNATHATY        60
TCHMDVFHFM ADDIFSVNIT DQSGNYSQEC GSFLLAESIK PAPPFNVTVT FSGQYNISWR       120
SDYEDPAFYM LKGKLQYELQ YRNRGDPWAV SPRRKLISVD SRSVSLLPLE FRKDSSYELQ       180
VRAGPMPGSS YQGTWSEWSD PVIFQTQSEE LKEPILLTIS ILSFFSVALL VILACVLWVK       240
RIFYQNVPSP AMFFQPLYSV HNGNFQTWMG AHGAGVLLSQ DCAGTPQGAL EPCVQEATAL       300
LTCGPARPWK SVALEEEQEG PGTRLPGNLS SEDVLPAGCT EWRVQTLAYL PQEDWAPTSL       360
TRPAPPDSEG SRSSSSSSSS NNNNYCALGC YGGWHLSALP GNTQSSGPIP ALACGLSCDH       420
QGLETQQGVA WVLAGHCQRP GLHEDLQGML LPSVLSKARS WTF                        463

SEQ ID NO: 65           moltype = AA  length = 463
FEATURE                 Location/Qualifiers
REGION                  1..463
                        note = MISC_FEATURE - IL21r/IL9R/IL2RbTM
source                  1..463
                        mol_type = protein
                        organism = synthetic construct
SEQUENCE: 65
CPDLVCYTDY LQTVICILEM WNLHPSTLTL TWQDQYEELK DEATSCSLHR SAHNATHATY        60
TCHMDVFHFM ADDIFSVNIT DQSGNYSQEC GSFLLAESIK PAPPFNVTVT FSGQYNISWR       120
SDYEDPAFYM LKGKLQYELQ YRNRGDPWAV SPRRKLISVD SRSVSLLPLE FRKDSSYELQ       180
VRAGPMPGSS YQGTWSEWSD PVIFQTQSEE LKEIPWLGHL LVGLSGAFGF IILVYLLIVK       240
RIFYQNVPSP AMFFQPLYSV HNGNFQTWMG AHGAGVLLSQ DCAGTPQGAL EPCVQEATAL       300
LTCGPARPWK SVALEEEQEG PGTRLPGNLS SEDVLPAGCT EWRVQTLAYL PQEDWAPTSL       360
TRPAPPDSEG SRSSSSSSSS NNNNYCALGC YGGWHLSALP GNTQSSGPIP ALACGLSCDH       420
QGLETQQGVA WVLAGHCQRP GLHEDLQGML LPSVLSKARS WTF                        463

SEQ ID NO: 66           moltype = AA  length = 434
FEATURE                 Location/Qualifiers
REGION                  1..434
                        note = MISC_FEATURE - IL15r-alpha/IL9R
source                  1..434
                        mol_type = protein
                        organism = synthetic construct
SEQUENCE: 66
ITCPPPMSVE HADIWVKSYS LYSRERYICN SGFKRKAGTS SLTECVLNKA TNVAHWTTPS        60
LKCIRDPALV HQRPAPPSTV TTAGVTPQPE SLSPSGKEPA ASSPSSNNTA ATTAAIVPGS       120
```

```
QLMPSKSPST GTTEISSHES SHGTPSQTTA KNWELTASAS HQPPGVYPQG HSDTTLIPPW    180
GWPGNTLVAV SIFLLLTGPT YLLFKLSPRV KRIFYQNVPS PAMFFQPLYS VHNGNFQTWM    240
GAHGAGVLLS QDCAGTPQGA LEPCVQEATA LLTCGPARPW KSVALEEEQE GPGTRLPGNL    300
SSEDVLPAGC TEWRVQTLAY LPQEDWAPTS LTRPAPPDSE GSRSSSSSSS SNNNNYCALG    360
CYGGWHLSAL PGNTQSSGPI PALACGLSCD HQGLETQQGV AWVLAGHCQR PGLHEDLQGM    420
LLPSVLSKAR SWTF                                                     434

SEQ ID NO: 67          moltype = AA  length = 425
FEATURE                Location/Qualifiers
REGION                 1..425
                       note = MISC_FEATURE - IL15r-alpha/IL9R/IL7RaTM
source                 1..425
                       mol_type = protein
                       organism = synthetic construct
SEQUENCE: 67
ITCPPPMSVE HADIWVKSYS LYSRERYICN SGFKRKAGTS SLTECVLNKA TNVAHWTTPS     60
LKCIRDPALV HQRPAPPSTV TTAGVTPQPE SLSPSGKEPA ASSPSSNNTA ATTAAIVPGS    120
QLMPSKSPST GTTEISSHES SHGTPSQTTA KNWELTASAS HQPPGVYPQG HSDTTPILLT    180
ISILSFFSVA LLVILACVLW VKRIFYQNVP SPAMFFQPLY SVHNGNFQTW MGAHGAGVLL    240
SQDCAGTPQG ALEPCVQEAT ALLTCGPARP WKSVALEEEQ EGPGTRLPGN LSSEDVLPAG    300
CTEWRVQTLA YLPQEDWAPT SLTRPAPPDS EGSRSSSSSS SSNNNNYCAL GCYGGWHLSA    360
LPGNTQSSGP IPALACGLSC DHQGLETQQG VAWVLAGHCQ RPGLHEDLQG MLLPSVLSKA    420
RSWTF                                                               425

SEQ ID NO: 68          moltype = AA  length = 425
FEATURE                Location/Qualifiers
REGION                 1..425
                       note = MISC_FEATURE - IL15r-alpha/IL9R/IL2RbTM
source                 1..425
                       mol_type = protein
                       organism = synthetic construct
SEQUENCE: 68
ITCPPPMSVE HADIWVKSYS LYSRERYICN SGFKRKAGTS SLTECVLNKA TNVAHWTTPS     60
LKCIRDPALV HQRPAPPSTV TTAGVTPQPE SLSPSGKEPA ASSPSSNNTA ATTAAIVPGS    120
QLMPSKSPST GTTEISSHES SHGTPSQTTA KNWELTASAS HQPPGVYPQG HSDTTIPWLG    180
HLLVGLSGAF GFIILVYLLI VKRIFYQNVP SPAMFFQPLY SVHNGNFQTW MGAHGAGVLL    240
SQDCAGTPQG ALEPCVQEAT ALLTCGPARP WKSVALEEEQ EGPGTRLPGN LSSEDVLPAG    300
CTEWRVQTLA YLPQEDWAPT SLTRPAPPDS EGSRSSSSSS SSNNNNYCAL GCYGGWHLSA    360
LPGNTQSSGP IPALACGLSC DHQGLETQQG VAWVLAGHCQ RPGLHEDLQG MLLPSVLSKA    420
RSWTF                                                               425

SEQ ID NO: 69          moltype = AA  length = 478
FEATURE                Location/Qualifiers
REGION                 1..478
                       note = MISC_FEATURE - IL7r-alpha /IL9R
source                 1..478
                       mol_type = protein
                       organism = synthetic construct
SEQUENCE: 69
ESGYAQNGDL EDAELDDYSF SCYSQLEVNG SQHSLTCAFE DPDVNITNLE FEICGALVEV     60
KCLNFRKLQE IYFIETKKFL LIGKSNICVK VGEKSLTCKK IDLTTTIVKPE APFDLSVVYR   120
EGANDFVVTF NTSHLQKKYV KVLMHDVAYR QEKDENKWTH VNLSSTKTL LQRKLQPAAM     180
YEIKVRSIPD HYFKGFWSEW SPSYYFRTPE INNSSGEMDL IPPWGWPGNT LVAVSIFLLL    240
TGPTYLLFKL SPRVKRIFYQ NVPSPAMFFQ PLYSVHNGNF QTWMGAHGAG VLLSQDCAGT    300
PQGALEPCVQ EATALLTCGP ARPWKSVALE EEQEGPGTRL PGNLSSEDVL PAGCTEWRVQ    360
TLAYLPQEDW APTSLTRPAP PDSEGSRSSS SSSSNNNNY CALGCYGGWH LSALPGNTQS     420
SGPIPALACG LSCDHQGLET QQGVAWVLAG HCQRPGLHED LQGMLLPSVL SKARSWTF      478

SEQ ID NO: 70          moltype = AA  length = 469
FEATURE                Location/Qualifiers
REGION                 1..469
                       note = MISC_FEATURE - IL7r-alpha /IL9R/IL7RaTM
source                 1..469
                       mol_type = protein
                       organism = synthetic construct
SEQUENCE: 70
ESGYAQNGDL EDAELDDYSF SCYSQLEVNG SQHSLTCAFE DPDVNITNLE FEICGALVEV     60
KCLNFRKLQE IYFIETKKFL LIGKSNICVK VGEKSLTCKK IDLTTTIVKPE APFDLSVVYR   120
EGANDFVVTF NTSHLQKKYV KVLMHDVAYR QEKDENKWTH VNLSSTKTL LQRKLQPAAM     180
YEIKVRSIPD HYFKGFWSEW SPSYYFRTPE INNSSGEMDP ILLTISILSF FSVALLVILA    240
CVLWVKRIFY QNVPSPAMFF QPLYSVHNGN FQTWMGAHGA GVLLSQDCAG TPQGALEPCV    300
QEATALLTCG PARPWKSVAL EEEQEGPGTR LPGNLSSEDV LPAGCTEWRV QTLAYLPQED    360
WAPTSLTRPA PPDSEGSRSS SSSSSNNNN YCALGCYGGW HLSALPGNTQ SSGPIPALAC     420
GLSCDHQGLE TQQGVAWVLA GHCQRPGLHE DLQGMLLPSV LSKARSWTF                469

SEQ ID NO: 71          moltype = AA  length = 469
FEATURE                Location/Qualifiers
REGION                 1..469
                       note = MISC_FEATURE - IL7r-alpha /IL9R/IL2RbTM
```

| | | |
|---|---|---|
| source | 1..469 | |
| | mol_type = protein | |
| | organism = synthetic construct | |

SEQUENCE: 71

```
ESGYAQNGDL EDAELDDYSF SCYSQLEVNG SQHSLTCAFE DPDVNITNLE FEICGALVEV   60
KCLNFRKLQE IYFIETKKFL LIGKSNICVK VGEKSLTCKK IDLTTIVKPE APFDLSVVYR  120
EGANDFVVTF NTSHLQKKYV KVLMHDVAYR QEKDENKWTH VNLSSTKLTL LQRKLQPAAM  180
YEIKVRSIPD HYFKGFWSEW SPSYYFRTPE INNSSGEMDI PWLGHLLVGL SGAFGFIILV  240
YLLIVKRIFY QNVPSPAMFF QPLYSVHNGN FQTWMGAHGA GVLLSQDCAG TPQGALEPCV  300
QEATALLTCG PARPWKSVAL EEEQEGPGTR LPGNLSSEDV LPAGCTEWRV QTLAYLPQED  360
WAPTSLTRPA PPDSEGSRSS SSSSSSNNNN YCALGCYGGW HLSALPGNTQ SSGPIPALAC  420
GLSCDHQGLE TQQGVAWVLA GHCQRPGLHE DLQGMLLPSV LSKARSWTF              469
```

| SEQ ID NO: 72 | moltype = AA  length = 466 |
|---|---|
| FEATURE | Location/Qualifiers |
| REGION | 1..466 |
| | note = MISC_FEATURE - IL4r-alpha/IL9R |
| source | 1..466 |
| | mol_type = protein |
| | organism = synthetic construct |

SEQUENCE: 72

```
MKVLQEPTCV SDYMSISTCE WKMNGPTNCS TELRLLYQLV FLLSEAHTCI PENNGGAGCV   60
CHLLMDDVVS ADNYTLDLWA GQQLLWKGSF KPSEHVKPRA PGNLTVHTNV SDTLLLTWSN  120
PYPPDNYLYN HLTYAVNIWS ENDPADFRIY NVTYLEPSLR IAASTLKSGI SYRARVRAWA  180
QCYNTTWSEW SPSTKWHNSY REPFEQHLIP PWGWPGNTLV AVSIFLLLTG PTYLLFKLSP  240
RVKRIFYQNV PSPAMFFQPL YSVHNGNFQT WMGAHGAGVL LSQDCAGTPQ GALEPCVQEA  300
TALLTCGPAR PWKSVALEEE QEGPGTRLPG NLSSEDVLPA GCTEWRVQTL AYLPQEDWAP  360
TSLTRPAPPD SEGSRSSSSS SSSNNNNYCA LGCYGGWHLS ALPGNTQSSG PIPALACGLS  420
CDHQGLETQQ GVAWVLAGHC QRPGLHEDLQ GMLLPSVLSK ARSWTF                 466
```

| SEQ ID NO: 73 | moltype = AA  length = 457 |
|---|---|
| FEATURE | Location/Qualifiers |
| REGION | 1..457 |
| | note = MISC_FEATURE - IL4r-alpha/IL9R/IL7RaTM |
| source | 1..457 |
| | mol_type = protein |
| | organism = synthetic construct |

SEQUENCE: 73

```
MKVLQEPTCV SDYMSISTCE WKMNGPTNCS TELRLLYQLV FLLSEAHTCI PENNGGAGCV   60
CHLLMDDVVS ADNYTLDLWA GQQLLWKGSF KPSEHVKPRA PGNLTVHTNV SDTLLLTWSN  120
PYPPDNYLYN HLTYAVNIWS ENDPADFRIY NVTYLEPSLR IAASTLKSGI SYRARVRAWA  180
QCYNTTWSEW SPSTKWHNSY REPFEQHPIL LTISILSFFS VALLVILACV LWIKRIFYQN  240
VPSPAMFFQP LYSVHNGNFQ TWMGAHGAGV LLSQDCAGTP QGALEPCVQE ATALLTCGPA  300
RPWKSVALEE EQEGPGTRLP GNLSSEDVLP AGCTEWRVQT LAYLPQEDWA PTSLTRPAPP  360
DSEGSRSSSS SSSSNNNNYC ALGCYGGWHL SALPGNTQSS GPIPALACGL SCDHQGLETQ  420
QGVAWVLAGH CQRPGLHEDL QGMLLPSVLS KARSWTF                           457
```

| SEQ ID NO: 74 | moltype = AA  length = 457 |
|---|---|
| FEATURE | Location/Qualifiers |
| REGION | 1..457 |
| | note = MISC_FEATURE - IL4r-alpha/IL9R/IL2RbTM |
| source | 1..457 |
| | mol_type = protein |
| | organism = synthetic construct |

SEQUENCE: 74

```
MKVLQEPTCV SDYMSISTCE WKMNGPTNCS TELRLLYQLV FLLSEAHTCI PENNGGAGCV   60
CHLLMDDVVS ADNYTLDLWA GQQLLWKGSF KPSEHVKPRA PGNLTVHTNV SDTLLLTWSN  120
PYPPDNYLYN HLTYAVNIWS ENDPADFRIY NVTYLEPSLR IAASTLKSGI SYRARVRAWA  180
QCYNTTWSEW SPSTKWHNSY REPFEQHIPW LGHLLVGLSG AFGFIILVYL LIVKRIFYQN  240
VPSPAMFFQP LYSVHNGNFQ TWMGAHGAGV LLSQDCAGTP QGALEPCVQE ATALLTCGPA  300
RPWKSVALEE EQEGPGTRLP GNLSSEDVLP AGCTEWRVQT LAYLPQEDWA PTSLTRPAPP  360
DSEGSRSSSS SSSSNNNNYC ALGCYGGWHL SALPGNTQSS GPIPALACGL SCDHQGLETQ  420
QGVAWVLAGH CQRPGLHEDL QGMLLPSVLS KARSWTF                           457
```

| SEQ ID NO: 75 | moltype = AA  length = 473 |
|---|---|
| FEATURE | Location/Qualifiers |
| REGION | 1..473 |
| | note = MISC_FEATURE - IL2r-beta Ectodomain /IL9R |
| source | 1..473 |
| | mol_type = protein |
| | organism = synthetic construct |

SEQUENCE: 75

```
AVNGTSQFTC FYNSRANISC VWSQDGALQD TSCQVHAWPD RRRWNQTCEL LPVSQASWAC   60
NLILGAPDSQ KLTTVDIVTL RVLCREGVRW RVMAIQDFKP FENLRLMAPI SLQVVHVETH  120
RCNISWEISQ ASHYFERHLE FEARTLSPGH TWEEAPLLTL KQKQEWICLE TLTPDTQYEF  180
QVRVKPLQGE FTTWSPWSQP LAFRTKPAAL GKDTLIPPWG WPGNTLVAVS IPLLLTGPTY  240
LLFKLSPRVK RIFYQNVPSP AMFFQPLYSV HNGNFQTWMG AHGAGVLLSQ DCAGTPQGAL  300
EPCVQEATAL LTCGPARPWK SVALEEEQEG PGTRLPGNLS SEDVLPAGCT EWRVQTLAYL  360
PQEDWAPTSL TRPAPPDSEG SRSSSSSSSS NNNNYCALGC YGGWHLSALP GNTQSSGPIP  420
```

```
ALACGLSCDH QGLETQQGVA WVLAGHCQRP GLHEDLQGML LPSVLSKARS WTF        473

SEQ ID NO: 76           moltype = AA  length = 464
FEATURE                 Location/Qualifiers
REGION                  1..464
                        note = MISC_FEATURE - IL2r-beta Ectodomain /IL9R/IL7RaTM
source                  1..464
                        mol_type = protein
                        organism = synthetic construct
SEQUENCE: 76
AVNGTSQFTC FYNSRANISC VWSQDGALQD TSCQVHAWPD RRRWNQTCEL LPVSQASWAC   60
NLILGAPDSQ KLTTVDIVTL RVLCREGVRW RVMAIQDFKP FENLRLMAPI SLQVVHVETH  120
RCNISWEISQ ASHYFERHLE FEARTLSPGH TWEEAPLLTL KQKQEWICLE TLTPDTQYEF  180
QVRVKPLQGE FTTWSPWSQP LAFRTKPAAL GKDTPILLTI SILSFFSVAL LVILACVLWV  240
KRIFYQNVPS PAMFFQPLYS VHNGNFQTWM GAHGAGVLLS QDCAGTPQGA LEPCVQEATA  300
LLTCGPARPW KSVALEEEQE GPGTRLPGNL SSEDVLPAGC TEWRVQTLAY LPQEDWAPTS  360
LTRPAPPDSE GSRSSSSSSS SNNNNYCALG CYGGWHLSAL PGNTQSSGPI PALACGLSCD  420
HQGLETQQGV AWVLAGHCQR PGLHEDLQGM LLPSVLSKAR SWTF                  464

SEQ ID NO: 77           moltype = AA  length = 464
FEATURE                 Location/Qualifiers
REGION                  1..464
                        note = MISC_FEATURE - IL2r-beta Ectodomain /IL9R/IL2RbTM
source                  1..464
                        mol_type = protein
                        organism = synthetic construct
SEQUENCE: 77
AVNGTSQFTC FYNSRANISC VWSQDGALQD TSCQVHAWPD RRRWNQTCEL LPVSQASWAC   60
NLILGAPDSQ KLTTVDIVTL RVLCREGVRW RVMAIQDFKP FENLRLMAPI SLQVVHVETH  120
RCNISWEISQ ASHYFERHLE FEARTLSPGH TWEEAPLLTL KQKQEWICLE TLTPDTQYEF  180
QVRVKPLQGE FTTWSPWSQP LAFRTKPAAL GKDTIPWLGH LLVGLSGAFG FIILVYLLIV  240
KRIFYQNVPS PAMFFQPLYS VHNGNFQTWM GAHGAGVLLS QDCAGTPQGA LEPCVQEATA  300
LLTCGPARPW KSVALEEEQE GPGTRLPGNL SSEDVLPAGC TEWRVQTLAY LPQEDWAPTS  360
LTRPAPPDSE GSRSSSSSSS SNNNNYCALG CYGGWHLSAL PGNTQSSGPI PALACGLSCD  420
HQGLETQQGV AWVLAGHCQR PGLHEDLQGM LLPSVLSKAR SWTF                  464

SEQ ID NO: 78           moltype = AA  length = 478
FEATURE                 Location/Qualifiers
REGION                  1..478
                        note = MISC_FEATURE - IL2r-alpha Ectodomain/IL9R
source                  1..478
                        mol_type = protein
                        organism = synthetic construct
SEQUENCE: 78
ELCDDDPPEI PHATFKAMAY KEGTMLNCEC KRGFRRIKSG SLYMLCTGNS SHSSWDNQCQ   60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTPQP LICTGEMETS QFPGEEKPQA  180
SPEGRPESET SCLVTTTDFQ IQTEMAATME TSIFTTEYQL IPPWGWPGNT LVAVSIFLLL  240
TGPTYLLFKL SPRVKRIFYQ NVPSPAMFFQ PLYSVHNGNF QTWMGAHGAG VLLSQDCAGT  300
PQGALEPCVQ EATALLTCGP ARPWKSVALE EEQEGPGTRL PGNLSSEDVL PAGCTEWRVQ  360
TLAYLPQEDW APTSLTRPAP PDSEGSRSSS SSSSNNNNY CALGCYGGWH LSALPGNTQS  420
SGPIPALACG LSCDHQGLET QQGVAWVLAG HCQRPGLHED LQGMLLPSVL SKARSWTF   478

SEQ ID NO: 79           moltype = AA  length = 469
FEATURE                 Location/Qualifiers
REGION                  1..469
                        note = MISC_FEATURE - IL2r-alpha Ectodomain/IL9R/IL7RaTM
source                  1..469
                        mol_type = protein
                        organism = synthetic construct
SEQUENCE: 79
ELCDDDPPEI PHATFKAMAY KEGTMLNCEC KRGFRRIKSG SLYMLCTGNS SHSSWDNQCQ   60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTPQP LICTGEMETS QFPGEEKPQA  180
SPEGRPESET SCLVTTTDFQ IQTEMAATME TSIFTTEYQP ILLTISILSF FSVALLVILA  240
CVLWVKRIFY QNVPSPAMFF QPLYSVHNGN FQTWMGAHGA GVLLSQDCAG TPQGALEPCV  300
QEATALLTCG PARPWKSVAL EEEQEGPGTR LPGNLSSEDV LPAGCTEWRV QTLAYLPQED  360
WAPTSLTRPA PPDSEGSRSS SSSSSNNNN YCALGCYGGW HLSALPGNTQ SSGPIPALAC  420
GLSCDHQGLE TQQGVAWVLA GHCQRPGLHE DLQGMLLPSV LSKARSWTF             469

SEQ ID NO: 80           moltype = AA  length = 469
FEATURE                 Location/Qualifiers
REGION                  1..469
                        note = MISC_FEATURE - IL2r-alpha Ectodomain/IL9R/IL2RbTM
source                  1..469
                        mol_type = protein
                        organism = synthetic construct
SEQUENCE: 80
ELCDDDPPEI PHATFKAMAY KEGTMLNCEC KRGFRRIKSG SLYMLCTGNS SHSSWDNQCQ   60
```

```
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTGEMETS QFPGEEKPQA    180
SPEGRPESET SCLVTTTDFQ IQTEMAATME TSIFTTEYQI PWLGHLLVGL SGAFGFIILV    240
YLLIVKRIFY QNVPSPAMFF QPLYSVHNGN FQTWMGAHGA GVLLSQDCAG TPQGALEPCV    300
QEATALLTCG PARPWKSVAL EEEQEGPGTR LPGNLSSEDV LPAGCTEWRV QTLAYLPQED    360
WAPTSLTRPA PPDSEGSRSS SSSSSSNNNN YCALGCYGGW HLSALPGNTQ SSGPIPALAC    420
GLSCDHQGLE TQQGVAWVLA GHCQRPGLHE DLQGMLLPSV LSKARSWTF               469

SEQ ID NO: 81           moltype = AA  length = 780
FEATURE                 Location/Qualifiers
REGION                  1..780
                        note = MISC_FEATURE - ILT5/IL9R/cGC-F
source                  1..780
                        mol_type = protein
                        organism = synthetic construct
SEQUENCE: 81
GPFPKPTLWA EPGSVISWGS PVTIWCQGSQ EAQEYRLHKE GSPEPLDRNN PLEPKNKARF     60
SIPSMTEHHA GRYRCHYYSS AGWSEPSDPL EMVMTGAYSK PTLSALPSPV VASGGNMTLR    120
CGSQKGYHHF VLMKEGEHQL PRTLDSQQLH SRGFQALFPV GPVTPSHRWR FTCYYYYTNT    180
PWVWSHPSDP LEILPSGVSR KPSLLTLQGP VLAPGQSLTL QCGSDVGYNR FVLYKEGERD    240
FLQRPGQQPQ AGLSQANFTL GPVSPSNGGQ YRCYGAHNLS SEWSAPSDPL NILMAGQIYD    300
TVSLSAQPGP TVASGENVTL LCQSWWQFDT FLLTKEGAAH PPLRLRSMYG AHKYQAEFPM    360
SPVTSAHAGT YRCYGSYSSN PHLLSHPSEP LELVVSGHSG GSSLPPTGPP STPGLGRYLE    420
LIPPWGWPGN TLVAVSIFLL LTGPTYLLFK LSPRVKRIFY QNVPSPAMFF QPLYSVHNGN    480
FQTWMGAHGA GVLLSQDCAG TPQGALEPCV QEATALLTCG PARPWKSVAL EEEQEGPGTR    540
LPGNLSSEDV LPAGCTEWRV QTLAYLPQED WAPTSLTRPA PPDSEGSRSS SSSSSSNNNN    600
YCALGCYGGW HLSALPGNTQ SSGPIPALAC GLSCDHQGLE TQQGVAWVLA GHCQRPGLHE    660
DLQGMLLPSV LSKARSWTFG GGGSGGGGSG GGGSERTMPR IPTLKNLEDL VTEYHGNFSA    720
WSGVSKGLAE SLQPDYSERL CLVSEIPPKG GALGEGPGAS PCNQHSPYWA PPCYTLKPET    780

SEQ ID NO: 82           moltype = AA  length = 777
FEATURE                 Location/Qualifiers
REGION                  1..777
                        note = MISC_FEATURE - ILT5/IL9R/cGC-S
source                  1..777
                        mol_type = protein
                        organism = synthetic construct
SEQUENCE: 82
GPFPKPTLWA EPGSVISWGS PVTIWCQGSQ EAQEYRLHKE GSPEPLDRNN PLEPKNKARF     60
SIPSMTEHHA GRYRCHYYSS AGWSEPSDPL EMVMTGAYSK PTLSALPSPV VASGGNMTLR    120
CGSQKGYHHF VLMKEGEHQL PRTLDSQQLH SRGFQALFPV GPVTPSHRWR FTCYYYYTNT    180
PWVWSHPSDP LEILPSGVSR KPSLLTLQGP VLAPGQSLTL QCGSDVGYNR FVLYKEGERD    240
FLQRPGQQPQ AGLSQANFTL GPVSPSNGGQ YRCYGAHNLS SEWSAPSDPL NILMAGQIYD    300
TVSLSAQPGP TVASGENVTL LCQSWWQFDT FLLTKEGAAH PPLRLRSMYG AHKYQAEFPM    360
SPVTSAHAGT YRCYGSYSSN PHLLSHPSEP LELVVSGHSG GSSLPPTGPP STPGLGRYLE    420
LIPPWGWPGN TLVAVSIFLL LTGPTYLLFK LSPRVKRIFY QNVPSPAMFF QPLYSVHNGN    480
FQTWMGAHGA GVLLSQDCAG TPQGALEPCV QEATALLTCG PARPWKSVAL EEEQEGPGTR    540
LPGNLSSEDV LPAGCTEWRV QTLAYLPQED WAPTSLTRPA PPDSEGSRSS SSSSSSNNNN    600
YCALGCYGGW HLSALPGNTQ SSGPIPALAC GLSCDHQGLE TQQGVAWVLA GHCQRPGLHE    660
DLQGMLLPSV LSKARSWTFQ PQPQPQPQPQ PERTMPRIPT LKNLEDLVTE YHGNFSAWSG    720
VSKGLAESLQ PDYSERLCLV SEIPPKGGAL GEGPGASPCN QHSPYWAPPC YTLKPET      777

SEQ ID NO: 83           moltype = AA  length = 598
FEATURE                 Location/Qualifiers
REGION                  1..598
                        note = MISC_FEATURE - ILT3/IL9R/cGC-F
source                  1..598
                        mol_type = protein
                        organism = synthetic construct
SEQUENCE: 83
QAGPLPKPTL WAEPGSVISW GNSVTIWCQG TLEAREYRLD KEESPAPWDR QNPLEPKNKA     60
RFSIPSMTED YAGRYRCYYR SPVGWSQPSD PLELVMTGAY SKPTLSALPS PLVTSGKSVT    120
LLCQSRSPMD TFLLIKERAA HPLLHLRSEH GAQQHQAEFP MSPTVSVHGG TYRCFSSHGF    180
SHYLLSHPSD PLELIVSGSL EDPRPSPTRS VSTAAGPEDQ PLMPTGSVPH SGLRRHWELI    240
PPWGWPGNTL VAVSIFLLLT GPTYLLFKLS PRVKRIFYQN VPSPAMFFQP LYSVHNGNFQ    300
TWMGAHGAGV LLSQDCAGTP QGALEPCVQE ATALLTCGPA RPWKSVALEE EQEGPGTRLP    360
GNLSSEDVLP AGCTEWRVQT LAYLPQEDWA PTSLTRPAPP DSEGSRSSSS SSSSNNNNYC    420
ALGCYGGWHL SALPGNTQSS GPIPALACGL SCDHQGLETQ QGVAWVLAGH CQRPGLHEDL    480
QGMLLPSVLS KARSWTFGGG GSGGGGSGGG GSERTMPRIP TLKNLEDLVT EYHGNFSAWS    540
GVSKGLAESL QPDYSERLCL VSEIPPKGGA LGEGPGASPC NQHSPYWAPP CYTLKPET     598

SEQ ID NO: 84           moltype = AA  length = 595
FEATURE                 Location/Qualifiers
REGION                  1..595
                        note = MISC_FEATURE - ILT3/IL9R/cGC-S
source                  1..595
                        mol_type = protein
                        organism = synthetic construct
SEQUENCE: 84
```

```
QAGPLPKPTL WAEPGSVISW GNSVTIWCQG TLEAREYRLD KEESPAPWDR QNPLEPKNKA    60
RFSIPSMTED YAGRYRCYYR SPVGWSQPSD PLELVMTGAY SKPTLSALPS PLVTSGKSVT   120
LLCQSRSPMD TFLLIKERAA HPLLHLRSEH GAQQHQAEFP MSPVTSVHGG TYRCFSSHGF   180
SHYLLSHPSD PLELIVSGSL EDPRPSPTRS VSTAAGPEDQ PLMPTGSVPH SGLRRHWELI   240
PPWGWPGNTL VAVSIFLLLT GPTYLLFKLS PRVKRIFYQN VPSPAMFFQP LYSVHNGNFQ   300
TWMGAHGAGV LLSQDCAGTP QGALEPCVQE ATALLTCGPA RPWKSVALEE EQEGPGTRLP   360
GNLSSEDVLP AGCTEWRVQT LAYLPQEDWA PTSLTRPAPP DSEGSRSSSS SSSSNNNNYC   420
ALGCYGGWHL SALPGNTQSS GPIPALACGL SCDHQGLETQ QGVAWVLAGH CQRPGLHEDL   480
QGMLLPSVLS KARSWTFQPQ PQPQPQPQPE RTMPRIPTLK NLEDLVTEYH GNFSAWSGVS   540
KGLAESLQPD YSERLCLVSE IPPKGGALGE GPGASPCNQH SPYWAPPCYT LKPET        595

SEQ ID NO: 85            moltype = AA  length = 800
FEATURE                  Location/Qualifiers
REGION                   1..800
                         note = MISC_FEATURE - ILT4 IL9R/cGC-F
source                   1..800
                         mol_type = protein
                         organism = synthetic construct
SEQUENCE: 85
QTGTIPKPTL WAEPDSVITQ GSPVTLSCQG SLEAQEYRLY REKKSASWIT RIRPELVKNG    60
QFHIPSITWE HTGRYGCQYY SRARWSELSD PLVLVMTGAY PKPTLSAQPS PVVTSGGRVT   120
LQCESQVAFG GFILCKEGEE EHPQCLNSQP HARGSSRAIF SVGPVSPNRR WSHRCYGYDL   180
NSPYVWSSPS DLLELLVPGV SKKPSLSVQP GPVVAPGESL TLQCVSDVGY DRFVLYKEGE   240
RDLRQLPGRQ PQAGLSQANF TLGPVSRSYG GQYRCYGAHN LSSECSAPSD PLDILITGQI   300
RGTPFISVQP GPTVASGENV TLLCQSWRQF HTFLLTKAGA ADAPLRLRSI HEYPKYQAEF   360
PMSPVTSAHA GTYRCYGSLN SDPYLLSHPS EPLELVVSGP SMGSSPPPTG PISTPAGPED   420
QPLTPTGSDP QSGLGRHLGV LIPPWGWPGN TLVAVSIFLL LTGPTYLLFK LSPRVKRIFY   480
QNVPSPAMFF QPLYSVHNGN FQTWMGAHGA GVLLSQDCAG TPQGALEPCV QEATALLTCG   540
PARPWKSVAL EEEQEGPGTR LPGNLSSEDV LPAGCTEWRV QTLAYLPQED WAPTSLTRPA   600
PPDSEGSRSS SSSSSSNNNN YCALGCYGGW HLSALPGNTQ SSGPIPALAC GLSCDHQGLE   660
TQQGVAWVLA GHCQRPGLHE DLQGMLLPSV LSKARSWTFG GGGSGGGGSG GGGSERTMPR   720
IPTLKNLEDL VTEYHGNFSA WSGVSKGLAE SLQPDYSERL CLVSEIPPKG GALGEGPGAS   780
PCNQHSPYWA PPCYTLKPET                                              800

SEQ ID NO: 86            moltype = AA  length = 797
FEATURE                  Location/Qualifiers
REGION                   1..797
                         note = MISC_FEATURE - ILT4 IL9R/cGC-S
source                   1..797
                         mol_type = protein
                         organism = synthetic construct
SEQUENCE: 86
QTGTIPKPTL WAEPDSVITQ GSPVTLSCQG SLEAQEYRLY REKKSASWIT RIRPELVKNG    60
QFHIPSITWE HTGRYGCQYY SRARWSELSD PLVLVMTGAY PKPTLSAQPS PVVTSGGRVT   120
LQCESQVAFG GFILCKEGEE EHPQCLNSQP HARGSSRAIF SVGPVSPNRR WSHRCYGYDL   180
NSPYVWSSPS DLLELLVPGV SKKPSLSVQP GPVVAPGESL TLQCVSDVGY DRFVLYKEGE   240
RDLRQLPGRQ PQAGLSQANF TLGPVSRSYG GQYRCYGAHN LSSECSAPSD PLDILITGQI   300
RGTPFISVQP GPTVASGENV TLLCQSWRQF HTFLLTKAGA ADAPLRLRSI HEYPKYQAEF   360
PMSPVTSAHA GTYRCYGSLN SDPYLLSHPS EPLELVVSGP SMGSSPPPTG PISTPAGPED   420
QPLTPTGSDP QSGLGRHLGV LIPPWGWPGN TLVAVSIFLL LTGPTYLLFK LSPRVKRIFY   480
QNVPSPAMFF QPLYSVHNGN FQTWMGAHGA GVLLSQDCAG TPQGALEPCV QEATALLTCG   540
PARPWKSVAL EEEQEGPGTR LPGNLSSEDV LPAGCTEWRV QTLAYLPQED WAPTSLTRPA   600
PPDSEGSRSS SSSSSNNNN YCALGCYGGW HLSALPGNTQ SSGPIPALAC GLSCDHQGLE    660
TQQGVAWVLA GHCQRPGLHE DLQGMLLPSV LSKARSWTFQ PQPQPQPQPQ PERTMPRIPT   720
LKNLEDLVTE YHGNFSAWSG VSKGLAESLQ PDYSERLCLV SEIPPKGGAL GEGPGASPCN   780
QHSPYWAPPC YTLKPET                                                 797

SEQ ID NO: 87            moltype = AA  length = 798
FEATURE                  Location/Qualifiers
REGION                   1..798
                         note = MISC_FEATURE - ILT2 IL9R/cGC-F
source                   1..798
                         mol_type = protein
                         organism = synthetic construct
SEQUENCE: 87
GHLPKPTLWA EPGSVITQGS PVTLRCQGGQ ETQEYRLYRE KKTALWITRI PQELVKKGQF    60
PIPSITWEHA GRYRCYYGSD TAGRSESSDP LELVVTGAYI KPTLSAQPSP VVNSGGNVIL   120
QCDSQVAFDG FSLCKEGEDE HPQCLNSQPH ARGSSRAIFS VGPVSPSRRW WYRCYAYDSN   180
SPYEWSLPSD LLELLVLGVS KKPSLSVQPG PIVAPEETLT LQCGSDAGYN RFVLYKDGER   240
DFLQLAGAQP QAGLSQANFT LGPVSRSYGG QYRCYGAHNL SSEWSAPSDP LDILIAGQFY   300
DRVSLSVQPG PTVASGENVT LLCQSQGWMQ TFLLTKEGAA DDPWRLRSTY QSQKYQAEFP   360
MGPVTSAHAG TYRCYGSQSS KPYLLTHPSD PLELVVSGPS GGPSSPTTGP TSTSGPEDQP   420
LTPTGSDPQS GLGRHLGVLI PPWGWPGNTL VAVSIFLLLT GPTYLLFKLS PRVKRIFYQN   480
VPSPAMFFQP LYSVHNGNFQ TWMGAHGAGV LLSQDCAGTP QGALEPCVQE ATALLTCGPA   540
RPWKSVALEE EQEGPGTRLP GNLSSEDVLP AGCTEWRVQT LAYLPQEDWA PTSLTRPAPP   600
DSEGSRSSSS SSSSNNNNYC ALGCYGGWHL SALPGNTQSS GPIPALACGL SCDHQGLETQ   660
QGVAWVLAGH CQRPGLHEDL QGMLLPSVLS KARSWTFGGG GSGGGGSGGG GSERTMPRIP   720
TLKNLEDLVT EYHGNFSAWS GVSKGLAESL QPDYSERLCL VSEIPPKGGA LGEGPGASPC   780
NQHSPYWAPP CYTLKPET                                                798
```

```
SEQ ID NO: 88            moltype = AA  length = 795
FEATURE                  Location/Qualifiers
REGION                   1..795
                         note = MISC_FEATURE - ILT2 IL9R/cGC-S
source                   1..795
                         mol_type = protein
                         organism = synthetic construct
SEQUENCE: 88
GHLPKPTLWA EPGSVITQGS PVTLRCQGGQ ETQEYRLYRE KKTALWITRI PQELVKKGQF    60
PIPSITWEHA GRYRCYYGSD TAGRSESSDP LELVVTGAYI KPTLSAQPSP VVNSGGNVIL   120
QCDSQVAFDG FSLCKEGEDE HPQCLNSQPH ARGSSRAIFS VGPVSPSRRW WYRCYAYDSN   180
SPYEWSLPSD LLELLVLGVS KKPSLSVQPG PIVAPEETLT LQCGSDAGYN RFVLYKDGER   240
DFLQLAGAQP QAGLSQANFT LGPVSRSYGG QYRCYGAHNL SSEWSAPSDP LDILIAGQFY   300
DRVSLSVQPG PTVASGENVT LLCQSQGWMQ TFLLTKEGAA DDPWRLRSTY QSQKYQAEFP   360
MGPVTSAHAG TYRCYGSQSS KPYLLTHPSD PLELVVSGPS GGPSSPTTGP TSTSGPEDQP   420
LTPTGSDPQS GLGRHLGVLI PPWGWPGNTL VAVSIFLLLT GPTYLLFKLS PRVKRIFYQN   480
VPSPAMFFQP LYSVHNGNFQ TWMGAHGAGV LLSQDCAGTP QGALEPCVQE ATALLTCGPA   540
RPWKSVALEE EQEGPGTRLP GNLSSEDVLP AGCTEWRVQT LAYLPQEDWA PTSLTRPAPP   600
DSEGSRSSSS SSSSNNNNYC ALGCYGGWHL SALPGNTQSS GPIPALACGL SCDHQGLETQ   660
QGVAWVLAGH CQRPGLHEDL QGMLLPSVLS KARSWTFQPQ PQPQPQPQPE RTMPRIPTLK   720
NLEDLVTEYH GNFSAWSGVS KGLAESLQPD YSERLCLVSE IPPKGGALGE GPGASPCNQH   780
SPYWAPPCYT LKPET                                                   795

SEQ ID NO: 89            moltype = AA  length = 486
FEATURE                  Location/Qualifiers
REGION                   1..486
                         note = MISC_FEATURE - CTLA4 IL9R/cGC-F
source                   1..486
                         mol_type = protein
                         organism = synthetic construct
SEQUENCE: 89
KAMHVAQPAV VLASSRGIAS FVCEYASPGK ATEVRVTVLR QADSQVTEVC AATYMMGNEL    60
TFLDDSICTG TSSGNQVNLT IQGLRAMDTG LYICKVELMY PPPYYLGIGN GTQIYVIDPE   120
PCPDSDLIPP WGWPGNTLVA VSIFLLLTGP TYLLFKLSPR VKRIFYQNVP SPAMFFQPLY   180
SVHNGNFQTW MGAHGAGVLL SQDCAGTPQG ALEPCVQEAT ALLTCGPARP WKSVALEEEQ   240
EGPGTRLPGN LSSEDVLPAG CTEWRVQTLA YLPQEDWAPT SLTRPAPPDS EGSRSSSSSS   300
SSNNNNYCAL GCYGGWHLSA LPGNTQSSGP IPALACGLSC DHQGLETQQG VAWVLAGHCQ   360
RPGLHEDLQG MLLPSVLSKA RSWTFGGGGS GGGGSGGGGS ERTMPRIPTL KNLEDLVTEY   420
HGNFSAWSGV SKGLAESLQP DYSERLCLVS EIPPKGGALG EGPGASPCNQ HSPYWAPPCY   480
TLKPET                                                             486

SEQ ID NO: 90            moltype = AA  length = 483
FEATURE                  Location/Qualifiers
REGION                   1..483
                         note = MISC_FEATURE - CTLA4 IL9R/cGC-S
source                   1..483
                         mol_type = protein
                         organism = synthetic construct
SEQUENCE: 90
KAMHVAQPAV VLASSRGIAS FVCEYASPGK ATEVRVTVLR QADSQVTEVC AATYMMGNEL    60
TFLDDSICTG TSSGNQVNLT IQGLRAMDTG LYICKVELMY PPPYYLGIGN GTQIYVIDPE   120
PCPDSDLIPP WGWPGNTLVA VSIFLLLTGP TYLLFKLSPR VKRIFYQNVP SPAMFFQPLY   180
SVHNGNFQTW MGAHGAGVLL SQDCAGTPQG ALEPCVQEAT ALLTCGPARP WKSVALEEEQ   240
EGPGTRLPGN LSSEDVLPAG CTEWRVQTLA YLPQEDWAPT SLTRPAPPDS EGSRSSSSSS   300
SSNNNNYCAL GCYGGWHLSA LPGNTQSSGP IPALACGLSC DHQGLETQQG VAWVLAGHCQ   360
RPGLHEDLQG MLLPSVLSKA RSWTFQPQPQ PQPQPQPERT MPRIPTLKNL EDLVTEYHGN   420
FSAWSGVSKG LAESLQPDYS ERLCLVSEIP PKGGALGEGP GASPCNQHSP YWAPPCYTLK   480
PET                                                                483

SEQ ID NO: 91            moltype = AA  length = 541
FEATURE                  Location/Qualifiers
REGION                   1..541
                         note = MISC_FEATURE - TIM3/IL9R/cGC-F
source                   1..541
                         mol_type = protein
                         organism = synthetic construct
SEQUENCE: 91
SEVEYRAEVG QNAYLPCFYT PAAPGNLVPV CWGKGACPVF ECGNVVLRTD ERDVNYWTSR    60
YWLNGDFRKG DVSLTIENVT LADSGIYCCR IQIPGIMNDE KFNLKLVIKP AKVTPAPTRQ   120
RDFTAAFPRM LTTRGHGPAE TQTLGSLPDI NLTQISTLAN ELRDSRLAND LRDSGATIRI   180
GLIPPWGWPG NTLVAVSIFL LLTGPTYLLF KLSPRVKRIF YQNVPSPAMF FQPLYSVHNG   240
NFQTWMGAHG AGVLLSQDCA GTPQGALEPC VQEATALLTC GPARPWKSVA LEEEQEGPGT   300
RLPGNLSSED VLPAGCTEWR VQTLAYLPQE DWAPTSLTRP APPDSEGSRS SSSSSSSNNN   360
NYCALGCYGG WHLSALPGNT QSSGPIPALA CGLSCDHQGL ETQQGVAWVL AGHCQRPGLH   420
EDLQGMLLPS VLSKARSWTF GGGGSGGGGS GGGGSERTMP RIPTLKNLED LVTEYHGNFS   480
AWSGVSKGLA ESLQPDYSER LCLVSEIPPK GGALGEGPGA SPCNQHSPYW APPCYTLKPE   540
T                                                                  541
```

```
SEQ ID NO: 92              moltype = AA  length = 538
FEATURE                    Location/Qualifiers
REGION                     1..538
                           note = MISC_FEATURE - TIM3/IL9R/cGC-S
source                     1..538
                           mol_type = protein
                           organism = synthetic construct
SEQUENCE: 92
SEVEYRAEVG QNAYLPCFYT PAAPGNLPV  CWGKGACPVF ECGNVVLRTD ERDVNYWTSR   60
YWLNGDFRKG DVSLTIENVT LADSGIYCCR IQIPGIMNDE KFNLKLVIKP AKVTPAPTRQ  120
RDFTAAFPRM LTTRGHGPAE TQTLGSLPDI NLTQISTLAN ELRDSRLAND LRDSGATIRI  180
GLIPPWGWPG NTLVAVSIFL LLTGPTYLLF KLSPRVKRIF YQNVPSPAMF FQPLYSVHNG  240
NFQTWMGAHG AGVLLSQDCA GTPQGALEPC VQEATALLTC GPARPWKSVA LEEEQEGPGT  300
RLPGNLSSED VLPAGCTEWR VQTLAYLPQE DWAPTSLTRP APPDSEGSRS SSSSSSSNNN  360
NYCALGCYGG WHLSALPGNT QSSGPIPALA CGLSCDHQGL ETQQGVAWVL AGHCQRPGLH  420
EDLQGMLLPS VLSKARSWTF QPQPQPQPQP QPERTMPRIP TLKNLEDLVT EYHGNFSAWS  480
GVSKGLAESL QPDYSERLCL VSEIPPKGGA LGEGPGASPC NQHSPYWAPP CYTLKPET    538

SEQ ID NO: 93              moltype = AA  length = 785
FEATURE                    Location/Qualifiers
REGION                     1..785
                           note = MISC_FEATURE - LAG3/IL9R/cGC-S
source                     1..785
                           mol_type = protein
                           organism = synthetic construct
SEQUENCE: 93
LQPGAEVPVV WAQEGAPAQL PCSPTIPLQD LSLLRRAGVT WQHQPDSGPP AAAPGHPLAP   60
GPHPAAPSSW GPRPRRYTVL SVGPGGLRSG RLPLQPRVQL DERGRQRGDF SLWLRPARRA  120
DAGEYRAAVH LRDRALSCRL RLRLGQASMT ASPPGSLRAS DWVILNCSFS RPDRPASVHW  180
FRNRGQGRVP VRESPHHHLA ESFLFLPQVS PMDSGPWGCI LTYRDGFNVS IMYNLTVLGL  240
EPPTPLTVYA GAGSRVGLPC RLPAGVGTRS FLTAKWTPPG GGPDLLVTGD NGDFTLRLED  300
VSQAQAGTYT CHIHLQEQQL NATVTLAIIT VTPKSFGSPG SLGKLLCEVT PVSGQERFVW  360
SSLDTPSQRS FSGPWLEAQE AQLLSQPWQC QLYQGERLLG AAVYFTELSS PGAQRSGRAP  420
GALPAGHLLI PPWGWPGNTL VAVSIFLLLT GPTYLLFKLS PRVKRIFYQN VPSPAMFFQP  480
LYSVHNGNFQ TWMGAHGAGV LLSQDCAGTP QGALEPCVQE ATALLTCGPA RPWKSVALEE  540
EQEGPGTRLP GNLSSEDVLP AGCTEWRVQT LAYLPQEDWA PTSLTRPAPP DSEGSRSSSS  600
SSSSNNNNYC ALGCYGGWHL SALPGNTQSS GPIPALACGL SCDHQGLETQ QGVAWVLAGH  660
CQRPGLHEDL QGMLLPSVLS KARSWTFQPQ PQPQPQPQPQ RTMPRIPTLK NLEDLVTEYH  720
GNFSAWSGVS KGLAESLQPD YSERLCLVSE IPPKGGALGE GPGASPCNQH SPYWAPPCYT  780
LKPET                                                              785

SEQ ID NO: 94              moltype = AA  length = 788
FEATURE                    Location/Qualifiers
REGION                     1..788
                           note = MISC_FEATURE - LAG3/IL9R/cGC-F
source                     1..788
                           mol_type = protein
                           organism = synthetic construct
SEQUENCE: 94
LQPGAEVPVV WAQEGAPAQL PCSPTIPLQD LSLLRRAGVT WQHQPDSGPP AAAPGHPLAP   60
GPHPAAPSSW GPRPRRYTVL SVGPGGLRSG RLPLQPRVQL DERGRQRGDF SLWLRPARRA  120
DAGEYRAAVH LRDRALSCRL RLRLGQASMT ASPPGSLRAS DWVILNCSFS RPDRPASVHW  180
FRNRGQGRVP VRESPHHHLA ESFLFLPQVS PMDSGPWGCI LTYRDGFNVS IMYNLTVLGL  240
EPPTPLTVYA GAGSRVGLPC RLPAGVGTRS FLTAKWTPPG GGPDLLVTGD NGDFTLRLED  300
VSQAQAGTYT CHIHLQEQQL NATVTLAIIT VTPKSFGSPG SLGKLLCEVT PVSGQERFVW  360
SSLDTPSQRS FSGPWLEAQE AQLLSQPWQC QLYQGERLLG AAVYFTELSS PGAQRSGRAP  420
GALPAGHLLI PPWGWPGNTL VAVSIFLLLT GPTYLLFKLS PRVKRIFYQN VPSPAMFFQP  480
LYSVHNGNFQ TWMGAHGAGV LLSQDCAGTP QGALEPCVQE ATALLTCGPA RPWKSVALEE  540
EQEGPGTRLP GNLSSEDVLP AGCTEWRVQT LAYLPQEDWA PTSLTRPAPP DSEGSRSSSS  600
SSSSNNNNYC ALGCYGGWHL SALPGNTQSS GPIPALACGL SCDHQGLETQ QGVAWVLAGH  660
CQRPGLHEDL QGMLLPSVLS KARSWTFGGG GSGGGGSGGG GSERTMPRIP TLKNLEDLVT  720
EYHGNFSAWS GVSKGLAESL QPDYSERLCL VSEIPPKGGA LGEGPGASPC NQHSPYWAPP  780
CYTLKPET                                                           788

SEQ ID NO: 95              moltype = AA  length = 580
FEATURE                    Location/Qualifiers
REGION                     1..580
                           note = MISC_FEATURE - PD1/IL9R/cGC-F
source                     1..580
                           mol_type = protein
                           organism = synthetic construct
SEQUENCE: 95
FTVTVPKDLY VVEYGSNMTI ECKFPVEKQL DLAALIVYWE MEDKNIIQFV HGEEDLKVQH   60
SSYRQRARLL KDQLSLGNAA LQITDVKLQD AGVYRCMISY GGADYKRITV KVNAPYNKIN  120
QRILVVDPVT SEHELTCQAE GYPKAEVIWT SSDHQVLSGK TTTTNSKREE KLFNVTSTLR  180
INTTTNEIFY CTFRRLDPEE NHTAELVIPE LPLAHPPNER LIPPWGWPGN TLVAVSIFLL  240
LTGPTYLLFK LSPRVKRIFY QNVPSPAMFF QPLYSVHNGN FQTWMGAHGA GVLLSQDCAG  300
TPQGALEPCV QEATALLTCG PARPWKSVAL EEEQEGPGTR LPGNLSSEDV LPAGCTEWRV  360
QTLAYLPQED WAPTSLTRPA PPDSEGSRSS SSSSSSNNNN YCALGCYGGW HLSALPGNTQ  420
```

```
SSGPIPALAC GLSCDHQGLE TQQGVAWVLA GHCQRPGLHE DLQGMLLPSV LSKARSWTFG    480
GGGSGGGGSG GGGSERTMPR IPTLKNLEDL VTEYHGNFSA WSGVSKGLAE SLQPDYSERL    540
CLVSEIPPKG GALGEGPGAS PCNQHSPYWA PPCYTLKPET                          580

SEQ ID NO: 96              moltype = AA   length = 577
FEATURE                    Location/Qualifiers
REGION                     1..577
                           note = MISC_FEATURE - PD1/IL9R/cGC-S
source                     1..577
                           mol_type = protein
                           organism = synthetic construct
SEQUENCE: 96
FTVTVPKDLY VVEYGSNMTI ECKFPVEKQL DLAALIVYWE MEDKNIIQFV HGEEDLKVQH     60
SSYRQRARLL KDQLSLGNAA LQITDVKLQD AGVYRCMISY GGADYKRITV KVNAPYNKIN    120
QRILVVDPVT SEHELTCQAE GYPKAEVIWT SSDHQVLSGK TTTTNSKREE KLFNVTSTLR    180
INTTTNEIFY CTFRRLDPEE NHTAELVIPE LPLAHPPNER LIPPWGWPGN TLVAVSIFLL    240
LTGPTYLLFK LSPRVKRIFY QNVPSPAMFF QPLYSVHNGN FQTWMGAHGA GVLLSQDCAG    300
TPQGALEPCV QEATALLTCG PARPWKSVAL EEEQEGPGTR LPGNLSSEDV LPAGCTEWRV    360
QTLAYLPQED WAPTSLTRPA PPDSEGSRSS SSSSSSNNNN YCALGCYGGW HLSALPGNTQ    420
SSGPIPALAC GLSCDHQGLE TQQGVAWVLA GHCQRPGLHE DLQGMLLPSV LSKARSWTFQ    480
PQPQPQPQPQ PERTMPRIPT LKNLEDLVTE YHGNFSAWSG VSKGLAESLQ PDYSERLCLV    540
SEIPPKGGAL GEGPGASPCN QHSPYWAPPC YTLKPET                             577

SEQ ID NO: 97              moltype = AA   length = 740
FEATURE                    Location/Qualifiers
REGION                     1..740
                           note = MISC_FEATURE - OPG/IL9R/cGC-F
source                     1..740
                           mol_type = protein
                           organism = synthetic construct
SEQUENCE: 97
ETFPPKYLHY DEETSHQLLC DKCPPGTYLK QHCTAKWKTV CAPCPDHYYT DSWHTSDECL     60
YCSPVCKELQ YVKQECNRTH NRVCECKEGR YLEIEFCLKH RSCPPGFGVV QAGTPERNTV    120
CKRCPDGFFS NETSSKAPCR KHTNCSVFGL LLTQKGNATH DNICSGNSES TQKCGIDVTL    180
CEEAFFRFAV PTKFTPNWLS VLVDNLPGTK VNAESVERIK RQHSSQEQTF QLLKLWKHQN    240
KDQDIVKKII QDIDLCENSV QRHIGHANLT FEQLRSLMES LPGKKVGAED IEKTIKACKP    300
SDQILKLLSL WRIKNGDQDT LKGLMHALKH SKTYHFPKTV TQSLKKTIRF LHSFTMYKLY    360
QKLFLEMIGN QVQSVKISCL LIPPWGWPGN TLVAVSIFLL LTGPTYLLFK LSPRVKRIFY    420
QNVPSPAMFF QPLYSVHNGN FQTWMGAHGA GVLLSQDCAG TPQGALEPCV QEATALLTCG    480
PARPWKSVAL EEEQEGPGTR LPGNLSSEDV LPAGCTEWRV QTLAYLPQED WAPTSLTRPA    540
PPDSEGSRSS SSSSSSNNNN YCALGCYGGW HLSALPGNTQ SSGPIPALAC GLSCDHQGLE    600
TQQGVAWVLA GHCQRPGLHE DLQGMLLPSV LSKARSWTFG GGGSGGGGSG GGGSERTMPR    660
IPTLKNLEDL VTEYHGNFSA WSGVSKGLAE SLQPDYSERL CLVSEIPPKG GALGEGPGAS    720
PCNQHSPYWA PPCYTLKPET                                                740

SEQ ID NO: 98              moltype = AA   length = 737
FEATURE                    Location/Qualifiers
REGION                     1..737
                           note = MISC_FEATURE - OPG/IL9R/cGC-S
source                     1..737
                           mol_type = protein
                           organism = synthetic construct
SEQUENCE: 98
ETFPPKYLHY DEETSHQLLC DKCPPGTYLK QHCTAKWKTV CAPCPDHYYT DSWHTSDECL     60
YCSPVCKELQ YVKQECNRTH NRVCECKEGR YLEIEFCLKH RSCPPGFGVV QAGTPERNTV    120
CKRCPDGFFS NETSSKAPCR KHTNCSVFGL LLTQKGNATH DNICSGNSES TQKCGIDVTL    180
CEEAFFRFAV PTKFTPNWLS VLVDNLPGTK VNAESVERIK RQHSSQEQTF QLLKLWKHQN    240
KDQDIVKKII QDIDLCENSV QRHIGHANLT FEQLRSLMES LPGKKVGAED IEKTIKACKP    300
SDQILKLLSL WRIKNGDQDT LKGLMHALKH SKTYHFPKTV TQSLKKTIRF LHSFTMYKLY    360
QKLFLEMIGN QVQSVKISCL LIPPWGWPGN TLVAVSIFLL LTGPTYLLFK LSPRVKRIFY    420
QNVPSPAMFF QPLYSVHNGN FQTWMGAHGA GVLLSQDCAG TPQGALEPCV QEATALLTCG    480
PARPWKSVAL EEEQEGPGTR LPGNLSSEDV LPAGCTEWRV QTLAYLPQED WAPTSLTRPA    540
PPDSEGSRSS SSSSSSNNNN YCALGCYGGW HLSALPGNTQ SSGPIPALAC GLSCDHQGLE    600
TQQGVAWVLA GHCQRPGLHE DLQGMLLPSV LSKARSWTFQ PQPQPQPQPQ PERTMPRIPT    660
LKNLEDLVTE YHGNFSAWSG VSKGLAESLQ PDYSERLCLV SEIPPKGGAL GEGPGASPCN    720
QHSPYWAPPC YTLKPET                                                   737

SEQ ID NO: 99              moltype = AA   length = 525
FEATURE                    Location/Qualifiers
REGION                     1..525
                           note = MISC_FEATURE - TACI/IL9R/cGC-F
source                     1..525
                           mol_type = protein
                           organism = synthetic construct
SEQUENCE: 99
MSGLGRSRRG GRSRVDQEER FPQGLWTGVA MRSCPEEQYW DPLLGTCMSC KTICNHQSQR     60
TCAAFCRSLS CRKEQGKFYD HLLRDCISCA SICGQHPKQC AYFCENKLRS PVNLPPELRR    120
QRSGEVENNS DNSGRYQGLE HRGSEASPAL PGLKLSADQV ALVYSLIPPW GWPGNTLVAV    180
SIFLLLTGPT YLLFKLSPRV KRIFYQNVPS PAMFFQPLYS VHNGNFQTWM GAHGAGVLLS    240
```

```
QDCAGTPQGA LEPCVQEATA LLTCGPARPW KSVALEEEQE GPGTRLPGNL SSEDVLPAGC   300
TEWRVQTLAY LPQEDWAPTS LTRPAPPDSE GSRSSSSSSS SNNNNYCALG CYGGWHLSAL   360
PGNTQSSGPI PALACGLSCD HQGLETQQGV AWVLAGHCQR PGLHEDLQGM LLPSVLSKAR   420
SWTFGGGGSG GGGSGGGGSE RTMPRIPTLK NLEDLVTEYH GNFSAWSGVS KGLAESLQPD   480
YSERLCLVSE IPPKGGALGE GPGASPCNQH SPYWAPPCYT LKPET                   525

SEQ ID NO: 100           moltype = AA  length = 522
FEATURE                  Location/Qualifiers
REGION                   1..522
                         note = MISC_FEATURE - TACI/IL9R/cGC-S
source                   1..522
                         mol_type = protein
                         organism = synthetic construct
SEQUENCE: 100
MSGLGRSRRG GRSRVDQEER FPQGLWTGVA MRSCPEEQYW DPLLGTCMSC KTICNHQSQR    60
TCAAFCRSLS CRKEQGKFYD HLLRDCISCA SICGQHPKQC AYFCENKLRS PVNLPPELRR   120
QRSGEVENNS DNSGRYQGLE HRGSEASPAL PGLKLSADQV ALVYSLIPPW GWPGNTLVAV   180
SIFLLLTGPT YLLFKLSPRV KRIFYQNVPS PAMFFQPLYS VHNGNFQTWM GAHGAGVLLS   240
QDCAGTPQGA LEPCVQEATA LLTCGPARPW KSVALEEEQE GPGTRLPGNL SSEDVLPAGC   300
TEWRVQTLAY LPQEDWAPTS LTRPAPPDSE GSRSSSSSSS SNNNNYCALG CYGGWHLSAL   360
PGNTQSSGPI PALACGLSCD HQGLETQQGV AWVLAGHCQR PGLHEDLQGM LLPSVLSKAR   420
SWTFQPQPQP QPQPQPERTM PRIPTLKNLE DLVTEYHGNF SAWSGVSKGL AESLQPDYSE   480
RLCLVSEIPP KGGALGEGPG ASPCNHSPY WAPPCYTLKP ET                       522

SEQ ID NO: 101           moltype = AA  length = 414
FEATURE                  Location/Qualifiers
REGION                   1..414
                         note = MISC_FEATURE - BCMA/IL9R/cGC-F
source                   1..414
                         mol_type = protein
                         organism = synthetic construct
SEQUENCE: 101
MLQMAGQCSQ NEYFDSLLHA CIPCQLRCSS NTPPLTCQRY CNASVTNSVK GTNALIPPWG    60
WPGNTLVAVS IFLLLTGPTY LLFKLSPRVK RIFYQNVPSP AMFFQPLYSV HNGNFQTWMG   120
AHGAGVLLSQ DCAGTPQGAL EPCVQEATAL LTCGPARPWK SVALEEEQEG PGTRLPGNLS   180
SEDVLPAGCT EWRVQTLAYL PQEDWAPTSL TRPAPPDSEG SRSSSSSSSS NNNNYCALGC   240
YGGWHLSALP GNTQSSGPIP ALACGLSCDH QGLETQQGVA WVLAGHCQRP GLHEDLQGML   300
LPSVLSKARS WTFGGGGSGG GGSGGGGSER TMPRIPTLKN LEDLVTEYHG NFSAWSGVSK   360
GLAESLQPDY SERLCLVSEI PPKGGALGEG PGASPCNHSP YWAPPCYTL KPET           414

SEQ ID NO: 102           moltype = AA  length = 411
FEATURE                  Location/Qualifiers
REGION                   1..411
                         note = MISC_FEATURE - BCMA/IL9R/cGC-S
source                   1..411
                         mol_type = protein
                         organism = synthetic construct
SEQUENCE: 102
MLQMAGQCSQ NEYFDSLLHA CIPCQLRCSS NTPPLTCQRY CNASVTNSVK GTNALIPPWG    60
WPGNTLVAVS IFLLLTGPTY LLFKLSPRVK RIFYQNVPSP AMFFQPLYSV HNGNFQTWMG   120
AHGAGVLLSQ DCAGTPQGAL EPCVQEATAL LTCGPARPWK SVALEEEQEG PGTRLPGNLS   180
SEDVLPAGCT EWRVQTLAYL PQEDWAPTSL TRPAPPDSEG SRSSSSSSSS NNNNYCALGC   240
YGGWHLSALP GNTQSSGPIP ALACGLSCDH QGLETQQGVA WVLAGHCQRP GLHEDLQGML   300
LPSVLSKARS WTFQPQPQPQ PQPQPERTMP RIPTLKNLED LVTEYHGNFS AWSGVSKGLA   360
ESLQPDYSER LCLVSEIPPK GGALGEGPGA SPCNHSPYW APPCYTLKPE T              411

SEQ ID NO: 103           moltype = AA  length = 582
FEATURE                  Location/Qualifiers
REGION                   1..582
                         note = MISC_FEATURE - NGFR/IL9R/cGC-F
source                   1..582
                         mol_type = protein
                         organism = synthetic construct
SEQUENCE: 103
KEACPTGLYT HSGECCKACN LGEGVAQPCG ANQTVCEPCL DSVTFSDVVS ATEPCKPCTE    60
CVGLQSMSAP CVEADDAVCR CAYGYYQDET TGRCEACRVC EAGSGLVFSC QDKQNTVCEE   120
CPDGTYSDEA NHVDPCLPCT VCEDTERQLR ECTRWADAEC EEIPGRWITR STPPEGSDST   180
APSTQEPEAP PEQDLIASTV AGVVTTVMGS SQPVVTRGTT DNLIPPWGWP GNTLVAVSIF   240
LLLTGPTYLL FKLSPRVKRI FYQNVPSPAM FFQPLYSVHN GNFQTWMGAH GAGVLLSQDC   300
AGTPQGALEP CVQEATALLT CGPARPWKSV ALEEEQEGPG TRLPGNLSSE DVLPAGCTEW   360
RVQTLAYLPQ EDWAPTSLTR PAPPDSEGSR SSSSSSSSNN NNYCALGCYG GWHLSALPGN   420
TQSSGPIPAL ACGLSCDHQG LETQQGVAWV LAGHCQRPGL HEDLQGMLLP SVLSKARSWT   480
FGGGGSGGGG SGGGGSERTM PRIPTLKNLE DLVTEYHGNF SAWSGVSKGL AESLQPDYSE   540
RLCLVSEIPP KGGALGEGPG ASPCNHSPY WAPPCYTLKP ET                       582

SEQ ID NO: 104           moltype = AA  length = 579
FEATURE                  Location/Qualifiers
REGION                   1..579
                         note = MISC_FEATURE - NGFR/IL9R/cGC-S
```

```
source                     1..579
                           mol_type = protein
                           organism = synthetic construct
SEQUENCE: 104
KEACPTGLYT HSGECCKACN LGEGVAQPCG ANQTVCEPCL DSVTFSDVVS ATEPCKPCTE    60
CVGLQSMSAP CVEADDAVCR CAYGYYQDET TGRCEACRVC EAGSGLVFSC QDKQNTVCEE   120
CPDGTYSDEA NHVDPCLPCT VCEDTERQLR ECTRWADAEC EEIPGRWITR STPPEGSDST   180
APSTQEPEAP PEQDLIASTV AGVVTTVMGS SQPVVTRGTT DNLIPPWGWP GNTLVAVSIF   240
LLLTGPTYLL FKLSPRVKRI FYQNVPSPAM FFQPLYSVHN GNFQTWMGAH GAGVLLSQDC   300
AGTPQGALEP CVQEATALLT CGPARPWKSV ALEEEQEGPG TRLPGNLSSE DVLPAGCTEW   360
RVQTLAYLPQ EDWAPTSLTR PAPPDSEGSR SSSSSSSSNN NNYCALGCYG GWHLSALPGN   420
TQSSGPIPAL ACGLSCDHQG LETQQGVAWV LAGHCQRPGL HEDLQGMLLP SVLSKARSWT   480
FQPQPQPQPQ PQPERTMPRI PTLKNLEDLV TEYHGNFSAW SGVSKGLAES LQPDYSERLC   540
LVSEIPPKGG ALGEGPGASP CNQHSPYWAP PCYTLKPET                          579

SEQ ID NO: 105             moltype = AA   length = 521
FEATURE                    Location/Qualifiers
REGION                     1..521
                           note = MISC_FEATURE - EDAR/IL9R/cGC-F
source                     1..521
                           mol_type = protein
                           organism = synthetic construct
SEQUENCE: 105
EYSNCGENEY YNQTTGLCQE CPPCGPGEEP YLSCGYGTKD EDYGCVPCPA EKFSKGGYQI    60
CRRHKDCEGF FRATVLTPGD MENDAECGPC LPGYYMLENR PRNIYGMVCY SCLLAPPNTK   120
ECVGATSGAS ANFPGTSGSS TLSPFQHAHK ELSGQGHLAT ALIPPWGWPG NTLVAVSIFL   180
LLTGPTYLLF KLSPRVKRIF YQNVPSPAMF FQPLYSVHNG NFQTWMGAHG AGVLLSQDCA   240
GTPQGALEPC VQEATALLTC GPARPWKSVA LEEEQEGPGT RLPGNLSSED VLPAGCTEWR   300
VQTLAYLPQE DWAPTSLTRP APPDSEGSRS SSSSSSSNNN NYCALGCYGG WHLSALPGNT   360
QSSGPIPALA CGLSCDHQGL ETQQGVAWVL AGHCQRPGLH EDLQGMLLPS VLSKARSWTF   420
GGGGSGGGGS GGGGSERTMP RIPTLKNLED LVTEYHGNFS AWSGVSKGLA ESLQPDYSER   480
LCLVSEIPPK GGALGEGPGA SPCNQHSPYW APPCYTLKPE T                       521

SEQ ID NO: 106             moltype = AA   length = 518
FEATURE                    Location/Qualifiers
REGION                     1..518
                           note = MISC_FEATURE - EDAR/IL9R/cGC-S
source                     1..518
                           mol_type = protein
                           organism = synthetic construct
SEQUENCE: 106
EYSNCGENEY YNQTTGLCQE CPPCGPGEEP YLSCGYGTKD EDYGCVPCPA EKFSKGGYQI    60
CRRHKDCEGF FRATVLTPGD MENDAECGPC LPGYYMLENR PRNIYGMVCY SCLLAPPNTK   120
ECVGATSGAS ANFPGTSGSS TLSPFQHAHK ELSGQGHLAT ALIPPWGWPG NTLVAVSIFL   180
LLTGPTYLLF KLSPRVKRIF YQNVPSPAMF FQPLYSVHNG NFQTWMGAHG AGVLLSQDCA   240
GTPQGALEPC VQEATALLTC GPARPWKSVA LEEEQEGPGT RLPGNLSSED VLPAGCTEWR   300
VQTLAYLPQE DWAPTSLTRP APPDSEGSRS SSSSSSSNNN NYCALGCYGG WHLSALPGNT   360
QSSGPIPALA CGLSCDHQGL ETQQGVAWVL AGHCQRPGLH EDLQGMLLPS VLSKARSWTF   420
QPQPQPQPQP QPERTMPRIP TLKNLEDLVT EYHGNFSAWS GVSKGLAESL QPDYSERLCL   480
VSEIPPKGGA LGEGPGASPC NQHSPYWAPP CYTLKPET                           518

SEQ ID NO: 107             moltype = AA   length = 516
FEATURE                    Location/Qualifiers
REGION                     1..516
                           note = MISC_FEATURE - DCR2 (TNFRSF10D) /IL9R/cGC-F
source                     1..516
                           mol_type = protein
                           organism = synthetic construct
SEQUENCE: 107
ATIPRQDEVP QQTVAPQQQR RSLKEEECPA GSHRSEYTGA CNPCTEGVDY TIASNNLPSC    60
LLCTVCKSGQ TNKSSCTTTR DTVCQCEKGS FQDKNSPEMC RTCRTGCPRG MVKVSNCTPR   120
SDIKCKNESA ASSTGKTPAA EETVTTILGM LASPYHLIPP WGWPGNTLVA VSIFLLLTGP   180
TYLLFKLSPR VKRIFYQNVP SPAMFFQPLY SVHNGNFQTW MGAHGAGVLL SQDCAGTPQG   240
ALEPCVQEAT ALLTCGPARP WKSVALEEEQ EGPGTRLPGN LSSEDVLPAG CTEWRVQTLA   300
YLPQEDWAPT SLTRPAPPDS EGSRSSSSSS SSNNNNYCAL GCYGGWHLSA LPGNTQSSGP   360
IPALACGLSC DHQGLETQQG VAWVLAGHCQ RPGLHEDLQG MLLPSVLSKA RSWTFGGGGS   420
GGGGSGGGGS ERTMPRIPTL KNLEDLVTEY HGNFSAWSGV SKGLAESLQP DYSERLCLVS   480
EIPPKGGALG EGPGASPCNQ HSPYWAPPCY TLKPET                             516

SEQ ID NO: 108             moltype = AA   length = 513
FEATURE                    Location/Qualifiers
REGION                     1..513
                           note = MISC_FEATURE - DCR2 (TNFRSF10D) /IL9R/cGC-S
source                     1..513
                           mol_type = protein
                           organism = synthetic construct
SEQUENCE: 108
ATIPRQDEVP QQTVAPQQQR RSLKEEECPA GSHRSEYTGA CNPCTEGVDY TIASNNLPSC    60
LLCTVCKSGQ TNKSSCTTTR DTVCQCEKGS FQDKNSPEMC RTCRTGCPRG MVKVSNCTPR   120
```

```
SDIKCKNESA ASSTGKTPAA EETVTTILGM LASPYHLIPP WGWPGNTLVA VSIFLLLTGP    180
TYLLFKLSPR VKRIFYQNVP SPAMFFQPLY SVHNGNFQTW MGAHGAGVLL SQDCAGTPQG    240
ALEPCVQEAT ALLTCGPARP WKSVALEEEQ EGPGTRLPGN LSSEDVLPAG CTEWRVQTLA    300
YLPQEDWAPT SLTRPAPPDS EGSRSSSSSS SSNNNNYCAL GCYGGWHLSA LPGNTQSSGP    360
IPALACGLSC DHQGLETQQG VAWVLAGHCQ RPGLHEDLQG MLLPSVLSKA RSWTFQPQPQ    420
PQPQPQPERT MPRIPTLKNL EDLVTEYHGN FSAWSGVSKG LAESLQPDYS ERLCLVSEIP    480
PKGGALGEGP GASPCNQHSP YWAPPCYTLK PET                                513

SEQ ID NO: 109            moltype = AA  length = 571
FEATURE                   Location/Qualifiers
REGION                    1..571
                          note = MISC_FEATURE - DCR1 (TNFRSF10C) /IL9R/cGC-F
source                    1..571
                          mol_type = protein
                          organism = synthetic construct
SEQUENCE: 109
ATTARQEEVP QQTVAPQQQR HSFKGEECPA GSHRSEHTGA CNPCTEGVDY TNASNNEPSC     60
FPCTVCKSDQ KHKSSCTMTR DTVCQCKEGT FRNENSPEMC RKCSRCPSGE VQVSNCTSWD    120
DIQCVEEFGA NATVETPAAE ETMNTSPGTP APAAEETMNT SPGTPAPAAE ETMTTSPGTP    180
APAAEETMTT SPGTPAPAAE ETMITSPGTP ALIPPWGWPG NTLVAVSIFL LLTGPTYLLF    240
KLSPRVKRIF YQNVPSPAMF FQPLYSVHNG NFQTWMGAHG AGVLLSQDCA GTPQGALEPC    300
VQEATALLTC GPARPWKSVA LEEEQEGPGT RLPGNLSSED VLPAGCTEWR VQTLAYLPQE    360
DWAPTSLTRP APPDSEGSRS SSSSSSSNNN NYCALGCYGG WHLSALPGNT QSSGPIPALA    420
CGLSCDHQGL ETQQGVAWVL AGHCQRPGLH EDLQGMLLPS VLSKARSWTF GGGGSGGGGS    480
GGGGSERTMP RIPTLKNLED LVTEYHGNFS AWSGVSKGLA ESLQPDYSER LCLVSEIPPK    540
GGALGEGPGA SPCNQHSPYW APPCYTLKPE T                                  571

SEQ ID NO: 110            moltype = AA  length = 568
FEATURE                   Location/Qualifiers
REGION                    1..568
                          note = MISC_FEATURE - DCR1 (TNFRSF10C) /IL9R/cGC-S
source                    1..568
                          mol_type = protein
                          organism = synthetic construct
SEQUENCE: 110
ATTARQEEVP QQTVAPQQQR HSFKGEECPA GSHRSEHTGA CNPCTEGVDY TNASNNEPSC     60
FPCTVCKSDQ KHKSSCTMTR DTVCQCKEGT FRNENSPEMC RKCSRCPSGE VQVSNCTSWD    120
DIQCVEEFGA NATVETPAAE ETMNTSPGTP APAAEETMNT SPGTPAPAAE ETMTTSPGTP    180
APAAEETMTT SPGTPAPAAE ETMITSPGTP ALIPPWGWPG NTLVAVSIFL LLTGPTYLLF    240
KLSPRVKRIF YQNVPSPAMF FQPLYSVHNG NFQTWMGAHG AGVLLSQDCA GTPQGALEPC    300
VQEATALLTC GPARPWKSVA LEEEQEGPGT RLPGNLSSED VLPAGCTEWR VQTLAYLPQE    360
DWAPTSLTRP APPDSEGSRS SSSSSSSNNN NYCALGCYGG WHLSALPGNT QSSGPIPALA    420
CGLSCDHQGL ETQQGVAWVL AGHCQRPGLH EDLQGMLLPS VLSKARSWTF QPQPQPQPQP    480
QPERTMPRIP TLKNLEDLVT EYHGNFSAWS GVSKGLAESL QPDYSERLCL VSEIPPKGGA    540
LGEGPGASPC NQHSPYWAPP CYTLKPET                                      568

SEQ ID NO: 111            moltype = AA  length = 533
FEATURE                   Location/Qualifiers
REGION                    1..533
                          note = MISC_FEATURE - CD40/IL9R/cGC-F
source                    1..533
                          mol_type = protein
                          organism = synthetic construct
SEQUENCE: 111
EPPTACREKQ YLINSQCCSL CQPGQKLVSD CTEFTETECL PCGESEFLDT WNRETHCHQH     60
KYCDPNLGLR VQQKGTSETD TICTCEEGWH CTSEACESCV LHRSCSPGFG VKQIATGVSD    120
TICEPCPVGF FSNVSSAFEK CHPWTSCETK DLVVQQAGTN KTDVVCGPQD RLRLIPPWGW    180
PGNTLVAVSI FLLLTGPTYL LFKLSPRVKR IFYQNVPSPA MFFQPLYSVH NGNFQTWMGA    240
HGAGVLLSQD CAGTPQGALE PCVQEATALL TCGPARPWKS VALEEEQEGP GTRLPGNLSS    300
EDVLPAGCTE WRVQTLAYLP QEDWAPTSLT RPAPPDSEGS RSSSSSSSSN NNYCALGCY     360
GGWHLSALPG NTQSSGPIPA LACGLSCDHQ GLETQQGVAW VLAGHCQRPG LHEDLQGMLL    420
PSVLSKARSW TFGGGGSGGG GSGGGGSERT MPRIPTLKNL EDLVTEYHGN FSAWSGVSKG    480
LAESLQPDYS ERLCLVSEIP PKGGALGEGP GASPCNQHSP YWAPPCYTLK PET           533

SEQ ID NO: 112            moltype = AA  length = 530
FEATURE                   Location/Qualifiers
REGION                    1..530
                          note = MISC_FEATURE - CD40/IL9R/cGC-S
source                    1..530
                          mol_type = protein
                          organism = synthetic construct
SEQUENCE: 112
EPPTACREKQ YLINSQCCSL CQPGQKLVSD CTEFTETECL PCGESEFLDT WNRETHCHQH     60
KYCDPNLGLR VQQKGTSETD TICTCEEGWH CTSEACESCV LHRSCSPGFG VKQIATGVSD    120
TICEPCPVGF FSNVSSAFEK CHPWTSCETK DLVVQQAGTN KTDVVCGPQD RLRLIPPWGW    180
PGNTLVAVSI FLLLTGPTYL LFKLSPRVKR IFYQNVPSPA MFFQPLYSVH NGNFQTWMGA    240
HGAGVLLSQD CAGTPQGALE PCVQEATALL TCGPARPWKS VALEEEQEGP GTRLPGNLSS    300
EDVLPAGCTE WRVQTLAYLP QEDWAPTSLT RPAPPDSEGS RSSSSSSSSN NNYCALGCY     360
GGWHLSALPG NTQSSGPIPA LACGLSCDHQ GLETQQGVAW VLAGHCQRPG LHEDLQGMLL    420
```

```
PSVLSKARSW TFQPQPQPQP QPQPERTMPR IPTLKNLEDL VTEYHGNFSA WSGVSKGLAE    480
SLQPDYSERL CLVSEIPPKG GALGEGPGAS PCNQHSPYWA PPCYTLKPET               530

SEQ ID NO: 113              moltype = AA  length = 508
FEATURE                     Location/Qualifiers
REGION                      1..508
                            note = MISC_FEATURE - FAS/IL9R/cGC-F
source                      1..508
                            mol_type = protein
                            organism = synthetic construct
SEQUENCE: 113
QVTDINSKGL ELRKTVTTVE TQNLEGLHHD GQFCHKPCPP GERKARDCTV NGDEPDCVPC    60
QEGKEYTDKA HFSSKCRRCR LCDEGHGLEV EINCTRTQNT KCRCKPNFFC NSTVCEHCDP    120
CTKCEHGIIK ECTLTSNTKC KEEGSRSNLI PPWGWPGNTL VAVSIFLLLT GPTYLLFKLS    180
PRVKRIFYQN VPSPAMFFQP LYSVHNGNFQ TWMGAHGAGV LLSQDCAGTP QGALEPCVQE    240
ATALLTCGPA RPWKSVALEE EQEGPGTRLP GNLSSEDVLP AGCTEWRVQT LAYLPQEDWA    300
PTSLTRPAPP DSEGSRSSSS SSSSNNNNYC ALGCYGGWHL SALPGNTQSS GPIPALACGL    360
SCDHQGLETQ QGVAWVLAGH CQRPGLHEDL QGMLLPSVLS KARSWTFGGG GSGGGGSGGG    420
GSERTMPRIP TLKNLEDLVT EYHGNFSAWS GVSKGLAESL QPDYSERLCL VSEIPPKGGA    480
LGEGPGASPC NQHSPYWAPP CYTLKPET                                      508

SEQ ID NO: 114              moltype = AA  length = 505
FEATURE                     Location/Qualifiers
REGION                      1..505
                            note = MISC_FEATURE - FAS/IL9R/cGC-S
source                      1..505
                            mol_type = protein
                            organism = synthetic construct
SEQUENCE: 114
QVTDINSKGL ELRKTVTTVE TQNLEGLHHD GQFCHKPCPP GERKARDCTV NGDEPDCVPC    60
QEGKEYTDKA HFSSKCRRCR LCDEGHGLEV EINCTRTQNT KCRCKPNFFC NSTVCEHCDP    120
CTKCEHGIIK ECTLTSNTKC KEEGSRSNLI PPWGWPGNTL VAVSIFLLLT GPTYLLFKLS    180
PRVKRIFYQN VPSPAMFFQP LYSVHNGNFQ TWMGAHGAGV LLSQDCAGTP QGALEPCVQE    240
ATALLTCGPA RPWKSVALEE EQEGPGTRLP GNLSSEDVLP AGCTEWRVQT LAYLPQEDWA    300
PTSLTRPAPP DSEGSRSSSS SSSSNNNNYC ALGCYGGWHL SALPGNTQSS GPIPALACGL    360
SCDHQGLETQ QGVAWVLAGH CQRPGLHEDL QGMLLPSVLS KARSWTFQPQ PQPQPQPQPE    420
RTMPRIPTLK NLEDLVTEYH GNFSAWSGVS KGLAESLQPD YSERLCLVSE IPPKGGALGE    480
GPGASPCNQH SPYWAPPCYT LKPET                                         505

SEQ ID NO: 115              moltype = AA  length = 576
FEATURE                     Location/Qualifiers
REGION                      1..576
                            note = MISC_FEATURE - DR4/IL9R/cGC-F
source                      1..576
                            mol_type = protein
                            organism = synthetic construct
SEQUENCE: 115
ASGTEAAAAT PSKVWGSSAG RIEPRGGGRG ALPTSMGQHG PSARARAGRA PGPRPAREAS    60
PRLRVHKTFK FVVVGVLLQV VPSSAATIKL HDQSIGTQQW EHSPLGELCP PGSHRSEHPG    120
ACNRCTEGVG YTNASNNLFA CLPCTACKSD EEERSPCTTT RNTACQCKPG TFRNDNSAEM    180
CRKCSRGCPR GMVKVKDCTP WSDIECVHKE SGNGHNLIPP WGWPGNTLVA VSIFLLLTGP    240
TYLLFKLSPR VKRIFYQNVP SPAMFFQPLY SVHNGNFQTW MGAHGAGVLL SQDCAGTPQG    300
ALEPCVQEAT ALLTCGPARP WKSVALEEEQ EGPGTRLPGN LSSEDVLPAG CTEWRVQTLA    360
YLPQEDWAPT SLTRPAPPDS EGSRSSSSSS SSNNNNYCAL GCYGGWHLSA LPGNTQSSGP    420
IPALACGLSC DHQGLETQQG VAWVLAGHCQ RPGLHEDLQG MLLPSVLSKA RSWTFGGGGS    480
GGGGSGGGGS ERTMPRIPTL KNLEDLVTEY HGNFSAWSGV SKGLAESLQP DYSERLCLVS    540
EIPPKGGALG EGPGASPCNQ HSPYWAPPCY TLKPET                             576

SEQ ID NO: 116              moltype = AA  length = 573
FEATURE                     Location/Qualifiers
REGION                      1..573
                            note = MISC_FEATURE - DR4/IL9R/cGC-S
source                      1..573
                            mol_type = protein
                            organism = synthetic construct
SEQUENCE: 116
ASGTEAAAAT PSKVWGSSAG RIEPRGGGRG ALPTSMGQHG PSARARAGRA PGPRPAREAS    60
PRLRVHKTFK FVVVGVLLQV VPSSAATIKL HDQSIGTQQW EHSPLGELCP PGSHRSEHPG    120
ACNRCTEGVG YTNASNNLFA CLPCTACKSD EEERSPCTTT RNTACQCKPG TFRNDNSAEM    180
CRKCSRGCPR GMVKVKDCTP WSDIECVHKE SGNGHNLIPP WGWPGNTLVA VSIFLLLTGP    240
TYLLFKLSPR VKRIFYQNVP SPAMFFQPLY SVHNGNFQTW MGAHGAGVLL SQDCAGTPQG    300
ALEPCVQEAT ALLTCGPARP WKSVALEEEQ EGPGTRLPGN LSSEDVLPAG CTEWRVQTLA    360
YLPQEDWAPT SLTRPAPPDS EGSRSSSSSS SSNNNNYCAL GCYGGWHLSA LPGNTQSSGP    420
IPALACGLSC DHQGLETQQG VAWVLAGHCQ RPGLHEDLQG MLLPSVLSKA RSWTFQPQPQ    480
PQPQPQPERT MPRIPTLKNL EDLVTEYHGN FSAWSGVSKG LAESLQPDYS ERLCLVSEIP    540
PKGGALGEGP GASPCNQHSP YWAPPCYTLK PET                                573

SEQ ID NO: 117              moltype = AA  length = 668
FEATURE                     Location/Qualifiers
```

| REGION | 1..668 |
| --- | --- |
| | note = MISC_FEATURE - DR6/IL9R/cGC-F |
| source | 1..668 |
| | mol_type = protein |
| | organism = synthetic construct |

SEQUENCE: 117

```
QPEQKASNLI GTYRHVDRAT GQVLTCDKCP AGTYVSEHCT NTSLRVCSSC PVGTFTRHEN    60
GIEKCHDCSQ PCPWPMIEKL PCAALTDREC TCPPGMFQSN ATCAPHTVCP VGWGVRKKGT   120
ETEDVRCKQC ARGTFSDVPS SVMKCCKAYTD CLSQNLVVIK PGTKETDNVC GTLPSFSSST   180
SPSPGTAIFP RPEHMETHEV PSSTYVPKGM NSTESNSSAS VRPKVLSSIQ EGTVPDNTSS   240
ARGKEDVNKT LPNLQVVNHQ QGPHHRHILK LLPSMEATGG EKSSTPIKGP KRGHPRQNLH   300
KHFDINEHLI PPWGWPGNTL VAVSIFLLLT GPTYLLFKLS PRVKRIFYQN VPSPAMFFQP   360
LYSVHNGNFQ TWMGAHGAGV LLSQDCAGTP QGALEPCVQE ATALLTCGPA RPWKSVALEE   420
EQEGPGTRLP GNLSSEDVLP AGCTEWRVQT LAYLPQEDWA PTSLTRPAPP DSEGSRSSSS   480
SSSSNNNNYC ALGCYGGWHL SALPGNTQSS GPIPALACGL SCDHQGLETQ QGVAWWLAGH   540
CQRPGLHEDL QGMLLPSVLS KARSWTFGGG GSGGGGSGGG GSERTMPRIP TLKNLEDLVT   600
EYHGNFSAWS GVSKGLAESL QPDYSERLCL VSEIPPKGGA LGEGPGASPC NQHSPYWAPP   660
CYTLKPET                                                            668
```

| SEQ ID NO: 118 | moltype = AA   length = 665 |
| --- | --- |
| FEATURE | Location/Qualifiers |
| REGION | 1..665 |
| | note = MISC_FEATURE - DR6/IL9R/cGC-S |
| source | 1..665 |
| | mol_type = protein |
| | organism = synthetic construct |

SEQUENCE: 118

```
QPEQKASNLI GTYRHVDRAT GQVLTCDKCP AGTYVSEHCT NTSLRVCSSC PVGTFTRHEN    60
GIEKCHDCSQ PCPWPMIEKL PCAALTDREC TCPPGMFQSN ATCAPHTVCP VGWGVRKKGT   120
ETEDVRCKQC ARGTFSDVPS SVMKCCKAYTD CLSQNLVVIK PGTKETDNVC GTLPSFSSST   180
SPSPGTAIFP RPEHMETHEV PSSTYVPKGM NSTESNSSAS VRPKVLSSIQ EGTVPDNTSS   240
ARGKEDVNKT LPNLQVVNHQ QGPHHRHILK LLPSMEATGG EKSSTPIKGP KRGHPRQNLH   300
KHFDINEHLI PPWGWPGNTL VAVSIFLLLT GPTYLLFKLS PRVKRIFYQN VPSPAMFFQP   360
LYSVHNGNFQ TWMGAHGAGV LLSQDCAGTP QGALEPCVQE ATALLTCGPA RPWKSVALEE   420
EQEGPGTRLP GNLSSEDVLP AGCTEWRVQT LAYLPQEDWA PTSLTRPAPP DSEGSRSSSS   480
SSSSNNNNYC ALGCYGGWHL SALPGNTQSS GPIPALACGL SCDHQGLETQ QGVAWWLAGH   540
CQRPGLHEDL QGMLLPSVLS KARSWTFQPQ PQPQPQPQPE RTMPRIPTLK NLEDLVTEYH   600
GNFSAWSGVS KGLAESLQPD YSERLCLVSE IPPKGGALGE GPGASPCNQH SPYWAPPCYT   660
LKPET                                                               665
```

| SEQ ID NO: 119 | moltype = AA   length = 515 |
| --- | --- |
| FEATURE | Location/Qualifiers |
| REGION | 1..515 |
| | note = MISC_FEATURE - DR5/IL9R/cGC-F |
| source | 1..515 |
| | mol_type = protein |
| | organism = synthetic construct |

SEQUENCE: 119

```
ITQQDLAPQQ RAAPQQKRSS PSEGLCPPGH HISEDGRDCI SCKYGQDYST HWNDLLFCLR    60
CTRCDSGEVE LSPCTTTRNT VCQCEEGTFR EEDSPEMCRK CRTGCPRGMV KVGDCTPWSD   120
IECVHKESGT KHSGEVPAVE ETVTSSPGTP ASPCSLIPPW GWPGNTLVAV SIFLLLTGPT   180
YLLFKLSPRV KRIFYQNVPS PAMFFQPLYS VHNGNFQTWM GAHGAGVLLS QDCAGTPQGA   240
LEPCVQEATA LLTCGPARPW KSVALEEEQE GPGTRLPGNL SSEDVLPAGC TEWRVQTLAY   300
LPQEDWAPTS LTRPAPPDSE GSRSSSSSSS SNNNNYCALG CYGGWHLSAL PGNTQSSGPI   360
PALACGLSCD HQGLETQQGV AWVLAGHCQR PGLHEDLQGM LLPSVLSKAR SWTFGGGGSG   420
GGGSGGGGSE RTMPRIPTLK NLEDLVTEYH GNFSAWSGVS KGLAESLQPD YSERLCLVSE   480
IPPKGGALGE GPGASPCNQH SPYWAPPCYT LKPET                              515
```

| SEQ ID NO: 120 | moltype = AA   length = 512 |
| --- | --- |
| FEATURE | Location/Qualifiers |
| REGION | 1..512 |
| | note = MISC_FEATURE - DR5/IL9R/cGC-S |
| source | 1..512 |
| | mol_type = protein |
| | organism = synthetic construct |

SEQUENCE: 120

```
ITQQDLAPQQ RAAPQQKRSS PSEGLCPPGH HISEDGRDCI SCKYGQDYST HWNDLLFCLR    60
CTRCDSGEVE LSPCTTTRNT VCQCEEGTFR EEDSPEMCRK CRTGCPRGMV KVGDCTPWSD   120
IECVHKESGT KHSGEVPAVE ETVTSSPGTP ASPCSLIPPW GWPGNTLVAV SIFLLLTGPT   180
YLLFKLSPRV KRIFYQNVPS PAMFFQPLYS VHNGNFQTWM GAHGAGVLLS QDCAGTPQGA   240
LEPCVQEATA LLTCGPARPW KSVALEEEQE GPGTRLPGNL SSEDVLPAGC TEWRVQTLAY   300
LPQEDWAPTS LTRPAPPDSE GSRSSSSSSS SNNNNYCALG CYGGWHLSAL PGNTQSSGPI   360
PALACGLSCD HQGLETQQGV AWVLAGHCQR PGLHEDLQGM LLPSVLSKAR SWTFQPQPQP   420
QPQPQPERTM PRIPTLKNLE DLVTEYHGNF SAWSGVSKGL AESLQPDYSE RLCLVSEIPP   480
KGGALGEGPG ASPCNQHSPY WAPPCYTLKP ET                                 512
```

| SEQ ID NO: 121 | moltype = AA   length = 535 |
| --- | --- |
| FEATURE | Location/Qualifiers |
| REGION | 1..535 |

```
                            note = MISC_FEATURE - DR3/IL9R/cGC-F
source                      1..535
                            mol_type = protein
                            organism = synthetic construct
SEQUENCE: 121
QGGTRSPRCD CAGDFHKKIG LFCCRGCPAG HYLKAPCTEP CGNSTCLVCP QDTFLAWENH    60
HNSECARCQA CDEQASQVAL ENCSAVADTR CGCKPGWFVE CQVSQCVSSS PFYCQPCLDC   120
GALHRHTRLL CSRRDTDCGT CLPGFYEHGD GCVSCPTSTL GSCPERCAAV CGWRQLIPPW   180
GWPGNTLVAV SIFLLLTGPT YLLFKLSPRV KRIFYQNVPS PAMFFQPLYS VHNGNFQTWM   240
GAHGAGVLLS QDCAGTPQGA LEPCVQEATA LLTCGPARPW KSVALEEEQE GPGTRLPGNL   300
SSEDVLPAGC TEWRVQTLAY LPQEDWAPTS LTRPAPPDSE GSRSSSSSSS SNNNNYCALG   360
CYGGWHLSAL PGNTQSSGPI PALACGLSCD HQGLETQQGV AWVLAGHCQR PGLHEDLQGM   420
LLPSVLSKAR SWTFGGGGSG GGGSGGGGSE RTMPRIPTLK NLEDLVTEYH GNFSAWSGVS   480
KGLAESLQPD YSERLCLVSE IPPKGGALGE GPGASPCNQH SPYWAPPCYT LKPET        535

SEQ ID NO: 122              moltype = AA  length = 532
FEATURE                     Location/Qualifiers
REGION                      1..532
                            note = MISC_FEATURE - DR3/IL9R/cGC-S
source                      1..532
                            mol_type = protein
                            organism = synthetic construct
SEQUENCE: 122
QGGTRSPRCD CAGDFHKKIG LFCCRGCPAG HYLKAPCTEP CGNSTCLVCP QDTFLAWENH    60
HNSECARCQA CDEQASQVAL ENCSAVADTR CGCKPGWFVE CQVSQCVSSS PFYCQPCLDC   120
GALHRHTRLL CSRRDTDCGT CLPGFYEHGD GCVSCPTSTL GSCPERCAAV CGWRQLIPPW   180
GWPGNTLVAV SIFLLLTGPT YLLFKLSPRV KRIFYQNVPS PAMFFQPLYS VHNGNFQTWM   240
GAHGAGVLLS QDCAGTPQGA LEPCVQEATA LLTCGPARPW KSVALEEEQE GPGTRLPGNL   300
SSEDVLPAGC TEWRVQTLAY LPQEDWAPTS LTRPAPPDSE GSRSSSSSSS SNNNNYCALG   360
CYGGWHLSAL PGNTQSSGPI PALACGLSCD HQGLETQQGV AWVLAGHCQR PGLHEDLQGM   420
LLPSVLSKAR SWTFQPQPQP QPQPQPERTM PRIPTLKNLE DLVTEYHGNF SAWSGVSKGL   480
AESLQPDYSE RLCLVSEIPP KGGALGEGPG ASPCNQHSPY WAPPCYTLKP ET           532

SEQ ID NO: 123              moltype = AA  length = 595
FEATURE                     Location/Qualifiers
REGION                      1..595
                            note = MISC_FEATURE - TNFRSF1B/IL9R/cGC-F
source                      1..595
                            mol_type = protein
                            organism = synthetic construct
SEQUENCE: 123
LPAQVAFTPY APEPGSTCRL REYYDQTAQM CCSKCSPGQH AKVFCTKTSD TVCDSCEDST    60
YTQLWNWVPE CLSCGSRCSS DQVETQACTR EQNRICTCRP GWYCALSKQE GCRLCAPLRK   120
CRPGFGVARP GTETSDVVCK PCAPGTFSNT TSSTDICRPH QICNVVAIPG NASMDAVCTS   180
TSPTRSMAPG AVHLPQPVST RSQHTQPTPE PSTAPSTSFL LPMGPSPPAE GSTGDLIPPW   240
GWPGNTLVAV SIFLLLTGPT YLLFKLSPRV KRIFYQNVPS PAMFFQPLYS VHNGNFQTWM   300
GAHGAGVLLS QDCAGTPQGA LEPCVQEATA LLTCGPARPW KSVALEEEQE GPGTRLPGNL   360
SSEDVLPAGC TEWRVQTLAY LPQEDWAPTS LTRPAPPDSE GSRSSSSSSS SNNNNYCALG   420
CYGGWHLSAL PGNTQSSGPI PALACGLSCD HQGLETQQGV AWVLAGHCQR PGLHEDLQGM   480
LLPSVLSKAR SWTFGGGGSG GGGSGGGGSE RTMPRIPTLK NLEDLVTEYH GNFSAWSGVS   540
KGLAESLQPD YSERLCLVSE IPPKGGALGE GPGASPCNQH SPYWAPPCYT LKPET        595

SEQ ID NO: 124              moltype = AA  length = 592
FEATURE                     Location/Qualifiers
REGION                      1..592
                            note = MISC_FEATURE - TNFRSF1B/IL9R/cGC-S
source                      1..592
                            mol_type = protein
                            organism = synthetic construct
SEQUENCE: 124
LPAQVAFTPY APEPGSTCRL REYYDQTAQM CCSKCSPGQH AKVFCTKTSD TVCDSCEDST    60
YTQLWNWVPE CLSCGSRCSS DQVETQACTR EQNRICTCRP GWYCALSKQE GCRLCAPLRK   120
CRPGFGVARP GTETSDVVCK PCAPGTFSNT TSSTDICRPH QICNVVAIPG NASMDAVCTS   180
TSPTRSMAPG AVHLPQPVST RSQHTQPTPE PSTAPSTSFL LPMGPSPPAE GSTGDLIPPW   240
GWPGNTLVAV SIFLLLTGPT YLLFKLSPRV KRIFYQNVPS PAMFFQPLYS VHNGNFQTWM   300
GAHGAGVLLS QDCAGTPQGA LEPCVQEATA LLTCGPARPW KSVALEEEQE GPGTRLPGNL   360
SSEDVLPAGC TEWRVQTLAY LPQEDWAPTS LTRPAPPDSE GSRSSSSSSS SNNNNYCALG   420
CYGGWHLSAL PGNTQSSGPI PALACGLSCD HQGLETQQGV AWVLAGHCQR PGLHEDLQGM   480
LLPSVLSKAR SWTFQPQPQP QPQPQPERTM PRIPTLKNLE DLVTEYHGNF SAWSGVSKGL   540
AESLQPDYSE RLCLVSEIPP KGGALGEGPG ASPCNQHSPY WAPPCYTLKP ET           592

SEQ ID NO: 125              moltype = AA  length = 542
FEATURE                     Location/Qualifiers
REGION                      1..542
                            note = MISC_FEATURE - TNFRSF1/IL9R/cGC-F
source                      1..542
                            mol_type = protein
                            organism = synthetic construct
SEQUENCE: 125
```

```
                                           -continued

LVPHLGDREK RDSVCPQGKY IHPQNNSICC TKCHKGTYLY NDCPGPGQDT DCRECESGSF    60
TASENHLRHC LSCSKCRKEM GQVEISSCTV DRDTVCGCRK NQYRHYWSEN LFQCFNCSLC   120
LNGTVHLSCQ EKQNTVCTCH AGFFLRENEC VSCSNCKKSL ECTKLCLPQI ENVKGTEDSG   180
TTLIPPWGWP GNTLVAVSIF LLLTGPTYLL FKLSPRVKRI FYQNVPSPAM FFQPLYSVHN   240
GNFQTWMGAH GAGVLLSQDC AGTPQGALEP CVQEATALLT CGPARPWKSV ALEEEQEGPG   300
TRLPGNLSSE DVLPAGCTEW RVQTLAYLPQ EDWAPTSLTR PAPPDSEGSR SSSSSSSSNN   360
NNYCALGCYG GWHLSALPGN TQSSGPIPAL ACGLSCDHQG LETQQGVAWV LAGHCQRPGL   420
HEDLQGMLLP SVLSKARSWT FGGGGSGGGG SGGGGSERTM PRIPTLKNLE DLVTEYHGNF   480
SAWSGVSKGL AESLQPDYSE RLCLVSEIPP KGGALGEGPG ASPCNQHSPY WAPPCYTLKP   540
ET                                                                 542

SEQ ID NO: 126          moltype = AA   length = 539
FEATURE                 Location/Qualifiers
REGION                  1..539
                        note = MISC_FEATURE - TNFRSF1/IL9R/cGC-S
source                  1..539
                        mol_type = protein
                        organism = synthetic construct
SEQUENCE: 126
LVPHLGDREK RDSVCPQGKY IHPQNNSICC TKCHKGTYLY NDCPGPGQDT DCRECESGSF    60
TASENHLRHC LSCSKCRKEM GQVEISSCTV DRDTVCGCRK NQYRHYWSEN LFQCFNCSLC   120
LNGTVHLSCQ EKQNTVCTCH AGFFLRENEC VSCSNCKKSL ECTKLCLPQI ENVKGTEDSG   180
TTLIPPWGWP GNTLVAVSIF LLLTGPTYLL FKLSPRVKRI FYQNVPSPAM FFQPLYSVHN   240
GNFQTWMGAH GAGVLLSQDC AGTPQGALEP CVQEATALLT CGPARPWKSV ALEEEQEGPG   300
TRLPGNLSSE DVLPAGCTEW RVQTLAYLPQ EDWAPTSLTR PAPPDSEGSR SSSSSSSSNN   360
NNYCALGCYG GWHLSALPGN TQSSGPIPAL ACGLSCDHQG LETQQGVAWV LAGHCQRPGL   420
HEDLQGMLLP SVLSKARSWT FQPQPQPQPQ PQPERTMPRI PTLKNLEDLV TEYHGNFSAW   480
SGVSKGLAES LQPDYSERLC LVSEIPPKGG ALGEGPGASP CNQHSPYWAP PCYTLKPET   539

SEQ ID NO: 127          moltype = AA   length = 473
FEATURE                 Location/Qualifiers
REGION                  1..473
                        note = MISC_FEATURE - BMPR1B/IL9R/cGC-F
source                  1..473
                        mol_type = protein
                        organism = synthetic construct
SEQUENCE: 127
KKEDGESTAP TPRPKVLRCK CHHHCPEDSV NNICSTDGYC FTMIEEDDSG LPVVTSGCLG    60
LEGSDFQCRD TPIPHQRRSI ECCTERNECN KDLHPTLPPL KNRDFVDGPI HHRLIPPWGW   120
PGNTLVAVSI FLLLTGPTYL LFKLSPRVKR IFYQNVPSPA MFFQPLYSVH NGNFQTWMGA   180
HGAGVLLSQD CAGTPQGALE PCVQEATALL TCGPARPWKS VALEEEQEGP GTRLPGNLSS   240
EDVLPAGCTE WRVQTLAYLP QEDWAPTSLT RPAPPDSEGS RSSSSSSSSN NNNYCALGCY   300
GGWHLSALPG NTQSSGPIPA LACGLSCDHQ GLETQQGVAW VLAGHCQRPG LHEDLQGMLL   360
PSVLSKARSW TFGGGGSGGG GSGGGGSERT MPRIPTLKNL EDLVTEYHGN FSAWSGVSKG   420
LAESLQPDYS ERLCLVSEIP PKGGALGEGP GASPCNQHSP YWAPPCYTLK PET          473

SEQ ID NO: 128          moltype = AA   length = 470
FEATURE                 Location/Qualifiers
REGION                  1..470
                        note = MISC_FEATURE - BMPR1B/IL9R/cGC-S
source                  1..470
                        mol_type = protein
                        organism = synthetic construct
SEQUENCE: 128
KKEDGESTAP TPRPKVLRCK CHHHCPEDSV NNICSTDGYC FTMIEEDDSG LPVVTSGCLG    60
LEGSDFQCRD TPIPHQRRSI ECCTERNECN KDLHPTLPPL KNRDFVDGPI HHRLIPPWGW   120
PGNTLVAVSI FLLLTGPTYL LFKLSPRVKR IFYQNVPSPA MFFQPLYSVH NGNFQTWMGA   180
HGAGVLLSQD CAGTPQGALE PCVQEATALL TCGPARPWKS VALEEEQEGP GTRLPGNLSS   240
EDVLPAGCTE WRVQTLAYLP QEDWAPTSLT RPAPPDSEGS RSSSSSSSSN NNNYCALGCY   300
GGWHLSALPG NTQSSGPIPA LACGLSCDHQ GLETQQGVAW VLAGHCQRPG LHEDLQGMLL   360
PSVLSKARSW TFQPQPQPQP QPQPERTMPR IPTLKNLEDL VTEYHGNFSA WSGVSKGLAE   420
SLQPDYSERL CLVSEIPPKG GALGEGPGAS PCNQHSPYWA PPCYTLKPET              470

SEQ ID NO: 129          moltype = AA   length = 489
FEATURE                 Location/Qualifiers
REGION                  1..489
                        note = MISC_FEATURE - BMPR1A/IL9R/cGC-F
source                  1..489
                        mol_type = protein
                        organism = synthetic construct
SEQUENCE: 129
QNLDSMLHGT GMKSDSDQKK SENGVTLAPE DTLPFLKCYC SGHCPDDAIN NTCITNGHCF    60
AIIEEDDQGE TTLASGCMKY EGSDFQCKDS PKAQLRRTIE CCRTNLCNQY LQPTLPPVVI   120
GPFFDGSIRL IPPWGWPGNT LVAVSIFLLL TGPTYLLFKL SPRVKRIFYQ NVPSPAMFFQ   180
PLYSVHNGNF QTWMGAHGAG VLLSQDCAGT PQGALEPCVQ EATALLTCGP ARPWKSVALE   240
EEQEGPGTRL PGNLSSEDVL PAGCTEWRVQ TLAYLPQEDW APTSLTRPAP PDSEGSRSSS   300
SSSSSNNNNY CALGCYGGWH LSALPGNTQS SGPIPALACG LSCDHQGLET QQGVAWVLAG   360
HCQRPGLHED LQGMLLPSVL SKARSWTFGG GGSGGGGSGG GGSERTMPRI PTLKNLEDLV   420
TEYHGNFSAW SGVSKGLAES LQPDYSERLC LVSEIPPKGG ALGEGPGASP CNQHSPYWAP   480
```

```
PCYTLKPET                                                                 489

SEQ ID NO: 130          moltype = AA  length = 486
FEATURE                 Location/Qualifiers
REGION                  1..486
                        note = MISC_FEATURE - BMPR1A/IL9R/cGC-S
source                  1..486
                        mol_type = protein
                        organism = synthetic construct
SEQUENCE: 130
QNLDSMLHGT GMKSDSDQKK SENGVTLAPE DTLPFLKCYC SGHCPDDAIN NTCITNGHCF   60
AIIEEDDQGE TTLASGCMKY EGSDFQCKDS PKAQLRRTIE CCRTNLCNQY LQPTLPPVVI  120
GPFFDGSIRL IPPWGWPGNT LVAVSIFLLL TGPTYLLFKL SPRVKRIFYQ NVPSPAMFFQ  180
PLYSVHNGNF QTWMGAHGAG VLLSQDCAGT PQGALEPCVQ EATALLTCGP ARPWKSVALE  240
EEQEGPGTRL PGNLSSEDVL PAGCTEWRVQ TLAYLPQEDW APTSLTRPAP PDSEGSRSSS  300
SSSSSNNNNY CALGCYGGWH LSALPGNTQS SGPIPALACG LSCDHQGLET QQGVAWVLAG  360
HCQRPGLHED LQGMLLPSVL SKARSWTFQP QPQPQPQPQP ERTMPRIPTL KNLEDLVTEY  420
HGNFSAWSGV SKGLAESLQP DYSERLCLVS EIPPKGGALG EGPGASPCNQ HSPYWAPPCY  480
TLKPET                                                              486

SEQ ID NO: 131          moltype = AA  length = 484
FEATURE                 Location/Qualifiers
REGION                  1..484
                        note = MISC_FEATURE - BMPR2/IL9R/cGC-F
source                  1..484
                        mol_type = protein
                        organism = synthetic construct
SEQUENCE: 131
SQNQERLCAF KDPYQQDLGI GESRISHENG TILCSKGSTC YGLWEKSKGD INLVKQGCWS   60
HIGDPQECHY EECVVTTTPP SIQNGTYRFC CCSTDLCNVN FTENFPPPDT TPLSPPHSFN  120
RDETLIPPWG WPGNTLVAVS IFLLLTGPTY LLFKLSPRVK RIFYQNVPSP AMFFQPLYSV  180
HNGNFQTWMG AHGAGVLLSQ DCAGTPQGAL EPCVQEATAL LTCGPARPWK SVALEEEQEG  240
PGTRLPGNLS SEDVLPAGCT EWRVQTLAYL PQEDWAPTSL TRPAPPDSEG SRSSSSSSSS  300
NNNNYCALGC YGGWHLSALP GNTQSSGPIP ALACGLSCDH QGLETQQGVA WVLAGHCQRP  360
GLHEDLQGML LPSVLSKARS WTFGGGGSGG GGSGGGGSER TMPRIPTLKN LEDLVTEYHG  420
NFSAWSGVSK GLAESLQPDY SERLCLVSEI PPKGGALGEG PGASPCNQHS PYWAPPCYTL  480
KPET                                                                484

SEQ ID NO: 132          moltype = AA  length = 481
FEATURE                 Location/Qualifiers
REGION                  1..481
                        note = MISC_FEATURE - BMPR2/IL9R/cGC-S
source                  1..481
                        mol_type = protein
                        organism = synthetic construct
SEQUENCE: 132
SQNQERLCAF KDPYQQDLGI GESRISHENG TILCSKGSTC YGLWEKSKGD INLVKQGCWS   60
HIGDPQECHY EECVVTTTPP SIQNGTYRFC CCSTDLCNVN FTENFPPPDT TPLSPPHSFN  120
RDETLIPPWG WPGNTLVAVS IFLLLTGPTY LLFKLSPRVK RIFYQNVPSP AMFFQPLYSV  180
HNGNFQTWMG AHGAGVLLSQ DCAGTPQGAL EPCVQEATAL LTCGPARPWK SVALEEEQEG  240
PGTRLPGNLS SEDVLPAGCT EWRVQTLAYL PQEDWAPTSL TRPAPPDSEG SRSSSSSSSS  300
NNNNYCALGC YGGWHLSALP GNTQSSGPIP ALACGLSCDH QGLETQQGVA WVLAGHCQRP  360
GLHEDLQGML LPSVLSKARS WTFQPQPQPQ PQPQPERTMP RIPTLKNLED LVTEYHGNFS  420
AWSGVSKGLA ESLQPDYSER LCLVSEIPPK GGALGEGPGA SPCNQHSPYW APPCYTLKPE  480
T                                                                   481

SEQ ID NO: 133          moltype = AA  length = 963
FEATURE                 Location/Qualifiers
REGION                  1..963
                        note = MISC_FEATURE - CSF3R/IL9R/cGC-F
source                  1..963
                        mol_type = protein
                        organism = synthetic construct
SEQUENCE: 133
ECGHISVSAP IVHLGDPITA SCIIKQNCSH LDPEPQILWR LGAELQPGGR QQRLSDGTQE   60
SIITLPHLNH TQAFLSCCLN WGNSLQILDQ VELRAGYPPA IPHNLSCLMN LTTSSLICQW  120
EPGPETHLPT SFTLKSFKSR GNCQTQGDSI LDCVPKDGQS HCCIPRKHLL LYQNMGIWVQ  180
AENALGTSMS PQLCLDPMDV VKLEPPMLRT MDPSPEAAPP QAGCLQLCWE PWQPGLHINQ  240
KCELRHKPQR GEASWALVGP LPLEALQYEL CGLLPATAYT LQIRCIRWPL PGHWSDWSPS  300
LELRTTERAP TVRLDTWWRQ RQLDPRTVQL FWKPVPLEED SGRIQGYVVS WRPSGQAGAI  360
LPLCNTTELS CTFHLPSEAQ EVALVAYNSA GTSRPTPVVF SESRGPALTR LHAMARDPHS  420
LWVGWEPPNP WPQGYVIEWG LGPPSASNSN KTWRMEQNGR ATGFLLKENI RPFQLYEIIV  480
TPLYQDTMGP SQHVYAYSQE MAPSHAPELH LKHIGKTWAQ LEWVPEPPEL GKSPLTHYTI  540
FWTNAQNQSF SAILNASSRG FVLHGLEPAS LYHIHLMAAS QAGATNSTVL TLMTLTPEGS  600
ELHLIPPWGW PGNTLVAVSI FLLLTGPTYL LFKLSPRVKR IFYQNVPSPA MFFQPLYSVH  660
NGNFQTWMGA HGAGVLLSQD CAGTPQGALE PCVQEATALL TCGPARPWKS VALEEEQEGP  720
GTRLPGNLSS EDVLPAGCTE WRVQTLAYLP QEDWAPTSLT RPAPPDSEGS RSSSSSSSSN  780
NNNYCALGCY GGWHLSALPG NTQSSGPIPA LACGLSCDHQ GLETQQGVAW VLAGHCQRPG  840
LHEDLQGMLL PSVLSKARSW TFGGGGSGGG GSGGGGSERT MPRIPTLKNL EDLVTEYHGN  900
```

```
FSAWSGVSKG LAESLQPDYS ERLCLVSEIP PKGGALGEGP GASPCNQHSP YWAPPCYTLK  960
PET                                                                963

SEQ ID NO: 134          moltype = AA  length = 960
FEATURE                 Location/Qualifiers
REGION                  1..960
                        note = MISC_FEATURE - CSF3R/IL9R/cGC-S
source                  1..960
                        mol_type = protein
                        organism = synthetic construct
SEQUENCE: 134
ECGHISVSAP IVHLGDPITA SCIIKQNCSH LDPEPQILWR LGAELQPGGR QQRLSDGTQE   60
SIITLPHLNH TQAFLSCCLN WGNSLQILDQ VELRAGYPPA IPHNLSCLMN LTTSSLICQW  120
EPGPETHLPT SFTLKSFKSR GNCQTQGDSI LDCVPKDGQS HCCIPRKHLL LYQNMGIWVQ  180
AENALGTSMS PQLCLDPMDV VKLEPPMLRT MDPSPEAAPP QAGCLQLCWE PWQPGLHINQ  240
KCELRHKPQR GEASWALVGP LPLEALQYEL CGLLPATAYT LQIRCIRWPL PGHWSDWSPS  300
LELRTTERAP TVRLDTWWRQ RQLDPRTVQL FWKPVPLEEG SGRIQGYVVS WRPSGQAGAI  360
LPLCNTTELS CTFHLPSEAQ EVALVAYNSA GTSRPTPVVF SESRGPALTR LHAMARDPHS  420
LWVGWEPPNP WPQGYVIEWG LGPPSASNSN KTWRMEQNGR ATGFLLKENI RPFQLYEIIV  480
TPLYQDTMGP SQHVYAYSQE MAPSHAPELH LKHIGKTWAQ LEWVPEPPEL GKSPLTHYTI  540
FWTNAQNQSF SAILNASSRG FVLHGLEPAS LYHIHLMAAS QAGATNSTVL TLMTLTPEGS  600
ELHLIPPWGW PGNTLVAVSI FLLLTGPTYL LFKLSPRVKR IFYQNVPSPA MFFQPLYSVH  660
NGNFQTWMGA HGAGVLLSQD CAGTPQGALE PCVQEATALL TCGPARPWKS VALEEEQEGP  720
GTRLPGNLSS EDVLPAGCTE WRVQTLAYLP QEDWAPTSLT RPAPPDSEGS RSSSSSSSSN  780
NNNYCALGCY GGWHLSALPG NTQSSGPIPA LACGLSCDHQ GLETQQGVAW VLAGHCQRPG  840
LHEDLQGMLL PSVLSKARSW TFQPQPQPQP QPQPERTMPR IPTLKNLEDL VTEYHGNFSA  900
WSGVSKGLAE SLQPDYSERL CLVSEIPPKG GALGEGPGAS PCNQHSPYWA PPCYTLKPET  960

SEQ ID NO: 135          moltype = AA  length = 858
FEATURE                 Location/Qualifiers
REGION                  1..858
                        note = MISC_FEATURE - CSF1R/IL9R/cGC-F
source                  1..858
                        mol_type = protein
                        organism = synthetic construct
SEQUENCE: 135
IPVIEPSVPE LVVKPGATVT LRCVGNGSVE WDGPPSPHWT LYSDGSSSIL STNNATFQNT   60
GTYRCTEPGD PLGGSAAIHL YVKDPARPWN VLAQEVVVFE DQDALLPCLL TDPVLEAGVS  120
LVRVRGRPLM RHTNYSFSPW HGFTIHRAKF IQSQDYQCSA LMGGRKVMSI SIRLKVQKVI  180
PGPPALTLVP AELVRIRGEA AQIVCSASSV DVNFDVFLQH NNTKLAIPQQ SDFHNNRYQK  240
VLTLNLDQVD FQHAGNYSCV ASNVQGKHST SMFFRVVESA YLNLSSEQNL IQEVTVGEGL  300
NLKVMVEAYP GLQGFNWTYL GPFSDHQPEP KLANATTKDT YRHTFTLSLP RLKPSEAGRY  360
SFLARNPGGW RALTFELTLR YPPEVSVIWT FINGSGTLLC AASGYPQPNV TWLQCSGHTD  420
RCDEAQVLQV WDDPYPEVLS QEPFHKVTVQ SLLTVETLEH NQTYECRAHN SVGSGSWAFI  480
PISAGAHTHP PDEFLFTPLI PPWGWPGNTL VAVSIFLLLT GPTYLLFKLS PRVKRIFYQN  540
VPSPAMFFQP LYSVHNGNFQ TWMGAHGAGV LLSQDCAGTP QGALEPCVQE ATALLTCGPA  600
RPWKSVALEE EQEGPGTRLP GNLSSEDVLP AGCTEWRVQT LAYLPQEDWA PTSLTRPAPP  660
DSEGSRSSSS SSSSNNNYC ALGCYGGWHL SALPGNTQSS GPIPALACGL SCDHQGLETQ  720
QGVAWVLAGH CQRPGLHEDL QGMLLPSVLS KARSWTFGGG GSGGGGSGGG GSERTMPRIP  780
TLKNLEDLVT EYHGNFSAWS GVSKGLAESL QPDYSERLCL VSEIPPKGGA LGEGPGASPC  840
NQHSPYWAPP CYTLKPET                                                858

SEQ ID NO: 136          moltype = AA  length = 855
FEATURE                 Location/Qualifiers
REGION                  1..855
                        note = MISC_FEATURE - CSF1R/IL9R/cGC-S
source                  1..855
                        mol_type = protein
                        organism = synthetic construct
SEQUENCE: 136
IPVIEPSVPE LVVKPGATVT LRCVGNGSVE WDGPPSPHWT LYSDGSSSIL STNNATFQNT   60
GTYRCTEPGD PLGGSAAIHL YVKDPARPWN VLAQEVVVFE DQDALLPCLL TDPVLEAGVS  120
LVRVRGRPLM RHTNYSFSPW HGFTIHRAKF IQSQDYQCSA LMGGRKVMSI SIRLKVQKVI  180
PGPPALTLVP AELVRIRGEA AQIVCSASSV DVNFDVFLQH NNTKLAIPQQ SDFHNNRYQK  240
VLTLNLDQVD FQHAGNYSCV ASNVQGKHST SMFFRVVESA YLNLSSEQNL IQEVTVGEGL  300
NLKVMVEAYP GLQGFNWTYL GPFSDHQPEP KLANATTKDT YRHTFTLSLP RLKPSEAGRY  360
SFLARNPGGW RALTFELTLR YPPEVSVIWT FINGSGTLLC AASGYPQPNV TWLQCSGHTD  420
RCDEAQVLQV WDDPYPEVLS QEPFHKVTVQ SLLTVETLEH NQTYECRAHN SVGSGSWAFI  480
PISAGAHTHP PDEFLFTPLI PPWGWPGNTL VAVSIFLLLT GPTYLLFKLS PRVKRIFYQN  540
VPSPAMFFQP LYSVHNGNFQ TWMGAHGAGV LLSQDCAGTP QGALEPCVQE ATALLTCGPA  600
RPWKSVALEE EQEGPGTRLP GNLSSEDVLP AGCTEWRVQT LAYLPQEDWA PTSLTRPAPP  660
DSEGSRSSSS SSSSNNNYC ALGCYGGWHL SALPGNTQSS GPIPALACGL SCDHQGLETQ  720
QGVAWVLAGH CQRPGLHEDL QGMLLPSVLS KARSWTFQPQ PQPQPQPQPE RTMPRIPTLK  780
NLEDLVTEYH GNFSAWSGVS KGLAESLQPD YSERLCLVSE IPPKGGALGE GPGASPCNQH  840
SPYWAPPCYT LKPET                                                   855

SEQ ID NO: 137          moltype = AA  length = 1092
FEATURE                 Location/Qualifiers
REGION                  1..1092
```

```
                        note = MISC_FEATURE - VEGF Receptor 1/IL9R/cGC-F
source                  1..1092
                        mol_type = protein
                        organism = synthetic construct
SEQUENCE: 137
SKLKDPELSL KGTQHIMQAG QTLHLQCRGE AAHKWSLPEM VSKESERLSI TKSACGRNGK    60
QFCSTLTLNT AQANHTGFYS CKYLAVPTSK KKETESAIYI FISDTGRPFV EMYSEIPEII   120
HMTEGRELVI PCRVTSPNIT VTLKKFPLDT LIPDGKRIIW DSRKGFIISN ATYKEIGLLT   180
CEATVNGHLY KTNYLTHRQT NTIIDVQIST PRPVKLLRGH TLVLNCTATT PLNTRVQMTW   240
SYPDEKNKRA SVRRRIDQSN SHANIFYSVL TIDKMQNKDK GLYTCRVRSG PSFKSVNTSV   300
HIYDKAFITV KHRKQQVLET VAGKRSYRLS MKVKAFPSPE VVWLKDGLPA TEKSARYLTR   360
GYSLIIKDVT EEDAGNYTIL LSIKQSNVFK NLTATLIVNV KPQIYEKAVS SFPDPALYPL   420
GSRQILTCTA YGIPQPTIKW FWHPCNHNHS EARCDFCSNN EESFILDADS NMGNRIESIT   480
QRMAIIEGKN KMASTLVVAD SRISGIYICI ASNKVGTVGR NISFYITDVP NGFHVNLEKM   540
PTEGEDLKLS CTVNKFLYRD VTWILLRTVN NRTMHYSISK QKMAITKEHS ITLNLTIMNV   600
SLQDSGTYAC RARNVYTGEE ILQKKEITIR DQEAPYLLRN LSDHTVAISS STTLDCHANG   660
VPEPQITWFK NNHKIQQEPG IILGPGSSTL FIERVTEEDE GVYHCKATNQ KGSVESSAYL   720
TVQGTSDKSN LELIPPWGWP GNTLVAVSIF LLLTGPTYLL FKLSPRVKRI FYQNVPSPAM   780
FFQPLYSVHN GNFQTWMGAH GAGVLLSQDC AGTPQGALEP CVQEATALLT CGPARPWKSV   840
ALEEEQEGPG TRLPGNLSSE DVLPAGCTEW RVQTLAYLPQ EDWAPTSLTR PAPPDSEGSR   900
SSSSSSSSNN NNYCALGCYG GWHLSALPGN TQSSGPIPAL ACGLSCDHQG LETQQGVAWV   960
LAGHCQRPGL HEDLQGMLLP SVLSKARSWT FGGGGSGGGG SGGGGSERTM PRIPTLKNLE  1020
DLVTEYHGNF SAWSGVSKGL AESLQPDYSE RLCLVSEIPP KGGALGEGPG ASPCNQHSPY  1080
WAPPCYTLKP ET                                                     1092

SEQ ID NO: 138          moltype = AA   length = 1089
FEATURE                 Location/Qualifiers
REGION                  1..1089
                        note = MISC_FEATURE - VEGF Receptor 1/IL9R/cGC-S
source                  1..1089
                        mol_type = protein
                        organism = synthetic construct
SEQUENCE: 138
SKLKDPELSL KGTQHIMQAG QTLHLQCRGE AAHKWSLPEM VSKESERLSI TKSACGRNGK    60
QFCSTLTLNT AQANHTGFYS CKYLAVPTSK KKETESAIYI FISDTGRPFV EMYSEIPEII   120
HMTEGRELVI PCRVTSPNIT VTLKKFPLDT LIPDGKRIIW DSRKGFIISN ATYKEIGLLT   180
CEATVNGHLY KTNYLTHRQT NTIIDVQIST PRPVKLLRGH TLVLNCTATT PLNTRVQMTW   240
SYPDEKNKRA SVRRRIDQSN SHANIFYSVL TIDKMQNKDK GLYTCRVRSG PSFKSVNTSV   300
HIYDKAFITV KHRKQQVLET VAGKRSYRLS MKVKAFPSPE VVWLKDGLPA TEKSARYLTR   360
GYSLIIKDVT EEDAGNYTIL LSIKQSNVFK NLTATLIVNV KPQIYEKAVS SFPDPALYPL   420
GSRQILTCTA YGIPQPTIKW FWHPCNHNHS EARCDFCSNN EESFILDADS NMGNRIESIT   480
QRMAIIEGKN KMASTLVVAD SRISGIYICI ASNKVGTVGR NISFYITDVP NGFHVNLEKM   540
PTEGEDLKLS CTVNKFLYRD VTWILLRTVN NRTMHYSISK QKMAITKEHS ITLNLTIMNV   600
SLQDSGTYAC RARNVYTGEE ILQKKEITIR DQEAPYLLRN LSDHTVAISS STTLDCHANG   660
VPEPQITWFK NNHKIQQEPG IILGPGSSTL FIERVTEEDE GVYHCKATNQ KGSVESSAYL   720
TVQGTSDKSN LELIPPWGWP GNTLVAVSIF LLLTGPTYLL FKLSPRVKRI FYQNVPSPAM   780
FFQPLYSVHN GNFQTWMGAH GAGVLLSQDC AGTPQGALEP CVQEATALLT CGPARPWKSV   840
ALEEEQEGPG TRLPGNLSSE DVLPAGCTEW RVQTLAYLPQ EDWAPTSLTR PAPPDSEGSR   900
SSSSSSSSNN NNYCALGCYG GWHLSALPGN TQSSGPIPAL ACGLSCDHQG LETQQGVAWV   960
LAGHCQRPGL HEDLQGMLLP SVLSKARSWT FQPQPQPQPQ PQPERTMPRI PTLKNLEDLV  1020
TEYHGNFSAW SGVSKGLAES LQPDYSERLC LVSEIPPKGG ALGEGPGASP CNQHSPYWAP  1080
PCYTLKPET                                                         1089

SEQ ID NO: 139          moltype = AA   length = 1105
FEATURE                 Location/Qualifiers
REGION                  1..1105
                        note = MISC_FEATURE - VEGF Receptor 2/IL9R/cGC-F
source                  1..1105
                        mol_type = protein
                        organism = synthetic construct
SEQUENCE: 139
ASVGLPSVSL DLPRLSIQKD ILTIKANTTL QITCRGQRDL DWLWPNNQSG SEQRVEVTEC    60
SDGLFCKTLT IPKVIGNDTG AYKCFYRETD LASVIYVYVQ DYRSPFIASV SDQHGVVYIT   120
ENKNKTVVIP CLGSISNLNV SLCARYPEKR FVPDGNRISW DSKKGFTIPS YMISYAGMVF   180
CEAKINDESY QSIMYIVVVV GYRIYDVVLS PSHGIELSVG EKLVLNCTAR TELNVGIDFN   240
WEYPSSKHQH KKLVNRDLKT QSGSEMKKFL STLTIDGVTR SDQGLYTCAA SSGLMTKKNS   300
TFVRVHEKPF VAFGSGMESL VEATVGERVR IPAKYLGYPP PEIKWYKNGI PLESNHTIKA   360
GHVLTIMEVS ERDTGNYTVI LTNPISKEKQ SHVVSLVVYV PPQIGEKSLI SPVDSYQYGT   420
TQTLTCTVYA IPPPHHIHWY WQLEEECANE PSQAVSVTNP YPCEEWRSVE DFQGGNKIEV   480
NKNQFALIEG KNKTVSTLVI QAANVSALYK CEAVNKVGRG ERVISFHVTR GPEITLQPDM   540
QPTEQESVSL WCTADRSTFE NLTWYKLGPQ PLPIHVGELP TPVCKNLDTL WKLNATMFSN   600
STNDILIMEL KNASLQDGD YVCLAQDRKT KKRHCVVRQL TVLERVAPTI TGNLENQTTS    660
IGESIEVSCT ASGNPPPQIM WFKDNETLVE DSGIVLKDGN RNLTIRRVRK EDEGLYTCQA   720
CSVLGCAKVE AFFIIEGAQE KTNLELIPPW GWPGNTLVAV SIFLLLTGPT YLLFKLSPRV   780
KRIFYQNVPS PAMFFQPLYS VHNGNFQTWM GAHGAGVLLS QDCAGTPQGA LEPCVQEATA   840
LLTCGPARPW KSVALEEEQE GPGTRLPGNL SSEDVLPAGC TEWRVQTLAY LPQEDWAPTS   900
LTRPAPPDSE GSRSSSSSSS SNNNNYCALG CYGGWHLSAL PGNTQSSGPI PALACGLSCD   960
HQGLETQQGV AWVLAGHCQR PGLHEDLQGM LLPSVLSKAR SWTFGGGGSG GGGSGGGGSE  1020
RTMPRIPTLK NLEDLVTEYH GNFSAWSGVS KGLAESLQPD YSERLCLVSE IPPKGGALGE  1080
```

```
GPGASPCNQH SPYWAPPCYT LKPET                                            1105

SEQ ID NO: 140          moltype = AA   length = 1102
FEATURE                 Location/Qualifiers
REGION                  1..1102
                        note = MISC_FEATURE - VEGF Receptor 2/IL9R/cGC-S
source                  1..1102
                        mol_type = protein
                        organism = synthetic construct
SEQUENCE: 140
ASVGLPSVSL DLPRLSIQKD ILTIKANTTL QITCRGQRDL DWLWPNNQSG SEQRVEVTEC    60
SDGLFCKTLT IPKVIGNDTG AYKCFYRETD LASVIYVYVQ DYRSPFIASV SDQHGVVYIT   120
ENKNKTVVIP CLGSISNLNV SLCARYPEKR FVPDGNRISW DSKKGFTIPS YMISYAGMVF   180
CEAKINDESY QSIMYIVVVV GYRIYDVVLS PSHGIELSVG EKLVLNCTAR TELNVGIDFN   240
WEYPSSKHQH KKLVNRDLKT QSGSEMKKFL STLTIDGVTR SDQGLYTCAA SSGLMTKKNS   300
TFVRVHEKPF VAFGSGMESL VEATVGERVR IPAKYLGYPP PEIKWYKNGI PLESNHTIKA   360
GHVLTIMEVS ERDTGNYTVI LTNPISKEKQ SHVVSLVVYV PPQIGEKSLI SPVDSYQYGT   420
TQTLTCTVYA IPPPHHIHWY WQLEEECANE PSQAVSVTNP YPCEEWRSVE DFQGGNKIEV   480
NKNQFALIEG KNKTVSTLVI QAANVSALYK CEAVNKVGRG ERVISFHVTR GPEITLQPDM   540
QPTEQESVSL WCTADRSTFE NLTWYKLGPQ PLPIHVGELP TPVCKNLDTL WKLNATMFSN   600
STNDILIMEL KNASLQDQGD YVCLAQDRKT KKRHCVVRQL TVLERVAPTI TGNLENQTTS   660
IGESIEVSCT ASGNPPPQIM WFKDNETLVE DSGIVLKDGN RNLTIRRVRK EDEGLYTCQA   720
CSVLGCAKVE AFFIIEGAQE KTNLELIPPW GWPGNTLVAV SIFLLLTGPT YLLFKLSPRV   780
KRIFYQNVPS PAMFFQPLYS VHNGNFQTWM GAHGAGVLLS QDCAGTPQGA LEPCVQEATA   840
LLTCGPARPW KSVALEEEQE GPGTRLPGNL SSEDVLPAGC TEWRVQTLAY LPQEDWAPTS   900
LTRPAPPDSE GSRSSSSSSS SNNNNYCALG CYGGWHLSAL PGNTQSSGPI PALACGLSCD   960
HQGLETQQGV AWVLAGHCQR PGLHEDLQGM LLPSVLSKAR SWTFQPQPQP QPQPQPERTM  1020
PRIPTLKNLE DLVTEYHGNF SAWSGVSKGL AESLQPDYSE RLCLVSEIPP KGGALGEGPG  1080
ASPCNQHSPY WAPPCYTLKP ET                                          1102

SEQ ID NO: 141          moltype = AA   length = 1108
FEATURE                 Location/Qualifiers
REGION                  1..1108
                        note = MISC_FEATURE - VEGF Receptor 3/IL9R/cGC-S
source                  1..1108
                        mol_type = protein
                        organism = synthetic construct
SEQUENCE: 141
YSMTPPTLNI TEESHVIDTG DSLSISCRGQ HPLEWAWPGA QEAPATGDKD SEDTGVVRDC    60
EGTDARPYCK VLLLHEVHAN DTGSYVCYYK YIKARIEGTT AASSYVFVRD FEQPFINKPD   120
TLLVNRKDAM WVPCLVSIPG LNVTLRSQSS VLWPDGQEVV WDDRRGMLVS TPLLHDALYL   180
QCETTWGDQD FLSNPFLVHI TGNELYDIQL LPRKSLELLV GEKLVLNCTV WAEFNSGVTF   240
DWDYPGKQAE RGKWVPERRS QQTHTELSSI LTIHNVSQHD LGSYVCKANN GIQRFRESTE   300
VIVHENPFIS VEWLKGPILE ATAGDELVKL PVKLAAYPPP EFQWYKDGKA LSGRHSPHAL   360
VLKEVTEAST GTYTLALWNS AAGLRRNISL ELVVNVPPQI HEKEASSPSI YSRHSRQALT   420
CTAYGVPLPL SIQWHWRPWT PCKMFAQRSL RRRQQQDLMP QCRDWRAVTT QDAVNPIESL   480
DTWTEFVEGK NKTVSKLVIQ NANVSAMYKC VVSNKVGQDE RLIYFYVTTI PDGFTIESKP   540
SEELLEGQPV LLSCQADSYK YEHLRWYRLN LSTLHDAHGN PLLLDCKNVH LFATPLAASL   600
EEVAPGRHA TLSLSIPRVA PEHEGHYVCE VQDRRSHDKH CHKKYLSVQA LEAPRLTQNL   660
TDLLVNVSDS LEMQCLVAGA HAPSIVWYKD ERLLEEKSGV DLADSNQKLS IQRVREEDAG   720
RYLCSVCNAK GCVNSSASVA VEGSEDKGSM ELIPPWGWPG NTLVAVSIFL LLTGPTYLLF   780
KLSPRVKRIF YQNVPSPAMF FQPLYSVHNG NFQTWMGAHG AGVLLSQDCA GTPQGALEPC   840
VQEATALLTC GPARPWKSVA LEEEQEGPGT RLPGNLSSED VLPAGCTEWR VQTLAYLPQE   900
DWAPTSLTRP APPDSEGSRS SSSSSSSSNN NYCALGCYGG WHLSALPGNT QSSGPIPALA   960
CGLSCDHQGL ETQQGVAWVL AGHCQRPGLH EDLQGMLLPS VLSKARSWTF QPQPQPQPQP  1020
QPERTMPRIP TLKNLEDLVT EYHGNFSAWS GVSKGLAESL QPDYSERLCL VSEIPPKGGA  1080
LGEGPGASPC NQHSPYWAPP CYTLKPET                                    1108

SEQ ID NO: 142          moltype = AA   length = 1111
FEATURE                 Location/Qualifiers
REGION                  1..1111
                        note = MISC_FEATURE - VEGF Receptor 3/IL9R/cGC-F
source                  1..1111
                        mol_type = protein
                        organism = synthetic construct
SEQUENCE: 142
YSMTPPTLNI TEESHVIDTG DSLSISCRGQ HPLEWAWPGA QEAPATGDKD SEDTGVVRDC    60
EGTDARPYCK VLLLHEVHAN DTGSYVCYYK YIKARIEGTT AASSYVFVRD FEQPFINKPD   120
TLLVNRKDAM WVPCLVSIPG LNVTLRSQSS VLWPDGQEVV WDDRRGMLVS TPLLHDALYL   180
QCETTWGDQD FLSNPFLVHI TGNELYDIQL LPRKSLELLV GEKLVLNCTV WAEFNSGVTF   240
DWDYPGKQAE RGKWVPERRS QQTHTELSSI LTIHNVSQHD LGSYVCKANN GIQRFRESTE   300
VIVHENPFIS VEWLKGPILE ATAGDELVKL PVKLAAYPPP EFQWYKDGKA LSGRHSPHAL   360
VLKEVTEAST GTYTLALWNS AAGLRRNISL ELVVNVPPQI HEKEASSPSI YSRHSRQALT   420
CTAYGVPLPL SIQWHWRPWT PCKMFAQRSL RRRQQQDLMP QCRDWRAVTT QDAVNPIESL   480
DTWTEFVEGK NKTVSKLVIQ NANVSAMYKC VVSNKVGQDE RLIYFYVTTI PDGFTIESKP   540
SEELLEGQPV LLSCQADSYK YEHLRWYRLN LSTLHDAHGN PLLLDCKNVH LFATPLAASL   600
EEVAPGRHA TLSLSIPRVA PEHEGHYVCE VQDRRSHDKH CHKKYLSVQA LEAPRLTQNL   660
TDLLVNVSDS LEMQCLVAGA HAPSIVWYKD ERLLEEKSGV DLADSNQKLS IQRVREEDAG   720
RYLCSVCNAK GCVNSSASVA VEGSEDKGSM ELIPPWGWPG NTLVAVSIFL LLTGPTYLLF   780
```

```
KLSPRVKRIF YQNVPSPAMF FQPLYSVHNG NFQTWMGAHG AGVLLSQDCA GTPQGALEPC    840
VQEATALLTC GPARPWKSVA LEEEQEGPGT RLPGNLSSED VLPAGCTEWR VQTLAYLPQE    900
DWAPTSLTRP APPDSEGSRS SSSSSSSNNN NYCALGCYGG WHLSALPGNT QSSGPIPALA    960
CGLSCDHQGL ETQQGVAWVL AGHCQRPGLH EDLQGMLLPS VLSKARSWTF GGGGSGGGGS   1020
GGGGSERTMP RIPTLKNLED LVTEYHGNFS AWSGVSKGLA ESLQPDYSER LCLVSEIPPK   1080
GGALGEGPGA SPCNQHSPYW APPCYTLKPE T                                 1111

SEQ ID NO: 143          moltype = AA  length = 463
FEATURE                 Location/Qualifiers
REGION                  1..463
                        note = MISC_FEATURE - Activin R1A ectodomain/IL9R/cGC-F
source                  1..463
                        mol_type = protein
                        organism = synthetic construct
SEQUENCE: 143
MEDEKPKVNP KLYMCVCEGL SCGNEDHCEG QQCFSSLSIN DGFHVYQKGC FQVYEQGKMT    60
CKTPPSPGQA VECCQGDWCN RNITAQLPTK GKSFPGTQNF HLELIPPWGW PGNTLVAVSI   120
FLLLTGPTYL LFKLSPRVKR IFYQNVPSPA MFFQPLYSVH NGNFQTWMGA HGAGVLLSQD   180
CAGTPQGALE PCVQEATALL TCGPARPWKS VALEEEQEGP GTRLPGNLSS EDVLPAGCTE   240
WRVQTLAYLP QEDWAPTSLT RPAPPDSEGS RSSSSSSSSN NNNYCALGCY GGWHLSALPG   300
NTQSSGPIPA LACGLSCDHQ GLETQQGVAW VLAGHCQRPG LHEDLQGMLL PSVLSKARSW   360
TFGGGGSGGG GSGGGGSERT MPRIPTLKNL EDLVTEYHGN FSAWSGVSKG LAESLQPDYS   420
ERLCLVSEIP PKGGALGEGP GASPCNQHSP YWAPPCYTLK PET                    463

SEQ ID NO: 144          moltype = AA  length = 460
FEATURE                 Location/Qualifiers
REGION                  1..460
                        note = MISC_FEATURE - Activin R1A ectodomain/IL9R/cGC-S
source                  1..460
                        mol_type = protein
                        organism = synthetic construct
SEQUENCE: 144
MEDEKPKVNP KLYMCVCEGL SCGNEDHCEG QQCFSSLSIN DGFHVYQKGC FQVYEQGKMT    60
CKTPPSPGQA VECCQGDWCN RNITAQLPTK GKSFPGTQNF HLELIPPWGW PGNTLVAVSI   120
FLLLTGPTYL LFKLSPRVKR IFYQNVPSPA MFFQPLYSVH NGNFQTWMGA HGAGVLLSQD   180
CAGTPQGALE PCVQEATALL TCGPARPWKS VALEEEQEGP GTRLPGNLSS EDVLPAGCTE   240
WRVQTLAYLP QEDWAPTSLT RPAPPDSEGS RSSSSSSSSN NNNYCALGCY GGWHLSALPG   300
NTQSSGPIPA LACGLSCDHQ GLETQQGVAW VLAGHCQRPG LHEDLQGMLL PSVLSKARSW   360
TFQPQPQPQP QPQPERTMPR IPTLKNLEDL VTEYHGNFSA WSGVSKGLAE SLQPDYSERL   420
CLVSEIPPKG GALGEGPGAS PCNQHSPYWA PPCYTLKPET                        460

SEQ ID NO: 145          moltype = AA  length = 463
FEATURE                 Location/Qualifiers
REGION                  1..463
                        note = MISC_FEATURE - Activin R1B ectodomain/IL9R/cGC-F
source                  1..463
                        mol_type = protein
                        organism = synthetic construct
SEQUENCE: 145
SGPRGVQALL CACTSCLQAN YTCETDGACM VSIFNLDGME HHVRTCIPKV ELVPAGKPFY    60
CLSSEDLRNT HCCYTDYCNR IDLRVPSGHL KEPEHPSMWG PVELIPPWGW PGNTLVAVSI   120
FLLLTGPTYL LFKLSPRVKR IFYQNVPSPA MFFQPLYSVH NGNFQTWMGA HGAGVLLSQD   180
CAGTPQGALE PCVQEATALL TCGPARPWKS VALEEEQEGP GTRLPGNLSS EDVLPAGCTE   240
WRVQTLAYLP QEDWAPTSLT RPAPPDSEGS RSSSSSSSSN NNNYCALGCY GGWHLSALPG   300
NTQSSGPIPA LACGLSCDHQ GLETQQGVAW VLAGHCQRPG LHEDLQGMLL PSVLSKARSW   360
TFGGGGSGGG GSGGGGSERT MPRIPTLKNL EDLVTEYHGN FSAWSGVSKG LAESLQPDYS   420
ERLCLVSEIP PKGGALGEGP GASPCNQHSP YWAPPCYTLK PET                    463

SEQ ID NO: 146          moltype = AA  length = 460
FEATURE                 Location/Qualifiers
REGION                  1..460
                        note = MISC_FEATURE - Activin R1B ectodomain/IL9R/cGC-S
source                  1..460
                        mol_type = protein
                        organism = synthetic construct
SEQUENCE: 146
SGPRGVQALL CACTSCLQAN YTCETDGACM VSIFNLDGME HHVRTCIPKV ELVPAGKPFY    60
CLSSEDLRNT HCCYTDYCNR IDLRVPSGHL KEPEHPSMWG PVELIPPWGW PGNTLVAVSI   120
FLLLTGPTYL LFKLSPRVKR IFYQNVPSPA MFFQPLYSVH NGNFQTWMGA HGAGVLLSQD   180
CAGTPQGALE PCVQEATALL TCGPARPWKS VALEEEQEGP GTRLPGNLSS EDVLPAGCTE   240
WRVQTLAYLP QEDWAPTSLT RPAPPDSEGS RSSSSSSSSN NNNYCALGCY GGWHLSALPG   300
NTQSSGPIPA LACGLSCDHQ GLETQQGVAW VLAGHCQRPG LHEDLQGMLL PSVLSKARSW   360
TFQPQPQPQP QPQPERTMPR IPTLKNLEDL VTEYHGNFSA WSGVSKGLAE SLQPDYSERL   420
CLVSEIPPKG GALGEGPGAS PCNQHSPYWA PPCYTLKPET                        460

SEQ ID NO: 147          moltype = AA  length = 452
FEATURE                 Location/Qualifiers
REGION                  1..452
                        note = MISC_FEATURE - Activin R1C ectodomain/IL9R/cGC-F
```

```
                                                     117                                                118
                                                              -continued source                          1..452
                                mol_type = protein
                                organism = synthetic construct
SEQUENCE: 147
LSPGLKCVCL LCDSSNFTCQ TEGACWASVM LTNGKEQVIK SCVSLPELNA QVFCHSSNNV          60
TKTECCFTDF CNNITLHLPT ASPNAPKLGP MELIPPWGWP GNTLVAVSIF LLLTGPTYLL         120
FKLSPRVKRI FYQNVPSPAM FFQPLYSVHN GNFQTWMGAH GAGVLLSQDC AGTPQGALEP         180
CVQEATALLT CGPARPWKSV ALEEEQEGPG TRLPGNLSSE DVLPAGCTEW RVQTLAYLPQ         240
EDWAPTSLTR PAPPDSEGSR SSSSSSSSNN NNYCALGCYG GWHLSALPGN TQSSGPIPAL         300
ACGLSCDHQG LETQQGVAWV LAGHCQRPGL HEDLQGMLLP SVLSKARSWT FGGGGSGGGG         360
SGGGGSERTM PRIPTLKNLE DLVTEYHGNF SAWSGVSKGL AESLQPDYSE RLCLVSEIPP         420
KGGALGEGPG ASPCNQHSPY WAPPCYTLKP ET                                      452

SEQ ID NO: 148                  moltype = AA  length = 449
FEATURE                         Location/Qualifiers
REGION                          1..449
                                note = MISC_FEATURE - Activin R1C ectodomain/IL9R/cGC-S
source                          1..449
                                mol_type = protein
                                organism = synthetic construct
SEQUENCE: 148
LSPGLKCVCL LCDSSNFTCQ TEGACWASVM LTNGKEQVIK SCVSLPELNA QVFCHSSNNV          60
TKTECCFTDF CNNITLHLPT ASPNAPKLGP MELIPPWGWP GNTLVAVSIF LLLTGPTYLL         120
FKLSPRVKRI FYQNVPSPAM FFQPLYSVHN GNFQTWMGAH GAGVLLSQDC AGTPQGALEP         180
CVQEATALLT CGPARPWKSV ALEEEQEGPG TRLPGNLSSE DVLPAGCTEW RVQTLAYLPQ         240
EDWAPTSLTR PAPPDSEGSR SSSSSSSSNN NNYCALGCYG GWHLSALPGN TQSSGPIPAL         300
ACGLSCDHQG LETQQGVAWV LAGHCQRPGL HEDLQGMLLP SVLSKARSWT FQPQPQPQPQ         360
PQPERTMPRI PTLKNLEDLV TEYHGNFSAW SGVSKGLAES LQPDYSERLC LVSEIPPKGG         420
ALGEGPGASP CNQHSPYWAP PCYTLKPET                                          449

SEQ ID NO: 149                  moltype = AA  length = 479
FEATURE                         Location/Qualifiers
REGION                          1..479
                                note = MISC_FEATURE - Activin R2B ectodomain/IL9R/cGC-F
source                          1..479
                                mol_type = protein
                                organism = synthetic construct
SEQUENCE: 149
SGRGEAETRE CIYYNANWEL ERTNQSGLER CEGEQDKRLH CYASWRNSSG TIELVKKGCW          60
LDDFNCYDRQ ECVATEENPQ VYFCCCEGNF CNERFTHLPE AGGPEVTYEP PPTAPTLLTL         120
IPPWGWPGNT LVAVSIFLLL TGPTYLLFKL SPRVKRIFYQ NVPSPAMFFQ PLYSVHNGNF         180
QTWMGAHGAG VLLSQDCAGT PQGALEPCVQ EATALLTCGP ARPWKSVALE EEQEGPGTRL         240
PGNLSSEDVL PAGCTEWRVQ TLAYLPQEDW APTSLTRPAP PDSEGSRSSS SSSSNNNNY         300
CALGCYGGWH LSALPGNTQS SGPIPALACG LSCDHQGLET QQGVAWVLAG HCQRPGLHED         360
LQGMLLPSVL SKARSWTFGG GGSGGGGSGG GGSERTMPRI PTLKNLEDLV TEYHGNFSAW         420
SGVSKGLAES LQPDYSERLC LVSEIPPKGG ALGEGPGASP CNQHSPYWAP PCYTLKPET         479

SEQ ID NO: 150                  moltype = AA  length = 476
FEATURE                         Location/Qualifiers
REGION                          1..476
                                note = MISC_FEATURE - Activin R2B ectodomain/IL9R/cGC-S
source                          1..476
                                mol_type = protein
                                organism = synthetic construct
SEQUENCE: 150
SGRGEAETRE CIYYNANWEL ERTNQSGLER CEGEQDKRLH CYASWRNSSG TIELVKKGCW          60
LDDFNCYDRQ ECVATEENPQ VYFCCCEGNF CNERFTHLPE AGGPEVTYEP PPTAPTLLTL         120
IPPWGWPGNT LVAVSIFLLL TGPTYLLFKL SPRVKRIFYQ NVPSPAMFFQ PLYSVHNGNF         180
QTWMGAHGAG VLLSQDCAGT PQGALEPCVQ EATALLTCGP ARPWKSVALE EEQEGPGTRL         240
PGNLSSEDVL PAGCTEWRVQ TLAYLPQEDW APTSLTRPAP PDSEGSRSSS SSSSNNNNY         300
CALGCYGGWH LSALPGNTQS SGPIPALACG LSCDHQGLET QQGVAWVLAG HCQRPGLHED         360
LQGMLLPSVL SKARSWTFQP QPQPQPQPQP ERTMPRIPTL KNLEDLVTEY HGNFSAWSGV         420
SKGLAESLQP DYSERLCLVS EIPPKGGALG EGPGASPCNQ HSPYWAPPCY TLKPET            476

SEQ ID NO: 151                  moltype = AA  length = 476
FEATURE                         Location/Qualifiers
REGION                          1..476
                                note = MISC_FEATURE - Activin R2A ectodomain/IL9R/cGC-F
source                          1..476
                                mol_type = protein
                                organism = synthetic construct
SEQUENCE: 151
AILGRSETQE CLFFNANWEK DRTNQTGVEP CYGDKDKRRH CFATWKNISG SIEIVKQGCW          60
LDDINCYDRT DCVEKKDSPE VYFCCCEGNM CNEKFSYFPE MEVTQPTSNP VTPKPPLIPP         120
WGWPGNTLVA VSIFLLLTGP TYLLFKLSPR VKRIFYQNVP SPAMFFQPLY SVHNGNFQTW         180
MGAHGAGVLL SQDCAGTPQG ALEPCVQEAT ALLTCGPARP WKSVALEEEQ EGPGTRLPGN         240
LSSEDVLPAG CTEWRVQTLA YLPQEDWAPT SLTRPAPPDS EGSRSSSSSS SSNNNNYCAL         300
GCYGGWHLSA LPGNTQSSGP IPALACGLSC DHQGLETQQG VAWVLAGHCQ RPGLHEDLQG         360
MLLPSVLSKA RSWTFGGGGS GGGGSGGGGS ERTMPRIPTL KNLEDLVTEY HGNFSAWSGV         420
```

```
SKGLAESLQP DYSERLCLVS EIPPKGGALG EGPGASPCNQ HSPYWAPPCY TLKPET      476

SEQ ID NO: 152          moltype = AA  length = 473
FEATURE                 Location/Qualifiers
REGION                  1..473
                        note = MISC_FEATURE - Activin R2A ectodomain/IL9R/cGC-S
source                  1..473
                        mol_type = protein
                        organism = synthetic construct
SEQUENCE: 152
AILGRSETQE CLFFNANWEK DRTNQTGVEP CYGDKDKRRH CFATWKNISG SIEIVKQGCW   60
LDDINCYDRT DCVEKKDSPE VYFCCCEGNM CNEKFSYFPE MEVTQPTSNP VTPKPPLIPP  120
WGWPGNTLVA VSIFLLLTGP TYLLFKLSPR VKRIFYQNVP SPAMFFQPLY SVHNGNFQTW  180
MGAHGAVLL SQDCAGTPQG ALEPCVQEAT ALLTCGPARP WKSVALEEEQ EGPGTRLPGN   240
LSSEDVLPAG CTEWRVQTLA YLPQEDWAPT SLTRPAPPDS EGSRSSSSSS SSNNNNYCAL  300
GCYGGWHLSA LPGNTQSSGP IPALACGLSC DHQGLETQQG VAWVLAGHCQ RPGLHEDLQG  360
MLLPSVLSKA RSWTFQPQPQ PQPQPQPERT MPRIPTLKNL EDLVTEYHGN FSAWSGVSKG  420
LAESLQPDYS ERLCLVSEIP PKGGALGEGP GASPCNQHSP YWAPPCYTLK PET         473

SEQ ID NO: 153          moltype = AA  length = 574
FEATURE                 Location/Qualifiers
REGION                  1..574
                        note = MISC_FEATURE - IL10R-alpha/IL9R/cGC-F
source                  1..574
                        mol_type = protein
                        organism = synthetic construct
SEQUENCE: 153
HGTELPSPPS VWFEAEFFHH ILHWTPIPNQ SESTCYEVAL LRYGIESWNS ISNCSQTLSY   60
DLTAVTLDLY HSNGYRARVR AVDGSRHSNW TVTNTRFSVD EVTLTVGSVN LEIHNGFILG  120
KIQLPRPKMA PANDTYESIF SHFREYEIAI RKVPGNFTFT HKKVKHENFS LLTSGEVGEF  180
CVQVKPSVAS RSNKGMWSKE ECISLTRQYF TVTNLIPPWG WPGNTLVAVS IFLLLTGPTY  240
LLFKLSPRVK RIFYQNVPSP AMFFQPLYSV HNGNFQTWMG AHGAGVLLSQ DCAGTPQGAL  300
EPCVQEATAL LTCGPARPWK SVALEEEQEG PGTRLPGNLS SEDVLPAGCT EWRVQTLAYL  360
PQEDWAPTSL TRPAPPDSEG SRSSSSSSSS NNNNYCALGC YGGWHLSALP GNTQSSGPIP  420
ALACGLSCDH QGLETQQGVA WVLAGHCQRP GLHEDLQGML LPSVLSKARS WTFGGGGSGG  480
GGSGGGGSER TMPRIPTLKN LEDLVTEYHG NFSAWSGVSK GLAESLQPDY SERLCLVSEI  540
PPKGGALGEG PGASPCNQHS PYWAPPCYTL KPET                              574

SEQ ID NO: 154          moltype = AA  length = 571
FEATURE                 Location/Qualifiers
REGION                  1..571
                        note = MISC_FEATURE - IL10R-alpha/IL9R/cGC-S
source                  1..571
                        mol_type = protein
                        organism = synthetic construct
SEQUENCE: 154
HGTELPSPPS VWFEAEFFHH ILHWTPIPNQ SESTCYEVAL LRYGIESWNS ISNCSQTLSY   60
DLTAVTLDLY HSNGYRARVR AVDGSRHSNW TVTNTRFSVD EVTLTVGSVN LEIHNGFILG  120
KIQLPRPKMA PANDTYESIF SHFREYEIAI RKVPGNFTFT HKKVKHENFS LLTSGEVGEF  180
CVQVKPSVAS RSNKGMWSKE ECISLTRQYF TVTNLIPPWG WPGNTLVAVS IFLLLTGPTY  240
LLFKLSPRVK RIFYQNVPSP AMFFQPLYSV HNGNFQTWMG AHGAGVLLSQ DCAGTPQGAL  300
EPCVQEATAL LTCGPARPWK SVALEEEQEG PGTRLPGNLS SEDVLPAGCT EWRVQTLAYL  360
PQEDWAPTSL TRPAPPDSEG SRSSSSSSSS NNNNYCALGC YGGWHLSALP GNTQSSGPIP  420
ALACGLSCDH QGLETQQGVA WVLAGHCQRP GLHEDLQGML LPSVLSKARS WTFQPQPQPQ  480
PQPQPERTMP RIPTLKNLED LVTEYHGNFS AWSGVSKGLA ESLQPDYSER LCLVSEIPPK  540
GGALGEGPGA SPCNQHSPYW APPCYTLKPE T                                 571

SEQ ID NO: 155          moltype = AA  length = 504
FEATURE                 Location/Qualifiers
REGION                  1..504
                        note = MISC_FEATURE - TGFBR2 ectodomain/IL9R/cGC-F
source                  1..504
                        mol_type = protein
                        organism = synthetic construct
SEQUENCE: 155
TIPPHVQKSV NNDMIVTDNN GAVKFPQLCK FCDVRFSTCD NQKSCMSNCS ITSICEKPQE   60
VCVAVWRKND ENITLETVCH DPKLPYHDFI LEDAASPKCI MKEKKKPGET FFMCSCSSDE  120
CNDNIIFSEE YNTSNPDLLL VIFQLIPPWG WPGNTLVAVS IFLLLTGPTY LLFKLSPRVK  180
RIFYQNVPSP AMFFQPLYSV HNGNFQTWMG AHGAGVLLSQ DCAGTPQGAL EPCVQEATAL  240
LTCGPARPWK SVALEEEQEG PGTRLPGNLS SEDVLPAGCT EWRVQTLAYL PQEDWAPTSL  300
TRPAPPDSEG SRSSSSSSSS NNNNYCALGC YGGWHLSALP GNTQSSGPIP ALACGLSCDH  360
QGLETQQGVA WVLAGHCQRP GLHEDLQGML LPSVLSKARS WTFGGGGSGG GGSGGGGSER  420
TMPRIPTLKN LEDLVTEYHG NFSAWSGVSK GLAESLQPDY SERLCLVSEI PPKGGALGEG  480
PGASPCNQHS PYWAPPCYTL KPET                                         504

SEQ ID NO: 156          moltype = AA  length = 501
FEATURE                 Location/Qualifiers
REGION                  1..501
                        note = MISC_FEATURE - TGFBR2 ectodomain/IL9R/cGC-S
```

```
                        source          1..501
                                        mol_type = protein
                                        organism = synthetic construct
SEQUENCE: 156
TIPPHVQKSV NNDMIVTDNN GAVKFPQLCK FCDVRFSTCD NQKSCMSNCS ITSICEKPQE    60
VCVAVWRKND ENITLETVCH DPKLPYHDFI LEDAASPKCI MKEKKKPGET FFMCSCSSDE   120
CNDNIIFSEE YNTSNPDLLL VIFQLIPPWG WPGNTLVAVS IFLLLTGPTY LLFKLSPRVK   180
RIFYQNVPSP AMFFQPLYSV HNGNFQTWMG AHGAGVLLSQ DCAGTPQGAL EPCVQEATAL   240
LTCGPARPWK SVALEEEQEG PGTRLPGNLS SEDVLPAGCT EWRVQTLAYL PQEDWAPTSL   300
TRPAPPDSEG SRSSSSSSSS NNNNYCALGC YGGWHLSALP GNTQSSGPIP ALACGLSCDH   360
QGLETQQGVA WVLAGHCQRP GLHEDLQGML LPSVLSKARS WTFQPQPQPQ PQPQPERTMP   420
RIPTLKNLED LVTEYHGNFS AWSGVSKGLA ESLQPDYSER LCLVSEIPPK GGALGEGPGA   480
SPCNQHSPYW APPCYTLKPE T                                            501

SEQ ID NO: 157          moltype = AA  length = 453
FEATURE                 Location/Qualifiers
REGION                  1..453
                        note = MISC_FEATURE - TGFBR1 ectodomain/IL9R/cGC-F
source                  1..453
                        mol_type = protein
                        organism = synthetic construct
SEQUENCE: 157
LQCFCHLCTK DNFTCVTDGL CFVSVTETTD KVIHNSMCIA EIDLIPRDRP FVCAPSSKTG    60
SVTTTYCCNQ DHCNKIELPT TVKSSPGLGP VELLIPPWGW PGNTLVAVSI FLLLTGPTYL   120
LFKLSPRVKR IFYQNVPSPA MFFQPLYSVH NGNFQTWMGA HGAGVLLSQD CAGTPQGALE   180
PCVQEATALL TCGPARPWKS VALEEEQEGP GTRLPGNLSS EDVLPAGCTE WRVQTLAYLP   240
QEDWAPTSLT RPAPPDSEGS RSSSSSSSSN NNNYCALGCY GGWHLSALPG NTQSSGPIPA   300
LACGLSCDHQ GLETQQGVAW VLAGHCQRPG LHEDLQGMLL PSVLSKARSW TFGGGGSGGG   360
GSGGGGSERT MPRIPTLKNL EDLVTEYHGN FSAWSGVSKG LAESLQPDYS ERLCLVSEIP   420
PKGGALGEGP GASPCNQHSP YWAPPCYTLK PET                                453

SEQ ID NO: 158          moltype = AA  length = 450
FEATURE                 Location/Qualifiers
REGION                  1..450
                        note = MISC_FEATURE - TGFBR1 ectodomain/IL9R/cGC-S
source                  1..450
                        mol_type = protein
                        organism = synthetic construct
SEQUENCE: 158
LQCFCHLCTK DNFTCVTDGL CFVSVTETTD KVIHNSMCIA EIDLIPRDRP FVCAPSSKTG    60
SVTTTYCCNQ DHCNKIELPT TVKSSPGLGP VELLIPPWGW PGNTLVAVSI FLLLTGPTYL   120
LFKLSPRVKR IFYQNVPSPA MFFQPLYSVH NGNFQTWMGA HGAGVLLSQD CAGTPQGALE   180
PCVQEATALL TCGPARPWKS VALEEEQEGP GTRLPGNLSS EDVLPAGCTE WRVQTLAYLP   240
QEDWAPTSLT RPAPPDSEGS RSSSSSSSSN NNNYCALGCY GGWHLSALPG NTQSSGPIPA   300
LACGLSCDHQ GLETQQGVAW VLAGHCQRPG LHEDLQGMLL PSVLSKARSW TFQPQPQPQP   360
QPQPERTMPR IPTLKNLEDL VTEYHGNFSA WSGVSKGLAE SLQPDYSERL CLVSEIPPKG   420
GALGEGPGAS PCNQHSPYWA PPCYTLKPET                                    450

SEQ ID NO: 159          moltype = AA  length = 480
FEATURE                 Location/Qualifiers
REGION                  1..480
                        note = MISC_FEATURE - TIGIT/IL9R/cGC-F
source                  1..480
                        mol_type = protein
                        organism = synthetic construct
SEQUENCE: 159
MMTGTIETTG NISAEKGGSI ILQCHLSSTT AQVTQVNWEQ QDQLLAICNA DLGWHISPSF    60
KDRVAPGPGL GLTLQSLTVN DTGEYFCIYH TYPDGTYTGR IFLEVLESSV AEHGARFQIP   120
LIPPWGWPGN TLVAVSIFLL LTGPTYLLFK LSPRVKRIFY QNVPSPAMFF QPLYSVHNGN   180
FQTWMGAHGA GVLLSQDCAG TPQGALEPCV QEATALLTCG PARPWKSVAL EEEQEGPGTR   240
LPGNLSSEDV LPAGCTEWRV QTLAYLPQED WAPTSLTRPA PPDSEGSRSS SSSSSSNNNN   300
YCALGCYGGW HLSALPGNTQ SSGPIPALAC GLSCDHQGLE TQQGVAWVLA GHCQRPGLHE   360
DLQGMLLPSV LSKARSWTFG GGGSGGGGSG GGGSERTMPR IPTLKNLEDL VTEYHGNFSA   420
WSGVSKGLAE SLQPDYSERL CLVSEIPPKG GALGEGPGAS PCNQHSPYWA PPCYTLKPET   480

SEQ ID NO: 160          moltype = AA  length = 477
FEATURE                 Location/Qualifiers
REGION                  1..477
                        note = MISC_FEATURE - TIGIT/IL9R/cGC-S
source                  1..477
                        mol_type = protein
                        organism = synthetic construct
SEQUENCE: 160
MMTGTIETTG NISAEKGGSI ILQCHLSSTT AQVTQVNWEQ QDQLLAICNA DLGWHISPSF    60
KDRVAPGPGL GLTLQSLTVN DTGEYFCIYH TYPDGTYTGR IFLEVLESSV AEHGARFQIP   120
LIPPWGWPGN TLVAVSIFLL LTGPTYLLFK LSPRVKRIFY QNVPSPAMFF QPLYSVHNGN   180
FQTWMGAHGA GVLLSQDCAG TPQGALEPCV QEATALLTCG PARPWKSVAL EEEQEGPGTR   240
LPGNLSSEDV LPAGCTEWRV QTLAYLPQED WAPTSLTRPA PPDSEGSRSS SSSSSSNNNN   300
YCALGCYGGW HLSALPGNTQ SSGPIPALAC GLSCDHQGLE TQQGVAWVLA GHCQRPGLHE   360
```

```
DLQGMLLPSV LSKARSWTFQ PQPQPQPQPQ PERTMPRIPT LKNLEDLVTE YHGNFSAWSG   420
VSKGLAESLQ PDYSERLCLV SEIPPKGGAL GEGPGASPCN QHSPYWAPPC YTLKPET      477

SEQ ID NO: 161            moltype = AA  length = 535
FEATURE                   Location/Qualifiers
REGION                    1..535
                          note = MISC_FEATURE - FCGR2B/IL9R/cGC-F
source                    1..535
                          mol_type = protein
                          organism = synthetic construct
SEQUENCE: 161
TPAAPPKAVL KLEPQWINVL QEDSVTLTCR GTHSPESDSI QWFHNGNLIP THTQPSYRFK   60
ANNNDSGEYT CQTGQTSLSD PVHLTVLSEW LVLQTPHLEF QEGETIVLRC HSWKDKPLVK   120
VTFFQNGKSK KFSRSDPNFS IPQANHSHSG DYHCTGNIGY TLYSSKPVTI TVQAPLIPPW   180
GWPGNTLVAV SIFLLLTGPT YLLFKLSPRV KRIFYQNVPS PAMFFQPLYS VHNGNFQTWM   240
GAHGAGVLLS QDCAGTPQGA LEPCVQEATA LLTCGPARPW KSVALEEEQE GPGTRLPGNL   300
SSEDVLPAGC TEWRVQTLAY LPQEDWAPTS LTRPAPPDSE GSRSSSSSSS SNNNNYCALG   360
CYGGWHLSAL PGNTQSSGPI PALACGLSCD HQGLETQQGV AWVLAGHCQR PGLHEDLQGM   420
LLPSVLSKAR SWTFGGGGSG GGGSGGGGSE RTMPRIPTLK NLEDLVTEYH GNFSAWSGVS   480
KGLAESLQPD YSERLCLVSE IPPKGGALGE GPGASPCNQH SPYWAPPCYT LKPET         535

SEQ ID NO: 162            moltype = AA  length = 532
FEATURE                   Location/Qualifiers
REGION                    1..532
                          note = MISC_FEATURE - FCGR2B/IL9R/cGC-S
source                    1..532
                          mol_type = protein
                          organism = synthetic construct
SEQUENCE: 162
TPAAPPKAVL KLEPQWINVL QEDSVTLTCR GTHSPESDSI QWFHNGNLIP THTQPSYRFK   60
ANNNDSGEYT CQTGQTSLSD PVHLTVLSEW LVLQTPHLEF QEGETIVLRC HSWKDKPLVK   120
VTFFQNGKSK KFSRSDPNFS IPQANHSHSG DYHCTGNIGY TLYSSKPVTI TVQAPLIPPW   180
GWPGNTLVAV SIFLLLTGPT YLLFKLSPRV KRIFYQNVPS PAMFFQPLYS VHNGNFQTWM   240
GAHGAGVLLS QDCAGTPQGA LEPCVQEATA LLTCGPARPW KSVALEEEQE GPGTRLPGNL   300
SSEDVLPAGC TEWRVQTLAY LPQEDWAPTS LTRPAPPDSE GSRSSSSSSS SNNNNYCALG   360
CYGGWHLSAL PGNTQSSGPI PALACGLSCD HQGLETQQGV AWVLAGHCQR PGLHEDLQGM   420
LLPSVLSKAR SWTFQPQPQP QPQPQPERTM PRIPTLKNLE DLVTEYHGNF SAWSGVSKGL   480
AESLQPDYSE RLCLVSEIPP KGGALGEGPG ASPCNQHSPY WAPPCYTLKP ET           532

SEQ ID NO: 163            moltype = AA  length = 637
FEATURE                   Location/Qualifiers
REGION                    1..637
                          note = MISC_FEATURE - FCGR1/IL9R/cGC-F
source                    1..637
                          mol_type = protein
                          organism = synthetic construct
SEQUENCE: 163
QVDTTKAVIT LQPPWVSVFQ EETVTLHCEV LHLPGSSSTQ WFLNGTATQT STPSYRITSA   60
SVNDSGEYRC QRGLSGRSDP IQLEIHRGWL LLQVSSRVFT EGEPLALRCH AWKDKLVYNV   120
LYYRNGKAFK FFHWNSNLTI LKTNISHNGT YHCSGMGKHR YTSAGISVTV KELFPAPVLN   180
ASVTSPLLEG NLVTLSCETK LLLQRPGLQL YFSFYMGSKT LRGRNTSSEY QILTARREDS   240
GLYWCEAATE DGNVLKRSPE LELQVLGLQL PTPVWFHLIP PWGWPGNTLV AVSIFLLLTG   300
PTYLLFKLSP RVKRIFYQNV PSPAMFFQPL YSVHNGNFQT WMGAHGAGVL LSQDCAGTPQ   360
GALEPCVQEA TALLTCGPAR PWKSVALEEE QEGPGTRLPG NLSSEDVLPA GCTEWRVQTL   420
AYLPQEDWAP TSLTRPAPPD SEGSRSSSSS SSSNNNNYCA LGCYGGWHLS ALPGNTQSSG   480
PIPALACGLS CDHQGLETQQ GVAWVLAGHC QRPGLHEDLQ GMLLPSVLSK ARSWTFGGGG   540
SGGGGSGGGG SERTMPRIPT LKNLEDLVTE YHGNFSAWSG VSKGLAESLQ PDYSERLCLV   600
SEIPPKGGAL GEGPGASPCN QHSPYWAPPC YTLKPET                            637

SEQ ID NO: 164            moltype = AA  length = 634
FEATURE                   Location/Qualifiers
REGION                    1..634
                          note = MISC_FEATURE - FCGR1/IL9R/cGC-S
source                    1..634
                          mol_type = protein
                          organism = synthetic construct
SEQUENCE: 164
QVDTTKAVIT LQPPWVSVFQ EETVTLHCEV LHLPGSSSTQ WFLNGTATQT STPSYRITSA   60
SVNDSGEYRC QRGLSGRSDP IQLEIHRGWL LLQVSSRVFT EGEPLALRCH AWKDKLVYNV   120
LYYRNGKAFK FFHWNSNLTI LKTNISHNGT YHCSGMGKHR YTSAGISVTV KELFPAPVLN   180
ASVTSPLLEG NLVTLSCETK LLLQRPGLQL YFSFYMGSKT LRGRNTSSEY QILTARREDS   240
GLYWCEAATE DGNVLKRSPE LELQVLGLQL PTPVWFHLIP PWGWPGNTLV AVSIFLLLTG   300
PTYLLFKLSP RVKRIFYQNV PSPAMFFQPL YSVHNGNFQT WMGAHGAGVL LSQDCAGTPQ   360
GALEPCVQEA TALLTCGPAR PWKSVALEEE QEGPGTRLPG NLSSEDVLPA GCTEWRVQTL   420
AYLPQEDWAP TSLTRPAPPD SEGSRSSSSS SSSNNNNYCA LGCYGGWHLS ALPGNTQSSG   480
PIPALACGLS CDHQGLETQQ GVAWVLAGHC QRPGLHEDLQ GMLLPSVLSK ARSWTFQPQP   540
QPQPQPQPER TMPRIPTLKN LEDLVTEYHG NFSAWSGVSK GLAESLQPDY SERLCLVSEI   600
PPKGGALGEG PGASPCNQHS PYWAPPCYTL KPET                               634
```

```
SEQ ID NO: 165          moltype = AA  length = 568
FEATURE                 Location/Qualifiers
REGION                  1..568
                        note = MISC_FEATURE - 2B4/IL9R/cCG-F
source                  1..568
                        mol_type = protein
                        organism = synthetic construct
SEQUENCE: 165
CQGSADHVVS ISGVPLQLQP NSIQTKVDSI AWKKLLPSQN GFHHILKWEN GSLPSNTSND    60
RFSFIVKNLS LLIKAAQQQD SGLYCLEVTS ISGKVQTATF QVFVFESLLP DKVEKPRLQG   120
QGKILDRGRC QVALSCLVSR DGNVSYAWYR GSKLIQTAGN LTYLDEEVDI NGTHTYTCNV   180
SNPVSWESHT LNLTQDCQNA HQEFRFWPLI PPWGWPGNTL VAVSIFLLLT GPTYLLFKLS   240
PRVKRIFYQN VPSPAMFFQP LYSVHNGNFQ TWMGAHGAGV LLSQDCAGTP QGALEPCVQE   300
ATALLTCGPA RPWKSVALEE EQEGPGTRLP GNLSSEDVLP AGCTEWRVQT LAYLPQEDWA   360
PTSLTRPAPP DSEGSRSSSS SSSSNNNNYC ALGCYGGWHL SALPGNTQSS GPIPALACGL   420
SCDHQGLETQ QGVAWVLAGH CQRPGLHEDL QGMLLPSVLS KARSWTFGGG GSGGGGSGGG   480
GSERTMPRIP TLKNLEDLVT EYHGNFSAWS GVSKGLAESL QPDYSERLCL VSEIPPKGGA   540
LGEGPGASPC NQHSPYWAPP CYTLKPET                                     568

SEQ ID NO: 166          moltype = AA  length = 565
FEATURE                 Location/Qualifiers
REGION                  1..565
                        note = MISC_FEATURE - 2B4/IL9R/cCG-S
source                  1..565
                        mol_type = protein
                        organism = synthetic construct
SEQUENCE: 166
CQGSADHVVS ISGVPLQLQP NSIQTKVDSI AWKKLLPSQN GFHHILKWEN GSLPSNTSND    60
RFSFIVKNLS LLIKAAQQQD SGLYCLEVTS ISGKVQTATF QVFVFESLLP DKVEKPRLQG   120
QGKILDRGRC QVALSCLVSR DGNVSYAWYR GSKLIQTAGN LTYLDEEVDI NGTHTYTCNV   180
SNPVSWESHT LNLTQDCQNA HQEFRFWPLI PPWGWPGNTL VAVSIFLLLT GPTYLLFKLS   240
PRVKRIFYQN VPSPAMFFQP LYSVHNGNFQ TWMGAHGAGV LLSQDCAGTP QGALEPCVQE   300
ATALLTCGPA RPWKSVALEE EQEGPGTRLP GNLSSEDVLP AGCTEWRVQT LAYLPQEDWA   360
PTSLTRPAPP DSEGSRSSSS SSSSNNNNYC ALGCYGGWHL SALPGNTQSS GPIPALACGL   420
SCDHQGLETQ QGVAWVLAGH CQRPGLHEDL QGMLLPSVLS KARSWTFQPQ PQPQPQPQPE   480
RTMPRIPTLK NLEDLVTEYH GNFSAWSGVS KGLAESLQPD YSERLCLVSE IPPKGGALGE   540
GPGASPCNQH SPYWAPPCYT LKPET                                        565

SEQ ID NO: 167          moltype = AA  length = 504
FEATURE                 Location/Qualifiers
REGION                  1..504
                        note = MISC_FEATURE - LAIR1/IL9R/cGC-F
source                  1..504
                        mol_type = protein
                        organism = synthetic construct
SEQUENCE: 167
QEEDLPRPSI SAEPGTVIPL GSHVTFVCRG PVGVQTFRLE RESRSTYNDT EDVSQASPSE    60
SEARFRIDSV SEGNAGPYRC IYYKPPKWSE QSDYLELLVK ETSGGPDSPD TEPGSSAGPT   120
QRPSDNSHNE HAPASQGLKA EHLYLIPPWG WPGNTLVAVS IFLLLTGPTY LLFKLSPRVK   180
RIFYQNVPSP AMFFQPLYSV HNGNFQTWMG AHGAGVLLSQ DCAGTPQGAL EPCVQEATAL   240
LTCGPARPWK SVALEEEQEG PGTRLPGNLS SEDVLPAGCT EWRVQTLAYL PQEDWAPTSL   300
TRPAPPDSEG SRSSSSSSSS NNNNYCALGC YGGWHLSALP GNTQSSGPIP ALACGLSCDH   360
QGLETQQGVA WVLAGHCQRP GLHEDLQGML LPSVLSKARS WTFGGGGSGG GGSGGGGSER   420
TMPRIPTLKN LEDLVTEYHG NFSAWSGVSK GLAESLQPDY SERLCLVSEI PPKGGALGEG   480
PGASPCNQHS PYWAPPCYTL KPET                                         504

SEQ ID NO: 168          moltype = AA  length = 501
FEATURE                 Location/Qualifiers
REGION                  1..501
                        note = MISC_FEATURE - LAIR1/IL9R/cGC-S
source                  1..501
                        mol_type = protein
                        organism = synthetic construct
SEQUENCE: 168
QEEDLPRPSI SAEPGTVIPL GSHVTFVCRG PVGVQTFRLE RESRSTYNDT EDVSQASPSE    60
SEARFRIDSV SEGNAGPYRC IYYKPPKWSE QSDYLELLVK ETSGGPDSPD TEPGSSAGPT   120
QRPSDNSHNE HAPASQGLKA EHLYLIPPWG WPGNTLVAVS IFLLLTGPTY LLFKLSPRVK   180
RIFYQNVPSP AMFFQPLYSV HNGNFQTWMG AHGAGVLLSQ DCAGTPQGAL EPCVQEATAL   240
LTCGPARPWK SVALEEEQEG PGTRLPGNLS SEDVLPAGCT EWRVQTLAYL PQEDWAPTSL   300
TRPAPPDSEG SRSSSSSSSS NNNNYCALGC YGGWHLSALP GNTQSSGPIP ALACGLSCDH   360
QGLETQQGVA WVLAGHCQRP GLHEDLQGML LPSVLSKARS WTFQPQPQPQ PQPQPERTMP   420
RIPTLKNLED LVTEYHGNFS AWSGVSKGLA ESLQPDYSER LCLVSEIPPK GGALGEGPGA   480
SPCNQHSPYW APPCYTLKPE T                                            501

SEQ ID NO: 169          moltype = AA  length = 708
FEATURE                 Location/Qualifiers
REGION                  1..708
                        note = MISC_FEATURE - CD5/IL-9R/cGC-F
source                  1..708
```

```
                           mol_type = protein
                           organism = synthetic construct
SEQUENCE: 169
RLSWYDPDFQ ARLTRSNSKC QGQLEVYLKD GWHMVCSQSW GRSSKQWEDP SQASKVCQRL   60
NCGVPLSLGP FLVTYTPQSS IICYGQLGSF SNCSHSRNDM CHSLGLTCLE PQKTTPPTTR  120
PPPTTTPEPT APPRLQLVAQ SGGQHCAGVV EFYSGSLGGT ISYEAQDKTQ DLENFLCNNL  180
QCGSFLKHLP ETEAGRAQDP GEPREHQPLP IQWKIQNSSC TSLEHCFRKI KPQKSGRVLA  240
LLCSGFQPKV QSRLVGGSSI CEGTVEVRQG AQWAALCDSS SARSSLRWEE VCREQQCGSV  300
NSYRVLDAGD PTSRGLFCPH QKLSQCHELW ERNSYCKKVF VTCQDPNPLI PPWGWPGNTL  360
VAVSIFLLLT GPTYLLFKLS PRVKRIFYQN VPSPAMFFQP LYSVHNGNFQ TWMGAHGAGV  420
LLSQDCAGTP QGALEPCVQE ATALLTCGPA RPWKSVALEE EQEGPGTRLP GNLSSEDVLP  480
AGCTEWRVQT LAYLPQEDWA PTSLTRPAPP DSEGSRSSSS SSSSNNNNYC ALGCYGGWHL  540
SALPGNTQSS GPIPALACGL SCDHQGLETQ QGVAWVLAGH CQRPGLHEDL QGMLLPSVLS  600
KARSWTFGGG GSGGGGSGGG GSERTMPRIP TLKNLEDLVT EYHGNFSAWS GVSKGLAESL  660
QPDYSERLCL VSEIPPKGGA LGEGPGASPC NQHSPYWAPP CYTLKPET              708

SEQ ID NO: 170             moltype = AA   length = 705
FEATURE                    Location/Qualifiers
REGION                     1..705
                           note = MISC_FEATURE - CD5/IL-9R/cGC-S
source                     1..705
                           mol_type = protein
                           organism = synthetic construct
SEQUENCE: 170
RLSWYDPDFQ ARLTRSNSKC QGQLEVYLKD GWHMVCSQSW GRSSKQWEDP SQASKVCQRL   60
NCGVPLSLGP FLVTYTPQSS IICYGQLGSF SNCSHSRNDM CHSLGLTCLE PQKTTPPTTR  120
PPPTTTPEPT APPRLQLVAQ SGGQHCAGVV EFYSGSLGGT ISYEAQDKTQ DLENFLCNNL  180
QCGSFLKHLP ETEAGRAQDP GEPREHQPLP IQWKIQNSSC TSLEHCFRKI KPQKSGRVLA  240
LLCSGFQPKV QSRLVGGSSI CEGTVEVRQG AQWAALCDSS SARSSLRWEE VCREQQCGSV  300
NSYRVLDAGD PTSRGLFCPH QKLSQCHELW ERNSYCKKVF VTCQDPNPLI PPWGWPGNTL  360
VAVSIFLLLT GPTYLLFKLS PRVKRIFYQN VPSPAMFFQP LYSVHNGNFQ TWMGAHGAGV  420
LLSQDCAGTP QGALEPCVQE ATALLTCGPA RPWKSVALEE EQEGPGTRLP GNLSSEDVLP  480
AGCTEWRVQT LAYLPQEDWA PTSLTRPAPP DSEGSRSSSS SSSSNNNNYC ALGCYGGWHL  540
SALPGNTQSS GPIPALACGL SCDHQGLETQ QGVAWVLAGH CQRPGLHEDL QGMLLPSVLS  600
KARSWTFQPQ PQPQPQPQPE RTMPRIPTLK NLEDLVTEYH GNFSAWSGVS KGLAESLQPD  660
YSERLCLVSE IPPKGGALGE GPGASPCNQH SPYWAPPCYT LKPET                 705

SEQ ID NO: 171             moltype = AA   length = 413
FEATURE                    Location/Qualifiers
REGION                     1..413
                           note = MISC_FEATURE - TWEAKR/IL9R/cGC-F
source                     1..413
                           mol_type = protein
                           organism = synthetic construct
SEQUENCE: 171
EQAPGTAPCS RGSSWSADLD KCMDCASCRA RPHSDFCLGC AAAPPAPFRL LWPLIPPWGW   60
PGNTLVAVSI FLLLTGPTYL LFKLSPRVKR IFYQNVPSPA MFFQPLYSVH NGNFQTWMGA  120
HGAGVLLSQD CAGTPQGALE PCVQEATALL TCGPARPWKS VALEEEQEGP GTRLPGNLSS  180
EDVLPAGCTE WRVQTLAYLP QEDWAPTSLT RPAPPDSEGS RSSSSSSSSN NNNYCALGCY  240
GGWHLSALPG NTQSSGPIPA LACGLSCDHQ GLETQQGVAW VLAGHCQRPG LHEDLQGMLL  300
PSVLSKARSW TFGGGGSGGG GSGGGGSERT MPRIPTLKNL EDLVTEYHGN FSAWSGVSKG  360
LAESLQPDYS ERLCLVSEIP PKGGALGEGP GASPCNQHSP YWAPPCYTLK PET         413

SEQ ID NO: 172             moltype = AA   length = 410
FEATURE                    Location/Qualifiers
REGION                     1..410
                           note = MISC_FEATURE - TWEAKR/IL9R/cGC-S
source                     1..410
                           mol_type = protein
                           organism = synthetic construct
SEQUENCE: 172
EQAPGTAPCS RGSSWSADLD KCMDCASCRA RPHSDFCLGC AAAPPAPFRL LWPLIPPWGW   60
PGNTLVAVSI FLLLTGPTYL LFKLSPRVKR IFYQNVPSPA MFFQPLYSVH NGNFQTWMGA  120
HGAGVLLSQD CAGTPQGALE PCVQEATALL TCGPARPWKS VALEEEQEGP GTRLPGNLSS  180
EDVLPAGCTE WRVQTLAYLP QEDWAPTSLT RPAPPDSEGS RSSSSSSSSN NNNYCALGCY  240
GGWHLSALPG NTQSSGPIPA LACGLSCDHQ GLETQQGVAW VLAGHCQRPG LHEDLQGMLL  300
PSVLSKARSW TFQPQPQPQP QPQPERTMPR IPTLKNLEDL VTEYHGNFSA WSGVSKGLAE  360
SLQPDYSERL CLVSEIPPKG GALGEGPGAS PCNQHSPYWA PPCYTLKPET             410

SEQ ID NO: 173             moltype = AA   length = 402
FEATURE                    Location/Qualifiers
REGION                     1..402
                           note = MISC_FEATURE - TWEAKR/IL9R/cGC-F/TNFR1-TM
source                     1..402
                           mol_type = protein
                           organism = synthetic construct
SEQUENCE: 173
EQAPGTAPCS RGSSWSADLD KCMDCASCRA RPHSDFCLGC AAAPPAPFRL LWPVLLPLVI   60
FFGLCLLSLL FIGLMYVKRI FYQNVPSPAM FFQPLYSVHN GNFQTWMGAH GAGVLLSQDC  120
```

```
AGTPQGALEP CVQEATALLT CGPARPWKSV ALEEEQEGPG TRLPGNLSSE DVLPAGCTEW    180
RVQTLAYLPQ EDWAPTSLTR PAPPDSEGSR SSSSSSSSNN NNYCALGCYG GWHLSALPGN    240
TQSSGPIPAL ACGLSCDHQG LETQQGVAWV LAGHCQRPGL HEDLQGMLLP SVLSKARSWT    300
FGGGGSGGGG SGGGGSERTM PRIPTLKNLE DLVTEYHGNF SAWSGVSKGL AESLQPDYSE    360
RLCLVSEIPP KGGALGEGPG ASPCNQHSPY WAPPCYTLKP ET                      402

SEQ ID NO: 174         moltype = AA  length = 399
FEATURE                Location/Qualifiers
REGION                 1..399
                       note = MISC_FEATURE - TWEAKR/IL9R/cGC-S/TNFR1-TM
source                 1..399
                       mol_type = protein
                       organism = synthetic construct
SEQUENCE: 174
EQAPGTAPCS RGSSWSADLD KCMDCASCRA RPHSDFCLGC AAAPPAPFRL LWPVLLPLVI    60
FFGLCLLSLL FIGLMYVKRI FYQNVPSPAM FFQPLYSVHN GNFQTWMGAH GAGVLLSQDC    120
AGTPQGALEP CVQEATALLT CGPARPWKSV ALEEEQEGPG TRLPGNLSSE DVLPAGCTEW    180
RVQTLAYLPQ EDWAPTSLTR PAPPDSEGSR SSSSSSSSNN NNYCALGCYG GWHLSALPGN    240
TQSSGPIPAL ACGLSCDHQG LETQQGVAWV LAGHCQRPGL HEDLQGMLLP SVLSKARSWT    300
FQPQPQPQPQ PQPERTMPRI PTLKNLEDLV TEYHGNFSAW SGVSKGLAES LQPDYSERLC    360
LVSEIPPKGG ALGEGPGASP CNQHSPYWAP PCYTLKPET                          399

SEQ ID NO: 175         moltype = AA  length = 729
FEATURE                Location/Qualifiers
REGION                 1..729
                       note = MISC_FEATURE - OPG/IL9R/cGC-F/TNFR1-TM
source                 1..729
                       mol_type = protein
                       organism = synthetic construct
SEQUENCE: 175
ETFPPKYLHY DEETSHQLLC DKCPPGTYLK QHCTAKWKTV CAPCPDHYYT DSWHTSDECL    60
YCSPVCKELQ YVKQECNRTH NRVCECKEGR YLEIEFCLKH RSCPPGFVV QAGTPERNTV     120
CKRCPDGFFS NETSSKAPCR KHTNCSVFGL LLTQKGNATH DNICSGNSES TQKCGIDVTL    180
CEEAFFRFAV PTKFTPNWLS VLVDNLPGTK VNAESVERIK RQHSSQEQTF QLLKLWKHQN    240
KDQDIVKKII QDIDLCENSV QRHIGHANLT FEQLRSLMES LPGKKVGAED IEKTIKACKP    300
SDQILKLLSL WRIKNGDQDT LKGLMHALKH SKTYHFPKTV TQSLKKTIRF LHSFTMYKLY    360
QKLFLEMIGN QVQSVKISCL VLLPLVIFFG LCLLSLLFIG LMYVKRIFYQ NVPSPAMFFQ    420
PLYSVHNGNF QTWMGAHGAG VLLSQDCAGT PQGALEPCVQ EATALLTCGP ARPWKSVALE    480
EEQEGPGTRL PGNLSSEDVL PAGCTEWRVQ TLAYLPQEDW APTSLTRPAP PDSEGSRSSS    540
SSSSSNNNNY CALGCYGGWH LSALPGNTQS SGPIPALACG LSCDHQGLET QQGVAWVLAG    600
HCQRPGLHED LQGMLLPSVL SKARSWTFGG GGSGGGGSGG GGSERTMPRI PTLKNLEDLV    660
TEYHGNFSAW SGVSKGLAES LQPDYSERLC LVSEIPPKGG ALGEGPGASP CNQHSPYWAP    720
PCYTLKPET                                                            729

SEQ ID NO: 176         moltype = AA  length = 726
FEATURE                Location/Qualifiers
REGION                 1..726
                       note = MISC_FEATURE - OPG/IL9R/cGC-S/TNFR1-TM
source                 1..726
                       mol_type = protein
                       organism = synthetic construct
SEQUENCE: 176
ETFPPKYLHY DEETSHQLLC DKCPPGTYLK QHCTAKWKTV CAPCPDHYYT DSWHTSDECL    60
YCSPVCKELQ YVKQECNRTH NRVCECKEGR YLEIEFCLKH RSCPPGFVV QAGTPERNTV     120
CKRCPDGFFS NETSSKAPCR KHTNCSVFGL LLTQKGNATH DNICSGNSES TQKCGIDVTL    180
CEEAFFRFAV PTKFTPNWLS VLVDNLPGTK VNAESVERIK RQHSSQEQTF QLLKLWKHQN    240
KDQDIVKKII QDIDLCENSV QRHIGHANLT FEQLRSLMES LPGKKVGAED IEKTIKACKP    300
SDQILKLLSL WRIKNGDQDT LKGLMHALKH SKTYHFPKTV TQSLKKTIRF LHSFTMYKLY    360
QKLFLEMIGN QVQSVKISCL VLLPLVIFFG LCLLSLLFIG LMYVKRIFYQ NVPSPAMFFQ    420
PLYSVHNGNF QTWMGAHGAG VLLSQDCAGT PQGALEPCVQ EATALLTCGP ARPWKSVALE    480
EEQEGPGTRL PGNLSSEDVL PAGCTEWRVQ TLAYLPQEDW APTSLTRPAP PDSEGSRSSS    540
SSSSSNNNNY CALGCYGGWH LSALPGNTQS SGPIPALACG LSCDHQGLET QQGVAWVLAG    600
HCQRPGLHED LQGMLLPSVL SKARSWTFQP QPQPQPQPQP ERTMPRIPTL KNLEDLVTEY    660
HGNFSAWSGV SKGLAESLQP DYSERLCLVS EIPPKGGALG EGPGASPCNQ HSPYWAPPCY    720
TLKPET                                                               726

SEQ ID NO: 177         moltype = AA  length = 514
FEATURE                Location/Qualifiers
REGION                 1..514
                       note = MISC_FEATURE - TACI/IL9R/cGC-F/TNFR1-TM
source                 1..514
                       mol_type = protein
                       organism = synthetic construct
SEQUENCE: 177
MSGLGRSRRG GRSRVDQEER FPQGLWTGVA MRSCPEEQYW DPLLGTCMSC KTICNHQSQR    60
TCAAFCRSLS CRKEQGKFYD HLLRDCISCA SICGQHPKQC AYFCENKLRS PVNLPPELRR    120
QRSGEVENNS DNSGRYQGLE HRGSEASPAL PGLKLSADQV ALVYSVLLPL VIFFGLCLLS    180
LLFIGLMYVK RIFYQNVPSP AMFFQPLYSV HNGNFQTWMG AHGAGVLLSQ DCAGTPQGAL    240
EPCVQEATAL LTCGPARPWK SVALEEEQEG PGTRLPGNLS SEDVLPAGCT EWRVQTLAYL    300
```

```
PQEDWAPTSL TRPAPPDSEG SRSSSSSSSS NNNNYCALGC YGGWHLSALP GNTQSSGPIP    360
ALACGLSCDH QGLETQQGVA WVLAGHCQRP GLHEDLQGML LPSVLSKARS WTFGGGGSGG    420
GGSGGGGSER TMPRIPTLKN LEDLVTEYHG NFSAWSGVSK GLAESLQPDY SERLCLVSEI    480
PPKGGALGEG PGASPCNQHS PYWAPPCYTL KPET                                514

SEQ ID NO: 178          moltype = AA   length = 511
FEATURE                 Location/Qualifiers
REGION                  1..511
                        note = MISC_FEATURE - TACI/IL9R/cGC-S/TNFR1-TM
source                  1..511
                        mol_type = protein
                        organism = synthetic construct
SEQUENCE: 178
MSGLGRSRRG GRSRVDQEER FPQGLWTGVA MRSCPEEQYW DPLLGTCMSC KTICNHQSQR     60
TCAAFCRSLS CRKEQGKFYD HLLRDCISCA SICGQHPKQC AYFCENKLRS PVNLPPELRR    120
QRSGEVENNS DNSGRYQGLE HRGSEASPAL PGLKLSADQV ALVYSVLLPL VIFFGLCLLS    180
LLFIGLMYVK RIFYQNVPSP AMFFQPLYSV HNGNFQTWMG AHGAGVLLSQ DCAGTPQGAL    240
EPCVQEATAL LTCGPARPWK SVALEEEQEG PGTRLPGNLS SEDVLPAGCT EWRVQTLAYL    300
PQEDWAPTSL TRPAPPDSEG SRSSSSSSSS NNNNYCALGC YGGWHLSALP GNTQSSGPIP    360
ALACGLSCDH QGLETQQGVA WVLAGHCQRP GLHEDLQGML LPSVLSKARS WTFQPQPQPQ    420
PQPQPERTMP RIPTLKNLED LVTEYHGNFS AWSGVSKGLA ESLQPDYSER LCLVSEIPPK    480
GGALGEGPGA SPCNQHSPYW APPCYTLKPE T                                   511

SEQ ID NO: 179          moltype = AA   length = 403
FEATURE                 Location/Qualifiers
REGION                  1..403
                        note = MISC_FEATURE - BCMA/IL9R/cGC-F/TNFR1-TM
source                  1..403
                        mol_type = protein
                        organism = synthetic construct
SEQUENCE: 179
MLQMAGQCSQ NEYFDSLLHA CIPCQLRCSS NTPPLTCQRY CNASVTNSVK GTNAVLLPLV     60
IFFGLCLLSL LFIGLMYVKR IFYQNVPSPA MFFQPLYSVH NGNFQTWMGA HGAGVLLSQD    120
CAGTPQGALE PCVQEATALL TCGPARPWKS VALEEEQEGP GTRLPGNLSS EDVLPAGCTE    180
WRVQTLAYLP QEDWAPTSLT RPAPPDSEGS RSSSSSSSSN NNNYCALGCY GGWHLSALPG    240
NTQSSGPIPA LACGLSCDHQ GLETQQGVAW VLAGHCQRPG LHEDLQGMLL PSVLSKARSW    300
TFGGGGSGGG GSGGGGSERT MPRIPTLKNL EDLVTEYHGN FSAWSGVSKG LAESLQPDYS    360
ERLCLVSEIP PKGGALGEGP GASPCNQHSP YWAPPCYTLK PET                      403

SEQ ID NO: 180          moltype = AA   length = 400
FEATURE                 Location/Qualifiers
REGION                  1..400
                        note = MISC_FEATURE - BCMA/IL9R/cGC-S/TNFR1-TM
source                  1..400
                        mol_type = protein
                        organism = synthetic construct
SEQUENCE: 180
MLQMAGQCSQ NEYFDSLLHA CIPCQLRCSS NTPPLTCQRY CNASVTNSVK GTNAVLLPLV     60
IFFGLCLLSL LFIGLMYVKR IFYQNVPSPA MFFQPLYSVH NGNFQTWMGA HGAGVLLSQD    120
CAGTPQGALE PCVQEATALL TCGPARPWKS VALEEEQEGP GTRLPGNLSS EDVLPAGCTE    180
WRVQTLAYLP QEDWAPTSLT RPAPPDSEGS RSSSSSSSSN NNNYCALGCY GGWHLSALPG    240
NTQSSGPIPA LACGLSCDHQ GLETQQGVAW VLAGHCQRPG LHEDLQGMLL PSVLSKARSW    300
TFQPQPQPQP QPQPERTMPR IPTLKNLEDL VTEYHGNFSA WSGVSKGLAE SLQPDYSERL    360
CLVSEIPPKG GALGEGPGAS PCNQHSPYWA PPCYTLKPET                          400

SEQ ID NO: 181          moltype = AA   length = 571
FEATURE                 Location/Qualifiers
REGION                  1..571
                        note = MISC_FEATURE - NGFR/IL9R/cGC-F/TNFR1-TM
source                  1..571
                        mol_type = protein
                        organism = synthetic construct
SEQUENCE: 181
KEACPTGLYT HSGECCKACN LGEGVAQPCG ANQTVCEPCL DSVTFSDVVS ATEPCKPCTE     60
CVGLQSMSAP CVEADDAVCR CAYGYYQDET TGRCEACRVC EAGSGLVFSC QDKQNTVCEE    120
CPDGTYSDEA NHVDPCLPCT VCEDTERQLR ECTRWADAEC EEIPGRWITR STPPEGSDST    180
APSTQEPEAP PEQDLIASTV AGVVTTVMGS SQPVVTRGTT DNVLLPLVIF FGLCLLSLLF    240
IGLMYVKRIF YQNVPSPAMF FQPLYSVHNG NFQTWMGAHG AGVLLSQDCA GTPQGALEPC    300
VQEATALLTC GPARPWKSVA LEEEQEGPGT RLPGNLSSED VLPAGCTEWR VQTLAYLPQE    360
DWAPTSLTRP APPDSEGSRS SSSSSSSNNN NYCALGCYGG WHLSALPGNT QSSGPIPALA    420
CGLSCDHQGL ETQQGVAWVL AGHCQRPGLH EDLQGMLLPS VLSKARSWTF GGGGSGGGGS    480
GGGGSERTMP RIPTLKNLED LVTEYHGNFS AWSGVSKGLA ESLQPDYSER LCLVSEIPPK    540
GGALGEGPGA SPCNQHSPYW APPCYTLKPE T                                   571

SEQ ID NO: 182          moltype = AA   length = 568
FEATURE                 Location/Qualifiers
REGION                  1..568
                        note = MISC_FEATURE - NGFR/IL9R/cGC-S/TNFR1-TM
source                  1..568
```

```
                        mol_type = protein
                        organism = synthetic construct
SEQUENCE: 182
KEACPTGLYT HSGECCKACN LGEGVAQPCG ANQTVCEPCL DSVTFSDVVS ATEPCKPCTE    60
CVGLQSMSAP CVEADDAVCR CAYGYYQDET TGRCEACRVC EAGSGLVFSC QDKQNTVCEE   120
CPDGTYSDEA NHVDPCLPCT VCEDTERQLR ECTRWADAEC EEIPGRWITR STPPEGSDST   180
APSTQEPEAP PEQDLIASTV AGVVTTVMGS SQPVVTRGTT DNVLLPLVIF FGLCLLSLLF   240
IGLMYVKRIF YQNVPSPAMF FQPLYSVHNG NFQTWMGAHG AGVLLSQDCA GTPQGALEPC   300
VQEATALLTC GPARPWKSVA LEEEQEGPGT RLPGNLSSED VLPAGCTEWR VQTLAYLPQE   360
DWAPTSLTRP APPDSEGSRS SSSSSSSNNN NYCALGCYGG WHLSALPGNT QSSGPIPALA   420
CGLSCDHQGL ETQQGVAWVL AGHCQRPGLH EDLQGMLLPS VLSKARSWTF QPQPQPQPQP   480
QPERTMPRIP TLKNLEDLVT EYHGNFSAWS GVSKGLAESL QPDYSERLCL VSEIPPKGGA   540
LGEGPGASPC NQHSPYWAPP CYTLKPET                                    568

SEQ ID NO: 183          moltype = AA  length = 510
FEATURE                 Location/Qualifiers
REGION                  1..510
                        note = MISC_FEATURE - EDAR/IL9R/cGC-F/TNFR1-TM
source                  1..510
                        mol_type = protein
                        organism = synthetic construct
SEQUENCE: 183
EYSNCGENEY YNQTTGLCQE CPPCGPGEEP YLSCGYGTKD EDYGCVPCPA EKFSKGGYQI    60
CRRHKDCEGF FRATVLTPGD MENDAECGPC LPGYYMLENR PRNIYGMVCY SCLLAPPNTK   120
ECVGATSGAS ANFPGTSGSS TLSPFQHAHK ELSGQGHLAT AVLLPLVIFF GLCLLSLLFI   180
GLMYVKRIFY QNVPSPAMFF QPLYSVHNGN FQTWMGAHGA GVLLSQDCAG TPQGALEPCV   240
QEATALLTCG PARPWKSVAL EEEQEGPGTR LPGNLSSEDV LPAGCTEWRV QTLAYLPQED   300
WAPTSLTRPA PPDSEGSRSS SSSSSSNNNN YCALGCYGGW HLSALPGNTQ SSGPIPALAC   360
GLSCDHQGLE TQQGVAWVLA GHCQRPGLHE DLQGMLLPSV LSKARSWTFG GGGSGGGGSG   420
GGGSERTMPR IPTLKNLEDL VTEYHGNFSA WSGVSKGLAE SLQPDYSERL CLVSEIPPKG   480
GALGEGPGAS PCNQHSPYWA PPCYTLKPET                                  510

SEQ ID NO: 184          moltype = AA  length = 507
FEATURE                 Location/Qualifiers
REGION                  1..507
                        note = MISC_FEATURE - EDAR/IL9R/cGC-S/TNFR1-TM
source                  1..507
                        mol_type = protein
                        organism = synthetic construct
SEQUENCE: 184
EYSNCGENEY YNQTTGLCQE CPPCGPGEEP YLSCGYGTKD EDYGCVPCPA EKFSKGGYQI    60
CRRHKDCEGF FRATVLTPGD MENDAECGPC LPGYYMLENR PRNIYGMVCY SCLLAPPNTK   120
ECVGATSGAS ANFPGTSGSS TLSPFQHAHK ELSGQGHLAT AVLLPLVIFF GLCLLSLLFI   180
GLMYVKRIFY QNVPSPAMFF QPLYSVHNGN FQTWMGAHGA GVLLSQDCAG TPQGALEPCV   240
QEATALLTCG PARPWKSVAL EEEQEGPGTR LPGNLSSEDV LPAGCTEWRV QTLAYLPQED   300
WAPTSLTRPA PPDSEGSRSS SSSSSSNNNN YCALGCYGGW HLSALPGNTQ SSGPIPALAC   360
GLSCDHQGLE TQQGVAWVLA GHCQRPGLHE DLQGMLLPSV LSKARSWTFQ PQPQPQPQPQ   420
PERTMPRIPT LKNLEDLVTE YHGNFSAWSG VSKGLAESLQ PDYSERLCLV SEIPPKGGAL   480
GEGPGASPCN QHSPYWAPPC YTLKPET                                     507

SEQ ID NO: 185          moltype = AA  length = 505
FEATURE                 Location/Qualifiers
REGION                  1..505
                        note = MISC_FEATURE - DCR2 (TNFRSF10D) /IL9R/cGC-F/TNFR1-TM
source                  1..505
                        mol_type = protein
                        organism = synthetic construct
SEQUENCE: 185
ATIPRQDEVP QQTVAPQQQR RSLKEEECPA GSHRSEYTGA CNPCTEGVDY TIASNNLPSC    60
LLCTVCKSGQ TNKSSCTTTR DTVCQCEKGS FQDKNSPEMC RTCRTGCPRG MVKVSNCTPR   120
SDIKCKNESA ASSTGKTPAA EETVTTILGM LASPYHVLLP LVIFFGLCLL SLLFIGLMYV   180
KRIFYQNVPS PAMFFQPLYS VHNGNFQTWM GAHGAGVLLS QDCAGTPQGA LEPCVQEATA   240
LLTCGPARPW KSVALEEEQE GPGTRLPGNL SSEDVLPAGC TEWRVQTLAY LPQEDWAPTS   300
LTRPAPPDSE GSRSSSSSSS SNNNNYCALG CYGGWHLSAL PGNTQSSGPI PALACGLSCD   360
HQGLETQQGV AWVLAGHCQR PGLHEDLQGM LLPSVLSKAR SWTFGGGGSG GGGSGGGGSE   420
RTMPRIPTLK NLEDLVTEYH GNFSAWSGVS KGLAESLQPD YSERLCLVSE IPPKGGALGE   480
GPGASPCNQH SPYWAPPCYT LKPET                                       505

SEQ ID NO: 186          moltype = AA  length = 502
FEATURE                 Location/Qualifiers
REGION                  1..502
                        note = MISC_FEATURE - DCR2 (TNFRSF10D) /IL9R/cGC-S/TNFR1-TM
source                  1..502
                        mol_type = protein
                        organism = synthetic construct
SEQUENCE: 186
ATIPRQDEVP QQTVAPQQQR RSLKEEECPA GSHRSEYTGA CNPCTEGVDY TIASNNLPSC    60
LLCTVCKSGQ TNKSSCTTTR DTVCQCEKGS FQDKNSPEMC RTCRTGCPRG MVKVSNCTPR   120
SDIKCKNESA ASSTGKTPAA EETVTTILGM LASPYHVLLP LVIFFGLCLL SLLFIGLMYV   180
```

```
KRIFYQNVPS PAMFFQPLYS VHNGNFQTWM GAHGAGVLLS QDCAGTPQGA LEPCVQEATA    240
LLTCGPARPW KSVALEEEQE GPGTRLPGNL SSEDVLPAGC TEWRVQTLAY LPQEDWAPTS    300
LTRPAPPDSE GSRSSSSSSS SNNNNYCALG CYGGWHLSAL PGNTQSSGPI PALACGLSCD    360
HQGLETQQGV AWVLAGHCQR PGLHEDLQGM LLPSVLSKAR SWTFQPQPQP QPQPQPERTM    420
PRIPTLKNLE DLVTEYHGNF SAWSGVSKGL AESLQPDYSE RLCLVSEIPP KGGALGEGPG    480
ASPCNQHSPY WAPPCYTLKP ET                                            502

SEQ ID NO: 187          moltype = AA  length = 560
FEATURE                 Location/Qualifiers
REGION                  1..560
                        note = MISC_FEATURE - DCR1 (TNFRSF10C) /IL9R/cGC-F/TNFR1-TM
source                  1..560
                        mol_type = protein
                        organism = synthetic construct
SEQUENCE: 187
ATTARQEEVP QQTVAPQQQR HSFKGEECPA GSHRSEHTGA CNPCTEGVDY TNASNNEPSC    60
FPCTVCKSDQ KHKSSCTMTR DTVCQCKEGT FRNENSPEMC RKCSRCPSGE VQVSNCTSWD    120
DIQCVEEFGA NATVETPAAE ETMNTSPGTP APAAEETMNT SPGTPAPAAE ETMTTSPGTP    180
APAAEETMTT SPGTPAPAAE ETMITSPGTP AVLLPLVIFF GLCLLSLLFI GLMYVKRIFY    240
QNVPSPAMFF QPLYSVHNGN FQTWMGAHGA GVLLSQDCAG TPQGALEPCV QEATALLTCG    300
PARPWKSVAL EEEQEGPGTR LPGNLSSEDV LPAGCTEWRV QTLAYLPQED WAPTSLTRPA    360
PPDSEGSRSS SSSSSSNNNN YCALGCYGGW HLSALPGNTQ SSGPIPALAC GLSCDHQGLE    420
TQQGVAWVLA GHCQRPGLHE DLQGMLLPSV LSKARSWTFG GGGSGGGGSG GGGSERTMPR    480
IPTLKNLEDL VTEYHGNFSA WSGVSKGLAE SLQPDYSERL CLVSEIPPKG GALGEGPGAS    540
PCNQHSPYWA PPCYTLKPET                                               560

SEQ ID NO: 188          moltype = AA  length = 557
FEATURE                 Location/Qualifiers
REGION                  1..557
                        note = MISC_FEATURE - DCR1 (TNFRSF10C) /IL9R/cGC-S/TNFR1-TM
source                  1..557
                        mol_type = protein
                        organism = synthetic construct
SEQUENCE: 188
ATTARQEEVP QQTVAPQQQR HSFKGEECPA GSHRSEHTGA CNPCTEGVDY TNASNNEPSC    60
FPCTVCKSDQ KHKSSCTMTR DTVCQCKEGT FRNENSPEMC RKCSRCPSGE VQVSNCTSWD    120
DIQCVEEFGA NATVETPAAE ETMNTSPGTP APAAEETMNT SPGTPAPAAE ETMTTSPGTP    180
APAAEETMTT SPGTPAPAAE ETMITSPGTP AVLLPLVIFF GLCLLSLLFI GLMYVKRIFY    240
QNVPSPAMFF QPLYSVHNGN FQTWMGAHGA GVLLSQDCAG TPQGALEPCV QEATALLTCG    300
PARPWKSVAL EEEQEGPGTR LPGNLSSEDV LPAGCTEWRV QTLAYLPQED WAPTSLTRPA    360
PPDSEGSRSS SSSSSSNNNN YCALGCYGGW HLSALPGNTQ SSGPIPALAC GLSCDHQGLE    420
TQQGVAWVLA GHCQRPGLHE DLQGMLLPSV LSKARSWTFQ PQPQPQPQPQ PERTMPRIPT    480
LKNLEDLVTE YHGNFSAWSG VSKGLAESLQ PDYSERLCLV SEIPPKGGAL GEGPGASPCN    540
QHSPYWAPPC YTLKPET                                                  557

SEQ ID NO: 189          moltype = AA  length = 522
FEATURE                 Location/Qualifiers
REGION                  1..522
                        note = MISC_FEATURE - CD40/IL9R/cGC-F/TNFR1-TM
source                  1..522
                        mol_type = protein
                        organism = synthetic construct
SEQUENCE: 189
EPPTACREKQ YLINSQCCSL CQPGQKLVSD CTEFTETECL PCGESEFLDT WNRETHCHQH    60
KYCDPNLGLR VQQKGTSETD TICTCEEGWH CTSEACESCV LHRSCSPGFG VKQIATGVSD    120
TICEPCPVGF FSNVSSAFEK CHPWTSCETK DLVVQQAGTN KTDVVCGPQD RLRVLLPLVI    180
FFGLCLLSLL FIGLMYVKRI FYQNVPSPAM FFQPLYSVHN GNFQTWMGAH GAGVLLSQDC    240
AGTPQGALEP CVQEATALLT CGPARPWKSV ALEEEQEGPG TRLPGNLSSE DVLPAGCTEW    300
RVQTLAYLPQ EDWAPTSLTR PAPPDSEGSR SSSSSSSSNN NNYCALGCYG GWHLSALPGN    360
TQSSGPIPAL ACGLSCDHQG LETQQGVAWV LAGHCQRPGL HEDLQGMLLP SVLSKARSWT    420
FGGGGSGGGG SGGGGSERTM PRIPTLKNLE DLVTEYHGNF SAWSGVSKGL AESLQPDYSE    480
RLCLVSEIPP KGGALGEGPG ASPCNQHSPY WAPPCYTLKP ET                      522

SEQ ID NO: 190          moltype = AA  length = 519
FEATURE                 Location/Qualifiers
REGION                  1..519
                        note = MISC_FEATURE - CD40/IL9R/cGC-S/TNFR1-TM
source                  1..519
                        mol_type = protein
                        organism = synthetic construct
SEQUENCE: 190
EPPTACREKQ YLINSQCCSL CQPGQKLVSD CTEFTETECL PCGESEFLDT WNRETHCHQH    60
KYCDPNLGLR VQQKGTSETD TICTCEEGWH CTSEACESCV LHRSCSPGFG VKQIATGVSD    120
TICEPCPVGF FSNVSSAFEK CHPWTSCETK DLVVQQAGTN KTDVVCGPQD RLRVLLPLVI    180
FFGLCLLSLL FIGLMYVKRI FYQNVPSPAM FFQPLYSVHN GNFQTWMGAH GAGVLLSQDC    240
AGTPQGALEP CVQEATALLT CGPARPWKSV ALEEEQEGPG TRLPGNLSSE DVLPAGCTEW    300
RVQTLAYLPQ EDWAPTSLTR PAPPDSEGSR SSSSSSSSNN NNYCALGCYG GWHLSALPGN    360
TQSSGPIPAL ACGLSCDHQG LETQQGVAWV LAGHCQRPGL HEDLQGMLLP SVLSKARSWT    420
FQPQPQPQPQ PQPERTMPRI PTLKNLEDLV TEYHGNFSAW SGVSKGLAES LQPDYSERLC    480
```

```
LVSEIPPKGG ALGEGPGASP CNQHSPYWAP PCYTLKPET                      519

SEQ ID NO: 191          moltype = AA   length = 497
FEATURE                 Location/Qualifiers
REGION                  1..497
                        note = MISC_FEATURE - FAS/IL9R/cGC-F/TNFR1-TM
source                  1..497
                        mol_type = protein
                        organism = synthetic construct
SEQUENCE: 191
QVTDINSKGL ELRKTVTTVE TQNLEGLHHD GQFCHKPCPP GERKARDCTV NGDEPDCVPC   60
QEGKEYTDKA HFSSKCRRCR LCDEGHGLEV EINCTRTQNT KCRCKPNFFC NSTVCEHCDP  120
CTKCEHGIIK ECTLTSNTKC KEEGSRSNVL LPLVIFFGLC LLSLLFIGLM YVKRIFYQNV  180
PSPAMFFQPL YSVHNGNFQT WMGAHGAGVL LSQDCAGTPQ GALEPCVQEA TALLTCGPAR  240
PWKSVALEEE QEGPGTRLPG NLSSEDVLPA GCTEWRVQTL AYLPQEDWAP TSLTRPAPPD  300
SEGSRSSSSS SSSNNNNYCA LGCYGGWHLS ALPGNTQSSG PIPALACGLS CDHQGLETQQ  360
GVAWVLAGHC QRPGLHEDLQ GMLLPSVLSK ARSWTFGGGG SGGGGSGGGG SERTMPRIPT  420
LKNLEDLVTE YHGNFSAWSG VSKGLAESLQ PDYSERLCLV SEIPPKGGAL GEGPGASPCN  480
QHSPYWAPPC YTLKPET                                                497

SEQ ID NO: 192          moltype = AA   length = 494
FEATURE                 Location/Qualifiers
REGION                  1..494
                        note = MISC_FEATURE - FAS/IL9R/cGC-S/TNFR1-TM
source                  1..494
                        mol_type = protein
                        organism = synthetic construct
SEQUENCE: 192
QVTDINSKGL ELRKTVTTVE TQNLEGLHHD GQFCHKPCPP GERKARDCTV NGDEPDCVPC   60
QEGKEYTDKA HFSSKCRRCR LCDEGHGLEV EINCTRTQNT KCRCKPNFFC NSTVCEHCDP  120
CTKCEHGIIK ECTLTSNTKC KEEGSRSNVL LPLVIFFGLC LLSLLFIGLM YVKRIFYQNV  180
PSPAMFFQPL YSVHNGNFQT WMGAHGAGVL LSQDCAGTPQ GALEPCVQEA TALLTCGPAR  240
PWKSVALEEE QEGPGTRLPG NLSSEDVLPA GCTEWRVQTL AYLPQEDWAP TSLTRPAPPD  300
SEGSRSSSSS SSSNNNNYCA LGCYGGWHLS ALPGNTQSSG PIPALACGLS CDHQGLETQQ  360
GVAWVLAGHC QRPGLHEDLQ GMLLPSVLSK ARSWTFQPQP QPQPQPQPER TMPRIPTLKN  420
LEDLVTEYHG NFSAWSGVSK GLAESLQPDY SERLCLVSEI PPKGGALGEG PGASPCNQHS  480
PYWAPPCYTL KPET                                                   494

SEQ ID NO: 193          moltype = AA   length = 565
FEATURE                 Location/Qualifiers
REGION                  1..565
                        note = MISC_FEATURE - DR4/IL9R/cGC-F/TNFR1-TM
source                  1..565
                        mol_type = protein
                        organism = synthetic construct
SEQUENCE: 193
ASGTEAAAAT PSKVWGSSAG RIEPRGGGRG ALPTSMGQHG PSARARAGRA PGPRPAREAS   60
PRLRVHKTFK FVVVGVLLQV VPSSAATIKL HDQSIGTQQW EHSPLGELCP PGSHRSEHPG  120
ACNRCTEGVG YTNASNNLFA CLPCTACKSD EEERSPCTTT RNTACQCKPG TFRNDNSAEM  180
CRKCSRGCPR GMVKVKDCTP WSDIECVHKE SGNGHNVLLP LVIFFGLCLL SLLFIGLMYV  240
KRIFYQNVPS PAMFFQPLYS VHNGNFQTWM GAHGAGVLLS QDCAGTPQGA LEPCVQEATA  300
LLTCGPARPW KSVALEEEQE GPGTRLPGNL SSEDVLPAGC TEWRVQTLAY LPQEDWAPTS  360
LTRPAPPDSE GSRSSSSSSS SNNNNYCALG CYGGWHLSAL PGNTQSSGPI PALACGLSCD  420
HQGLETQQGV AWVLAGHCQR PGLHEDLQGM LLPSVLSKAR SWTFGGGGSG GGGSGGGGSE  480
RTMPRIPTLK NLEDLVTEYH GNFSAWSGVS KGLAESLQPD YSERLCLVSE IPPKGGALGE  540
GPGASPCNQH SPYWAPPCYT LKPET                                       565

SEQ ID NO: 194          moltype = AA   length = 562
FEATURE                 Location/Qualifiers
REGION                  1..562
                        note = MISC_FEATURE - DR4/IL9R/cGC-S/TNFR1-TM
source                  1..562
                        mol_type = protein
                        organism = synthetic construct
SEQUENCE: 194
ASGTEAAAAT PSKVWGSSAG RIEPRGGGRG ALPTSMGQHG PSARARAGRA PGPRPAREAS   60
PRLRVHKTFK FVVVGVLLQV VPSSAATIKL HDQSIGTQQW EHSPLGELCP PGSHRSEHPG  120
ACNRCTEGVG YTNASNNLFA CLPCTACKSD EEERSPCTTT RNTACQCKPG TFRNDNSAEM  180
CRKCSRGCPR GMVKVKDCTP WSDIECVHKE SGNGHNVLLP LVIFFGLCLL SLLFIGLMYV  240
KRIFYQNVPS PAMFFQPLYS VHNGNFQTWM GAHGAGVLLS QDCAGTPQGA LEPCVQEATA  300
LLTCGPARPW KSVALEEEQE GPGTRLPGNL SSEDVLPAGC TEWRVQTLAY LPQEDWAPTS  360
LTRPAPPDSE GSRSSSSSSS SNNNNYCALG CYGGWHLSAL PGNTQSSGPI PALACGLSCD  420
HQGLETQQGV AWVLAGHCQR PGLHEDLQGM LLPSVLSKAR SWTFQPQPQP QPQPQPERTM  480
PRIPTLKNLE DLVTEYHGNF SAWSGVSKGL AESLQPDYSE RLCLVSEIPP KGGALGEGPG  540
ASPCNQHSPY WAPPCYTLKP ET                                          562

SEQ ID NO: 195          moltype = AA   length = 654
FEATURE                 Location/Qualifiers
REGION                  1..654
```

```
                          note = MISC_FEATURE - DR6/IL9R/cGC-S/TNFR1-TM
source                    1..654
                          mol_type = protein
                          organism = synthetic construct
SEQUENCE: 195
QPEQKASNLI GTYRHVDRAT GQVLTCDKCP AGTYVSEHCT NTSLRVCSSC PVGTFTRHEN    60
GIEKCHDCSQ PCPWPMIEKL PCAALTDREC TCPPGMFQSN ATCAPHTVCP VGWGVRKKGT   120
ETEDVRCKQC ARGTFSDVPS SVMKCKAYTD CLSQNLVVIK PGTKETDNVC GTLPSFSSST   180
SPSPGTAIFP RPEHMETHEV PSSTYVPKGM NSTESNSSAS VRPKVLSSIQ EGTVPDNTSS   240
ARGKEDVNKT LPNLQVVNHQ QGPHHRHILK LLPSMEATGG EKSSTPIKGP KRGHPRQNLH   300
KHFDINEHVL LPLVIFFGLC LLSLLFIGLM YVKRIFYQNV PSPAMFFQPL YSVHNGNFQT   360
WMGAHGAGVL LSQDCAGTPQ GALEPCVQEA TALLTCGPAR PWKSVALEEE QEGPGTRLPG   420
NLSSEDVLPA GCTEWRVQTL AYLPQEDWAP TSLTRPAPPD SEGSRSSSSS SSSNNNNYCA   480
LGCYGGWHLS ALPGNTQSSG PIPALACGLS CDHQGLETQQ GVAWVLAGHC QRPGLHEDLQ   540
GMLLPSVLSK ARSWTFQPQP QPQPQPQPER TMPRIPTLKN LEDLVTEYHG NFSAWSGVSK   600
GLAESLQPDY SERLCLVSEI PPKGGALGEG PGASPCNQHS PYWAPPCYTL KPET         654

SEQ ID NO: 196          moltype = AA  length = 504
FEATURE                 Location/Qualifiers
REGION                  1..504
                        note = MISC_FEATURE - DR5/IL9R/cGC-F/TNFR1-TM
source                  1..504
                        mol_type = protein
                        organism = synthetic construct
SEQUENCE: 196
ITQQDLAPQQ RAAPQQKRSS PSEGLCPPGH HISEDGRDCI SCKYGQDYST HWNDLLFCLR    60
CTRCDSGEVE LSPCTTTRNT VCQCEEGTFR EEDSPEMCRK CRTGCPRGMV KVGDCTPWSD   120
IECVHKESGT KHSGEVPAVE ETVTSSPGTP ASPCSVLLPL VIFFGLCLLS LLFIGLMYVK   180
RIFYQNVPSP AMFFQPLYSV HNGNFQTWMG AHGAGVLLSQ DCAGTPQGAL EPCVQEATAL   240
LTCGPARPWK SVALEEEQEG PGTRLPGNLS SEDVLPAGCT EWRVQTLAYL PQEDWAPTSL   300
TRPAPPDSEG SRSSSSSSSS NNNNYCALGC YGGWHLSALP GNTQSSGPIP ALACGLSCDH   360
QGLETQQGVA WVLAGHCQRP GLHEDQGML LPSVLSKARS WTGGGGSGG GGSGGGGSER    420
TMPRIPTLKN LEDLVTEYHG NFSAWSGVSK GLAESLQPDY SERLCLVSEI PPKGGALGEG   480
PGASPCNQHS PYWAPPCYTL KPET                                          504

SEQ ID NO: 197          moltype = AA  length = 501
FEATURE                 Location/Qualifiers
REGION                  1..501
                        note = MISC_FEATURE - DR5/IL9R/cGC-S/TNFR1-TM
source                  1..501
                        mol_type = protein
                        organism = synthetic construct
SEQUENCE: 197
ITQQDLAPQQ RAAPQQKRSS PSEGLCPPGH HISEDGRDCI SCKYGQDYST HWNDLLFCLR    60
CTRCDSGEVE LSPCTTTRNT VCQCEEGTFR EEDSPEMCRK CRTGCPRGMV KVGDCTPWSD   120
IECVHKESGT KHSGEVPAVE ETVTSSPGTP ASPCSVLLPL VIFFGLCLLS LLFIGLMYVK   180
RIFYQNVPSP AMFFQPLYSV HNGNFQTWMG AHGAGVLLSQ DCAGTPQGAL EPCVQEATAL   240
LTCGPARPWK SVALEEEQEG PGTRLPGNLS SEDVLPAGCT EWRVQTLAYL PQEDWAPTSL   300
TRPAPPDSEG SRSSSSSSSS NNNNYCALGC YGGWHLSALP GNTQSSGPIP ALACGLSCDH   360
QGLETQQGVA WVLAGHCQRP GLHEDQGML LPSVLSKARS WTFQPQPQPQ PQPQPERTMP   420
RIPTLKNLED LVTEYHGNFS AWSGVSKGLA ESLQPDYSER LCLVSEIPPK GGALGEGPGA   480
SPCNQHSPYW APPCYTLKPE T                                             501

SEQ ID NO: 198          moltype = AA  length = 524
FEATURE                 Location/Qualifiers
REGION                  1..524
                        note = MISC_FEATURE - DR3/IL9R/cGC-F/TNFR1-TM
source                  1..524
                        mol_type = protein
                        organism = synthetic construct
SEQUENCE: 198
QGGTRSPRCD CAGDFHKKIG LFCCRGCPAG HYLKAPCTEP CGNSTCLVCP QDTFLAWENH    60
HNSECARCQA CDEQASQVAL ENCSAVADTR CGCKPGWFVE CQVSQCVSSS PFYCQPCLDH   120
GALHRHTRLL CSRRDTDCGT CLPGFYEHGD GCVSCPTSTL GSCPERCAAV CGWRQVLLPL   180
VIFFGLCLLS LLFIGLMYVK RIFYQNVPSP AMFFQPLYSV HNGNFQTWMG AHGAGVLLSQ   240
DCAGTPQGAL EPCVQEATAL LTCGPARPWK SVALEEEQEG PGTRLPGNLS SEDVLPAGCT   300
EWRVQTLAYL PQEDWAPTSL TRPAPPDSEG SRSSSSSSSS NNNNYCALGC YGGWHLSALP   360
GNTQSSGPIP ALACGLSCDH QGLETQQGVA WVLAGHCQRP GLHEDQGML LPSVLSKARS   420
WTFGGGGSGG GGSGGGGSER TMPRIPTLKN LEDLVTEYHG NFSAWSGVSK GLAESLQPDY   480
SERLCLVSEI PPKGGALGEG PGASPCNQHS PYWAPPCYTL KPET                    524

SEQ ID NO: 199          moltype = AA  length = 521
FEATURE                 Location/Qualifiers
REGION                  1..521
                        note = MISC_FEATURE - DR3/IL9R/cGC-S/TNFR1-TM
source                  1..521
                        mol_type = protein
                        organism = synthetic construct
SEQUENCE: 199
```

```
QGGTRSPRCD CAGDFHKKIG LFCCRGCPAG HYLKAPCTEP CGNSTCLVCP QDTFLAWENH  60
HNSECARCQA CDEQASQVAL ENCSAVADTR CGCKPGWFVE CQVSQCVSSS PFYCQPCLDC 120
GALHRHTRLL CSRRDTDCGT CLPGFYEHGD GCVSCPTSTL GSCPERCAAV CGWRQVLLPL 180
VIFFGLCLLS LLFIGLMYVK RIFYQNVPSP AMFFQPLYSV HNGNFQTWMG AHGAGVLLSQ 240
DCAGTPQGAL EPCVQEATAL LTCGPARPWK SVALEEEQEG PGTRLPGNLS SEDVLPAGCT 300
EWRVQTLAYL PQEDWAPTSL TRPAPPDSEG SRSSSSSSSS NNNNYCALGC YGGWHLSALP 360
GNTQSSGPIP ALACGLSCDH QGLETQQGVA WVLAGHCQRP GLHEDLQGML LPSVLSKARS 420
WTFQPQPQPQ PQPQPERTMP RIPTKNLED LVTEYHGNFS AWSGVSKGLA ESLQPDYSER 480
LCLVSEIPPK GGALGEGPGA SPCNQHSPYW APPCYTLKPE T                   521

SEQ ID NO: 200          moltype = AA  length = 584
FEATURE                 Location/Qualifiers
REGION                  1..584
                        note = MISC_FEATURE - TNFRSF1B/IL9R/cGC-F/TNFR1-TM
source                  1..584
                        mol_type = protein
                        organism = synthetic construct
SEQUENCE: 200
LPAQVAFTPY APEPGSTCRL REYYDQTAQM CCSKCSPGQH AKVFCTKTSD TVCDSCEDST  60
YTQLWNWVPE CLSCGSRCSS DQVETQACTR EQNRICTCRP GWYCALSKQE GCRLCAPLRK 120
CRPGFGVARP GTETSDVVCK PCAPGTFSNT TSSTDICRPH QICNVVAIPG NASMDAVCTS 180
TSPTRSMAPG AVHLPQPVST RSQHTQPTPE PSTAPSTSFL LPMGPSPPAE GSTGDVLLPL 240
VIFFGLCLLS LLFIGLMYVK RIFYQNVPSP AMFFQPLYSV HNGNFQTWMG AHGAGVLLSQ 300
DCAGTPQGAL EPCVQEATAL LTCGPARPWK SVALEEEQEG PGTRLPGNLS SEDVLPAGCT 360
EWRVQTLAYL PQEDWAPTSL TRPAPPDSEG SRSSSSSSSS NNNNYCALGC YGGWHLSALP 420
GNTQSSGPIP ALACGLSCDH QGLETQQGVA WVLAGHCQRP GLHEDLQGML LPSVLSKARS 480
WTFGGGGSGG GGSGGGGSER TMPRIPTLKN LEDLVTEYHG NFSAWSGVSK GLAESLQPDY 540
SERLCLVSEI PPKGGALGEG PGASPCNQHS PYWAPPCYTL KPET                584

SEQ ID NO: 201          moltype = AA  length = 581
FEATURE                 Location/Qualifiers
REGION                  1..581
                        note = MISC_FEATURE - TNFRSF1B/IL9R/cGC-S/TNFR1-TM
source                  1..581
                        mol_type = protein
                        organism = synthetic construct
SEQUENCE: 201
LPAQVAFTPY APEPGSTCRL REYYDQTAQM CCSKCSPGQH AKVFCTKTSD TVCDSCEDST  60
YTQLWNWVPE CLSCGSRCSS DQVETQACTR EQNRICTCRP GWYCALSKQE GCRLCAPLRK 120
CRPGFGVARP GTETSDVVCK PCAPGTFSNT TSSTDICRPH QICNVVAIPG NASMDAVCTS 180
TSPTRSMAPG AVHLPQPVST RSQHTQPTPE PSTAPSTSFL LPMGPSPPAE GSTGDVLLPL 240
VIFFGLCLLS LLFIGLMYVK RIFYQNVPSP AMFFQPLYSV HNGNFQTWMG AHGAGVLLSQ 300
DCAGTPQGAL EPCVQEATAL LTCGPARPWK SVALEEEQEG PGTRLPGNLS SEDVLPAGCT 360
EWRVQTLAYL PQEDWAPTSL TRPAPPDSEG SRSSSSSSSS NNNNYCALGC YGGWHLSALP 420
GNTQSSGPIP ALACGLSCDH QGLETQQGVA WVLAGHCQRP GLHEDLQGML LPSVLSKARS 480
WTFQPQPQPQ PQPQPERTMP RIPTKNLED LVTEYHGNFS AWSGVSKGLA ESLQPDYSER 540
LCLVSEIPPK GGALGEGPGA SPCNQHSPYW APPCYTLKPE T                   581

SEQ ID NO: 202          moltype = AA  length = 531
FEATURE                 Location/Qualifiers
REGION                  1..531
                        note = MISC_FEATURE - TNFRSF1/IL9R/cGC-F/TNFR1-TM
source                  1..531
                        mol_type = protein
                        organism = synthetic construct
SEQUENCE: 202
LVPHLGDREK RDSVCPQGKY IHPQNNSICC TKCHKGTYLY NDCPGPGQDT DCRECESGSF  60
TASENHLRHC LSCSKCRKEM GQVEISSCTV DRDTVCGCRK NQYRHYWSEN LFQCFNCSLC 120
LNGTVHLSCQ EKQNTVCTCH AGFFLRENEC VSCSNCKKSL ECTKLCLPQI ENVKGTEDSG 180
TTVLLPLVIF FGLCLLSLLF IGLMYVKRIF YQNVPSPAMF FQPLYSVHNG NFQTWMGAHG 240
AGVLLSQDCA GTPQGALEPC VQEATALLTC GPARPWKSVA LEEEQEGPGT RLPGNLSSED 300
VLPAGCTEWR VQTLAYLPQE DWAPTSLTRP APPDSEGSRS SSSSSSSNNN NYCALGCYGG 360
WHLSALPGNT QSSGPIPALA CGLSCDHQGL ETQQGVAWVL AGHCQRPGLH EDLQGMLLPS 420
VLSKARSWTF GGGSGGGGS GGGSERTMP RIPTKNLED LVTEYHGNFS AWSGVSKGLA 480
ESLQPDYSER LCLVSEIPPK GGALGEGPGA SPCNQHSPYW APPCYTLKPE T         531

SEQ ID NO: 203          moltype = AA  length = 528
FEATURE                 Location/Qualifiers
REGION                  1..528
                        note = MISC_FEATURE - TNFRSF1/IL9R/cGC-S/TNFR1-TM
source                  1..528
                        mol_type = protein
                        organism = synthetic construct
SEQUENCE: 203
LVPHLGDREK RDSVCPQGKY IHPQNNSICC TKCHKGTYLY NDCPGPGQDT DCRECESGSF  60
TASENHLRHC LSCSKCRKEM GQVEISSCTV DRDTVCGCRK NQYRHYWSEN LFQCFNCSLC 120
LNGTVHLSCQ EKQNTVCTCH AGFFLRENEC VSCSNCKKSL ECTKLCLPQI ENVKGTEDSG 180
TTVLLPLVIF FGLCLLSLLF IGLMYVKRIF YQNVPSPAMF FQPLYSVHNG NFQTWMGAHG 240
AGVLLSQDCA GTPQGALEPC VQEATALLTC GPARPWKSVA LEEEQEGPGT RLPGNLSSED 300
```

```
                                       -continued
VLPAGCTEWR VQTLAYLPQE DWAPTSLTRP APPDSEGSRS SSSSSSSNNN NYCALGCYGG  360
WHLSALPGNT QSSGPIPALA CGLSCDHQGL ETQQGVAWVL AGHCQRPGLH EDLQGMLLPS  420
VLSKARSWTF QPQPQPQPQP QPERTMPRIP TLKNLEDLVT EYHGNFSAWS GVSKGLAESL  480
QPDYSERLCL VSEIPPKGGA LGEGPGASPC NQHSPYWAPP CYTLKPET              528

SEQ ID NO: 204          moltype = AA  length = 489
FEATURE                 Location/Qualifiers
REGION                  1..489
                        note = MISC_FEATURE - anti-HER2 CAR (4D5)
source                  1..489
                        mol_type = protein
                        organism = synthetic construct
SEQUENCE: 204
MDFQVQIFSF LLISASVIMS RGDIQMTQSP SSLSASVGDR VTITCRASQD VNTAVAWYQQ   60
KPGKAPKLLI YSASFLYSGV PSRFSGSRSG TDFTLTISSL QPEDFATYYC QQHYTTPPTF  120
GQGTKVEIKR TGSTSGSGKP GSGEGSEVQL VESGGGLVQP GGSLRLSCAA SGFNIKDTYI  180
HWVRQAPGKG LEWVARIYPT NGYTRYADSV KGRFTISADT SKNTAYLQMN SLRAEDTAVY  240
YCSRWGGDGF YAMDVWGQGT LVTVSSTTTP APRPPTPAPT IASQPLSLRP EACRPAAGGA  300
VHTRGLDFAC DIYIWAPLAG TCGVLLLSLV ITLYCKRGRK KLLYIFKQPF MRPVQTTQEE  360
DGCSCRFPEE EEGGCELRVK FSRSADAPAY KQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                         489

SEQ ID NO: 205          moltype = AA  length = 657
FEATURE                 Location/Qualifiers
REGION                  1..657
                        note = MISC_FEATURE - DR6/IL9R/cGC-F/TNFR1-TM
source                  1..657
                        mol_type = protein
                        organism = synthetic construct
SEQUENCE: 205
QPEQKASNLI GTYRHVDRAT GQVLTCDKCP AGTYVSEHCT NTSLRVCSSC PVGTFTRHEN   60
GIEKCHDCSQ PCPWPMIEKL PCAALTDREC TCPPGMFQSN ATCAPHTVCP VGWGVRKKGT  120
ETEDVRCKQC ARGTFSDVPS SVMKCKAYTD CLSQNLVVIK PGTKETDNVC GTLPSFSSST  180
SPSPGTAIFP RPEHMETHEV PSSTYVPKGM NSTESNSSAS VRPKVLSSIQ EGTVPDNTSS  240
ARGKEDVNKT LPNLQVVNHQ QGPHHRHILK LLPSMEATGG EKSSTPIKGP KRGHPRQNLH  300
KHFDINEHVL LPLVIFFGLC LLSLLFIGLM YVKRIFYQNV PSPAMFFQPL YSVHNGNFQT  360
WMGAHGAGVL LSQDCAGTPQ GALEPCVQEA TALLTCGPAR PWKSVALEEE QEGPGTRLPG  420
NLSSEDVLPA GCTEWRVQTL AYLPQEDWAP TSLTRPAPPD SEGSRSSSSS SSSNNNNYCA  480
LGCYGGWHLS ALPGNTQSSG PIPALACGLS CDHQGLETQQ GVAWVLAGHC QRPGLHEDLQ  540
GMLLPSVLSK ARSWTFGGGG SGGGGSGGGG SERTMPRIPT LKNLEDLVTE YHGNFSAWSG  600
VSKGLAESLQ PDYSERLCLV SEIPPKGGAL GEGPGASPCN QHSPYWAPPC YTLKPET    657
```